United States Patent
Fox et al.

(10) Patent No.: US 12,344,640 B2
(45) Date of Patent: Jul. 1, 2025

(54) INSECTICIDAL PROTEINS AND METHODS FOR THEIR USE

(71) Applicant: PIONEER HI-BRED INTERNATIONAL, INC., Johnston, IA (US)

(72) Inventors: Ellaine Anne Mariano Fox, San Francisco, CA (US); Naga Kishore Kakani, Fremont, CA (US); Kay Walter, Sunnyvale, CA (US); Takashi Yamamoto, Dublin, CA (US); Yi Zheng, Newark, CA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 0 days.

(21) Appl. No.: 18/544,571

(22) Filed: Dec. 19, 2023

(65) Prior Publication Data

US 2024/0150415 A1    May 9, 2024

Related U.S. Application Data

(62) Division of application No. 17/269,314, filed as application No. PCT/US2019/047660 on Aug. 22, 2019, now Pat. No. 11,878,999.

(60) Provisional application No. 62/724,276, filed on Aug. 29, 2018.

(51) Int. Cl.
| | |
|---|---|
| *C07K 14/325* | (2006.01) |
| *A01N 63/50* | (2020.01) |
| *A01P 7/04* | (2006.01) |
| *C12N 15/82* | (2006.01) |

(52) U.S. Cl.
CPC ........... *C07K 14/325* (2013.01); *A01N 63/50* (2020.01); *A01P 7/04* (2021.08); *C12N 15/8286* (2013.01)

(58) Field of Classification Search
None
See application file for complete search history.

(56) References Cited

U.S. PATENT DOCUMENTS

| | | |
|---|---|---|
| 5,273,746 A | 12/1993 | Payne et al. |
| 5,407,825 A | 4/1995 | Payne et al. |
| 5,468,483 A | 11/1995 | Thompson et al. |

(Continued)

FOREIGN PATENT DOCUMENTS

| | | |
|---|---|---|
| BR | PI9816295 B1 | 8/2017 |
| WO | 9002801 A2 | 3/1990 |

(Continued)

OTHER PUBLICATIONS

Bravo A., et al., "Evolution of Bacillus Thuringiensis Cry Toxins Insecticidal Activity," Evolution of the Bt toxins, Microbial Biotechnology, 2012, vol. 6, No. 1, pp. 17-26.

(Continued)

*Primary Examiner* — Matthew R Keogh
*Assistant Examiner* — Rebecca Stephens

(57) ABSTRACT

This disclosure relates to the field of molecular biology. Provided are novel genes that encode pesticidal proteins. These pesticidal proteins and the nucleic acid sequences that encode them are useful in preparing pesticidal formulations and in the production of transgenic pest-resistant plants. Methods to create or alter pesticidal proteins are provided for altered or enhanced pesticidal activity.

24 Claims, 13 Drawing Sheets

Specification includes a Sequence Listing.

(56) References Cited

U.S. PATENT DOCUMENTS

| | | |
|---|---|---|
| 5,521,286 A | 5/1996 | Payne et al. |
| 5,530,195 A | 6/1996 | Kramer et al. |
| 5,686,069 A | 11/1997 | Payne et al. |
| 6,017,534 A | 1/2000 | Malvar et al. |
| 6,033,874 A | 3/2000 | Baum et al. |
| 6,780,408 B1 | 8/2004 | Bosch et al. |
| 10,611,806 B2 | 4/2020 | Baum et al. |
| 10,634,675 B2 | 4/2020 | Cummings et al. |
| 10,669,319 B2 | 6/2020 | Kennedy et al. |
| 11,008,371 B2 | 5/2021 | Abad et al. |
| 11,447,531 B2 | 9/2022 | Carlson et al. |
| 11,492,639 B2 | 11/2022 | Abad et al. |
| 2003/0188335 A1 | 10/2003 | Tuli |
| 2005/0124803 A1 | 6/2005 | Dean et al. |
| 2012/0210462 A1 | 8/2012 | Bermudez et al. |
| 2012/0324605 A1 | 12/2012 | Meade et al. |
| 2014/0109263 A1 | 4/2014 | Sheets et al. |
| 2015/0232877 A1 | 8/2015 | Cong et al. |
| 2019/0270780 A1 | 9/2019 | Abad et al. |
| 2021/0181204 A1 | 6/2021 | Yarnell et al. |
| 2021/0277070 A1 | 9/2021 | Abad et al. |
| 2021/0347830 A1 | 11/2021 | Fox et al. |
| 2022/0243221 A1 | 8/2022 | Baum et al. |

FOREIGN PATENT DOCUMENTS

| | | | |
|---|---|---|---|
| WO | 9823641 A1 | 6/1998 | |
| WO | 0215701 A2 | 2/2002 | |
| WO | 03082910 A1 | 10/2003 | |
| WO | 2009002366 A1 | 12/2008 | |
| WO | 2014055881 A1 | 4/2014 | |
| WO | 2016061208 A1 | 4/2016 | |
| WO | 2016186986 A1 | 11/2016 | |
| WO | WO-2018075197 A1 * | 4/2018 | ............ A01N 37/46 |

OTHER PUBLICATIONS

International Preliminary Report on Patentability for International Application No. PCT/US2019/047660, mailed Mar. 11, 2021, 10 Pages.

International Search Report and Written Opinion for International Application No. PCT/US2019/047660, mailed Jan. 14, 2020, 19 Pages.

Liu X.S., et al., "Redesigning Bacillus Thuringiensis Cry I Aa Toxin into a Mosquito Toxin," Protein Engineering, Design Selection, Jan. 25, 2006, vol. 19, No. 3, pp. 107-111.

Rang C., et al.,"Exchange of domain I from Bacillus thuringiensis Cry1 Toxins Influences protoxin stability and crystal formation," Current Microbiology, Jul. 2001, vol. 43(1), pp. 1-6.

Torres-Quintero M-C., et al., "Engineering Bacillus Thuringiensis Cyt1Aa Toxin Specificity from Dipteran to Lepidopteran Toxicity," Scientific Reports, 2018, vol. 8, No. 1, Article No. 4989, 12 Pages, Published Online Mar. 21, 2018, DOI:10.1038/S41598-018-22740-9.

* cited by examiner

FIG. 1

Dm2 synthesized (QLTRE to SHRLS)

| Dm1 | Dm2 | Dm3 |

Dm1 synthesized (Met to QLTRE)   Dm3 synthesized (SHRLS to end of the toxin ie AQK or AKK)

FIG. 3

| ECF2 library | | | | | |
|---|---|---|---|---|---|
| Domain-1 | | | Domain 2 &3 | | |
| α1-2 | α3-5 | α6-7 | | | |
| 1Ea | MP372 | 1Ea | | | |
| 1Ea | MP294 | 1Ea | | | |
| 1Ea | GS047 | 1Ea | | | |
| 1Ea | Eb | 1Ea | | | |
| 1Ea | Ah | 1Ea | | | |
| 1Ea | Ae | 1Ea | X | 1Ea | 1Ca |
| 1Ea | Ad | 1Ea | | | |
| 1Ea | Ab | 1Ea | | | |
| 1Ea | Aa | 1Ea | | | |
| MP372Dm1 | | | | | |
| MP294Dm1 | | | | | |
| GS047Dm1 | | | | | |
| Dm2 and Dm3 were fused at WTHRS crossover region-2 | | | | | |

| ECF3 library | | | | | |
|---|---|---|---|---|---|
| Domain-1 | | | Domain 2 &3 | | |
| α1-2 | α3-5 | α6-7 | | | |
| 1Ea | MP372 | 1Ea | | | |
| 1Ea | MP294 | 1Ea | | | |
| 1Ea | GS047 | 1Ea | | | |
| 1Ea | Eb | 1Ea | | | |
| 1Ea | Ah | 1Ea | | | |
| 1Ea | Ae | 1Ea | X | 1Ea | 1Ca |
| 1Ea | Ad | 1Ea | | | |
| 1Ea | Ab | 1Ea | | | |
| 1Ea | Aa | 1Ea | | | |
| MP372Dm1 | | | | | |
| MP294Dm1 | | | | | |
| GS047Dm1 | | | | | |
| Dm2 and Dm3 were fused at ITQIP crossover region-3 | | | | | |

| ECF4 library | | | | | |
|---|---|---|---|---|---|
| Domain-1 | | | Domain 2 &3 | | |
| α1-2 | α3-5 | α6-7 | | | |
| 1Ea | MP372 | 1Ea | | | |
| 1Ea | MP294 | 1Ea | | | |
| 1Ea | GS047 | 1Ea | | | |
| 1Ea | Eb | 1Ea | | | |
| 1Ea | Ah | 1Ea | | | |
| 1Ea | Ae | 1Ea | X | 1Ea | 1Ca |
| 1Ea | Ad | 1Ea | | | |
| 1Ea | Ab | 1Ea | | | |
| 1Ea | Aa | 1Ea | | | |
| MP372Dm1 | | | | | |
| MP294Dm1 | | | | | |
| GS047Dm1 | | | | | |
| Dm2 and Dm3 were fused at GFTGG crossover region-4 | | | | | |

FIG. 7

| | | | | IPRS (Insect-active Proteins from Region Shuffling) Constructs | | | | | | | | | | | | | | |
|---|---|---|---|---|---|---|---|---|---|---|---|---|---|---|---|---|---|---|
| | Backbone | SEQ ID NO: | Name | Toxin Composition | | | | | | | Activity (ppm) | | | | | | | |
| | | | | Dm1 | | | | Dm2 | Dm3 | | CEW | | FAW | | ECB | | SBL | | VBC |
| | | | | α1-2 | α3 | α4 | α5 | α6-7 | | | IC50 | LC50 | IC50 | LC50 | ILC50 | LC50 | ILC50 | LC50 | ILC50 | LC50 |
| FAW actives | 1Ea | 59 | IPRS-C13 | 1Ea | | Aa | | 1Ea | 1Ea | 1CaF3 | N.A. | N.A. | 3.4 | 63 | N.A. | N.A. | <3 | <3 | <1 | 16 |
| | | 60 | IPRS-C14 | 1Ea | | Ab | | 1Ea | 1Ea | 1CaF3 | N.D. | N.D. | 4.52 | 185 | N.D. | N.D. | N.D. | N.D. | N.D. | N.D. |
| | | 61 | IPRS-C15 | 1Ea | | Eb | | 1Ea | 1Ea | 1CaF3 | N.D. | N.D. | 5.06 | 168 | N.D. | N.D. | N.D. | N.D. | N.D. | N.D. |
| | | 62 | IPRS-C16 | 1Ea | | MP294 | | 1Ea | 1Ea | 1CaF3 | N.A. | N.A. | <1 | 25 | N.A. | N.A. | <3 | <3 | <1 | 4 |
| | | 63 | IPRS-C17 | 1Ea | | Ad | | 1Ea | 1Ea | 1CaF3 | N.A. | N.A. | 4 | 69 | N.A. | N.A. | <2 | <2 | <1 | 4.5 |
| | | 64 | IPRS-C19 | 1Ea | | MP294 | | 1Ea | 1Ea | 1CaF4 | N.D. | N.D. | 35 | 282 | N.D. | N.D. | N.D. | N.D. | N.D. | N.D. |
| | | 65 | IPRS-C31 | 1Ea | | Eb | | 1Ea | 1Ea | 1CaF4 | N.D. | N.D. | 333 | N.M. | N.D. | N.D. | N.D. | N.D. | N.D. | N.D. |
| | | 66 | IPRS-C18 | 1Ea | | MP294 | | 1Ea | MP372_2F | 1CaF3 | N.A. | N.A. | <1 | 11 | N.A. | N.A. | <3 | <3 | <3 | <3 |
| | | 67 | IPRS-C32 | 1Ea | | MP294 | | 1Ea | 1Cb | 1CaF3 | 78 | 164 | 38.6 | N.M. | 19 | 2000 | <1 | <1 | 0.17 | 1 |
| | | 68 | IPRS-C33 | 1Ea | | MP294 | | 1Ea | 1Ea | IfF3 | N.D. | N.D. | 63 | N.M | N.A. | N.A. | 0.7 | 2.1 | 2 | N.A. |
| | | 69 | IPRS-C34 | 1Ea | | MP294 | | 1Ea | 1Ea | 9EbF3 | N.D. | N.D. | 5 | 234 | N.D. | N.D. | 0.75 | 1.3 | 2 | N.M |
| | | 70 | IPRS-C35 | 1Ea | | MP294 | | 1Ea | MP372_2F | 1CbF2 | 13 | 151 | 7 | 580 | 45 | N.M | 1 | 1 | 2 | 125 |
| | | 71 | IPRS-C56 | 1Ea | | MP294 | | 1Ea | MP372_2F | 1AeF3 | N.D. | N.D. | 17 | N.M | N.D. | N.D. | N.D. | N.D. | N.D. | N.D. |
| | | 72 | IPRS-C57 | 1Ea | | MP294 | | 1Ea | 1Ea | 1BbF3 | N.D. | N.D. | 14 | N.M | N.A. | N.A. | 1 | 1.1 | 2 | N.M |
| | | 73 | IPRS-C58 | 1Ea | | MP294 | | 1Ea | MP372_2F1 | 1CaF3 | N.D. | N.D. | 40 | N.M | N.D. | N.D. | N.D. | N.D. | N.D. | N.D. |
| | | 74 | IPRS-C59 | 1Ea | | MP294 | | 1Ea | 1Ga_2F1 | 1CaF3 | N.D. | N.D. | 168 | N.M | N.D. | N.D. | N.D. | N.D. | N.D. | N.D. |
| | | 75 | IPRS-C71 | 1Ea | | MP294 | | 1Ea | GS028_2F1 | 1CaF3 | N.D. | N.D. | 25 | 325 | N.D. | N.D. | N.D. | N.D. | N.D. | N.D. |
| | | 76 | IPRS-C72 | 1Ea | | MP294 | | 1Ea | 1Eb_2F1 | 1CaF3 | N.D. | N.D. | 7 | 47 | N.D. | N.D. | N.D. | N.D. | N.D. | N.D. |
| | | 77 | IPRS-C73 | 1Ea | | MP294 | | 1Ea | 1Eb_2F2 | 1CaF3 | N.D. | N.D. | 3.2 | 46 | N.D. | N.D. | N.D. | N.D. | N.D. | N.D. |
| | | 78 | IPRS-C74 | 1Ea | | MP294 | | 1Ea | GS028_2F2 | 1CaF3 | N.D. | N.D. | <1 | 24 | N.D. | N.D. | N.D. | N.D. | N.D. | N.D. |
| | | 79 | IPRS-C36 | 1Ea | Da | MP294 | | 1Ea | 1Ea | 1CaF3 | N.D. | N.D. | 15 | 51 | N.D. | N.D. | N.D. | N.D. | N.D. | N.D. |
| | | 80 | IPRS-C37 | 1Ea | MP294 | | Aa | 1Ea | 1Ea | 1CaF3 | N.D. | N.D. | 3.2 | N.M | N.D. | N.D. | N.D. | N.D. | N.D. | N.D. |
| | | 81 | IPRS-C38 | 1Ea | MP294 | Ad | MP294 | 1Ea | 1Ea | 1CaF3 | N.D. | N.D. | 5.1 | N.M | N.D. | N.D. | N.D. | N.D. | N.D. | N.D. |
| | | 82 | IPRS-C39 | 1Ea | MP294 | | Ae | 1Ea | 1Ea | 1CaF3 | N.D. | N.D. | 2.4 | N.M | N.D. | N.D. | N.D. | N.D. | N.D. | N.D. |
| | | 83 | IPRS-C52 | 1Ea | MP294 | | Db | 1Ea | 1Ea | 1CaF3 | N.D. | N.D. | 17 | N.M | N.D. | N.D. | N.D. | N.D. | N.D. | N.D. |
| | | 84 | IPRS-C53 | 1Ea | MP294 | | Dc | 1Ea | 1Ea | 1CaF3 | N.D. | N.D. | 6.2 | N.M | N.D. | N.D. | N.D. | N.D. | N.D. | N.D. |
| | | 85 | IPRS-C54 | 1Ea | MP294 | | Eb | 1Ea | 1Ea | 1CaF3 | N.D. | N.D. | 4.1 | N.M | N.D. | N.D. | N.D. | N.D. | N.D. | N.D. |
| | | 86 | IPRS-C55 | 1Ea | MP294 | | Hb | 1Ea | 1Ea | 1CaF3 | N.D. | N.D. | 42.5 | N.M | N.D. | N.D. | N.D. | N.D. | N.D. | N.D. |
| | 1Ja | 87 | IPRS-C51 | 1Ja | | 1Ca | | 1Ja | 1Ja | Ja | N.D. | N.D. | 376 | N.M | N.D. | N.D. | N.D. | N.D. | N.D. | N.D. |
| CEW actives | 1Jc | 88 | IPRS-C21 | 1Jc | | 1Ca | | 1Jc | 1Jc | Jc | <1 | 20 | N.A. | N.A. | 1.9 | 9 | <1 | <1 | N.A. | N.A. |
| | | 89 | IPRS-C66 | 1Jc | | 1Ca | | 1Jc | 1Jc | 1F2F3 | 20 | 209 | N.A. | N.A. | N.A. | N.A. | 10 | 29 | 865 | N.M |
| | | 90 | IPRS-C49 | 1Jc | 1Aa | 1Ca | | 1Jc | 1Jc | 1Jc | 9.20 | N.M | N.D. | N.D. | N.D. | N.D. | N.D. | N.D. | N.D. | N.D. |
| | | 91 | IPRS-C61 | 1Jc | 1Jc | 1Ca | | 1Jc | 1Jc | 1Jc | 6.37 | N.M | N.D. | N.D. | N.D. | N.D. | N.D. | N.D. | N.D. | N.D. |
| | | 92 | IPRS-C62 | 1Jc | | 1Ca | 1Ah | 1Jc | 1Jc | 1Jc | 3.95 | N.M | N.D. | N.D. | N.D. | N.D. | N.D. | N.D. | N.D. | N.D. |
| | | 93 | IPRS-C63 | 1Jc | | 1Ca | 1Ea | 1Jc | 1Jc | 1Jc | 3.07 | N.M | N.D. | N.D. | N.D. | N.D. | N.D. | N.D. | N.D. | N.D. |
| | | 94 | IPRS-C64 | 1Jc | | 1Ca | 1Jc | 1Jc | 1Jc | 1Jc | 4.18 | N.M | N.D. | N.D. | N.D. | N.D. | N.D. | N.D. | N.D. | N.D. |
| | | 95 | IPRS-C65 | 1Jc | | 1Ca | 1Jd | 1Jc | 1Jc | 1Jc | 2.39 | N.M | N.D. | N.D. | N.D. | N.D. | N.D. | N.D. | N.D. | N.D. |
| | GS062 | 112 | IPRS-C49 | | | GS002 | | | GS062 | GS062 | N.A. | N.A. | N.A. | N.A. | N.A. | N.A. | 12 | | 80 | N.D. |
| | | 97 | IPRS-C45 | | | GS002 | | | GS062 | 1Cb (F2) | 28 | 120 | N.A. | N.A. | 65 | 320 | <3 | <3 | <3 | <3 |
| | | 99 | IPRS-C47 | | | GS002 | | | GS062 | 1Be (F3) | 20 | 70 | N.A. | N.A. | 24 | 119 | <3 | <3 | <3 | <3 |
| | | 96 | IPRS-C46 | | | GS002 | | | GS062 | 1Cb (F1) | 12 | 43 | N.D | N.D. | N.D | N.D. | N.D | N.D. | N.D. | N.D. |
| | | 98 | IPRS-C48 | | | GS002 | | | GS062 | 1Da(F2) | 40 | N.M | N.D | N.D. | N.D | N.D. | N.D | N.D. | N.D. | N.D. |
| CEW & FAW actives | MP1068 | 100 | IPRS-C23 | MP1068 | | 1Aa | | MP1068 | MP1068 | MP1068 | 5.5 | 62 | 7 | N.M | <2 | 934 | N.D. | N.D. | N.D. | N.D. |
| | | 102 | IPRS-C24 | MP1068 | | 1Aa | | MP1068 | MP1068 | 1Cb (F2) | 2 | 14 | 7 | N.M | 1.12 | 930 | <3 | <3 | 2.3 | 3.5 |
| | | 103 | IPRS-C25 | MP1068 | | 1Aa | | MP1068 | MP1068 | 1Cb (F3) | <1 | 15 | 3 | N.M | 11 | 567 | <5 | <5 | 1 | 1 |
| | | 104 | IPRS-C26 | MP1068 | | 1Aa | | MP1068 | MP1068 | 1Da (F3) | 17 | 260 | 148 | N.M | N.D | N.D. | N.D | N.D. | N.D | N.D. |
| | | 105 | IPRS-C27 | MP1068 | | 1Aa | | MP1068 | MP1068 | 1Ja (F2) | 11 | N.M | 5 | N.M | N.D | N.D. | N.D | N.D. | N.D | N.D. |
| | | 106 | IPRS-C28 | MP1068 | | 1Aa | | MP1068 | MP1068 | 1Ja (F3) | 9 | 580 | <1 | N.M | N.D | N.D. | N.D | N.D. | N.D | N.D. |
| | | 107 | IPRS-C29 | MP1068 | | 1Aa | | MP1068 | MP1068 | MP258 (F4) | 2.19 | 27 | 5.5 | N.M | N.D | N.D. | N.D | N.D. | N.D | N.D. |
| | | 109 | IPRS-C41 | MP1068 | | 1Aa | | MP1068 | MP1068 | MP258 (F2) | 5 | 100 | 16 | N.M | N.D | N.D. | N.D | N.D. | N.D | N.D. |
| | | 108 | IPRS-C42 | MP1068 | | 1Aa | | MP1068 | MP1068 | MP258 (F3) | <1 | 25 | 3.6 | N.M | 1.2 | 105 | <2 | <2 | 120 | 1020 |
| | | 110 | IPRS-C43 | MP1068 | | 1Aa | | MP1068 | MP1068 | MP258 (F5) | <1 | 31 | 4.5 | N.M | 1 | 427 | <3 | <3 | 61 | 266 |
| | | 111 | IPRS-C44 | MP1068 | | 1Aa | | MP1068 | MP1068 | 1Bb (F3) | 11.4 | 224 | N.A. | N.A. | N.D. | N.D. | N.D. | N.D. | N.D. | N.D. |

FIG. 8

| Alpha 3 to part of Alpha 5 shuffling | | | | | | | | | |
|---|---|---|---|---|---|---|---|---|---|
| | Alpha-3, Alpha-4 and Part of Alpha-5 | | | | | | | | |
| Used in | | | | | | | | | |
| 1. Example 3: 1. Cry1J Alpha3-5 shuffling (for IPRS hits C21 and C51) | | | | | | | | | |
| 2. Example 4: Dm1Alpha3-5 and Dm3 shuffling on Cry1Ea backbone for IPRS hits: C13, 14, 15, 16, 17, 19 and 31 | | | | | | | | | |
| 3. Example 5: Sequential Alpha3-5 and Dm3 shuffling on MP1068 backbone | | | | | | | | | |
| Anchor sequences used in Alpha-3-5 shuffling of Cry toxins: | | | | | | | | | |
| 5' end | | | | | 3' end | | | | |
| Q | I | E | Q | L | A | N | L | H | L |
| H | V | L | R | I | V | F | F | | |
| R | M | | E | | | | | | |
| | L | | L | | | | | | |
| | | | S | | | | | | |

Alpha 3, Alpha 4, Alpha 5 (complete), Alpha 3-4, Alpha 4-5 and Alpha 3-5 (complete alpha 5)

FIG. 10

| IPRS Variant Name | Amino Acid SEQ ID NO: | DNA SEQ ID NO: |
|---|---|---|
| IPRS-C11 | 57 | 1 |
| IPRS-C12 | 58 | 2 |
| IPRS-C13 | 59 | 3 |
| IPRS-C14 | 60 | 4 |
| IPRS-C15 | 61 | 5 |
| IPRS-C16 | 62 | 6 |
| IPRS-C17 | 63 | 7 |
| IPRS-C19 | 64 | 8 |
| IPRS-C31 | 65 | 9 |
| IPRS-C18 | 66 | 10 |
| IPRS-C32 | 67 | 11 |
| IPRS-C33 | 68 | 12 |
| IPRS-C34 | 69 | 13 |
| IPRS-C35 | 70 | 14 |
| IPRS-C56 | 71 | 15 |
| IPRS-C57 | 72 | 16 |
| IPRS-C58 | 73 | 17 |
| IPRS-C59 | 74 | 18 |
| IPRS-C71 | 75 | 19 |
| IPRS-C72 | 76 | 20 |
| IPRS-C73 | 77 | 21 |
| IPRS-C74 | 78 | 22 |
| IPRS-C36 | 79 | 23 |
| IPRS-C37 | 80 | 24 |
| IPRS-C38 | 81 | 25 |
| IPRS-C39 | 82 | 26 |
| IPRS-C52 | 83 | 27 |
| IPRS-C53 | 84 | 28 |

| IPRS Variant Name | Amino Acid SEQ ID NO: | DNA SEQ ID NO: |
|---|---|---|
| IPRS-C54 | 85 | 29 |
| IPRS-C55 | 86 | 30 |
| IPRS-C51 | 87 | 31 |
| IPRS-C21 | 88 | 32 |
| IPRS-C66 | 89 | 33 |
| IPRS-C49 | 90 | 34 |
| IPRS-C61 | 91 | 35 |
| IPRS-C62 | 92 | 36 |
| IPRS-C63 | 93 | 37 |
| IPRS-C64 | 94 | 38 |
| IPRS-C65 | 95 | 39 |
| IPRS-C46 | 96 | 40 |
| IPRS-C45 | 97 | 41 |
| IPRS-C48 | 98 | 42 |
| IPRS-C47 | 99 | 43 |
| IPRS-C23 | 100 | 44 |
| IPRS-C44 | 101 | 45 |
| IPRS-C24 | 102 | 46 |
| IPRS-C25 | 103 | 47 |
| IPRS-C26 | 104 | 48 |
| IPRS-C27 | 105 | 49 |
| IPRS-C28 | 106 | 50 |
| IPRS-C29 | 107 | 51 |
| IPRS-C42 | 108 | 52 |
| IPRS-C41 | 109 | 53 |
| IPRS-C43 | 110 | 54 |
| IPRS-C44 | 111 | 55 |
| IPRS-C49 | 112 | 56 |

FIG. 11

| Cry Variant Alpha Loop 3-5 Fragment | Amino Acid SEQ ID NO: | DNA SEQ ID NO: |
|---|---|---|
| 1Ac | 159 | 137 |
| 1Ab | 160 | 138 |
| 1Aa | 161 | 139 |
| 1Ag | 162 | 140 |
| TA009 | 163 | 141 |
| 1Db | 164 | 142 |
| 1Ea | 165 | 143 |
| 1Eb | 166 | 144 |
| 1Ah | 167 | 145 |
| 1Ca | 168 | 146 |
| 1Cb | 169 | 147 |
| 1Hb | 170 | 148 |
| 1Gc | 171 | 149 |
| 1Ja | 172 | 150 |
| 1Jb | 173 | 151 |
| 1Jd | 174 | 152 |
| 1Jc | 175 | 153 |
| 1Gb | 176 | 154 |
| 1Ga | 177 | 155 |
| 1La | 178 | 156 |
| 1Ka | 179 | 157 |
| 1Ma | 180 | 158 |

FIG. 12

| Proprietary Cry Toxin Name | DNA SEQ ID NO: | Amino Acid SEQ ID NO: |
|---|---|---|
| MP1068 | 181 | 214 |
| MP372 | 182 | 215 |
| GS062 | 183 | 216 |
| GS028 | 184 | 217 |
| MP294 | 185 | 218 |
| MP627 | 186 | 219 |
| MP265 | 187 | 220 |
| MP626 | 188 | 221 |
| MP596 | 189 | 222 |
| MP477 | 190 | 223 |
| GS062 | 191 | 224 |
| MP047 | 192 | 225 |
| GS030 | 193 | 226 |
| GS150 | 194 | 227 |
| GS074 | 195 | 228 |
| MP252 | 196 | 229 |
| GS135 | 197 | 230 |
| MP547 | 198 | 231 |
| GS148 | 199 | 232 |
| MP310 | 200 | 233 |
| GS155 | 201 | 234 |
| TA006 | 202 | 235 |
| GS018 | 203 | 236 |
| MP071 | 204 | 237 |
| MP448 | 205 | 238 |
| MP315 | 206 | 239 |
| MP310 | 207 | 240 |
| MP316 | 208 | 241 |
| MP327 | 209 | 242 |
| TA005 | 210 | 243 |
| GS128 | 211 | 244 |
| MP259 | 212 | 245 |
| MP250 | 213 | 246 |

FIG. 13

| Cry Toxin Domain 3 regions showing altered activity when swapped to another Cry toxin | Amino Acid SEQ ID NO: |
|---|---|
| Cry1F | 259 |
| Cry1Cb | 260 |
| Cry1Fa | 261 |
| Cry9Ea | 262 |
| Cry1Ae | 263 |
| Cry1Bb | 264 |
| Cry1Ca | 265 |
| Cry1Da | 268 |
| Cry1Ja | 269 |
| Cry1If | 270 |

SEQUENCE LISTING

```
Sequence total quantity: 278
SEQ ID NO: 1            moltype = DNA  length = 1944
FEATURE                 Location/Qualifiers
misc_feature            1..1944
                        note = Synthetic
source                  1..1944
                        mol_type = other DNA
                        organism = synthetic construct
SEQUENCE: 1
atgcctagca accgtaagaa cgagaacgaa atcatcaacg cagtaagcaa tcacagcgcg  60
caaatggacc tgagcctgga cgcgcgcatt gaggatagct tgtgcgttgc agaggtgaac  120
aacattgacc cgttcgttag cgcgtcgacg gtccaaaccg gcattagcat cgccggtcgc  180
atcctcggtg tgttgggtgt cccgttcgcg ggtcagctgg cgagcttcta cagcttcctg  240
gtgggcgagt tatggcctag cggtcgcgac ccgtgggaga tctttatgga gcacgtggag  300
caaatcgttc gtcaacagat cacggacagc gtgcgcgaca ccgcaattgc tcgtctggaa  360
ggcctgggtc gtggctaccg tagctatcag caagctctgg aaacctggct ggataatcgt  420
aatgacgcgc gttcccgcag cattattcgt gaacgttaca tcgcgctgga gctggacatt  480
acgaccgcta ttccgctgtt ctccattcgt aatcaagaag tgccgctgct gatggtctat  540
gcgcaagccg ccaatttgca tctgcttctg ctgcgtgacg caagcctgtt tggttctgag  600
tggggcatga gctctagcga tgtcaatcag tactatcaag agcagattcg ttacaccgaa  660
gaatacagca atcactgtgt tcagtggtac aataccggtt tgaacaatct gagaggcacc  720
aacgcggaaa gctggctgcg ctataatcag tttcgtcgtg atctgaccct gggcgtcttg  780
gatctggttg cactgttccc gtcttacgat acgcgcgtgt acccgatgaa tacctctgcc  840
cagctgacgc gcgaaattta caccaatcca gtattcgaaa actccccggt taatatcaac  900
ttggtgaacg gtttcaatcg ggttgaatat ggtgtgcgtc agccgcacct gatggatcac  960
cttatgaacg tgtcaatttc tgaagaagat tatcgtgggg atacgttctg gggcggccac  1020
tccattgcaa gcgtggatac cggaggtaac ctggtggggt ttccgttcta cggcaacttc  1080
gatcgttttc gttttcagac cattaatgcg caacaattcc cgcttttccg gacgcttagc  1140
gacccggttt ataatctgtc caccagcggg ggtcgtaatc gccttttcgc cctggaaggg  1200
attggcttcc agcaagccgt aactggtacc acgcgggcat ttcgccgtgt tggcaccatt  1260
gattcactga ttgagatccc gccacaagat gaaagtgaag taccttggaa tggttattcc  1320
catgtactga atcacatcac ctttattaat tggccggccg ttttcctgca aggcgaacgt  1380
attgcgtcgc cgatgtttag ctggacccat cgctccgcta ccttaacgaa tactattgat  1440
ccggagcgca tcaaccagat tccgttggtc aaaggtttcc gcgtctgggg tggtacgagc  1500
gtgattacgg gtccgggatt taccggcggt gatatcctgc gtcgtaacac ctttggtgac  1560
tttgttagcc tgcaagtgaa tatcaatagc ccgattactc agcgctaccg tctgcgtttc  1620
cgctatgcca gctcccgtga cgcacgcgtg atcgttctga cgggtgcggc aagcaccggt  1680
gtgggtggcc aggtttctgt taacatgccg ctgcagaaaa ccatggaaat cggtgaaaat  1740
ctgacgtcgc gtacctttcg ctataccgat ttctccaacc cattctcatt tcgtgcgaat  1800
ccggatatca tcggcattag cgagcaacct ctgtttggtg cgggcagcat tagcagcggt  1860
gagctgtaca ttgacaaaat tgagattatc ctggcagatg cgacgttcga agccgagtcc  1920
gatctggaac gcgcgcagaa gtaa                                          1944

SEQ ID NO: 2            moltype = DNA  length = 1986
FEATURE                 Location/Qualifiers
```

| | | |
|---|---|---|
| misc_feature | 1..1986 | |
| | note = Synthetic | |
| source | 1..1986 | |
| | mol_type = other DNA | |
| | organism = synthetic construct | |

SEQUENCE: 2

```
atgcctagca accgtaagaa cgagaacgaa atcatcaacg cagtaagcaa tcacagcgcg   60
caaatggacc tgagcctgga cgcgcgcatt gaggatagct tgtgcgttgc agaggtgaac  120
aacattgacc cgttcgttag cgcgtcgacg gtccaaaccg gcattagcat cgccggtcgc  180
atcctcggtg tgttgggtgt cccgttcgcg ggtcagctgg cgagcttcta cagcttcctg  240
gtgggcgagt tatggcctag cggtcgcgac ccgtgggaga tctttatgga gcacgtggag  300
caaatcgttc gtcaacagat cacggacagc gtgcgcgaca ccgcaattgc tcgtctggaa  360
ggcctgggtc gtggctaccg tagctatcag caagctctgg aaacctggct ggataatcgt  420
aatgacgcgc gttcccgcag cattattcgt gaacgttaca tcgcgctgga gctggaccat  480
acgaccgcta ttccgctgtt ctccattcgt aatcaagaag tgccgctgct gatggtctat  540
gcgcaagccg ccaatttgca tctgcttctg ctgcgtgacg caagcctgtt tggttctgag  600
tggggcatga gctctagcga tgtcaatcag tactatcaag agcagattcg ttacaccgaa  660
gaatacaatc catcactgtgt tcagtggtac aataccggtt gaacaatcct agagaggcacc  720
aacgcggaaa gctggctgcg ctataatcag tttcgtcgtg atctgaccct gggcgtcttg  780
gatctggttg cactgttccc gtcttacgat acgcgcgtgt acccgatgaa tacctctgcc  840
cagctgacgc gcgaaatcta caccgacccg atcggtcgca ctaacgctcc atccggtttc  900
gcgagcacca actggttcaa caataacgca ccgagctcg gcgcgatcga ggccgcgcag  960
tttcgtccgc cgcacctgat ggattttcca gagcagttaa ctatttatag caccctgtcc 1020
cgttggtcta cacgcagta tatgaacatt tgggtgggcc accgcctgga gagccgcact 1080
atcggaggtt cactgaatac ctccacgcaa ggttctacaa ataccagtat taaccccgta 1140
cgtttgcagt tcacggcgcg tgatgtttac cgtaccgaaa gcctggctgg ccttaacatt 1200
ttccttactc agccggttaa tggtgtacca tgggtgcgct tcaactggcg caatccgctg 1260
aattcgctgc gtgggtcctt gctgtatact attggctata ccggcgtggg cactcaactg 1320
caggattcag aaaccgagct gccgccagaa acaacgaac gtccgaacta cgaatcatat 1380
tcccatcgcc tgagccacat cgggctgatt agcagcgatc gtgtccgac attggtgtac 1440
agctggaccc atcgctccgc taccttaacg aatactattg atccggagcg catcaaccag 1500
attccgttgg tcaaaggttt ccgcgtctgg ggtggtacga gcgtgattac gggtccggga 1560
tttaccggcg gtgatatcct gcgtcgtaac acctttggtg actttgttag cctgcaagtg 1620
aatatccaata gcccgattac tcagcgctac cgtctgcgtt tccgctatgc cagctccgt 1680
gacgcacgcg tgatcgttct gacgggtgcg gcaagcaccg gtgtgggtgg ccaggtttct 1740
gttaacatgc cgctgcagaa aaccatggaa atcggtgaaa atctgacgtc gcgtaccttt 1800
cgctataccg atttctccaa cccattctca tttcgtgcga atccggatat catcggcatt 1860
agcgagcaac ctctgtttgg tgcgggcagc attagcagcg gtgagctgta cattgacaaa 1920
attgagatta tcctggcaga tgcgacgttc gaagccgagt ccgatctgga acgcgcgcag 1980
aagtaa                                                             1986
```

| | | |
|---|---|---|
| SEQ ID NO: 3 | moltype = DNA length = 1884 | |
| FEATURE | Location/Qualifiers | |
| misc_feature | 1..1884 | |
| | note = Synthetic | |
| source | 1..1884 | |
| | mol_type = other DNA | |
| | organism = synthetic construct | |

SEQUENCE: 3

```
atggaaatcg ttaataacca gaaccagtgc gttccgtaca actgtctgaa caaccctgaa   60
aacgaaatcc tggatatcga acgttccaac tccacggtgg ccaccaacat cgctctggaa  120
atttcccgcc tgctggcaag cgccactcca attggtggta ttctgctggg cctgttcgac  180
gccatttggg gttctatcgg cccgtctcaa tgggaccgt ttctggaaca gatcgaacag  240
ctgattaacc agcgtatcga agaattcgcg cgtaaccagg caatctcccg tctggaaggt  300
ctgtccaacc tgtaccagat ctacgcagag tccttccgtg aatggaaagt gatccgaac  360
aacccggcac tgcgcgaaga aatgcgtatc cagttcaacg acatgaactc tgctctgacg  420
acggccatcc ctctgctggc tgtgcagaat tatcaggtac cgctgctgtc tgtgtacgtg  480
caggcggcga acctgcatct gtccgtactg cgtgacgtgt ctgttttcgg ccaggcgtgg  540
ggtttcgaca ttgccactat caactctcgt taccatgacc tgaccgtctg gatcccgatc  600
tatacggact acgctgttcg ttggtacaac actggtctgg atcgtctgcc acgtaccggc  660
gtctgcgca attgggctcg tttcaaccag ttccgtcgtg agctgactat ctctgtgctg  720
gacatcatta gcttcttccg caactatgac tctgcctgt atcaatccc aaccagcagc  780
cagctgacgc gtgaagtgta tactgaccct gtcatcaaca ttaccgacta tcgtgttggt  840
ccgtctttcg aaaacatcga aactctgca atccgtttcc gcacctgat ggattttcct  900
aacaacctga ccattgacac cgatctgatc cgtggcgtga actacgtggc tggtcaccgt  960
gttacgtccc acttcactgg ctccagccag gtgatcacga ctccacagta cggcattact 1020
gcgaacgcgg aaccaccgcg caccatcgct ccgtccacgt tccgggtct gaacctgttc 1080
taccgcactc tgagcaaccc gttttttccgt cgttctgaaa acatcactcc aaccctgggt 1140
atcaacgtag ttcaggggtgt cggcttcatt cagccgaaca acgctgaagt actgtaccgt 1200
tcccgtggca ccgtagatag cctgaatgaa ctgccaattg atggtgagaa ctctctggtg 1260
ggttacagcc accgctgtc ccatgtaacg ctgacccgca gcctgtacaa taccaacatc 1320
accagcctgc cgactttcgt gtggactcat cattctgcga ccaacaccaa cactattaac 1380
ccggacatta tcacccagat cccgctggtg aagggctttc gtgtttgggg cggcacttcc 1440
gtaatcactg gtccgggttt cacgggtggc gatattctgc gcaacac gttcggcgac 1500
ttcgtttccc tgcaggtaaa catcaactct ccgatcaccc agcgctaccg cctgcgcttc 1560
cgttacgcct cttctcgtga tgcacgtgtt atcgtcctga ccgcgcagc aagcaccggc 1620
gttggtggtc aagtttctgt gaacatgcca ctgcagaaaa ccatgaaat cggcgaaaac 1680
ctgacgtccc gcactttccg ctataccgat tttagcaatc cgttctcctt tcgtgcaaac 1740
ccggacatca ttggcatctc tgagcaaccg ctgttcggtg ctggttccat ctcctctggt 1800
```

```
gagctgtata tcgacaagat cgaaattatc ctggcggacg ctaccttcga agcggagagc   1860
gacctggaac gcgcgcagaa ataa                                         1884

SEQ ID NO: 4             moltype = DNA  length = 1884
FEATURE                  Location/Qualifiers
misc_feature             1..1884
                         note = Synthetic
source                   1..1884
                         mol_type = other DNA
                         organism = synthetic construct
SEQUENCE: 4
atggaaatcg ttaataacca gaaccagtgc gttccgtaca actgtctgaa caaccctgaa     60
aacgaaatcc tggatatcga acgttccaac tccacggtgg ccaccaacat cgctctggaa   120
atttcccgcc tgctggcaag cgccactcca attggtggta ttctgctggg cctgttcgac   180
gccatttggg gttctatcgg cccgtctcaa tgggaccgct ttctggaaca gatcgaacag   240
ctgattaacc aacgtatcga agaattcgcg cgtaaccagg caatttcacg cctgaaggt   300
ctgagtaacc tttaccagat ttatgctgaa tcgttccggg aatgggaagc agaccctacc   360
aacccggcac ttcgtgagga aatgcgcatc cagttcaatg atatgaatag cgcgctgaca   420
actgctatcc cacttttcgc cgttcagaat tatcaagtcg cgctgctgtc tgtttacgtc   480
caggccgcga acctgcatct gtccgtactg cgtgacgtgt ctgttttcgg ccaggcgtgg   540
ggtttcgaca ttgccactat caactctcgt tacaatgacc tgaccgctct gatcccgatc   600
tatacggact acgctgttcg ttggtacaac actggtctgg atcgtctgcc acgtaccggc   660
ggtctgcgca attgggctcg tttcaaccag ttccgtcgtg agctgactat ctctgtgctg   720
gacatcatta gcttcttccg caactatgac tctcgcctgt atccaatccc aaccagcagc   780
cagctgacgc gtgaagtgta tactgaccct gtcatcaaca ttaccgacta tcgtgttggt   840
ccgtctttcg aaaacatcga aaactctgca atccgttccc gcacctgat ggattttctg   900
aacaacctga ccattgacac cgatctgatc cgtggcgtgc actactgggc tggtcaccgt   960
gttacgtccc acttcactgg ctccagccag gtgatcacga ctccacagta cggcattact  1020
gcgaacgcgg aaccacgccg caccatcgct ccgtccacgt tcccgggtct gaacctgttc  1080
taccgcactc tgagcaaccc gtttttccgt cgttctgaaa acatcactcc aaccctgggt  1140
atcaacgtag ttcagggtgt cggcttcatt cagccgaaca acgctgaagt actgtaccgt  1200
tcccgtggca ccgtagatag cctgaatgaa ctgccaattg atggtgagaa ctctctggtg  1260
ggttacagcc accgctgtc ccatgtaacg ctgacccgca gcctgtacaa taccaacatc  1320
accagcctgc cgactttcgt gtggactcat cattctgcga ccaacaccaa cactattaac  1380
ccggacatta tcacccagat cccgctggtg aagggctttc gtgtttgggg cggcacttcc  1440
gtaatcactg gtccgggttt cacgggtggc gatattctgc gtcgcaacac gttcggcgac  1500
ttcgtttccc tgcaggtaaa catcaactct ccgatcaccc agcgctaccg cctgcgcttc  1560
cgttacgcct cttctcgtga tgcacgtgtt atcgtcctga ccggcgcagc aagcaccggc  1620
gttggtggtc aagtttctgt gaacatgcca ctgcagaaaa ccatggaaat cggcgaaaac  1680
ctgacgtccc gcacttttccg ctataccgat tttagcaatc cgttctcctt tcgtgcaaac  1740
ccggacatca ttggcatctc tgagcaaccg cgtgttcggtg ctggttccat ctcctctggt  1800
gagctgtata tcgacaagat cgaaattatc ctggcggacg ctaccttcga agcggagagc  1860
gacctggaac gcgcgcagaa ataa                                         1884

SEQ ID NO: 5             moltype = DNA  length = 1884
FEATURE                  Location/Qualifiers
misc_feature             1..1884
                         note = Synthetic
source                   1..1884
                         mol_type = other DNA
                         organism = synthetic construct
SEQUENCE: 5
atggaaatcg ttaataacca gaaccagtgc gttccgtaca actgtctgaa caaccctgaa     60
aacgaaatcc tggatatcga acgttccaac tccacggtgg ccaccaacat cgctctggaa   120
atttcccgcc tgctggcaag cgccactcca attggtggta ttctgctggg cctgttcgac   180
gccatttggg gttctatcgg cccgtctcaa tgggaccgtt ttctggaaca gatcgaacag   240
ctgatcggcc agcgtatcga agaattcgca cgcaatcagg ccatttctcg tctgcaaggc   300
ctgtctaacc tgtatcgcat ctacaccaat gctttcaaaa attgggaagt agacccgact   360
aatccggctc tgcgcgaaga aatgcgcatt cagtttaacg atatgaactc cgcgctgacg   420
actgcaattc cgctgttctc tgttcagggt tacgaaatcc cgctgctgtc tgtctacgtt   480
caggccgcga acctgcatct gtccgtactg cgtgacgtgt ctgttttcgg ccaggcgtgg   540
ggtttcgaca ttgccactat caactctcgt tacaatgacc tgaccgctct gatcccgatc   600
tatacggact acgctgttcg ttggtacaac actggtctgg atcgtctgcc acgtaccggc   660
ggtctgcgca attgggctcg tttcaaccag ttccgtcgtg agctgactat ctctgtgctg   720
gacatcatta gcttcttccg caactatgac tctcgcctgt atccaatccc aaccagcagc   780
cagctgacgc gtgaagtgta tactgaccct gtcatcaaca ttaccgacta tcgtgttggt   840
ccgtctttcg aaaacatcga aaactctgca atccgttccc gcacctgat ggattttctg   900
aacaacctga ccattgacac cgatctgatc cgtggcgtgc actactgggc tggtcaccgt   960
gttacgtccc acttcactgg ctccagccag gtgatcacga ctccacagta cggcattact  1020
gcgaacgcgg aaccacgccg caccatcgct ccgtccacgt tcccgggtct gaacctgttc  1080
taccgcactc tgagcaaccc gtttttccgt cgttctgaaa acatcactcc aaccctgggt  1140
atcaacgtag ttcagggtgt cggcttcatt cagccgaaca acgctgaagt actgtaccgt  1200
tcccgtggca ccgtagatag cctgaatgaa ctgccaattg atggtgagaa ctctctggtg  1260
ggttacagcc accgctgtc ccatgtaacg ctgacccgca gcctgtacaa taccaacatc  1320
accagcctgc cgactttcgt gtggactcat cattctgcga ccaacaccaa cactattaac  1380
ccggacatta tcacccagat cccgctggtg aagggctttc gtgtttgggg cggcacttcc  1440
gtaatcactg gtccgggttt cacgggtggc gatattctgc gtcgcaacac gttcggcgac  1500
ttcgtttccc tgcaggtaaa catcaactct ccgatcaccc agcgctaccg cctgcgcttc  1560
cgttacgcct cttctcgtga tgcacgtgtt atcgtcctga ccggcgcagc aagcaccggc  1620
```

| | | |
|---|---|---|
| gttggtggtc aagtttctgt gaacatgcca ctgcagaaaa ccatggaaat cggcgaaaac | | 1680 |
| ctgacgtccc gcactttccg ctataccgat tttagcaatc cgttctcctt tcgtgcaaac | | 1740 |
| ccggacatca ttggcatctc tgagcaaccg ctgttcggtg ctggttccat ctcctctggt | | 1800 |
| gagctgtata tcgacaagat cgaaattatc ctggcggacg ctaccttcga agcggagagc | | 1860 |
| gacctggaac gcgcgcagaa ataa | | 1884 |

```
SEQ ID NO: 6            moltype = DNA  length = 1884
FEATURE                 Location/Qualifiers
misc_feature            1..1884
                        note = Synthetic
source                  1..1884
                        mol_type = other DNA
                        organism = synthetic construct
SEQUENCE: 6
```

| | | |
|---|---|---|
| atggaaatcg ttaataacca gaaccagtgc gttccgtaca actgtctgaa caaccctgaa | | 60 |
| aacgaaatcc tggatatcga acgttccaac tccacggtgg ccaccaacat cgctctggaa | | 120 |
| atttcccgcc tgctggcaag cgccactcca attggtggta ttctgctggg cctgttcgac | | 180 |
| gccatttggg gttctatcgg cccgtctcaa tgggacctgt ttctgaaca gatcgaacag | | 240 |
| ctgattggcc aacgtatcga agaattcgcg cgtaaccagg caatttcacg cctgaaggt | | 300 |
| ctgagtaacc tttaccggat ttatactaac gcgttcaaga actgggaagc agaccctacc | | 360 |
| aacccggtac ttcgtgagga aatgcgcatc cagttcaatg atatgaatag cgcgtttaca | | 420 |
| actgctatcc cacttttctc cgttcaggt tatgaaattc cgctgctggt tgtttacgtc | | 480 |
| caggccgcga acctgcatct gtccgtactg cgtgacgtgt ctgttttcgg ccaggcgtgg | | 540 |
| ggtttcgaca ttgccactat caactctcgt tacaatgacc tgaccgtct gatcccgatc | | 600 |
| tatacgact acgctgttcg ttggtacaac actggtctgg atcgtctgcc acgtaccggc | | 660 |
| ggtctgcgca attgggctcg tttcaaccag ttccgtcgtg agctgactat ctctgtgctg | | 720 |
| gacatcatta gcttcttccg caactatgac tctcgcctgt atccaatccc aaccagcagc | | 780 |
| cagctgacgc gtgaagtgta tactgaccct gtcatcaaca ttaccgacta tcgtgttggt | | 840 |
| ccgtctttcg aaaacatcga aaactctgca atccgttccc gcacctgat ggatttctg | | 900 |
| aacaacctga ccattgacac cgatctgatc cgtggcgtgc actactgggc tggtcaccgt | | 960 |
| gttacgtccc acttcactgg ctccagccag gtgatcacga ctccacagta cggcattact | | 1020 |
| gcgaacgcgg aaccacgccg caccatcgct ccgtccacgt tcccgggtct gaacctgttc | | 1080 |
| taccgcactc tgagcaaccc gtttttccgt cgttctgaaa acatcactcc aaccctgggt | | 1140 |
| atcaacgtag ttcagggtgt cggcttcatt cagccgaaca acgctgaagt actgtaccgt | | 1200 |
| tcccgtggca ccgtagatag cctgaatgaa ctgccaattg atggtgagaa ctctctggtg | | 1260 |
| ggttacagcc accgcctgtc ccatgtaacg ctgacccgca gctgtacaa taccaacatc | | 1320 |
| accagcctgc cgactttcgt gtggactcat cattctgcga ccaacaccaa cactattaac | | 1380 |
| ccggacatta tcacccagat cccgctggtg aagggctttc gtgtttgggg cggcacttcc | | 1440 |
| gtaatcactg gtccggggttt cacgggtggc gatattctgc gtcgcaacac gttcggcgac | | 1500 |
| ttcgttttccc tgcaggtaaa catcaactct ccgatcaccc agcgctaccg cctgcgcttc | | 1560 |
| cgttacgcct cttctcgtga tgcacgtgtt atcgtcctga ccggcgcagc aagcaccggc | | 1620 |
| gttggtggtc aagtttctgt gaacatgcca ctgcagaaaa ccatggaaat cggcgaaaac | | 1680 |
| ctgacgtccc gcactttccg ctataccgat tttagcaatc cgttctcctt tcgtgcaaac | | 1740 |
| ccggacatca ttggcatctc tgagcaaccg ctgttcggtg ctggttccat ctcctctggt | | 1800 |
| gagctgtata tcgacaagat cgaaattatc ctggcggacg ctaccttcga agcggagagc | | 1860 |
| gacctggaac gcgcgcagaa ataa | | 1884 |

```
SEQ ID NO: 7            moltype = DNA  length = 1884
FEATURE                 Location/Qualifiers
misc_feature            1..1884
                        note = Synthetic
source                  1..1884
                        mol_type = other DNA
                        organism = synthetic construct
SEQUENCE: 7
```

| | | |
|---|---|---|
| atggaaatcg ttaataacca gaaccagtgc gttccgtaca actgtctgaa caaccctgaa | | 60 |
| aacgaaatcc tggatatcga acgttccaac tccacggtgg ccaccaacat cgctctggaa | | 120 |
| atttcccgcc tgctggcaag cgccactcca attggtggta ttctgctggg cctgttcgac | | 180 |
| gccatttggg gttctatcgg cccgtctcaa tgggacctgt ttctgaaca gatcgaacag | | 240 |
| ctgattaacc aacgtatcga agaattcgcg cgtaaccagg caatttcacg cctgaaggt | | 300 |
| ctgagtaacc tttaccagat ttatgctgaa gcgttccggg aatgggaagc agaccctacc | | 360 |
| aacccggcac ttactgagga aatgcgcatc cagttcaatg atatgaatag cgcgctgaca | | 420 |
| actgctatcc cacttttcac cgttcagaat tatcaagtgc cgctgctgtc tgtttacgtc | | 480 |
| caggccgcga acctgcatct gtccgtactg cgtgacgtgt ctgttttcgg ccaggcgtgg | | 540 |
| ggtttcgaca ttgccactat caactctcgt tacaatgacc tgaccgtct gatcccgatc | | 600 |
| tatacgact acgctgttcg ttggtacaac actggtctgg atcgtctgcc acgtaccggc | | 660 |
| ggtctgcgca attgggctcg tttcaaccag ttccgtcgtg agctgactat ctctgtgctg | | 720 |
| gacatcatta gcttcttccg caactatgac tctcgcctgt atccaatccc aaccagcagc | | 780 |
| cagctgacgc gtgaagtgta tactgaccct gtcatcaaca ttaccgacta tcgtgttggt | | 840 |
| ccgtctttcg aaaacatcga aaactctgca atccgttccc gcacctgat ggatttctg | | 900 |
| aacaacctga ccattgacac cgatctgatc cgtggcgtgc actactgggc tggtcaccgt | | 960 |
| gttacgtccc acttcactgg ctccagccag gtgatcacga ctccacagta cggcattact | | 1020 |
| gcgaacgcgg aaccacgccg caccatcgct ccgtccacgt tcccgggtct gaacctgttc | | 1080 |
| taccgcactc tgagcaaccc gtttttccgt cgttctgaaa acatcactcc aaccctgggt | | 1140 |
| atcaacgtag ttcagggtgt cggcttcatt cagccgaaca acgctgaagt actgtaccgt | | 1200 |
| tcccgtggca ccgtagatag cctgaatgaa ctgccaattg atggtgagaa ctctctggtg | | 1260 |
| ggttacagcc accgcctgtc ccatgtaacg ctgacccgca gctgtacaa taccaacatc | | 1320 |
| accagcctgc cgactttcgt gtggactcat cattctgcga ccaacaccaa cactattaac | | 1380 |
| ccggacatta tcacccagat cccgctggtg aagggctttc gtgtttgggg cggcacttcc | | 1440 |

```
gtaatcactg gtccgggttt cacgggtggc gatattctgc gtcgcaacac gttcggcgac    1500
ttcgtttccc tgcaggtaaa catcaactct ccgatcaccc agcgctaccg cctgcgcttc    1560
cgttacgcct cttctcgtga tgcacgtgtt atcgtcctga ccggcgcagc aagcaccggc    1620
gttggtggtc aagtttctgt gaacatgcca ctgcagaaaa ccatggaaat cggcgaaaac    1680
ctgacgtccc gcacttttcc g ctataccgat tttagcaatc cgttctcctt tcgtgcaaac   1740
ccggacatca ttggcatctc tgagcaaccg ctgttcggtg ctggttccat ctcctctggt    1800
gagctgtata tcgacaagat cgaaattatc ctggcggacg ctaccttcga agcggagagc    1860
gacctggaac gcgcgcagaa ataa                                          1884

SEQ ID NO: 8             moltype = DNA   length = 1884
FEATURE                  Location/Qualifiers
misc_feature             1..1884
                         note = Synthetic
source                   1..1884
                         mol_type = other DNA
                         organism = synthetic construct
SEQUENCE: 8
atggaaatcg ttaataacca gaaccagtgc gttccgtaca actgtctgaa caaccctgaa     60
aacgaaatcc tggatatcga acgttccaac tccacggtgg ccaccaacat cgctctggaa    120
atttcccgcc tgctggcaag cgccactcca attggtggta ttctgctggg cctgttcgac    180
gccatttggg gttctatcgg cccgtctcaa tgggacctgt ttctggaaca gatcgaacag    240
ctgattggcc aacgtatcga agaattcgcg cgtaaccagg caatttcacg gctggaaggt    300
ctgagtaacc tttaccggat ttatactaac gcgttcaaga actgggaagc agaccctacc    360
aacccggtac ttcgtgagga aatgcgcatc cagttcaatg atatgaatag cgcgtttaca    420
actgctatcc cacttttctc cgttcagggt tatgaaattc cgctgctggg tgtttacgtc    480
caggccgcga acctgcatct gtccgtactg cgtgacgtgt ctgttttcgg ccaggcgtgg    540
ggtttcgaca ttgccactat caactctcgt tacaatgacc tgaccgtct gatcccgatc    600
tatacggact acgctgttcg ttggtacaac actggtctgg atcgtctgcc acgtaccggc    660
ggtctgcgca attgggctcg tttcaaccag ttccgtcgtg agctgactat ctctgtgctg    720
gacatcatta gcttcttccg caactatgac tctcgcctgt atccaatccc aaccagcagc    780
cagctgacgc gtgaagtgta tactgaccct gtcatcaaca ttaccgacta tcgtgttggt    840
ccgtctttcg aaaacatcga aaactctgca atccgttccc cgcacctgat ggattttctg    900
aacaacctga ccattgacac cgatctgatc cgtggcgtgc actactgggc tggtcaccgt    960
gttacgtccc acttcactgg ctccagccag gtgatcacga ctccacagta cggcattact   1020
gcgaacgcgg aaccacgccg caccatcgct ccgtccacgt tccgggtct gaacctgttc   1080
taccgcactc tgagcaaccc gtttttccgt cgttctgaaa acatcactcc aaccctgggt   1140
atcaacgtag ttcagggtgt cggcttcatt cagccgaaca acgctgaagt actgtaccgt   1200
tcccgtggca ccgtagatag cctgaatgaa ctgccaattg atggtgagaa ctctctggtg   1260
ggttacagcc accgcctgtc ccatgtaacg ctgacccgca gcctgtacaa taccaacatc   1320
accagcctgc cgacttttcgt gtggactcat cattctgcga ccaacaccaa cactattaac   1380
ccggacatta tcacccaaat cccgctggtg aagggctttc gtctgggtgg cggcacttcc   1440
gtaatcaaag gtccgggttt cacgggtggt gatattctgc gtcgcaacac gttcggcgac   1500
ttcgtttccc tgcaggtaaa catcaactct ccgatcaccc agcgctaccg cctgcgcttc   1560
cgttacgcct cttctcgtga tgcacgtgtt atcgtcctga ccggcgcagc aagcaccggc   1620
gttggtggtc aagtttctgt gaacatgcca ctgcagaaaa ccatggaaat cggcgaaaac   1680
ctgacgtccc gcacttttcc g ctataccgat tttagcaatc cgttctcctt tcgtgcaaac  1740
ccggacatca ttggcatctc tgagcaaccg ctgttcggtg ctggttccat ctcctctggt   1800
gagctgtata tcgacaagat cgaaattatc ctggcggacg ctaccttcga agcggagagc   1860
gacctggaac gcgcgcagaa ataa                                         1884

SEQ ID NO: 9             moltype = DNA   length = 1884
FEATURE                  Location/Qualifiers
misc_feature             1..1884
                         note = Synthetic
source                   1..1884
                         mol_type = other DNA
                         organism = synthetic construct
SEQUENCE: 9
atggaaatcg ttaataacca gaaccagtgc gttccgtaca actgtctgaa caaccctgaa     60
aacgaaatcc tggatatcga acgttccaac tccacggtgg ccaccaacat cgctctggaa    120
atttcccgcc tgctggcaag cgccactcca attggtggta ttctgctggg cctgttcgac    180
gccatttggg gttctatcgg cccgtctcaa tgggacctgt ttctggaaca gatcgaacag    240
ctgatcggcc agcgtatcga agaattcgca cgcaatcagg ccatttctcg tctgcaaggc    300
ctgtctaacc tgtatcgcat ctacaccaat gctttcaaaa attgggaagt agacccgact    360
aatccggctc tgcgcgaaga aatgcgcatt cagtttaacg atatgaactc cgcgctgacg    420
actgcaattc cgctgttctc tgttcagggt tacgaaatcc cgctgctgtc tgtctacgtt    480
caggccgcga acctgcatct gtccgtactg cgtgacgtgt ctgttttcgg ccaggcgtgg    540
ggtttcgaca ttgccactat caactctcgt tacaatgacc tgaccgtct gatcccgatc    600
tatacggact acgctgttcg ttggtacaac actggtctgg atcgtctgcc acgtaccggc    660
ggtctgcgca attgggctcg tttcaaccag ttccgtcgtg agctgactat ctctgtgctg    720
gacatcatta gcttcttccg caactatgac tctcgcctgt atccaatccc aaccagcagc    780
cagctgacgc gtgaagtgta tactgaccct gtcatcaaca ttaccgacta tcgtgttggt    840
ccgtctttcg aaaacatcga aaactctgca atccgttccc cgcacctgat ggattttctg    900
aacaacctga ccattgacac cgatctgatc cgtggcgtgc actactgggc tggtcaccgt    960
gttacgtccc acttcactgg ctccagccag gtgatcacga ctccacagta cggcattact   1020
gcgaacgcgg aaccacgccg caccatcgct ccgtccacgt tccgggtct gaacctgttc   1080
taccgcactc tgagcaaccc gtttttccgt cgttctgaaa acatcactcc aaccctgggt   1140
atcaacgtag ttcagggtgt cggcttcatt cagccgaaca acgctgaagt actgtaccgt   1200
tcccgtggca ccgtagatag cctgaatgaa ctgccaattg atggtgagaa ctctctggtg   1260
```

```
ggttacagcc accgcctgtc ccatgtaacg ctgacccgca gcctgtacaa taccaacatc   1320
accagcctgc cgactttcgt gtggactcat cattctgcga ccaacaccaa cactattaac   1380
ccggacatta tcacccaaat cccgctggtg aagggctttc gtctggtgg cggcacttcc    1440
gtaatcaaag gtccgggttt cacgggtggt gatattctgc gtcgcaacac gttcggcgac   1500
ttcgtttccc tgcaggtaaa catcaactct ccgatcaccc agcgctaccg cctgcgcttc   1560
cgttacgcct cttctcgtga tgcacgtgtt atcgtcctga ccggcgcagc aagcaccggc   1620
gttggtggtc aagtttctgt gaacatgcca ctgcagaaaa ccatgaaat cggcgaaaac   1680
ctgacgtccc gcacttttccg ctataccgat tttagcaatc cgttctcctt tcgtgcaaac   1740
ccggacatca ttggcatctc tgagcaaccg ctgttcggtg ctggttccat ctcctctggt   1800
gagctgtata tcgacaagat cgaaattatc ctggcggacg ctaccttcga agcggagagc   1860
gacctggaac gcgcgcagaa ataa                                          1884

SEQ ID NO: 10           moltype = DNA   length = 1893
FEATURE                 Location/Qualifiers
misc_feature            1..1893
                        note = Synthetic
source                  1..1893
                        mol_type = other DNA
                        organism = synthetic construct
SEQUENCE: 10
atggaaatcg tgaataacca gaaccagtgc gtgccgtaca attgtctgaa taaccccgaa   60
aacgagattc tggacatcga gcgcagtaac agcacagttc ctaccaacat cgcactggaa   120
atttcgcgtt tactgcctc cgccacgcca atcgggggga ttctgctggg tctgtttgat    180
gctatctggg gaagtattgg cccgagccaa tgggatctgt ttttgagca aattgaacag    240
ctgattggcc agcgcattga agaattcgca cgcaatcaag ccatctcccg cctggaaggg   300
ttgagtaacc tttatcgtat ctacacgaat gcctttaaga attgggaagc cgatccgacc   360
aatccagtgt tgcgggagga aatgcgcatt cagtttaatg atatgaatag tgcgttcacg   420
accgcaatcc cattattttc agtacaaggt tacgaaattc ctcttcttgg cgtctatgtg   480
caggctgcga acctgcattt gtcagtctta cgtgacgtta gtgtgtttgg ccaggcttgg   540
ggttttgaca ttgcgacaat taactcccgc tataacgatc tgacgcgtct gatccctatt   600
tatactgatt atgctgtccg ttggtacaat acgggtctgg atcgtttacc gcgcaccggc   660
gggttgcgta attgggcacg tttcaaccaa ttccgccggg aactgactat ttcggttctg   720
gacatcatta gtttttttccg taattacgat agtcggctgt atccgatccc cacgtcgtct   780
cagctgaccc gggaagtgta tacgaccct gttattaaca ttaccgatta tcgcgttggg   840
ccgagctttg aaaatattga aaattctgcc attcgttcgc cgcaccgat ggacttcctg    900
actaatatta tcatcgatac cgatctgatt cgtggcgtgt attactggg ggggcaccgc    960
attaacagtc gctttacggg aacagcattt ccgcacatta tcacgagtcc acagtacggt   1020
attacagcta acgccgagcc ccgccgcacc attgcaccag gccctttca aggtgtgcct   1080
tccctgttat accgtacgct gagtgatccg tttttccggc gctcagataa tatcagtccg   1140
accccttggta tcaatgtggt tcaaggagtc ggatttctgc agccaaacaa ttttgaatcc   1200
ctttaccgtc gtcgtgggac tgtcgatagt ctgaacgagt tacccattga tggagaaaac   1260
tcgttagtag gttactccca ccgcctgagt catgtgacgt tgacccgctc tttatacaac   1320
acgaacatta cgtctctgcc gactttcgtc tggacccatc attcagcgac caatacgaat   1380
accatcaacc ccgatattat cacccagatc ccactggtca aagttttcg tgtatgggga    1440
ggaacatcgg ttattactgg accgggatt accggcggtg atattcttcg ccgcaacacc   1500
tttgagact tgttagcct gcaagtgaac atcaatagtc caattacgca acgctatcgt    1560
ctgcgcttcc gttatgctag ctctcgtgac gcgcgtgtga ttctgctacg ggggcagcc    1620
agcacaggcg tgggcggtca agtctctgtg aacatgcctc tgcagaaaac gatggagatt   1680
ggggaaaatc tgaccagccg cacttttcgt tacacggatt tttctaatcc gttctccttc   1740
cgggccaatc cagacattat cgggatttca gaacagccat tattcggcgc gggtcaatt   1800
tcatctggag aactgtatat tgataaaatc gaaattattc tggcggatgc cacgttcgag   1860
gccgaagtg atttggaacg tgcccagaaa taa                                 1893

SEQ ID NO: 11           moltype = DNA   length = 1875
FEATURE                 Location/Qualifiers
misc_feature            1..1875
                        note = Synthetic
source                  1..1875
                        mol_type = other DNA
                        organism = synthetic construct
SEQUENCE: 11
atggaaatcg ttaataacca gaaccagtgc gttccgtaca actgtctgaa caaccctgaa    60
aacgaaatcc tggatatcga acgttccaac tccacggtgg ccaccaacat cgctctggaa   120
atttcccgcc tgctggcaag cgccactcca attggtggta ttctgctggg cctgttcgac   180
gccatttggg gttctatcgg cccgtctcaa tgggacctgt ttctggaaca gatcgaacag   240
ctgattggcc aacgtatcga agaattcgcg cgtaaccagg caatttcacg cctgaaggt    300
ctgagtaacc tttaccggat ttatactaac gcgttcaaga ctgggaagc agaccctacc    360
aacccggtac ttcgtgagga aatgcgcatc cagttcaata tatgaatag cgctgtttaca   420
actgctatcc cactttttctc cgttcagggt tatgaaattc gctgctgtg tgtttacgtg    480
caggccgcga acctgcatct gtccgtactg cgtgacgtgt ctgttttcgg ccaggcgtgg   540
ggtttcgaca ttgccactat caactctcgt tacaatgacc tgaccccgtc tgatcccgatc   600
tatacggact acgctgttcg ttggtacaac actggtctgg atcgtctgcc acgtaccggc   660
ggtctgcgca attgggctcg tttcaaccag ttccgtcgtg agctgactat ctctgtgctg   720
gacatcatta gcttcttccg caactatgac tctcgcctgt atccgatccc aacagcagc   780
cagctgacgc gtgaagtgta tactgaccct gtcatcaaca ttaccgacta tcgtgttggt   840
ccgtctttcg aaaacatcga aaactctgca atccgttccc cgcaccgtga tggatgttctt   900
aataacttaa ctattttttac ggattggttt tccgtcggcc gcaactttta tggggcggc    960
caccgcgtca ttagcaatcg catcgaggt ggaaacatta cgagcccaat ttatggtcgc   1020
gaagcaaacc aagagccgcc acgctcgttt accttcaatg gtccggtgtt ccggacgctt   1080
```

```
agcaatccga ctttccggcc actgcagcag ccgtgccgg cgcctccgtt caatctgcgc  1140
ggggtagagg gggtcgaatt ttcaactcca ctgaattctt ttacctatcg tggccgtggc  1200
accgtagata gcctgaatga actgccaatt gatggtgaga actctctggt gggttacagc  1260
caccgcctgt cccatgtaac gctgacccgc agcctgtaca ataccaacat caccagcctg  1320
ccgactttcg tgtggactca tcattctgcg accaacacca acactattaa cccggacatt  1380
atcacccaga tcccgctggt gaagggcttt cgtgtttggg cggcacttc cgtaatcact  1440
ggtccgggtt tcacgggtgg cgatattctg cgtcgcaaca cgttcggcga cttcgtttcc  1500
ctgcaggtaa acatcaactc tccgatcacc cagcgctacc gctgcgctt ccgttacgcc  1560
tcttctcgtg atgcacgtgt tatcgtcctg accggcgcga caagcaccgg cgttggtggt  1620
caagttctg tgaacatgcc actgcagaaa accatgaaa tcggcgaaaa cctgacgtcc  1680
cgcactttcc gctataccga ttttagcaat ccgttctcct ttcgtgcaaa cccggacatc  1740
attggcatct ctgagcaacc gctgttcggt gctggttcca tctcctctgg tgagctgtat  1800
atcgacaaga tcgaaattat cctggcggac gctaccttcg aagcggagag cgacctggaa  1860
cgcgcgcaga aataa                                                    1875

SEQ ID NO: 12        moltype = DNA  length = 1848
FEATURE              Location/Qualifiers
misc_feature         1..1848
                     note = Synthetic
source               1..1848
                     mol_type = other DNA
                     organism = synthetic construct
SEQUENCE: 12
atggaaatcg ttaataacca gaaccagtgc gttccgtaca actgtctgaa caaccctgaa   60
aacgaaatct ggatatcga acgttccaac tccacggtgg ccaccaacat cgctctggaa  120
atttcccgcc tgctggcaag cgccactcca attggtggta ttctgctgtt cctgttcgac  180
gccatttggg gttctatcgg cccgtctcaa tgggacctgt ttctggaaca gatcgaacag  240
ctgattggcc aacgtatcga agaattcgcg cgtaaccagg caatttcacg cctggaaggt  300
ctgagtaacc tttaccggat ttatactaac gcgttcaaga actgggaagc agaccctacc  360
aacccggtac ttcgtgagga aatgcgcatc cagttcaatg atatgaatag cgcgtttaca  420
actgctatcc cactttttctc cgttcagggt tatgaaattc gctgctggg tgtttacgtt  480
caggccgcga acctgcatct gtccgtactg cgtgacgtgt ctgttttcgg ccaggcgtgg  540
ggtttcgaca ttgccactat caactctcgt tacaatgacc tgaccgtct gatcccgatc  600
tatacggact acgctgttcg ttggtacaac actggtctgg atcgtctgcc acgtaccggc  660
ggtctgcgca attggctcg tttcaaccag ttccgtcgtg agctgactat ctctgtgctg  720
gacatcatta gcttcttccg caactatgac tctcgcctgt atcaatcccc aaccagcagc  780
cagctgacgc gtgaagtgta tactgaccct gtcatcaaca ttaccgacta tcgtgttggt  840
ccgtctttcg aaaacatcga aaactctgca atccgttccc cgcacctgat ggattttctg  900
aacaacctga ccattgacac cgatctgatc cgtggcgtgc actactgggc tggtcaccgt  960
gttacgtccc acttcactgg ctccagccag gtgatcacga ctccacagta cggcattact 1020
gcgaacgcgg aaccaccgcg caccatcgct ccgtccacgt tcccgggtct gaacctgttc 1080
taccgcactc tgagcaaccc gtttttccgt cgttctgaaa catcactcc aaccctgggt 1140
atcaacgtag ttcagggtgt cggcttcatt cagccgaaca acgctgaagt actgtaccgt 1200
tcccgtggca ccgtagatag cctgaatgaa ctgccaattg atggtgagaa ctctctggtg 1260
ggttacagcc accgcctgtc ccatgtaacg ctgacccgca gcctgtacaa taccaacatc 1320
accagcctgc cgactttcgt gtggactcat cattctgcga ccaacaccaa cactattaac 1380
ccggacatta tcacccagat cccgtagtg aagcctcca acttgtcctc cggtgcggct 1440
gtggttcgtg gtccaggctt cacagggggg gacattctgc gtcgtaaaaa cacagggacc 1500
tttggcgaca ttcgtgtcaa cattaaccct ccgttcgccc agcgctatcg tgtgcgtatt 1560
cgttatgcca gcacaaccga cctgcaattc catacctcta ttaacggaaa ggctatcaat 1620
cagggtaact ttagtgccac tatgaatcgt ggcgaggact tagattataa aaccttttgc 1680
accgtaggtt ttactacccc tttttcattt tccgacgttc aaagcacctt tacgatcggt 1740
gcctggaact ttagctcagg taatgaagtt tatatcgatc gcatcgaatt tgtaccggtg 1800
gaggtcaccct acgaggcgga atatgacttt gaaaagccc aggaataa            1848

SEQ ID NO: 13        moltype = DNA  length = 1848
FEATURE              Location/Qualifiers
misc_feature         1..1848
                     note = Synthetic
source               1..1848
                     mol_type = other DNA
                     organism = synthetic construct
SEQUENCE: 13
atggaaatcg ttaataacca gaaccagtgc gttccgtaca actgtctgaa caaccctgaa   60
aacgaaatcc tggatatcga acgttccaac tccacggtgg ccaccaacat cgctctggaa  120
atttcccgcc tgctggcaag cgccactcca attggtggta ttctgctggg cctgttcgac  180
gccatttggg gttctatcgg cccgtctcaa tgggacctgt ttctggaaca gatcgaacag  240
ctgattggcc aacgtatcga agaattcgcg cgtaaccagg caatttcacg cctggaaggt  300
ctgagtaacc tttaccggat ttatactaac gcgttcaaga actgggaagc agaccctacc  360
aacccggtac ttcgtgagga atgcgcatc cagttcaatg atatgaatag cgcgtttaca  420
actgctatcc cactttttctc cgttcagggt tatgaaattc gctgctgggt gtttacgtc  480
caggccgcga acctgcatct gtccgtactg cgtgacgtgt ctgttttcgg ccaggcgtgg  540
ggtttcgaca ttgccactat caactctcgt tacaatgacc tgaccgtct gatcccgatc  600
tatacggact acgctgttcg ttggtacaac actggtctgg atcgtctgcc acgtaccggc  660
ggtctgcgca attggctcg tttcaaccag ttccgtcgtg agctgactat ctctgtgctg  720
gacatcatta gcttcttccg caactatgac tctcgcctgt atcaatcccc aaccagcagc  780
cagctgacgc gtgaagtgta tactgaccct gtcatcaaca ttaccgacta tcgtgttggt  840
ccgtctttcg aaaacatcga aaactctgca atccgttccc cgcacctgat ggattttctg  900
aacaacctga ccattgacac cgatctgatc cgtggcgtgc actactgggc tggtcaccgt  960
```

```
gttacgtccc acttcactgg ctccagccag gtgatcacga ctccacagta cggcattact  1020
gcgaacgcgg aaccacgccg caccatcgct ccgtccacgt tcccgggtct gaacctgttc  1080
taccgcactc tgagcaaccc gttttccgt cgttctgaaa acatcactcc aaccctgggt  1140
atcaacgtag ttcagggtgt cggcttcatt cagccgaaca acgctgaagt actgtaccgt  1200
tccctggca ccgtagatag cctgaatgaa ctgccaattg atggtgagaa ctctctggtg  1260
ggttacagcc accgcctgtc ccatgtaacg ctgacccgca gcctgtacaa taccaacatc  1320
accagcctgc cgactttcgt gtggactcat cattctgcga ccaacaccaa cactattaac  1380
ccggacatta tcacccagat cccggttgta aaggcgtacg aactgagcag cggcgcgacc  1440
gtagttaaag gtccgggttt tactggcggc gacgttattc gtcgcaccaa cactggtggc  1500
ttcggcgcta tccgtgtatc tgtcactggc ccgctgaccc agcgttatcg cattcgtttt  1560
cgttatgcgt ccaccatcga tttcgattt tcgtgacgc gcggtggtac caccattaac  1620
aattttcgtt ttacccgtac tatgaaccgc ggtcaggaat cccgctacga aagctaccgc  1680
accgtagaat tcactacccc gttcaacttc acgcagtccc aggatatcat ccgtaccagc  1740
attcagggtc tgtccggcaa tggtgaggta tatctgacc gtatcgaaat catccctgtg  1800
aaccctaccc gtgaggccga ggaggatctg gaagcggcca aaaataa               1848

SEQ ID NO: 14            moltype = DNA  length = 1854
FEATURE                  Location/Qualifiers
misc_feature             1..1854
                         note = Synthetic
source                   1..1854
                         mol_type = other DNA
                         organism = synthetic construct
SEQUENCE: 14
atggaaatcg ttaataacca gaaccagtgc gttccgtaca actgtctgaa caaccctgaa    60
aacgaaatcc tggatatcga acgttccaac tccacggtgg ccaccaacat cgctctggaa   120
atttcccgcc tgctggcaag cgccactcca attggtggta ttctgctggg cctgttcgac   180
gccatttggg gttctatcgg cccgtctcaa tgggaccctgt ttctggaaca gatcgaacag   240
ctgattggcc aacgtatcga agaattcgcg cgtaaccagg caatttcacg cctggaaggt   300
ctgagtaacc tttaccggat ttatactaac gcgttcaaga actgggaagc agaccctacc   360
aacccggtac ttcgtgagga aatgcgcatc cagttcaatg atatgaatag cgcgtttaca   420
actgctatcc cacttttctc cgttcagggt tatgaaattc cgctgctggg tgtttacgtc   480
caggccgcga acctgcatct gtccgtactg cgtgacgtgt ctgttttcgg ccaggcgtgg   540
ggtttcgaca ttgccactat caactctcgt tacaatgacc tgaccgtct gatcccgatc   600
tatacggact acgctgttcg ttggtacaac actggtctgg atcgtctgcc acgtaccggc   660
ggtctgcgca attgggctcg tttcaaccag ttccgtcgtg agctgactat ctctgtgctg   720
gacatcatta gcttcttccg caactatgac tctcgcctgt atccaatccc aaccagcagc   780
cagctgacgc gtgaagtgta tactgaccct gtcatcaaca ttaccgacta tcgtgttggt   840
ccgtctttcg aaaacatcga aaactctgca atccgttccc gcacctgat ggatttctta   900
actaatataa ttattgacac tgatttaata gaggtgtttt actattgggc aggacatcgt   960
ataaattctc gctttaccgg gaccgcttt ccacatataa taacatctcc tcaatggaa   1020
ataactgcaa acgcagaacc aagacgtaca atagcgcctg gtccttttca aggtgtgcct  1080
tccctacttt atagaacact tcttcccgaa gatcagacaa tattagtcca               1140
accttaggga taaatgtagt acaggggta gggttcttac aaccaaataa ttttgaatct   1200
ctatatagaa ggcgtggcac cgtagatagc ctgaatgaac tgccaattga tggtgagaac  1260
tctctggtgg gttacagcca ccgcctgtcc catgtaacgc tgacccgcag cctgtacaat  1320
accaacatca ccagcctgcc gactttcgtg tggactcatc attctgcgac cgatccgaac  1380
atcatttacc cggacgttat caaccaaatc ccgctggtga aggcgtttaa cctgacctct  1440
ggcacttccg tagtgcgtgg tccgggtttc acggtggcg atattattcg tactaacgtg   1500
aacggcagcg tcctgtccat gtccctgaac ttcagcaaca ctactctgca gcgctaccgc  1560
gttcgcgttc gttacgccgc atctcagact atggtgatgc ccgtcaccgt tggcggttcc  1620
accaccggca accagggttt cccatctacc atgtctgcca atggcgcgct gacctcccag  1680
agcttccgtt tcgcagaatt tccggtaggc atctctgctt ctggttctca gggtgcgtcc  1740
atttctatcg caacaacgt aggccgtcag atgttccatc tggaccgcat cgaatttctg  1800
ccggtgacct ccaccttcga agaagaatac gatctgaaac gtgcgcaaga ataa        1854

SEQ ID NO: 15            moltype = DNA  length = 1857
FEATURE                  Location/Qualifiers
misc_feature             1..1857
                         note = Synthetic
source                   1..1857
                         mol_type = other DNA
                         organism = synthetic construct
SEQUENCE: 15
atggaaatcg ttaataacca gaaccagtgc gttccgtaca actgtctgaa caaccctgaa    60
aacgaaatcc tggatatcga acgttccaac tccacggtgg ccaccaacat cgctctggaa   120
atttcccgcc tgctggcaag cgccactcca attggtggta ttctgctggg cctgttcgac   180
gccatttggg gttctatcgg cccgtctcaa tgggaccctgt ttctggaaca gatcgaacag   240
ctgattggcc aacgtatcga agaattcgcg cgtaaccagg caatttcacg cctggaaggt   300
ctgagtaacc tttaccggat ttatactaac gcgttcaaga actgggaagc agaccctacc   360
aacccggtac ttcgtgagga aatgcgcatc cagttcaatg atatgaatag cgcgtttaca   420
actgctatcc cacttttctc cgttcagggt tatgaaattc cgctgctggg tgtttacgtc   480
caggccgcga acctgcatct gtccgtactg cgtgacgtgt ctgttttcgg ccaggcgtgg   540
ggtttcgaca ttgccactat caactctcgt tacaatgacc tgaccgtct gatcccgatc   600
tatacggact acgctgttcg ttggtacaac actggtctgg atcgtctgcc acgtaccggc   660
ggtctgcgca attgggctcg tttcaaccag ttccgtcgtg agctgactat ctctgtgctg   720
gacatcatta gcttcttccg caactatgac tctcgcctgt atccaatccc aaccagcagc   780
cagctgacgc gtgaagtgta tactgaccct gtcatcaaca ttaccgacta tcgtgttggt   840
ccgtctttcg aaaacatcga aaactctgca atccgttccc gcacctgat ggatttctta   900
```

```
actaatataa ttattgacac tgatttaata agaggtgttt actattgggc aggacatcgt   960
ataaattctc gctttaccgg gaccgctttt ccacatataa taacatctcc tcaatatgga  1020
ataactgcaa acgcagaacc aagacgtaca atagcgcctg gtccttttca aggtgtgcct  1080
tccctacttt atagaacact atcagaccct ttcttccgaa gatcagacaa tattagtcca  1140
accttaggga taaatgtagt acagggggta gggttcttac aaccaaataa ttttgaatct  1200
ctatatagaa ggcgtggcac cgtagatagc ctgaatgaac tgccaattga tggtgagaac  1260
tctctggtgg gttacagcca ccgcctgtcc catgtaacgc tgacccgcag cctgtacaat  1320
accaacatca ccagcctgcc gactttcgtg tggactcatc attctgcgga gtttaataac  1380
attattccgt cttctcaaat cacccagatc ccgctgacta aatccaccaa cctgggttcc  1440
ggcacctctg tagtaaaagg tcctggtttc accggtggtg atattctgcg ccgtacgagc  1500
ccgggtcaga tctccacgct gcgtgttaac attactgccc cgctgtctca gcgttatcgc  1560
gttcgcatcc gctacgcttc tactacgaac ctgcagttcc atacttccat cgacggtcgt  1620
ccgattaacc aaggtaactt cagcgcgact atgtcttccg gcggcaacct gcaatctggt  1680
tctttccgca ctgtgggttt cacgaccccg tttaacttca gcaacggctc ctctgttttc  1740
actctgagcg cccatgtttt taatagcggc aacgaggtgt acatcgaccg tattgaattc  1800
gttcctgctg aagttacttt cgaagctgaa tacgacctgg aacgtgcaca ggaataa     1857

SEQ ID NO: 16           moltype = DNA   length = 1845
FEATURE                 Location/Qualifiers
misc_feature            1..1845
                        note = Synthetic
source                  1..1845
                        mol_type = other DNA
                        organism = synthetic construct
SEQUENCE: 16
atggaaatcg ttaataacca gaaccagtgc gttccgtaca actgtctgaa caaccctgaa    60
aacgaaatcc tggatatcga acgttccaac tccacggtgg ccaccaacat cgctctggaa   120
atttcccgcc tgctggcaag cgccactcca attggtggta ttctgctggg cctgttcgac   180
gccatttggg gttctatcgg cccgtctcaa tgggacctgt ttctggaaca gatcgaacag   240
ctgattggcc aacgtatcga agaattcgcg cgtaaccagg caatttcacg cctggaaggt   300
ctgagtaacc tttaccggat ttatactaac gcgttcaaga actgggaagc agaccctacc   360
aacccggtac ttcgtgagga aatgcgcatc cagttcaatg atatgaatag cgcgtttaca   420
actgctatcc cacttttctc cgttcagggt tatgaaattc cgctgctggg tgtttacgtc   480
caggccgcga acctgcatct gtccgtactg cgtgacgtgt ctgttttcgg ccaggcgtgg   540
ggtttcgaca ttgccactat caactctcgt tacaatgacc tgacccgtct gatcccgatc   600
tatacggact acgctgttcg ttggtacaac actggtctgg atcgtctgcc acgtaccggc   660
ggtctgcgca attgggctcg tttcaaccag ttccgtcgtg agctgactat ctctgtgctg   720
gacatcatta gcttcttccg caactatgac tctcgcctgt atccaatccc aaccagcagc   780
cagctgacgc gtgaagtgta tactgaccct gtcatcaaca ttaccgacta tcgtgttggt   840
ccgtctttcg aaaacatcga aaactctgca atccgttccc cgcacctgat ggattttctg   900
aacaacctga ccattgacac cgatctgatc cgtggcgtgc actactgggc tggtcaccgt   960
gttacgtccc acttcactgg ctccagccag gtgatcacga ctccacagta cggcattact  1020
gcgaacgcga aaccacgccg caccatcgct ccgtccaccc ccgggtct gaacctgttc   1080
taccgcactc tgagcaaccc gtttttccgt cgttctgaaa acatcactcc aaccctgggt  1140
atcaactag ttcagggtgt cggcttcatt cagccgaaca acgctgaagt actgtaccgt  1200
tcccgtggca ccgtagatag cctgaatgaa ctgccaattg atggtgagaa ctctctggtg  1260
ggttacagcc accgcctgtc ccatgtaacg ctgacccgca gcctgtacaa taccaacatc  1320
accagcctgc cgactttcgt gtggactcat cattctgcga ccaacaccaa cactattaac  1380
ccggacatta tcacccagat cccgctgtt aaggctctga acctgcactc tggcgttacc  1440
gttgttggtg gtccggtttt caccggtggt gatatcctgc gccgtacgaa caccggcact  1500
ttcggcgaca tccgcctgaa tatcaatgta ccactgagcc aacgctaccg tgtacgcatt  1560
cgctacgctt ccactaccga cctgcagttc ttcactcgta tcaatggtac caccgttaac  1620
atcggcaact tctctcgcac catgaaccgt ggtgataacc tggaataccg ctcttccgt   1680
accgcaggtt tttctacgcc gtttaacttc ctgaacgccc agtctacttt cacgctgggc  1740
gcgcagtctt tcagcaacca ggaagtctac attgaccgtg tggaattcgt gccggcggaa  1800
gttaccttg aagcagaata tgacctgaa cgtgcgcaaa ataa                      1845

SEQ ID NO: 17           moltype = DNA   length = 1893
FEATURE                 Location/Qualifiers
misc_feature            1..1893
                        note = Synthetic
source                  1..1893
                        mol_type = other DNA
                        organism = synthetic construct
SEQUENCE: 17
atggaaatcg ttaataacca gaaccagtgc gttccgtaca actgtctgaa caaccctgaa    60
aacgaaatcc tggatatcga acgttccaac tccacggtgg ccaccaacat cgctctggaa   120
atttcccgcc tgctggcaag cgccactcca attggtggta ttctgctggg cctgttcgac   180
gccatttggg gttctatcgg cccgtctcaa tgggacctgt ttctggaaca gatcgaacag   240
ctgattggcc aacgtatcga agaattcgcg cgtaaccagg caatttcacg cctggaaggt   300
ctgagtaacc tttaccggat ttatactaac gcgttcaaga actgggaagc agaccctacc   360
aacccggtac ttcgtgagga aatgcgcatc cagttcaatg atatgaatag cgcgtttaca   420
actgctatcc cacttttctc cgttcagggt tatgaaattc cgctgctggg tgtttacgtc   480
caggccgcga acctgcatct gtccgtactg cgtgacgtgt ctgttttcgg ccaggcgtgg   540
ggtttcgaca ttgccactat caactctcgt tacaatgacc tgacccgtct gatcccgatc   600
tatacggact acgctgttcg ttggtacaac actggtctgg atcgtctgcc acgtaccggc   660
ggtctgcgca attgggctcg tttcaaccag ttccgtcgtg agctgactat ctctgtgctg   720
gacatcatta gcttcttccg caactatgac tctcgcctgt atccaatccc aaccagcagc   780
cagctgacgc gtgaagtgta tactgaccct gtcatcaaca ttaccgacta tcgtgttggt   840
```

```
ccgtctttcg aaaacatcga aaactctgca atccgttccc cgcacctgat ggatttctta   900
actaatataa ttattgacac tgatttaata agaggtgttt actattgggc aggacatcgt   960
ataaattctc gctttaccgg gaccgctttt ccacatataa taacatctcc tcaatatgga  1020
ataactgcaa acgcagaacc aagacgtaca atagcgcctg gtccttttca aggtgtgcct  1080
tccctacttt atcgcactct gagcaacccg ttttccggtc gttctgaaaa catcactcca  1140
accctgggta tcaacgtagt tcagggtgtc ggcttcattc agccgaacaa cgctgaagta  1200
ctgtaccgtt cccgtggcac cgtagatagc ctgaatgaac tgccaattga tggtgagaac  1260
tctctggtgg gttacagcca ccgcctgtcc catgtaacgc tgacccgcag cctgtacaat  1320
accaacatca ccagcctgcc gactttcgtg tggactcatc attctgcgac caacaccaac  1380
actattaacc cggacattat cacccagatc ccgctggtga agggctttcg tgtttggggc  1440
ggcacttccg taatcactgg tccgggtttc acgggtggcg atattctgcg tcgcaacacg  1500
ttcggcgact tcgtttccct gcaggtaaac atcaactctc cgatcaccca gcgctaccgc  1560
ctgcgcttcc gttacgcctc ttctcgtgat gcacgtgtta tcgtcctgac cggcgcagca  1620
agcaccggcg ttggtggtca agtttctgtg aacatgccag tgcagaaaac catggaaatc  1680
ggcgaaaacc tgacgtcccg cactttccgc tataccgatt ttagcaatcc gttctccttt  1740
cgtgcaaacc cggacatcat tggcatctct gagcaaccgc tgttcggtgc tggttccatc  1800
tcctctggtg agctgtatat cgacaagatc gaaattatcc tggcggacgc taccttcgaa  1860
gcggagagcg acctggaacg cgcgcagaaa taa                                1893

SEQ ID NO: 18          moltype = DNA  length = 1893
FEATURE                Location/Qualifiers
misc_feature           1..1893
                       note = Synthetic
source                 1..1893
                       mol_type = other DNA
                       organism = synthetic construct
SEQUENCE: 18
atggaaatcg ttaataacca gaaccagtgc gttccgtaca actgtctgaa caaccctgaa    60
aacgaaatcc tggatatcga acgttccaac tccacggtgg ccaccaacat cgctctggaa   120
atttcccgcc tgctggcaag cgccactcca attggtggta ttctgctggg cctgttcgac   180
gccatttggg gttctatcgg cccgtctcaa tgggacctgt ttctggaaca gatcgaacag   240
ctgattggcc aacgtatcga agaattcgcg cgtaaccagg caatttcacg cctggaaggt   300
ctgagtaacc tttaccggat ttatactaac gcgttcaaga actgggaagc agaccctacc   360
aacccggtac ttcgtgagga aatgcgcatc cagttcaatg atatgaatag cgcgtttaca   420
actgctatcc cacttttctc cgttcagggt atgaaattcc gctgctgggt gtttacgtc    480
caggccgcga acctgcatct gtccgtactg cgtgacgtgt ctgttttcgg ccaggcgtgg   540
ggtttcgaca ttgccactat caactctcgt tacaatgacc tgaccgtct gatcccgatc    600
tatacggact acgctgttcg ttggtacaac actggtctgg atcgtctgcc acgtaccggc   660
ggtctgcgca attgggctcg tttcaaccag ttccgtcacg agctgactat ctctgtgctg   720
gacatcatta gcttcttccg caactatgac tctcgcctgt atccaatccc aaccagcagc   780
cagctgacgc gtgaagtgta tactgaccct gtcatcaaca ttaccgacta tcgtgttggt   840
ccgtctttcg aaaacatcga aaactctgca atccgttccc cgcacctgat ggattttatt   900
gaccgtatcg tgatctacac taattctgtg cgttccacgc cgtactgggc gggccacgaa   960
gtgatctccc gtcgtactgg tcaaggtcag ggtaacgaaa ttcgtttccc gctgtatggc  1020
gtagcggcaa acgcggaacc accggtaacc atccgcccaa ccggtttcac cgatgaacag  1080
cgtcagtggt atcgcactct gagcaacccg ttttccgtc gttctgaaaa catcactcca  1140
accctgggta tcaacgtagt tcagggtgtc ggcttcattc agccgaacaa cgctgaagta  1200
ctgtaccgtt cccgtggcac cgtagatagc ctgaatgaac tgccaattga tggtgagaac  1260
tctctggtgg gttacagcca ccgcctgtcc catgtaacgc tgacccgcag cctgtacaat  1320
accaacatca ccagcctgcc gactttcgtg tggactcatc attctgcgac caacaccaac  1380
actattaacc cggacattat cacccagatc ccgctggtga agggctttcg tgtttggggc  1440
ggcacttccg taatcactgg tccgggtttc acgggtggcg atattctgcg tcgcaacacg  1500
ttcggcgact tcgtttccct gcaggtaaac atcaactctc cgatcaccca gcgctaccgc  1560
ctgcgcttcc gttacgcctc ttctcgtgat gcacgtgtta tcgtcctgac cggcgcagca  1620
agcaccggcg ttggtggtca agtttctgtg aacatgccag tgcagaaaac catggaaatc  1680
ggcgaaaacc tgacgtcccg cactttccgc tataccgatt ttagcaatcc gttctccttt  1740
cgtgcaaacc cggacatcat tggcatctct gagcaaccgc tgttcggtgc tggttccatc  1800
tcctctggtg agctgtatat cgacaagatc gaaattatcc tggcggacgc taccttcgaa  1860
gcggagagcg acctggaacg cgcgcagaaa taa                                1893

SEQ ID NO: 19          moltype = DNA  length = 1893
FEATURE                Location/Qualifiers
misc_feature           1..1893
                       note = Synthetic
source                 1..1893
                       mol_type = other DNA
                       organism = synthetic construct
SEQUENCE: 19
atggaaatcg ttaataacca gaaccagtgc gttccgtaca actgtctgaa caaccctgaa    60
aacgaaatcc tggatatcga acgttccaac tccacggtgg ccaccaacat cgctctggaa   120
atttcccgcc tgctggcaag cgccactcca attggtggta ttctgctggg cctgttcgac   180
gccatttggg gttctatcgg cccgtctcaa tgggacctgt ttctggaaca gatcgaacag   240
ctgattggcc aacgtatcga agaattcgcg cgtaaccagg caatttcacg cctggaaggt   300
ctgagtaacc tttaccggat ttatactaac gcgttcaaga actgggaagc agaccctacc   360
aacccggtac ttcgtgagga aatgcgcatc cagttcaatg atatgaatag cgcgtttaca   420
actgctatcc cacttttctc cgttcagggt atgaaattcc gctgctgggt gtttacgtc    480
caggccgcga acctgcatct gtccgtactg cgtgacgtgt ctgttttcgg ccaggcgtgg   540
ggtttcgaca ttgccactat caactctcgt tacaatgacc tgaccgtct gatcccgatc    600
tatacggact acgctgttcg ttggtacaac actggtctgg atcgtctgcc acgtaccggc   660
```

```
ggtctgcgca attgggctcg tttcaaccag ttccgtcgtg agctgactat ctctgtgctg   720
gacatcatta gcttcttccg caactatgac tctcgcctgt atccaatccc aaccagcagc   780
cagctgacgc gtgaagtgta tactgaccct gtcatcaaca ttaccgacta tcgtgttggt   840
ccgtctttcg aaaacatcga aaactctgca atccgttccc cgcacctgat ggatttctta   900
actaatataa ttattgacac tgatttaata agaggtgttt actattgggc aggacatcgt   960
ataaattctc gctttaccgg gaccgctttt ccacatataa taacatctcc tcaatatgga  1020
ataactgcaa acgcagaacc aagacgtaca atagtgcctg gtcctttttca aggtgtgcct  1080
tccctacttt atcgcactct gagcaacccg ttttccgtc gttctgaaaa catcactcca  1140
accctgggta tcaacgtagt tcagggtgtc ggcttcattc agccgaacaa cgctgaagta  1200
ctgtaccgtt cccgtggcac cgtagatagc ctgaatgaac tgccaattga tggtgagaac  1260
tctctggtgg gttacagcca ccgcctgtcc catgtaacgc tgacccgcag cctgtacaat  1320
accaacatca ccagcctgcc gactttcgtg tggactcatc attctgcgac caacaccaac  1380
actattaacc cggacattat cacccagatc ccgctggtga agggctttcg tgtttggggc  1440
ggcacttccg taatcactgg tccgggtttc acgggtggcg atattctgcg tcgcaacacg  1500
ttcggcgact tcgtttccct gcaggtaaac atcaactctc cgatcaccca gcgctaccgc  1560
ctgcgcttcc gttacgcctc ttctcgtgat gcacgtgtta tcgtcctgac cggcgcagca  1620
agcaccggcg ttggtggtca agtttctgtg aacatgccac tgcagaaaac catggaaatc  1680
ggcgaaaacc tgacgtcccg cactttccgc tataccgatt ttagcaatcc gttctccttt  1740
cgtgcaaacc cggacatcat tggcatctct gagcaaccgc tgttcggtgc tggttccatc  1800
tcctctggtg agctgtatat cgacaagatc gaaattatcc tggcggacgc taccttcgaa  1860
gcggagagcg acctggaacg cgcgcagaaa taa                                1893

SEQ ID NO: 20          moltype = DNA   length = 1884
FEATURE                Location/Qualifiers
misc_feature           1..1884
                       note = Synthetic
source                 1..1884
                       mol_type = other DNA
                       organism = synthetic construct
SEQUENCE: 20
atggaaatcg ttaataacca gaaccagtgc gttccgtaca actgtctgaa caaccctgaa    60
aacgaaatcc tggatatcga acgttccaac tccacggtgg ccaccaacat cgctctggaa   120
atttcccgcc tgctggcaag cgccactcca attggtggta ttctgctggg cctgttcgac   180
gccatttggg gttctatcgg cccgtctcaa tgggacctgt ttctggaaca gatcgaacag   240
ctgattggcc aacgtatcga agaattcgcg cgtaaccagg caatttcacg cctggaaggt   300
ctgagtaacc tttaccggat ttatactaac gcgttcaaga actgggaagc agaccctacc   360
aacccggtac ttcgtgagga aatgcgcatc cagttcaatg atatgaatag cgcgtttaca   420
actgctatcc cacttttctc cgttcagggt tatgaaattc gctgctggg tgtttacgtc   480
caggccgcga acctgcatct gtccgtactg cgtgacgtgt ctgttttcgg ccaggcgtgg   540
ggtttcgaca ttgccactat caactctcgt tacaatgacc tgacccgtct gatcccgatc   600
tatacggact acgctgttcg ttggtacaac actggtctgg atcgtctgcc acgtaccggc   660
ggtctgcgca attgggctcg tttcaaccag ttccgtcgtg agctgactat ctctgtgctg   720
gacatcatta gcttcttccg caactatgac tctcgcctgt atccaatccc aaccagcagc   780
cagctgacgc gtgaagtgta tactgaccct gtcatcaaca ttaccgacta tcgtgttggt   840
ccgtctttcg aaaacatcga aaactctgca atccgttccc cgcacctgat ggattttctg   900
aacaacatca tcattgacac cgatctgatc cgtggcgtgc actactgggc tggtcaccgt   960
gttacgtccc acttcactgg ctccagccag tgtgatctct cccacagta cggcattact  1020
gcgaacgcgg aaccatctcg caccatcgct ccgtccacgt tcccgggtct gaacctgttc  1080
taccgcactc tgagcaaccc gttttccgt cgttctgaaa acatcactcc aaccctgggt  1140
atcaacgtag ttcagggtgt cggcttcatt cagccgaaca acgctgaagt actgtaccgt  1200
tcccgtggca ccgtagatag cctgaatgaa ctgccaattg atggtgagaa ctctctggtg  1260
ggttacagcc accgcctgtc ccatgtaacg ctgacccgca gcctgtacaa taccaacatc  1320
accagcctgc cgactttcgt gtggactcat cattctgcga ccaacaccaa cactattaac  1380
ccggacatta tcacccagat cccgctggtg aagggctttc gtgtttgggg cggcacttcc  1440
gtaatcactg gtccgggttt cacgggtggc gatattctgc gtcgcaacac gttcggcgac  1500
ttcgtttccc tgcaggtaaa catcaactct ccgatcaccc agcgctaccg cctgcgcttc  1560
cgttacgcct cttctcgtga tgcacgtgtt atcgtcctga ccggcgcagc aagcaccggc  1620
gttggtggtc aagtttctgt gaacatgcca ctgcagaaaa ccatggaaat cggcgaaaac  1680
ctgacgtccc gcacttttcg ctataccgat tttagcaatc cgttctcctt tcgtgcaaac  1740
ccggacatca ttggcatctc tgagcaaccg ctgttcggtg ctggttccat ctcctctggt  1800
gagctgtata tcgacaagat cgaaattatc ctggcggacg ctaccttcga agcggagagc  1860
gacctggaac gcgcgcagaa ataa                                          1884

SEQ ID NO: 21          moltype = DNA   length = 1884
FEATURE                Location/Qualifiers
misc_feature           1..1884
                       note = Synthetic
source                 1..1884
                       mol_type = other DNA
                       organism = synthetic construct
SEQUENCE: 21
atggaaatcg ttaataacca gaaccagtgc gttccgtaca actgtctgaa caaccctgaa    60
aacgaaatcc tggatatcga acgttccaac tccacggtgg ccaccaacat cgctctggaa   120
atttcccgcc tgctggcaag cgccactcca attggtggta ttctgctggg cctgttcgac   180
gccatttggg gttctatcgg cccgtctcaa tgggacctgt ttctggaaca gatcgaacag   240
ctgattggcc aacgtatcga agaattcgcg cgtaaccagg caatttcacg cctggaaggt   300
ctgagtaacc tttaccggat ttatactaac gcgttcaaga actgggaagc agaccctacc   360
aacccggtac ttcgtgagga aatgcgcatc cagttcaatg atatgaatag cgcgtttaca   420
actgctatcc cacttttctc cgttcagggt tatgaaattc gctgctgggt gtttacgtc   480
```

```
caggccgcga acctgcatct gtccgtactg cgtgacgtgt ctgttttcgg ccaggcgtgg    540
ggtttcgaca ttgccactat caactctcgt tacaatgacc tgacccgtct gatcccgatc    600
tatacggact acgctgttcg ttggtacaac actggtctgg atcgtctgcc acgtaccggc    660
ggtctgcgca attgggctcg tttcaaccag ttccgtcgtg agctgactat ctctgtgctg    720
gacatcatta gcttcttccg caactatgac tctcgcctgt atccaatccc aaccagcagc    780
cagctgacgc gtgaagtgta tactgaccct gtcatcaaca ttaccgacta tcgtgttggt    840
ccgtctttcg aaaacatcga aaactctgca atccgttccc cgcacctgat ggattttctg    900
aacaacctga ccattgacac cgatctgatc cgtggcgtgc actactgggc tggtcaccgt    960
gttacgtccc acttcactgg ctccagccag gtgatcacga ctccacagta cggcattact   1020
gcgaacgcgg aaccacgccg caccatcgct ccgtccacgt tcccgggtct gaacctgttc   1080
taccgcactc tgagcaaccc gttttttccgt cgttctgata acatcatgcc aaccctgggt   1140
atcaacgtag ttcagggtgt cggcttcatt cagccgaaca acggtgaagt actgtaccgt   1200
cgccgtggca ccgtagatag cctgaatgaa ctgccaattg atggtgagaa ctctctggtg   1260
ggttacagcc accgcctgtc ccatgtaacg ctgacccgca gcctgtaccg taccaacatc   1320
accagcctgc cgactttcgt gtggactcat cattctgcga ccaacaccaa cactattaac   1380
ccggacatta tcacccagat cccgctggtg aagggctttc gtgtttgggg cggcacttcc   1440
gtaatcactg gtccgggttt cacgggtggc gatattctgc gtcgcaacac gttcggcgac   1500
ttcgtttccc tgcaggtaaa catcaactct ccgatcaccc agccgtaccg cctgcgcttc   1560
cgttacgcct cttctcgtga tgcacgtgtt atcgtcctga ccggcgcagc aagcaccggc   1620
gttggtggtc aagtttctgt gaacatgcca ctgcagaaaa ccatgaaaat cggcgaaaac   1680
ctgacgtccc gcacttttccg ctataccgat tttagcaatc cgttctcctt tcgtgcaaac   1740
ccggacatca ttggcatctc tgagcaaccg ctgttcggtg ctggttccat ctcctctggt   1800
gagctgtata tcgacaagat cgaaattatc ctggcggacg ctaccttcga agcggagagc   1860
gacctggaac gcgcgcagaa ataa                                           1884
```

```
SEQ ID NO: 22          moltype = DNA  length = 1884
FEATURE                Location/Qualifiers
misc_feature           1..1884
                       note = Synthetic
source                 1..1884
                       mol_type = other DNA
                       organism = synthetic construct
SEQUENCE: 22
atggaaatcg ttaataacca gaaccagtgc gttccgtaca actgtctgaa caaccctgaa     60
aacgaaatcc tggatatcga acgttccaac tccacggtgg ccaccaacat cgctctggaa    120
atttcccgcc tgctggcaag cgccactcca attggtggta ttctgctggg cctgttcgac    180
gccatttggg gttctatcgg cccgtctcaa tgggacctgt ttctggaaca gatcgaacag    240
ctgattggcc aacgtatcga agaattcgcg cgtaaccagg caatttcacg cctgtgaaggt    300
ctgagtaacc tttaccggat ttatactaac gcgttcagca actggaagc agaccctacc    360
aacccggtac ttcgtgagga aatgcgcatc cagttcaatg atatgaatag cgcgtttaca    420
actgctatcc cactttttctc cgttcagggt tatgaaattc cgctgctggg tgtttacgtc    480
caggccgcga acctgcatct gtccgtactg cgtgacgtgt ctgttttcgg ccaggcgtgg    540
ggtttcgaca ttgccactat caactctcgt tacaatgacc tgacccgtct gatcccgatc    600
tatacggact acgctgttcg ttggtacaac actggtctgg atcgtctgcc acgtaccggc    660
ggtctgcgca attgggctcg tttcaaccag ttccgtcgtg agctgactat ctctgtgctg    720
gacatcatta gcttcttccg caactatgac tctcgcctgt atccaatccc aaccagcagc    780
cagctgacgc gtgaagtgta tactgaccct gtcatcaaca ttaccgacta tcgtgttggt    840
ccgtctttcg aaaacatcga aaactctgca atccgttccc cgcacctgat ggattttctg    900
aacaacctga ccattgacac cgatctgatc cgtggcgtgc actactgggc tggtcaccgt    960
gttacgtccc acttcactgg ctccagccag gtgatcacga ctccacagta cggcattact   1020
gcgaacgcgg aaccacgccg caccatcgct ccgtccacgt tcccgggtct gaacctgttc   1080
taccgcactc tgagcaaccc tttcttccga agatcagaca atattagtcc aaccttaggg   1140
ataaatgtag tacagggggt agggttctta caaccaaata attttgaatc tctatataga   1200
aggcgtggca ccgtagatag cctgaatgaa ctgccaattg atggtgagaa ctctctggtg   1260
ggttacagcc accgcctgtc ccatgtaacg ctgacccgca gcctgtaccg taccaacatc   1320
accagcctgc cgactttcgt gtggactcat cattctgcga ccaacaccaa cactattaac   1380
ccggacatta tcacccagat cccgctggtg aagggctttc gtgtttgggg cggcacttcc   1440
gtaatcactg gtccgggttt cacgggtggc gatattctgc gtcgcaacac gttcggcgac   1500
ttcgtttccc tgcaggtaaa catcaactct ccgatcaccc agccgtaccg cctgcgcttc   1560
cgttacgcct cttctcgtga tgcacgtgtt atcgtcctga ccggcgcagc aagcaccggc   1620
gttggtggtc aagtttctgt gaacatgcca ctgcagaaaa ccatgaaaat cggcgaaaac   1680
ctgacgtccc gcacttttccg ctataccgat tttagcaatc cgttctcctt tcgtgcaaac   1740
ccggacatca ttggcatctc tgagcaaccg ctgttcggtg ctggttccat ctcctctggt   1800
gagctgtata tcgacaagat cgaaattatc ctggcggacg ctaccttcga agcggagagc   1860
gacctggaac gcgcgcagaa ataa                                           1884
```

```
SEQ ID NO: 23          moltype = DNA  length = 1884
FEATURE                Location/Qualifiers
misc_feature           1..1884
                       note = Synthetic
source                 1..1884
                       mol_type = other DNA
                       organism = synthetic construct
SEQUENCE: 23
atggaaatcg ttaataacca gaaccagtgc gttccgtaca actgtctgaa caaccctgaa     60
aacgaaatcc tggatatcga acgttccaac tccacggtgg ccaccaacat cgctctggaa    120
atttcccgcc tgctggcaag cgccactcca attggtggta ttctgctggg cctgttcgac    180
gccatttggg gttctatcgg cccgtctcaa tgggacctgt ttctggaaca gatcgaacag    240
ctgatttctc agcgtatcga ggaattcgcg cgtaaccagg caatttcccg tctggaaggt    300
```

```
ctgtccaacc tgtataaagt gtatgttcgt gcgttcagcg actgggaaaa agaccctacc   360
aacccggtac ttcgtgagga aatgcgcatc cagttcaatg atatgaatag cgcgtttaca   420
actgctatcc cacttttctc cgttcagggt tatgaaattc cgctgctggg tgtttacgtc   480
caggccgcga acctgcatct gtccgtactg cgtgacgtgt ctgttttcgg ccaggcgtgg   540
ggtttcgaca ttgccactat caactctcgt tacaatgacc tgacccgtct gatcccgatc   600
tatacggact acgctgttcg ttggtacaac actggtctgg atcgtctgcc acgtaccggc   660
ggtctgcgca attgggctcg tttcaaccag ttccgtcgtg agctgactat ctctgtgctg   720
gacatcatta gcttcttccg caactatgac tctcgcctgt atccaatccc aaccagcagc   780
cagctgacgc gtgaagtgta tactgaccct gtcatcaaca ttaccgacta tcgtgttggt   840
ccgtctttcg aaaacatcga aaactctgca atccgttccc cgcacctgat ggattttctg   900
aacaacctga ccattgacac cgatctgatc cgtggcgtgc actactgggc tggtcaccgt   960
gttacgtccc acttcactgg ctccagccag gtgatcacga ctccacagta cggcattact  1020
gcgaacgcgg aaccacgccg caccatcgct ccgtccacgt tcccgggtct gaacctgttc  1080
taccgcactc tgagcaaccc gttttccgt cgttctgaaa acatcactcc aacctgggt  1140
atcaacgtag ttcagggtgt cggcttcatt cagccgaaca cgctgaagt actgtaccgt  1200
tcccgtggca ccgtagatag cctgaatgaa ctgccaattg atggtgagaa ctctctggtg  1260
ggttacagcc accgctgtc catgtaacg ctgacccgca gcctgtacaa taccaacatc  1320
accagcctgc cgactttcgt gtggactcat cattctgcga ccaacaccaa cactattaac  1380
ccggacatta tcacccagat cccgctggtg aagggctttc gtgtttgggg cggcacttcc  1440
gtaatcactg gtccgggttt cacgggtggc gatattctgc gtcgcaacac gttcggcgac  1500
ttcgtttccc tgcaggtaaa catcaactct ccgatcaccc agcgctaccg cctgcgcttc  1560
cgttacgcct cttctcgtga tgcacgtgtt atcgtcctga ccggcgcagc aagcaccggc  1620
gttggtggtc aagtttctgt gaacatgcca ctgcagaaaa ccatgaaat cggcgaaaac  1680
ctgacgtccc gcactttccg ctataccgat tttagcaatc cgttctcctt tcgtgcaaac  1740
ccggacatca ttggcatctc tgagcaaccg ctgttcggtg ctggttccat ctcctctggt  1800
gagctgtata tcgacaagat cgaaattatc ctggcggacg ctaccttcga agcggagagc  1860
gacctggaac gcgcgcagaa ataa                                          1884

SEQ ID NO: 24           moltype = DNA   length = 1884
FEATURE                 Location/Qualifiers
misc_feature            1..1884
                        note = Synthetic
source                  1..1884
                        mol_type = other DNA
                        organism = synthetic construct
SEQUENCE: 24
atggaaatcg ttaataacca gaaccagtgc gttccgtaca actgtctgaa caaccctgaa    60
aacgaaatcc tggatatcga acgttccaac tccacggtgg ccaccaacat cgctctggaa   120
atttcccgcc tgctggcaag cgccactcca attggtggta ttctgctggg cctgttcgac   180
gccatttggg gttctatcgg cccgtctcaa tgggaccgt ttctggaaca gatcgaacag   240
ctgattggcc aacgtatcga agaattcgcg cgtaaccagg caatttcacg cctggaaggt   300
ctgagtaacc tttaccggat ttatactaac gcgttcaaga actgggaagc agaccctacc   360
aacccggtac ttcgtgagga aatgcgcatc cagttcaatg atatgaatag cgcgtttaca   420
actgctatcc cacttttctc cgttcagggt tatcaggtac cgctgctgtc tgtgtacgtc   480
caggcggcta acctgcacct gtccgtcctg cgtgacgttt ctgtattcgg ccaggcgtgg   540
ggtttcgaca ttgccactat caactctcgt tacaatgacc tgacccgtct gatcccgatc   600
tatacggact acgctgttcg ttggtacaac actggtctgg atcgtctgcc acgtaccggc   660
ggtctgcgca attgggctcg tttcaaccag ttccgtcgtg agctgactat ctctgtgctg   720
gacatcatta gcttcttccg caactatgac tctcgcctgt atccaatccc aaccagcagc   780
cagctgacgc gtgaagtgta tactgaccct gtcatcaaca ttaccgacta tcgtgttggt   840
ccgtctttcg aaaacatcga aaactctgca atccgttccc cgcacctgat ggattttctg   900
aacaacctga ccattgacac cgatctgatc cgtggcgtgc actactgggc tggtcaccgt   960
gttacgtccc acttcactgg ctccagccag gtgatcacga ctccacagta cggcattact  1020
gcgaacgcgg aaccacgccg caccatcgct ccgtccacgt tcccgggtct gaacctgttc  1080
taccgcactc tgagcaaccc gttttccgt cgttctgaaa acatcactcc aacctgggt  1140
atcaacgtag ttcagggtgt cggcttcatt cagccgaaca cgctgaagt actgtaccgt  1200
tcccgtggca ccgtagatag cctgaatgaa ctgccaattg atggtgagaa ctctctggtg  1260
ggttacagcc accgctgtc catgtaacg ctgacccgca gcctgtacaa taccaacatc  1320
accagcctgc cgactttcgt gtggactcat cattctgcga ccaacaccaa cactattaac  1380
ccggacatta tcacccagat cccgctggtg aagggctttc gtgtttgggg cggcacttcc  1440
gtaatcactg gtccgggttt cacgggtggc gatattctgc gtcgcaacac gttcggcgac  1500
ttcgtttccc tgcaggtaaa catcaactct ccgatcaccc agcgctaccg cctgcgcttc  1560
cgttacgcct cttctcgtga tgcacgtgtt atcgtcctga ccggcgcagc aagcaccggc  1620
gttggtggtc aagtttctgt gaacatgcca ctgcagaaaa ccatgaaat cggcgaaaac  1680
ctgacgtccc gcactttccg ctataccgat tttagcaatc cgttctcctt tcgtgcaaac  1740
ccggacatca ttggcatctc tgagcaaccg ctgttcggtg ctggttccat ctcctctggt  1800
gagctgtata tcgacaagat cgaaattatc ctggcggacg ctaccttcga agcggagagc  1860
gacctggaac gcgcgcagaa ataa                                          1884

SEQ ID NO: 25           moltype = DNA   length = 1884
FEATURE                 Location/Qualifiers
misc_feature            1..1884
                        note = Synthetic
source                  1..1884
                        mol_type = other DNA
                        organism = synthetic construct
SEQUENCE: 25
atggaaatcg ttaataacca gaaccagtgc gttccgtaca actgtctgaa caaccctgaa    60
aacgaaatcc tggatatcga acgttccaac tccacggtgg ccaccaacat cgctctggaa   120
```

```
atttcccgcc tgctggcaag cgccactcca attggtggta ttctgctggg cctgttcgac   180
gccatttggg gttctatcgg cccgtctcaa tgggacctgt ttctggaaca gatcgaacag   240
ctgattggcc aacgtatcga agaattcgcg cgtaaccagg caatttcacg cctgaaggt   300
ctgagtaacc tttaccggat ttatactaac gcgttcaaga actgggaagc agaccctacc   360
aacccggcac tgacggaaga aatgcgtatc cagttcaacg acatgaactc tgctctgacg   420
acggccatcc ctctgttctc cgttcagggt tatgaaattc cgctgctggg tgtttacgtc   480
caggccgcga acctgcatct gtccgtactg cgtgacgtgt ctgttttcgg ccaggcgtgg   540
ggtttcgaca ttgccactat caactctcgt tacaatgacc tgacccgtct gatcccgatc   600
tatacggact acgctgttcg ttggtacaac actggtctgg atcgtctgcc acgtaccggc   660
ggtctgcgca attgggctcg tttcaaccag ttccgtcgtg agctgactat ctctgtgctg   720
gacatcatta gcttcttccg caactatgac tctcgcctgt atccaatccc aaccagcagc   780
cagctgacgc gtgaagtgta tactgaccct gtcatcaaca ttaccgacta tcgtgttggt   840
ccgtctttcg aaaacatcga aaactctgca atccgttccc cgcacctgat ggattttctg   900
aacaacctga ccattgacac cgatctgatc cgtggcgtgc actactgggc tggtcaccgt   960
gttacgtccc acttcactgg ctccagccag gtgatcacga ctccacagta cggcattact  1020
gcgaacgcgg aaccacgccg caccatcgct ccgtccacgt tcccgggtct gaacctgttc  1080
taccgcactc tgagcaaccc gttttccgt cgttctgaaa acatcactcc aaccctgggt  1140
atcaacgtag ttcagggtgt cggcttcatt cagccgaaca acgtgaaagt actgtaccgt  1200
tcccgtggca ccgtagatag cctgaatgaa ctgccaattg atggtgagaa ctctctggtt  1260
ggttacagcc accgcctgtc ccatgtaacg ctgacccgca gcctgtacaa taccaacatc  1320
accagcctgc cgactttcgt gtggactcat cattctgcga ccaacaccaa cactattaac  1380
ccggacatta tcacccagat cccgctggtg aagggctttc gtgtttgggg cggcacttcc  1440
gtaatcactg gtccgggttt cacgggtggc gatattctgc gtcgcaacac gttcggcgac  1500
ttcgtttccc tgcaggtaaa catcaactct ccgatcaccc agcgctaccg cctgcgcttc  1560
cgttacgcct cttctcgtga tgcacgtgtt atcgtcctga ccggcgcagc aagcaccggc  1620
gttggtggtc aagtttctgt gaacatgcca ctgcagaaaa ccatgaaat cggcgaaaac  1680
ctgacgtccc gcacttttccg ctataccgat tttagcaatc cgttctcctt tcgtgcaaac  1740
ccggacatca ttggcatctc tgagcaaccg ctgttcggtg ctggttccat ctcctctggt  1800
gagctgtata tcgacaagat cgaaattatc ctggcggacg ctaccttcga agcggagagc  1860
gacctggaac gcgcgcagaa ataa                                        1884
```

SEQ ID NO: 26    moltype = DNA  length = 1884
FEATURE    Location/Qualifiers
misc_feature    1..1884
    note = Synthetic
source    1..1884
    mol_type = other DNA
    organism = synthetic construct
SEQUENCE: 26

```
atggaaatcg ttaataacca gaaccagtgc gttccgtaca actgtctgaa caaccctgaa    60
aacgaaatcc tggatatcga acgttccaac tccacggtgg ccaccaacat cgctctgaa   120
atttcccgcc tgctggcaag cgccactcca attggtggta ttctgctggg cctgttcgac   180
gccatttggg gttctatcgg cccgtctcaa tgggacctgt ttctggaaca gatcgaacag   240
ctgattggcc aacgtatcga agaattcgcg cgtaaccagg caatttcacg cctgaaggt   300
ctgagtaacc tttaccggat ttatactaac gcgttcaaga actgggaagc agaccctacc   360
aacccggtac ttcgtgagga aatgcgcatc cagttcaatg atatgaatag cgcgtttaca   420
actgctatcc cacttttctc cgttcagggt tatcaggtac tcgctgtgtc tgtgtacgtg   480
caggcggtaa acctgcacct gtccgtcctg cgtgacgttt ctgtattcgg ccaggcgtgg   540
ggtttcgaca ttgccactat caactctcgt tacaatgacc tgacccgtct gatcccgatc   600
tatacggact acgctgttcg ttggtacaac actggtctgg atcgtctgcc acgtaccggc   660
ggtctgcgca attgggctcg tttcaaccag ttccgtcgtg agctgactat ctctgtgctg   720
gacatcatta gcttcttccg caactatgac tctcgcctgt atccaatccc aaccagcagc   780
cagctgacgc gtgaagtgta tactgaccct gtcatcaaca ttaccgacta tcgtgttggt   840
ccgtctttcg aaaacatcga aaactctgca atccgttccc cgcacctgat ggattttctg   900
aacaacctga ccattgacac cgatctgatc cgtggcgtgc actactgggc tggtcaccgt   960
gttacgtccc acttcactgg ctccagccag gtgatcacga ctccacagta cggcattact  1020
gcgaacgcgg aaccacgccg caccatcgct ccgtccacgt tcccgggtct gaacctgttc  1080
taccgcactc tgagcaaccc gttttccgt cgttctgaaa acatcactcc aaccctgggt  1140
atcaacgtag ttcagggtgt cggcttcatt cagccgaaca acgtgaaagt actgtaccgt  1200
tcccgtggca ccgtagatag cctgaatgaa ctgccaattg atggtgagaa ctctctggtt  1260
ggttacagcc accgcctgtc ccatgtaacg ctgacccgca gcctgtacaa taccaacatc  1320
accagcctgc cgactttcgt gtggactcat cattctgcga ccaacaccaa cactattaac  1380
ccggacatta tcacccagat cccgctggtg aagggctttc gtgtttgggg cggcacttcc  1440
gtaatcactg gtccgggttt cacgggtggc gatattctgc gtcgcaacac gttcggcgac  1500
ttcgtttccc tgcaggtaaa catcaactct ccgatcaccc agcgctaccg cctgcgcttc  1560
cgttacgcct cttctcgtga tgcacgtgtt atcgtcctga ccggcgcagc aagcaccggc  1620
gttggtggtc aagtttctgt gaacatgcca ctgcagaaaa ccatgaaat cggcgaaaac  1680
ctgacgtccc gcacttttccg ctataccgat tttagcaatc cgttctcctt tcgtgcaaac  1740
ccggacatca ttggcatctc tgagcaaccg ctgttcggtg ctggttccat ctcctctggt  1800
gagctgtata tcgacaagat cgaaattatc ctggcggacg ctaccttcga agcggagagc  1860
gacctggaac gcgcgcagaa ataa                                        1884
```

SEQ ID NO: 27    moltype = DNA  length = 1884
FEATURE    Location/Qualifiers
misc_feature    1..1884
    note = Synthetic
source    1..1884
    mol_type = other DNA
    organism = synthetic construct

```
SEQUENCE: 27
atggaaatcg ttaataacca gaaccagtgc gttccgtaca actgtctgaa caaccctgaa    60
aacgaaatcc tggatatcga acgttccaac tccacggtgg ccaccaacat cgctctggaa   120
atttcccgcc tgctggcaag cgccactcca attggtggta ttctgctggg cctgttcgac   180
gccatttggg gttctatcgg cccgtctcaa tgggacctgt ttctggaaca gatcgaacag   240
ctgattggcc aacgtatcga agaattcgcg cgtaaccagg caatttcacg cctggaaggt   300
ctgagtaacc tttaccggat ttatactaac gcgttcaaga actgggaagc agaccctacc   360
aacccggtac ttcgtgagga aatgcgcatc cagttcaatg atatgaatag cgcgtttaca   420
actgctatcc cacttttctc cgttcagggt tatgaagtgg cactgctgtc tgtttacgtg   480
caggccgcga acctgcatct gtccgttctg cgcgatgttt ctgtttatgg ccaggcgtgg   540
ggtttcgaca ttgccactat caactctcgt tacaatgacc tgaccgtct gatcccgatc    600
tatacggact acgctgttcg ttggtacaac actggtctgg atcgtctgcc acgtaccggc   660
ggtctgcgca attgggctcg tttcaaccag ttccgtcgtg agctgactat ctctgtgctg   720
gacatcatta gcttcttccg caactatgac tctcgcctat atccaatccc aaccagcagc   780
cagctgacgc gtgaagtgta tactgaccct gtcatcaaca ttaccgacta tcgtgttggt   840
ccgtctttcg aaaacatcga aaactctgca atccgttccc cgcacctgat ggattttctg   900
aacaacctga ccattgacac cgatctgatc cgtggcgtgc actactgggc tggtcaccgt   960
gttacgtccc acttcactgg ctccagccag gtgatcacga ctccacagta cggcattact  1020
gcgaacgcgg aaccacgccg caccatcgct ccgtccacgt tcccgggtct gaacctgttc  1080
taccgcactc tgagcaaccc gttttccgt cgttctgaaa acatcactcc aaccctgggt  1140
atcaacgtag ttcagggtgt cggcttcatt cagccgaaca acgctgaagt actgtaccgt  1200
tcccgtggca ccgtagatag cctgaatgaa ctgccaattg atggtgagaa ctctctggtg  1260
ggttacagcc accgcctgtc ccatgtaacg ctgacccgca gcctgtacaa taccaacatc  1320
accagcctgc cgactttcgt gtggactcat cattctgcga ccaacaccaa cactattaac  1380
ccggacatta tcacccagat cccgctggtg aagggctttc gtgtttgggg cggcacttcc  1440
gtaatcactg gtccgggttt cacgggtggc gatattctgc gtcgcaacac gttcggcgac  1500
ttcgttccc tgcaggtaaa catcaactct ccgatcaccc agcgctaccg cctgcgcttc  1560
cgttacgcct cttctcgtga tgcacgtgtt atcgtcctga ccggcgcagc aagcaccggc  1620
gttggtggtc aagtttctgt gaacatgcca ctgcagaaaa ccatgaaat cggcgaaaac  1680
ctgacgtccc gcactttccg ctataccgat tttagcaatc cgttctcctt tcgtgcaaac  1740
ccggacatca ttggcatctc tgagcaaccg ctgttcggtg ctggttccat ctcctctggt  1800
gagctgtata tcgacaagat cgaaattatc ctggcggacg ctaccttcga agcggagagc  1860
gacctggaac gcgcgcagaa ataa                                          1884

SEQ ID NO: 28           moltype = DNA  length = 1884
FEATURE                 Location/Qualifiers
misc_feature            1..1884
                        note = Synthetic
source                  1..1884
                        mol_type = other DNA
                        organism = synthetic construct
SEQUENCE: 28
atggaaatcg ttaataacca gaaccagtgc gttccgtaca actgtctgaa caaccctgaa    60
aacgaaatcc tggatatcga acgttccaac tccacggtgg ccaccaacat cgctctggaa   120
atttcccgcc tgctggcaag cgccactcca attggtggta ttctgctggg cctgttcgac   180
gccatttggg gttctatcgg cccgtctcaa tgggacctgt ttctggaaca gatcgaacag   240
ctgattggcc aacgtatcga agaattcgcg cgtaaccagg caatttcacg cctggaaggt   300
ctgagtaacc tttaccggat ttatactaac gcgttcaaga actgggaagc agaccctacc   360
aacccggtac ttcgtgagga aatgcgcatc cagttcaatg atatgaatag cgcgtttaca   420
actgctatcc cacttttctc cgttcagggt tatgagattc cactgctgtc cgtgtatgtt   480
caggcagcga acctgcatct gtccatcctg cgtgacgtaa cgtattcgg ccaggcgtgg    540
ggtttcgaca ttgccactat caactctcgt tacaatgacc tgaccgtct gatcccgatc    600
tatacggact acgctgttcg ttggtacaac actggtctgg atcgtctgcc acgtaccggc   660
ggtctgcgca attgggctcg tttcaaccag ttccgtcgtg agctgactat ctctgtgctg   720
gacatcatta gcttcttccg caactatgac tctcgcctat atccaatccc aaccagcagc   780
cagctgacgc gtgaagtgta tactgaccct gtcatcaaca ttaccgacta tcgtgttggt   840
ccgtctttcg aaaacatcga aaactctgca atccgttccc cgcacctgat ggattttctg   900
aacaacctga ccattgacac cgatctgatc cgtggcgtgc actactgggc tggtcaccgt   960
gttacgtccc acttcactgg ctccagccag gtgatcacga ctccacagta cggcattact  1020
gcgaacgcgg aaccacgccg caccatcgct ccgtccacgt tcccgggtct gaacctgttc  1080
taccgcactc tgagcaaccc gttttccgt cgttctgaaa acatcactcc aaccctgggt  1140
atcaacgtag ttcagggtgt cggcttcatt cagccgaaca acgctgaagt actgtaccgt  1200
tcccgtggca ccgtagatag cctgaatgaa ctgccaattg atggtgagaa ctctctggtg  1260
ggttacagcc accgcctgtc ccatgtaacg ctgacccgca gcctgtacaa taccaacatc  1320
accagcctgc cgactttcgt gtggactcat cattctgcga ccaacaccaa cactattaac  1380
ccggacatta tcacccagat cccgctggtg aagggctttc gtgtttgggg cggcacttcc  1440
gtaatcactg gtccgggttt cacgggtggc gatattctgc gtcgcaacac gttcggcgac  1500
ttcgttccc tgcaggtaaa catcaactct ccgatcaccc agcgctaccg cctgcgcttc  1560
cgttacgcct cttctcgtga tgcacgtgtt atcgtcctga ccggcgcagc aagcaccggc  1620
gttggtggtc aagtttctgt gaacatgcca ctgcagaaaa ccatgaaat cggcgaaaac  1680
ctgacgtccc gcactttccg ctataccgat tttagcaatc cgttctcctt tcgtgcaaac  1740
ccggacatca ttggcatctc tgagcaaccg ctgttcggtg ctggttccat ctcctctggt  1800
gagctgtata tcgacaagat cgaaattatc ctggcggacg ctaccttcga agcggagagc  1860
gacctggaac gcgcgcagaa ataa                                          1884

SEQ ID NO: 29           moltype = DNA  length = 1884
FEATURE                 Location/Qualifiers
misc_feature            1..1884
                        note = Synthetic
```

| source | 1..1884 |
| | mol_type = other DNA |
| | organism = synthetic construct |

SEQUENCE: 29

```
atggaaatcg ttaataacca gaaccagtgc gttccgtaca actgtctgaa caaccctgaa    60
aacgaaatcc tggatatcga acgttccaac tccacggtgg ccaccaacat cgctctggaa   120
atttcccgcc tgctggcaag cgccactcca attggtggta ttctgctggg cctgttcgac   180
gccatttggg gttctatcgg cccgtctcaa tgggacctgt ttctggaaca gatcgaacag   240
ctgattggcc aacgtatcga agaattcgcg cgtaaccagg caatttcacg cctggaaggt   300
ctgagtaacc tttaccggat ttatactaac gcgttcaaga actgggaagc agaccctacc   360
aacccggtac ttcgtgagga aatgcgcatc cagttcaatg atatgaatag cgcgtttaca   420
actgctatcc cacttttctc cgttcagggt tatgaaatcc cgctgctgtc tgtctacgtt   480
caggccgcga acctgcacct gtccgttctg cgcgatgttt ctgttttcgg ccaggcgtgg   540
ggtttcgaca ttgccactat caactctcgt tacaatgacc tgacccgtct gatcccgatc   600
tatacggact acgctgttcg ttggtacaac actggtctgg atcgtctgcc acgtaccggc   660
ggtctgcgca attgggctcg tttcaaccag ttccgtcgtg agctgactat ctctgtgctg   720
gacatcatta gcttcttccg caactatgac tctcgcctgt atccaatccc aaccagcagc   780
cagctgacgc gtgaagtgta tactgaccct gtcatcaaca ttaccgacta tcgtgttggt   840
ccgtctttcg aaaacatcga aaactctgca atccgttccc cgcacctgat ggattttctg   900
aacaacctga ccattgacac cgatctgatc cgtggcgtgc actactgggc tggtcaccgt   960
gttacgtccc acttcactgg ctccagccag gtgatcacga ctcccacagta cggcattact  1020
gcgaacgcgg aaccacgccg caccatcgct ccgtccacgt tcccgggtct gaacctgttc  1080
taccgcactc tgagcaaccc gttttttccgt cgttctgaaa acatcactcc aaccctgggt  1140
atcaacgtag ttcagggtgt cggcttcatt cagccgaaca acgctgaagt actgtaccgt  1200
tcccgtggca ccgtagatag cctgaatgaa ctgccaattg atggtgagaa ctctctggtg  1260
ggttacagcc accgcctgtc ccatgtaacg ctgacccgca gcctgtacaa taccaacatc  1320
accagcctgc cgactttcgt gtggactcat cattctgcga ccaacaccaa cactattaac  1380
ccggacatta tcacccagat cccgctggtg aagggctttc gtgtttgggg cggcacttcc  1440
gtaatcactg gtccggggttt cacgggtggc gatattctgc gtcgcaacac gttcggcgac  1500
ttcgtttccc tgcaggtaaa catcaactct ccgatcaccc agcgctaccg cctgcgcttc  1560
cgttacgcct cttctcgtga tgcacgtgtt atcgtcctga ccggcgcagc aagcaccggc  1620
gttggtggtc aagtttctgt gaacatgcca ctgcagaaaa ccatgaaat cggcgaaaac  1680
ctgacgtccc gcacttttccg ctataccgat tttagcaatc cgttctcctt tcgtgcaaac  1740
ccggacatca ttggcatctc tgagcaaccg ctgttcggtg ctggttccat ctcctctggt  1800
gagctgtata tcgacaagat cgaaattatc ctggcggacg ctaccttcga agcggagagc  1860
gacctggaac gcgcgcagaa ataa                                          1884
```

| SEQ ID NO: 30 | moltype = DNA length = 1884 |
| FEATURE | Location/Qualifiers |
| misc_feature | 1..1884 |
| | note = Synthetic |
| source | 1..1884 |
| | mol_type = other DNA |
| | organism = synthetic construct |

SEQUENCE: 30

```
atggaaatcg ttaataacca gaaccagtgc gttccgtaca actgtctgaa caaccctgaa    60
aacgaaatcc tggatatcga acgttccaac tccacggtgg ccaccaacat cgctctggaa   120
atttcccgcc tgctggcaag cgccactcca attggtggta ttctgctggg cctgttcgac   180
gccatttggg gttctatcgg cccgtctcaa tgggacctgt ttctggaaca gatcgaacag   240
ctgattggcc aacgtatcga agaattcgcg cgtaaccagg caatttcacg cctggaaggt   300
ctgagtaacc tttaccggat ttatactaac gcgttcaaga actgggaagc agaccctacc   360
aacccggtac ttcgtgagga aatgcgcatc cagttcaatg atatgaatag cgcgtttaca   420
actgctatcc cacttttctc cgttcagggt tatgagattc ctctgctgac tgtatacgta   480
caggctgcca acctgcatct ttctctgtta cgcgacgcgg tgtatttcgg ccaggcgtgg   540
ggtttcgaca ttgccactat caactctcgt tacaatgacc tgacccgtct gatcccgatc   600
tatacggact acgctgttcg ttggtacaac actggtctgg atcgtctgcc acgtaccggc   660
ggtctgcgca attgggctcg tttcaaccag ttccgtcgtg agctgactat ctctgtgctg   720
gacatcatta gcttcttccg caactatgac tctcgcctgt atccaatccc aaccagcagc   780
cagctgacgc gtgaagtgta tactgaccct gtcatcaaca ttaccgacta tcgtgttggt   840
ccgtctttcg aaaacatcga aaactctgca atccgttccc cgcacctgat ggattttctg   900
aacaacctga ccattgacac cgatctgatc cgtggcgtgc actactgggc tggtcaccgt   960
gttacgtccc acttcactgg ctccagccag gtgatcacga ctcccacagta cggcattact  1020
gcgaacgcgg aaccacgccg caccatcgct ccgtccacgt tcccgggtct gaacctgttc  1080
taccgcactc tgagcaaccc gttttttccgt cgttctgaaa acatcactcc aaccctgggt  1140
atcaacgtag ttcagggtgt cggcttcatt cagccgaaca acgctgaagt actgtaccgt  1200
tcccgtggca ccgtagatag cctgaatgaa ctgccaattg atggtgagaa ctctctggtg  1260
ggttacagcc accgcctgtc ccatgtaacg ctgacccgca gcctgtacaa taccaacatc  1320
accagcctgc cgactttcgt gtggactcat cattctgcga ccaacaccaa cactattaac  1380
ccggacatta tcacccagat cccgctggtg aagggctttc gtgtttgggg cggcacttcc  1440
gtaatcactg gtccggggttt cacgggtggc gatattctgc gtcgcaacac gttcggcgac  1500
ttcgtttccc tgcaggtaaa catcaactct ccgatcaccc agcgctaccg cctgcgcttc  1560
cgttacgcct cttctcgtga tgcacgtgtt atcgtcctga ccggcgcagc aagcaccggc  1620
gttggtggtc aagtttctgt gaacatgcca ctgcagaaaa ccatgaaat cggcgaaaac  1680
ctgacgtccc gcacttttccg ctataccgat tttagcaatc cgttctcctt tcgtgcaaac  1740
ccggacatca ttggcatctc tgagcaaccg ctgttcggtg ctggttccat ctcctctggt  1800
gagctgtata tcgacaagat cgaaattatc ctggcggacg ctaccttcga agcggagagc  1860
gacctggaac gcgcgcagaa ataa                                          1884
```

| SEQ ID NO: 31 | moltype = DNA length = 1830 |

```
FEATURE                 Location/Qualifiers
misc_feature            1..1830
                        note = Synthetic
source                  1..1830
                        mol_type = other DNA
                        organism = synthetic construct
SEQUENCE: 31
atgccaatca acaaccagaa acagtgcatc ccatacaatt gcctgagtaa tcctgaggag    60
gttttactgg acggcgaacg tatcctgccg gacattgacc cactggaagt gagcctgtca   120
ctgttacaat tcttgctgaa taatttcgtg ccgggtggtg gcttcatctc tggattggtg   180
gataaaatct ggggtgccct tcgtccgagc gaatgggatc tgttttttagc gcagatcgaa   240
cagctgatta acgaacgtat cgccgaattc gcgcgtaacg ccgcaattgc aaacctggaa   300
ggtctgggta acaacttcaa tatttatgtt gaagcgttca aagaatggga agaagaccct   360
aacaacccgg aaacccgtac gcgcgttatc gaccgtttcc gtattctgga tggcctgctg   420
gaacgtgata tcccatcttt ccgcatttct ggttttgaag tgccgctgct gtctgtttac   480
gcccaggccg cgaacctgca tctggcgctt ctgcgtgatt ccgtaatttt tggcgaacgt   540
tggggtctga cgaccaagaa cgttaatgac atttacaacc ggcagatccg cgagattcac   600
gagtattcaa accactgtgt ggatacgtac aacacagaac tggaacgttt gggcttccgc   660
tctattgccc agtggcgtat ctacaatcaa tttcggcggg agttaacatt gacggttctg   720
gacattgtgg ccctgtttcc aaattatgat agccgcctgt atcctatcca gactttcagt   780
cagttaaccc gcgaaatcgt gacatcccca gtctcagagt tctattatgg cgttattaac   840
tccgggaaca tcattggcac cctgacagca cagcagatcc gtcgtccaca cctgatggac   900
tttttcaaca gcatgattat gtatacgtcg gataaccgtc gcgagcacta ctggtcaggc   960
ctggaaatga cggcatactt tactggattc gctggcgccc aagtaagttt tccgcttgta  1020
ggcacccgtg gcgagtctgc tcctcccctg acggtgcgca gcgttaatga tggaatttac  1080
cgcattttat cagctccatt ctattcagct ccgtttctgg gaaccatcgt cctggggtcg  1140
cggggcgaaa aattcgattt cgcgttaaat aatattagcc ctccgcctag cacaatttat  1200
cgtcacccag gtaccgttga cagtctggtc agcatcccgc ctcaggataa ttcggttccg  1260
ccgcaccgcg gctcatccca tcggctgagt cacgttacta tgcgtgcaag ttcgcctatc  1320
tttcattgga cccatcgttc cgccaccact acgaacacca ttaacccgaa cgcagattat  1380
cagattccgt tggtgaaggc gttcaacctt cactcgggcg cgacagtggt acgcgggccc  1440
ggtttcaccg gggcgatat cctgcgccgt acgaacactg gtacgttcgc ggatatgcgc  1500
gttaacatca ctgcccgtt gtcgcagcgg taccgtgtgc gtatccgcta cgcctccaca  1560
acggatctgc agttctttac ccgtatcaat ggtacatcgg tgaatcaggg gaacttccag  1620
cgcacgatga atcggggtga taaccttgag agcggcaact ttcgtaccgc cggcttctcg  1680
acaccgtttt cgttttctaa cgcgcagtct acttttacgc tgggcaccca agcgtttagc  1740
aaccaggaag tttatatcga ccgtatcgag tttgtgccag ccgaagtaac ctttgaggca  1800
gaaagtgatc tggaacgtgc gcaaaaataa                                   1830

SEQ ID NO: 32           moltype = DNA  length = 1833
FEATURE                 Location/Qualifiers
misc_feature            1..1833
                        note = Synthetic
source                  1..1833
                        mol_type = other DNA
                        organism = synthetic construct
SEQUENCE: 32
atgccaatca acaaccagaa ccagtgcatc ccatacaatt gcctgagtaa tcctgaggag    60
gttttcctgg acggcgaacg tatcctgccg gacattgacc cactggaagt gagcctgtca   120
ctgttacaat tcttgctgaa taatttcgtg ccgggtggtg gcttcatctc tggattgctg   180
gataaaatct ggggtgccct tcgtccgagc gattgggaac tgttttttaga gcagatcgaa   240
cagctgatta acgaacgtat cgccgaattc gcgcgtaacg ccgcaattgc aaacctggaa   300
ggtctgggta acaacttcaa tatttatgtt gaagcgttca aagaatggga agaagaccct   360
aacaacccgg aaacccgtac gcgcgttatc gaccgtttcc gtattctgga tggcctgctg   420
gaacgtgata tcccatcttt ccgcatttct ggttttgaag tgccgctgct gtctgtttac   480
gcccaggccg cgaacctgca tctggcgctt ctgcgtgatt ccgtagtgtt tggcgaacgt   540
tggggtctga cgaccaccaa cgttaatgac atttacaacc gacaggtgaa ccgcattggc   600
gagtattcaa acactgtgt ggatacgtac aagacagaac tggaacgttt gggcttccgc   660
tctattgccc agtggcgtat ctacaatcaa tttcggcggg agttaacatt gacggttctg   720
gacattgtgg ccgttttttcc aaattatgat agccgcctgt atcctatccg cactattagt   780
cagctgacgc gtgaaattta taccagccca gtgtcggagt tctactacgg tgtgatcaat   840
tctaacaata tcattgggac gcttacgaa cagcagatcc ggcggccgca cctgatggat   900
ttcttcaact caatgatcat gtatacctca gataaccgtc gtgaacacta ttggtcgggt   960
ttagagatga cggcgaccaa caccgaaggc catcaacgca gttttcctct tgcagggacc  1020
attgggaata gtgcacctcc agtcactgtt cgtaacaatg gtgaaggtat ctaccgtatt  1080
cttttctgagc cctttactc tgcacctttt ctgggtacca cgtgctggg cagccgtggt  1140
gaggaatttg ctttcgcgtc taacactact acaagtttgc cgagtaccat ttaccgcaac  1200
cgtggaactg ttgattctct tgtatcaatt ccaccacagg attatagcgt gcctcctcat  1260
cgtggctact cgcacttgtt gagtcatgtt acgatgcgta actcaagccg gattttcat  1320
tggattcacc gcagcgcgac gcctcgcaac acgatcgacc cagatagtat cacacagatt  1380
ccggcagtca aggggcata tattttcaat tcgccggtga ttacaggccc gggtcatacg  1440
ggtggtgata ttatccgttt caacccgaat acgcagaata cattcgtat cccctttccag  1500
tcgaacgccg tgcaacgtta tcgcattcgg atgcgttacg ctgccgaggc agactgtatc  1560
ctggagtcag gtgtgaacat cgtcacaggg gccgggtga cctttgcct tattccgatt  1620
aaagccacca tgaccccggg ctcgcctctg acctactata gttttccaata cgctgatctg  1680
aacatcaacc tgaccgcgcc gattgcccct aataactttg tgagtattcg gcgcagtaat  1740
cagccaggta atctgtatat tgatcgtatt gaattcatcc cgattgatcc aatccgtgag  1800
gctgaacatg acctggaacg tgcgcagaaa taa                                1833
```

```
SEQ ID NO: 33               moltype = DNA   length = 1827
FEATURE                     Location/Qualifiers
misc_feature                1..1827
                            note = Synthetic
source                      1..1827
                            mol_type = other DNA
                            organism = synthetic construct
SEQUENCE: 33
atgccaatca acaaccagaa ccagtgcatc ccatacaatt gcctgagtaa tcctgaggag    60
gttttcctgg acggcgaacg tatcctgccg gacattgacc cactggaagt gagcctgtca   120
ctgttacaat tcttgctgaa taatttcgtg ccgggtggtg gcttcatctc tggattgctg   180
gataaaatct ggggtgccct tcgtccgagc gattgggaac tgttttttaga gcagatcgaa   240
cagctgatta acgaacgtat cgccgaattc gcgcgtaacg ccgcaattgc aaacctggaa   300
ggtctgggta acaacttcaa tatttatgtt gaagcgttca aagaatggaa agaagaccct   360
aacaacccgg aaaccgtac gcgcgttatc gaccgtttcc gtattctgga tggcctgctg   420
gaacgtgata tcccatcttt ccgcatttct ggttttgaag tgccgctgct gtctgtttac   480
gcccaggccg cgaacctgca tctggcgctt ctgcgtgatt ccgtagtgtt tggcgaacgt   540
tggggtctga cgaccaccaa cgttaatgac atttacaacc gacaggtgaa ccgcattggc   600
gagtattcaa acactgtgt ggatacgtac aagacagaac tggaacgttt gggcttccgc   660
tctattgccc agtggcgtat ctacaatcaa tttcggcggg agttaacatt gacggttctg   720
gacattgtgg ccgttttcc aaattatgat agccgcctgt atcctatccg cactattagt   780
cagctgacgc gtgaaattta taccagccca gtgtcggagt tctactacgg tgtgatcaat   840
tctaacaata tcattgggac gcttacgaa cagcagatcc ggcggccgca cctgatggat   900
ttcttcaact caatgatcat gtatacctca gataaccgtc gtgaacacta ttggtcgggt   960
ttagagatga cggcgaccaa caccgaaggc catcaacgca gttttcctct gcagggacc   1020
attgggaata gtgcacctcc agtcactgtt cgtaacaatg gtgaaggtat ctaccgtatt   1080
ctttctgagc ccttttactc tgcacccttc ctgggtacca gcgtgctggg cagccgtggt   1140
gaggaatttg ctttcgcgtc taacactact acaagtttgc cgagtaccat ttaccgcaac   1200
cgtggaactg ttgattctct tgtatcaatt ccaccacagg attatagcgt gcctcctcat   1260
cgtggctact cgcacttgtt gagtcatgtt acgatgcgta actcaagccc gattttcat   1320
tggattcacc gcagcgcgac gcctcgcaac acgatcgacc cagatagtat cacacagatt   1380
ccgctggtta aagcgcatac cctgcaatcc ggcaccactg tagtacgtgg tcctggtttc   1440
accggtggtg atattctgcg ccgtacgagc ggcggtccgt tgcgtacac tatcgttaac   1500
attaatggtc agctgccgca gcgttatcgc gcgcgcatcc gctacgcttc tactacgaac   1560
ctgcgcatct acgttaccgt agcaggtgaa cgtattttcg ctggtcagtt caacaaaact   1620
atggacactg gcgacccgct gacgttccag tcttttctcct atgccactat taacaccgct   1680
tttactttcc cgatgtccca atcttctttc actgtaggcg ccgacacttt ttctagcggc   1740
aacgaggtgt acatcgaccg ttttgaactg atccctgtaa cggcgactt cgaagctgaa   1800
tacgacctgg aacgtgcaca gaaataa                                       1827
SEQ ID NO: 34               moltype = DNA   length = 1833
FEATURE                     Location/Qualifiers
misc_feature                1..1833
                            note = Synthetic
source                      1..1833
                            mol_type = other DNA
                            organism = synthetic construct
SEQUENCE: 34
atgccaatca acaaccagaa ccagtgcatc ccatacaatt gcctgagtaa tcctgaggag    60
gttttcctgg acggcgaacg tatcctgccg gacattgacc cactggaagt gagcctgtca   120
ctgttacaat tcttgctgaa taatttcgtg ccgggtggtg gcttcatctc tggattgctg   180
gataaaatct ggggtgccct tcgtccgagc gattgggaac tgttttttaga gcagatcgaa   240
cagctgatta accagcgtat cgaagaattc gcgcgtaacc aggcaatctc ccgtctggaa   300
ggtctgtcca acctgtacca gatctacgca gagtccttcc gtaatggga agctgaccct   360
aacaacccgg aaaccgtac gcgcgttatc gaccgtttcc gtattctgga tggcctgctg   420
gaacgtgata tcccatcttt ccgcatttct ggttttgaag tgccgctgct gtctgtttac   480
gcccaggccg cgaacctgca tctggcgctt ctgcgtgatt ccgtagtgtt tggcgaacgt   540
tggggtctga cgaccaccaa cgttaatgac atttacaacc gacaggtgaa ccgcattggc   600
gagtattcaa acactgtgt ggatacgtac aagacagaac tggaacgttt gggcttccgc   660
tctattgccc agtggcgtat ctacaatcaa tttcggcggg agttaacatt gacggttctg   720
gacattgtgg ccgttttcc aaattatgat agccgcctgt atcctatccg cactattagt   780
cagctgacgc gtgaaattta taccagccca gtgtcggagt tctactacgg tgtgatcaat   840
tctaacaata tcattgggac gcttacgaa cagcagatcc ggcggccgca cctgatggat   900
ttcttcaact caatgatcat gtatacctca gataaccgtc gtgaacacta ttggtcgggt   960
ttagagatga cggcgaccaa caccgaaggc catcaacgca gttttcctct gcagggacc   1020
attgggaata gtgcacctcc agtcactgtt cgtaacaatg gtgaaggtat ctaccgtatt   1080
ctttctgagc ccttttactc tgcacccttc ctgggtacca gcgtgctggg cagccgtggt   1140
gaggaatttg ctttcgcgtc taacactact acaagtttgc cgagtaccat ttaccgcaac   1200
cgtggaactg ttgattctct tgtatcaatt ccaccacagg attatagcgt gcctcctcat   1260
cgtggctact cgcacttgtt gagtcatgtt acgatgcgta actcaagccc gattttcat   1320
tggattcacc gcagcgcgac gcctcgcaac acgatcgacc cagatagtat cacacagatt   1380
ccggcagtca agggggcata tattttcaat cgccggtga ttacaggccc gggtcatacg   1440
ggtggtgata ttatccgttt caacccgaat acgcagaata acattcgtat cccctttcag   1500
tcgaacgccg tgcaacgtta tcgcattcgg atgcgttacg ctgccgaggc agactgtatc   1560
ctggagtcag gtgtgaacat cgtcacaggg gccgggtga ccttttcgtcc tattccgatt   1620
aaagccacca tgaccccggg ctcgcctctg acctactata gtttccaata cgctgatctg   1680
aacatcaacc tgaccgcgcc gattgcgcct aataacttg tgagtattcg gcgcagtaat   1740
cagccaggta atctgtatat tgatcgtatt gaattcatcc cgattgatcc aatccgtgag   1800
gctgaacatg acctggaacg tgcgcagaaa taa                                 1833
```

```
SEQ ID NO: 35          moltype = DNA  length = 1833
FEATURE                Location/Qualifiers
misc_feature           1..1833
                       note = Synthetic
source                 1..1833
                       mol_type = other DNA
                       organism = synthetic construct
SEQUENCE: 35
atgccaatca acaaccagaa ccagtgcatc ccatacaatt gcctgagtaa tcctgaggag    60
gttttcctgg acggcgaacg tatcctgccg gacattgacc cactggaagt gagcctgtca   120
ctgttacaat tcttgctgaa taatttcgtg ccgggtggtg gcttcatctc tggattgctg   180
gataaaatct ggggtgccct tcgtccgagc gattgggaac tgttttttaga gcagatcgaa  240
cagctgatcg accgtcgcat tgagcgtaca gttcgtcgca aagcgattgc cgagctggag   300
ggcctgggcc ggagttacca gctgtacggt gaagccttca aagagtggga aaaagaccct   360
aacaacccgg aaaccgtac gcgcgttatc gaccgtttcc gtattctgga tggcctgctg    420
gaacgtgata tcccatcttt ccgcatttct ggttttgaag tgccgctgct gtctgtttac   480
gcccaggccg cgaacctgca tctggcgctt ctgcgtgatt ccgtagtgtt tggcgaacgt   540
tggggtctga cgaccaccaa cgttaatgac atttacaacc gacaggtgaa ccgcattggc   600
gagtattcaa aacactgtgt ggatacgtac aagacagaac tggaacgttt gggcttccgc   660
tctattgccc agtggcgtat ctacaatcaa tttcggcggg agttaacatt gacggttctg   720
gacattgtgg ccgtttttcc aaattatgat agccgcctgt atcctatccg cactattagt   780
cagctgacgc gtgaaattta taccagccca gtgtcggagt tctactacgg tgtgatcaat   840
tctaacaata tcattgggac gcttacggaa cagcagatcc ggcggccgca cctgatggat   900
ttcttcaact caatgatcat gtatacctca gataaccgtc gtgaacacta ttggtcgggt   960
ttagagatga cggcgaccaa caccgaaggc catcaacgca gttttcctct tgcagggacc  1020
attgggaata gtgcacctcc agtcactgtt cgtaacaatg gtgaaggtat ctaccgtatt  1080
cttctctgagc cctttactc tgcacctttc ctgggtacca gcgtgctggg cagccgtggt  1140
gaggaatttg ctttcgcgtc taacactact acaagtttgc cgagtaccat ttaccgcaac  1200
cgtggaactg ttgattctct tgtatcaatt ccaccacagg attatagcgt gcctcctcat  1260
cgtggctact cgcacttgtt gagtcatgtt acgatgcgta actcaagccc gattttttcat  1320
tggattcacc gcagcgcgac gcctcgcaac acgatcgacc cagatagtat cacacagatt  1380
ccggcagtca agggggcata tattttcaat tcgccggtga ttacaggccc gggtcatacg  1440
ggtggtgata ttatccgttt caacccgaat acgcagaata acattcgtat ccccttccag  1500
tcgaacgccg tgcaacgtta tcgcattcgg atgcgttacg ctgccgaggc agactgtatc  1560
ctggagtcag gtgtgaacat cgtcacaggg gccggggtga cctttcgtcc tattccgatt  1620
aaagccacca tgaccccggg ctcgcctctg acctactata gtttcaaata cgctgatctg  1680
aacatcaacc tgaccgcgcc gattcgccct aataactttg tgagtattcg gcgcagtaat  1740
cagccaggta atctgtatat tgatcgtatt gaattcatcc cgattgatcc aatccgtgag  1800
gctgaacatg acctggaacg tgcgcagaaa taa                               1833

SEQ ID NO: 36          moltype = DNA  length = 1833
FEATURE                Location/Qualifiers
misc_feature           1..1833
                       note = Synthetic
source                 1..1833
                       mol_type = other DNA
                       organism = synthetic construct
SEQUENCE: 36
atgccaatca acaaccagaa ccagtgcatc ccatacaatt gcctgagtaa tcctgaggag    60
gttttcctgg acggcgaacg tatcctgccg gacattgacc cactggaagt gagcctgtca   120
ctgttacaat tcttgctgaa taatttcgtg ccgggtggtg gcttcatctc tggattgctg   180
gataaaatct ggggtgccct tcgtccgagc gattgggaac tgttttttaga gcagatcgaa  240
cagctgatta cgaacgtat cgccgaattc gcgcgtaacg ccgcaattgc aaacctggaa    300
ggtctgggta caacttcaa tatttatgtt gaagcgttca aagaatggga agagacccct   360
aacaacccgg aaaccgtac gcgcgttatc gaccgtttcc gtattctgga tggcctgctg    420
gaacgtgata tcccatcttt ccgcatttct ggttttgaag tacagctgct gtctgtgttt   480
gcgcaggcgc taacctgca cctgtccctg ctgcgtgacg ttgttttctt cggcgaacgt   540
tggggtctga cgaccaccaa cgttaatgac atttacaacc gacaggtgaa ccgcattggc   600
gagtattcaa aacactgtgt ggatacgtac aagacagaac tggaacgttt gggcttccgc   660
tctattgccc agtggcgtat ctacaatcaa tttcggcggg agttaacatt gacggttctg   720
gacattgtgg ccgtttttcc aaattatgat agccgcctgt atcctatccg cactattagt   780
cagctgacgc gtgaaattta taccagccca gtgtcggagt tctactacgg tgtgatcaat   840
tctaacaata tcattgggac gcttacggaa cagcagatcc ggcggccgca cctgatggat   900
ttcttcaact caatgatcat gtatacctca gataaccgtc gtgaacacta ttggtcgggt   960
ttagagatga cggcgaccaa caccgaaggc catcaacgca gttttcctct tgcagggacc  1020
attgggaata gtgcacctcc agtcactgtt cgtaacaatg gtgaaggtat ctaccgtatt  1080
cttctctgagc cctttactc tgcacctttc ctgggtacca gcgtgctggg cagccgtggt  1140
gaggaatttg ctttcgcgtc taacactact acaagtttgc cgagtaccat ttaccgcaac  1200
cgtggaactg ttgattctct tgtatcaatt ccaccacagg attatagcgt gcctcctcat  1260
cgtggctact cgcacttgtt gagtcatgtt acgatgcgta actcaagccc gattttttcat  1320
tggattcacc gcagcgcgac gcctcgcaac acgatcgacc cagatagtat cacacagatt  1380
ccggcagtca agggggcata tattttcaat tcgccggtga ttacaggccc gggtcatacg  1440
ggtggtgata ttatccgttt caacccgaat acgcagaata acattcgtat ccccttccag  1500
tcgaacgccg tgcaacgtta tcgcattcgg atgcgttacg ctgccgaggc agactgtatc  1560
ctggagtcag gtgtgaacat cgtcacaggg gccggggtga cctttcgtcc tattccgatt  1620
aaagccacca tgaccccggg ctcgcctctg acctactata gtttcaaata cgctgatctg  1680
aacatcaacc tgaccgcgcc gattcgccct aataactttg tgagtattcg gcgcagtaat  1740
cagccaggta atctgtatat tgatcgtatt gaattcatcc cgattgatcc aatccgtgag  1800
```

```
gctgaacatg acctggaacg tgcgcagaaa taa                              1833

SEQ ID NO: 37           moltype = DNA  length = 1833
FEATURE                 Location/Qualifiers
misc_feature            1..1833
                        note = Synthetic
source                  1..1833
                        mol_type = other DNA
                        organism = synthetic construct
SEQUENCE: 37
atgccaatca acaaccagaa ccagtgcatc ccatacaatt gcctgagtaa tcctgaggag   60
gttttcctgg acggcgaacg tatcctgccg gacattgacc cactggaagt gagcctgtca  120
ctgttacaat tcttgctgaa taatttcgtg ccgggtggtg gcttcatctc tggattgctg  180
gataaaatct ggggtgccct tcgtccgagc gattgggaac tgtttttaga gcagatcgaa  240
cagctgatta acgaacgtat cgccgaattc gcgcgtaacg ccgcaattgc aaacctggaa  300
ggtctgggta acaacttcaa tatttatgtt gaagcgttca agaatgggaa agaagaccct  360
aacaacccgg aaacccgtac gcgcgttatc gaccgtttcc gtattctgga tggcctgctg  420
gaacgtgata tcccatcttt ccgcatttct ggttttcaag tgcctttcct gagcgtgtac  480
gtgcaagcgg ccaacctgca cctgtccgta ctgcgtgacg tgtctgtttt cggcgaacgt  540
tggggtctga cgaccaccaa cgttaatgac atttacaacc gacaggtgaa ccgcattggc  600
gagtattcaa acactgtgt ggatacgtac aagacagaac tggaacgttt gggcttccgc  660
tctattgccc agtggcgtat ctacaatcaa tttcggcggg agttaacatt gacggttctg  720
gacattgtgg ccgttttcc aaattatgat agccgcctgt atcctatccg cactattagt  780
cagctgacgc gtgaaattta taccagccca gtgtcggagt tctactacgg tgtgatcaat  840
tctaacaata tcattgggac gcttacgaa cagcagatcc ggcggccgca cctgatggat  900
ttcttcaact caatgatcat gtatacctca gataaccgtc gtgaacacta ttggtcgggt  960
ttagagatga cggcgaccaa caccgaaggc catcaacgca gttttcctct tgcagggacc  1020
attgggaata gtgcacctcc agtcactgtt cgtaacaatg gtgaaggtat ctaccgtatt  1080
cttttctgagc cctttactc tgcacctttc ctgggtacca gcgtgctggg cagccgtggt  1140
gaggaatttg ctttcgcgtc taacactact acaagtttgc cgagtaccat ttaccgcaac  1200
cgtggaactg ttgattctct tgtatcaatt ccaccacagg attatagcgt gcctcctcat  1260
cgtggctact cgcacttgtt gagtcatgtt acgatgcgta actcaagccc gattttcat  1320
tggattcacc gcagcgcgac gcctcgcaac acgatcgacc cagatagtat cacacagatt  1380
ccggcagtca aggggggcata tattttcaat tcgccggtga ttacaggccc gggtcatacg  1440
ggtggtgata ttatccgttt caacccgaat acgcagaata acattcgtat ccccttccag  1500
tcgaacgccg tgcaacgtta tcgcattcgg atgcgttacg ctgccgaggc agactgtatc  1560
ctggagtcag gtgtgaacat cgtcacaggg gccggggtga cctttcgtcc tattccgatt  1620
aaagccacca tgacccgggg ctcgcctctg acctactata gttccaata cgctgatctg  1680
aacatcaacc tgaccgcgcc gattcgccct aataactttg tgagtattcg gcgcagtaat  1740
cagccaggta atctgtatat tgatcgtatt gaattcatcc cgattgatcc aatccgtgag  1800
gctgaacatg acctggaacg tgcgcagaaa taa                              1833

SEQ ID NO: 38           moltype = DNA  length = 1833
FEATURE                 Location/Qualifiers
misc_feature            1..1833
                        note = Synthetic
source                  1..1833
                        mol_type = other DNA
                        organism = synthetic construct
SEQUENCE: 38
atgccaatca acaaccagaa ccagtgcatc ccatacaatt gcctgagtaa tcctgaggag   60
gttttcctgg acggcgaacg tatcctgccg gacattgacc cactggaagt gagcctgtca  120
ctgttacaat tcttgctgaa taatttcgtg ccgggtggtg gcttcatctc tggattgctg  180
gataaaatct ggggtgccct tcgtccgagc gattgggaac tgtttttaga gcagatcgaa  240
cagctgatta acgaacgtat cgccgaattc gcgcgtaacg ccgcaattgc aaacctggaa  300
ggtctgggta acaacttcaa tatttatgtt gaagcgttca agaatgggaa agaagaccct  360
aacaacccgg aaacccgtac gcgcgttatc gaccgtttcc gtattctgga tggcctgctg  420
gaacgtgata tcccatcttt ccgcatttct ggttttgagg tgccgctgct gctggtttac  480
acgcaggctg cgaacctgca tttggcatta ctgcgtgact ctgtggtcgt cggcgaacgt  540
tggggtctga cgaccaccaa cgttaatgac atttacaacc gacaggtgaa ccgcattggc  600
gagtattcaa acactgtgt ggatacgtac aagacagaac tggaacgttt gggcttccgc  660
tctattgccc agtggcgtat ctacaatcaa tttcggcggg agttaacatt gacggttctg  720
gacattgtgg ccgttttcc aaattatgat agccgcctgt atcctatccg cactattagt  780
cagctgacgc gtgaaattta taccagccca gtgtcggagt tctactacgg tgtgatcaat  840
tctaacaata tcattgggac gcttacgaa cagcagatcc ggcggccgca cctgatggat  900
ttcttcaact caatgatcat gtatacctca gataaccgtc gtgaacacta ttggtcgggt  960
ttagagatga cggcgaccaa caccgaaggc catcaacgca gttttcctct tgcagggacc  1020
attgggaata gtgcacctcc agtcactgtt cgtaacaatg gtgaaggtat ctaccgtatt  1080
cttttctgagc cctttactc tgcacctttc ctgggtacca gcgtgctggg cagccgtggt  1140
gaggaatttg ctttcgcgtc taacactact acaagtttgc cgagtaccat ttaccgcaac  1200
cgtggaactg ttgattctct tgtatcaatt ccaccacagg attatagcgt gcctcctcat  1260
cgtggctact cgcacttgtt gagtcatgtt acgatgcgta actcaagccc gattttcat  1320
tggattcacc gcagcgcgac gcctcgcaac acgatcgacc cagatagtat cacacagatt  1380
ccggcagtca aggggggcata tattttcaat tcgccggtga ttacaggccc gggtcatacg  1440
ggtggtgata ttatccgttt caacccgaat acgcagaata acattcgtat ccccttccag  1500
tcgaacgccg tgcaacgtta tcgcattcgg atgcgttacg ctgccgaggc agactgtatc  1560
ctggagtcag gtgtgaacat cgtcacaggg gccggggtga cctttcgtcc tattccgatt  1620
aaagccacca tgacccgggg ctcgcctctg acctactata gttccaata cgctgatctg  1680
aacatcaacc tgaccgcgcc gattcgccct aataactttg tgagtattcg gcgcagtaat  1740
```

```
cagccaggta atctgtatat tgatcgtatt gaattcatcc cgattgatcc aatccgtgag   1800
gctgaacatg acctggaacg tgcgcagaaa taa                                1833

SEQ ID NO: 39          moltype = DNA   length = 1833
FEATURE                Location/Qualifiers
misc_feature           1..1833
                       note = Synthetic
source                 1..1833
                       mol_type = other DNA
                       organism = synthetic construct
SEQUENCE: 39
atgccaatca acaaccagaa ccagtgcatc ccatacaatt gcctgagtaa tcctgaggag   60
gttttcctgg acggcgaacg tatcctgccg gacattgacc cactggaagt gagcctgtca   120
ctgttacaat tcttgctgaa taatttcgtg ccgggtggtg gcttcatctc tggattgctg   180
gataaaatct ggggtgccct tcgtccgagc gattgggaac tgttttaga gcagatcgaa   240
cagctgatta acgaacgtat cgccgaattc gcgcgtaacg ccgcaattgc aaacctggaa   300
ggtctgggta acaacttcaa tatttatgtt gaagcgttca agaatgggaa agaagaccct   360
aacaacccgg aaacccgtac gcgcgttatc gaccgtttcc gtattctgga tggcctgctg   420
gaacgtgata tcccatcttt ccgcatttct ggttttgagg tgccgctgct gtccgtttac   480
acgcaggctg cgaacctgca tttggcatta ctgcgtgact ctgtgatttt cggcgaacgt   540
tggggtctga cgaccaccaa cgttaatgac atttacaacc gacaggtgaa ccgcattggc   600
gagtattcaa aacactgtgt ggatacgtac aagacagaat tggaacgttt gggcttccgc   660
tctattgccc agtggcgtat ctacaatcaa tttcggcggg agttaacatt gacggttctg   720
gacattgtgg ccgttttcc aaattatgat agccgcctgt atcctatccg cactattagt   780
cagctgacgc gtgaaattta taccagccca gtgtcggagt tctactacgg tgtgatcaat   840
tctaacaata tcattgggac gcttacgaca cagcagatcc gcgggccgca cctgatggat   900
ttcttcaact caatgatcat gtataccctca gataaccgtc gtgaacacta ttggtcgggt   960
ttagagatga cggcgaccaa caccgaaggc atcaacgca gttttcctct tgcagggacc   1020
attgggaata gtgcacctcc agtcactgtt cgtaacaatg gtgaaggtat ctaccgtatt   1080
ctttctgagc ccttttactc tgcaccttc ctgggtacga gctgctggg cagccgtgtg   1140
gaggaatttg ctttcgcgtc taacactact acaagtttgc cgagtaccat ttaccgcaac   1200
cgtggaactg ttgattctct tgtatcaatt ccaccacagg attatagcgt gcctcctcat   1260
cgtggctact cgcacttgtt gagtcatgtt acgatgcgta actcaagccc gatttttcat   1320
tggattcacc gcagcgcgac gcctcgcaac acgatccgca cagtagtat cacacagatt   1380
ccggcagtca aggggcata tattttcaat tcgccggtga ttacagggcc gggtcatacg   1440
ggtggtgata ttatccgttt caacccgaat acgcagaata acattcgtat ccccttccag   1500
tcgaacgccg tgcaacgtta tcgcattcgg atgcgttacg ctgccgaggc agactgtatc   1560
ctggagtcag gtgtgaacat cgtcacaggg gccggggtga cctttcgtcc tattccgatt   1620
aaagccacca tgccccgggg ctcgcctctg acctactata cgtttccaata cgctgatctg   1680
aacatcaacc tgaccgcgcc gattcgccct aataacttgt gagtattcg gcgcagtaat   1740
cagccaggta atctgtatat tgatcgtatt gaattcatcc cgattgatcc aatccgtgag   1800
gctgaacatg acctggaacg tgcgcagaaa taa                                1833

SEQ ID NO: 40          moltype = DNA   length = 1839
FEATURE                Location/Qualifiers
misc_feature           1..1839
                       note = Synthetic
source                 1..1839
                       mol_type = other DNA
                       organism = synthetic construct
SEQUENCE: 40
atgccctcaa atgaacatga ttatttgaaa gtttgtgatg atttaagtga aactaatatg   60
gagaggtttg acaaaaatga tgcactggaa attggtatgt ctattgtatc tgaacttctt   120
ggcatgattc caggcggagc agccttacaa tttgtgttta atcaattgtg gtcgcgttta   180
ggtgattctg gatggagtgc attcatggaa catgttgaag aattaattga tactaaaata   240
gaagggtatg caaaaaataa agccttatct gagttagcag gtatgcacag aaatcttgaa   300
acatatataa aattgcttaa tgaatgggaa aataatactg gaagttcaaa agcacaaggt   360
agagtagcta attattttga aagtcttgag caggcggttg aaagaggtat gcctcaattc   420
gcagttggta atttcgaaat accccttta actgtttatg tacaagctgc taaccttcat   480
ttattgttat taagagatgt ttcagtttat ggaaaacgct ggggatggtc agatcagaaa   540
attaagattt attatgagaa acaagttaag tatactcatg aatacaccaa tcattgttcg   600
acttggtata tagaggact agataaattg aaaaataagg ttcttcctta ccaagattgg   660
tacaactata atcgtttccg tagagaaatt actcttactg ttctgatat cgtcgctgta   720
ttcccacact atgatgtgaa agcatatcca attcaaacag ttggccaatt aacaagaaa   780
gtatatacag acccattaat taatttcaat ccgcagttac agtctgtagc tcaattgcct   840
acttttaacg ttatggaaag taacgcaatt agaaaccctc atttagttga cttcttgaat   900
aaccttagaa tttttacaga ttggtttagt gtcggacggc actattattg gggaggacat   960
cgagtgattt ccaaacgtgt aggaggaagg gagataacct tccctatata tggaagggag   1020
gcaaagcagg aaccttccaag atcccttact ttaatggac ctgttttag gacgttatca   1080
aatcctaccc taagaccatt acaacaacct gcaccagctc ctccttttaa tttacgtggc   1140
ttggaaggtg taaattttta tacacctaca aataccttta cgtatcgggg aagaggcccg   1200
cgtgattctt taactgaatt accgcctgga gatacaagtg tactaccctcg gaaggatat   1260
tctcaccgcc tgtgtcatgc cacgtttgtt cagcgttctg gtaccccgtt cctgaccacc   1320
ggtcggtat tctcttggac tcatcgtctt gcgaccgatc gcaacatcat ttacccgagt   1380
gttatcaacc aaatcccgct ggtgaaggcg tttaacctga cctctggcac ttccgtagtc   1440
cgtggtccgg gtttcacggg tggcgatatt attcgtacta acgtgaacgg cagcgtcctg   1500
tccatgtccc tgaacttcag caacactact ctgcagcgct accgcgttcg cgttcgttac   1560
gccgcatctc agactatggt gatgtccgtc accgttggcg gttccaccac cggcaaccag   1620
ggtttcccat ctaccatgtc tgccaatggc gcgctgacct cccagagctt ccgtttcgca   1680
```

```
gaatttccgg taggcatctc tgcttctggt tctcagggtg cgtccatttc tatcagcaac 1740
aacgtaggcc gtcagatgtt ccatctggac cgcatcgaat ttctgccggt gacctccacc 1800
ttcgaagaag aatacgatct ggaacgtgcg caagaataa                        1839

SEQ ID NO: 41           moltype = DNA   length = 1839
FEATURE                 Location/Qualifiers
misc_feature            1..1839
                        note = Synthetic
source                  1..1839
                        mol_type = other DNA
                        organism = synthetic construct
SEQUENCE: 41
atgccctcaa atgaacatga ttatttgaaa gtttgtgatg atttaagtga aactaatatg  60
gagaggtttg acaaaaatga tgcactggag attggtatgt ctattgtatc tgaacttctt 120
ggcatgattc caggcggagc agccttacaa tttgtgttta atcaattgtg gtcgcgttta 180
ggtgattctg gatggagtgc attcatgaaa catgttgaag aattaattga tactaaaata 240
gaagggtatg caaaaaataa agccttatct gagttagcag gtatgcacag aaatcttgaa 300
acatatataa aattgcttaa tgaatgggaa aataatactg gaagttcaaa agcacaaggt 360
agagtagcta attattttga aagtcttgag caggcggttg aaagaggtat gcctcaattc 420
gcagttggta atttcgaaat accccttttta actgtttatg tacaagctgc taaccttcat 480
ttattgttat taagagatgt ttcagtttat ggaaaacgct ggggatggtc agatcagaaa 540
attaagattt attatgagaa acaccttaag tatactcatg aatacaccaa tcattgttcg 600
acttggtata atagaggact agataaattg aaaaataagg gttcttctta ccaagattgg 660
tacaactata atcgtttccg tagagaaatt actcttactg ttctagatat cgtcgctgta 720
ttcccacact atgatgtgaa agcatatcca attcaaacag ttggccaatt aacaagagaa 780
gtatatacag acccattaat taatttcaat ccgcagttac agtctgtagc tcaattgcct 840
acttttaacg ttatgaaaag taacgcaatt agaaaccctc atttagttga cttcttgaat 900
aaccttagaa tttttacaga ttggtttagt gtcggacggc actattattg ggaggacat 960
cgagtgattt ccaaacgtgt aggaggaagg gagataacct tccctatata tggaagggag 1020
gcaaagcagg aacctccaag atcctttact tttaatggac ctgttttttag gacgttatca 1080
aatcctaccc taagaccatt acaacaacct gcaccagctc ctcctttta tttacgtggc 1140
ttggaaggtg taaaattta cacctaca aatacctttta cgtatcgggg aagaggcccg 1200
cgtgattctt taactgaatt accgcctgga gatacaagtg tactacctcg gaaggatat 1260
agtcaccggt tatgtcatgc aacatttatt caaagatcatg cacacctttt tttaacaaca 1320
ggcgtagtct tttcttggac tcatcgttct gcgaccgatc gcaacatcat ttacccggac 1380
gttatcaacc aaatcccgct ggtgaaggcg tttaacctga cctctggcac ttccgtagtg 1440
cgtggtccgg gtttcacggg tggcgatatt ttcgtacta acgtgaacgg cagcgtcctg 1500
tccatgtccc tgaacttcag caacactact ctgcagcgct accgcgttcg cgttcgttac 1560
gccgcatctc agactatggt gatgtccgtc accgttgcg gttccaccac cggcaaccag 1620
ggtttcccat ctaccatgtc tgccaatggc gcgctgacct cccagagctt ccgtttcgca 1680
gaatttccgg taggcatctc tgcttctggt tctcagggtg cgtccatttc tatcagcaac 1740
aacgtaggcc gtcagatgtt ccatctggac cgcatcgaat ttctgccggt gacctccacc 1800
ttcgaagaag aatacgatct ggaacgtgcg caagaataa                        1839

SEQ ID NO: 42           moltype = DNA   length = 1827
FEATURE                 Location/Qualifiers
misc_feature            1..1827
                        note = Synthetic
source                  1..1827
                        mol_type = other DNA
                        organism = synthetic construct
SEQUENCE: 42
atgccctcaa atgaacatga ttatttgaaa gtttgtgatg atttaagtga aactaatatg  60
gagaggtttg acaaaaatga tgcactggag attggtatgt ctattgtatc tgaacttctt 120
ggcatgattc caggcggagc agccttacaa tttgtgttta atcaattgtg gtcgcgttta 180
ggtgattctg gatggagtgc attcatgaaa catgttgaag aattaattga tactaaaata 240
gaagggtatg caaaaaataa agccttatct gagttagcag gtatgcacag aaatcttgaa 300
acatatataa aattgcttaa tgaatgggaa aataatactg gaagttcaaa agcacaaggt 360
agagtagcta attattttga aagtcttgag caggcggttg aaagaggtat gcctcaattc 420
gcagttggta atttcgaaat accccttttta actgtttatg tacaagctgc taaccttcat 480
ttattgttat taagagatgt ttcagtttat ggaaaacgct ggggatggtc agatcagaaa 540
attaagattt attatgagaa acaagttaag tatactcatg aatacaccaa tcattgttcg 600
acttggtata atagaggact agataaattg aaaaataagg gttcttctta ccaagattgg 660
tacaactata atcgtttccg tagagaaatt actcttactg ttctagatat cgtcgctgta 720
ttcccacact atgatgtgaa agcatatcca attcaaacag ttggccaatt aacaagagaa 780
gtatatacag acccattaat taatttcaat ccgcagttac agtctgtagc tcaattgcct 840
acttttaacg ttatgaaaag taacgcaatt agaaaccctc atttagttga cttcttgaat 900
aaccttagaa tttttacaga ttggtttagt gtcggacggc actattattg ggaggacat 960
cgagtgattt ccaaacgtgt aggaggaagg gagataacct tccctatata tggaagggag 1020
gcaaagcagg aacctccaag atcctttact tttaatggac ctgttttttag gacgttatca 1080
aatcctaccc taagaccatt acaacaacct gcaccagctc ctcctttta tttacgtggc 1140
ttggaaggtg taaaattta cacctaca aatacctttta cgtatcgggg aagaggcccg 1200
cgtgattctt taactgaatt accgcctgga gatacaagtg tactacctcg gaaggatat 1260
agtcaccggt tatgtcatgc aacatttatt caaagatcatg cacacctttt tttaacaaca 1320
ggcgtagtct tttcttggac tcatcgttct gcgtctccga ccaatgaggt gtctccgtcc 1380
cgtattaccc agattccgtg ggttaaggca cacactctgg cgtccggcgc ctccgtgatt 1440
aaaggccctg gttttaccgg tggtgacatt ctgacgcgta actctatggg cgaactgggc 1500
actctgcgtg tcacgttcac ctggtcgtctg ccgcagagct attacatccg tttccgctat 1560
gcatctgtcg caaccgttc cggtaccttc cgctattctc agccgccgag ctacggcatc 1620
```

```
tccttcccaa aaaccatgga tgcgggtgaa ccgctgacct ctcgttcttt cgcacacacc   1680
acgctgttta ctcctattac gttttcccgt gctcaggagg agttcgatct gtacatccag   1740
tctggcgtat acatcgatcg tatcgagttc attccggtaa cggccacctt tgaagctgag   1800
tacgatctgg aacgtgcgca gaaataa                                       1827

SEQ ID NO: 43          moltype = DNA  length = 1839
FEATURE                Location/Qualifiers
misc_feature           1..1839
                       note = Synthetic
source                 1..1839
                       mol_type = other DNA
                       organism = synthetic construct
SEQUENCE: 43
atgccctcaa atgaacatga ttatttgaaa gtttgtgatg atttaagtga aactaatatg    60
gagaggtttg acaaaaatga tgcactggag attggtatgt ctattgtatc tgaacttctt   120
ggcatgattc caggcggagc agccttacaa tttgtgttta atcaattgtg gtcgcgttta   180
ggtgattctg gatggagtgc attcatggaa catgttgaag aattaattga tactaaaata   240
gaagggtatg caaaaaataa agcctatct gagttagcag gtatgcacag aaatcttgaa    300
acatatataa aattgcttaa tgaatgggaa aataatactg gaagttcaaa agcacaaggt   360
agagtagcta attattttga aagtcttgag caggcgttg aaagaggtat gcctcaattc    420
gcagttggta atttcgaaat acccctttta actgtttatg tacaagctgc taaccttcat   480
ttattgttat taagagatgt ttcagtttat ggaaaacgat gggatggtc agatcagaaa    540
attaagattt attatgagaa acaagttaag tatactcatg aatacaccaa tcattgttcg   600
acttggtata atagaggact agataaattg aaaataagg gttcttctta ccaagattgg    660
tacaactata atcgtttccg tagagaaatt actcttactg ttctagatat cgtcgctgta   720
ttcccacact atgatgtgaa agcatatcca attcaaacag ttggccaatt aacaagagaa   780
gtatatacag acccattaat taatttcaat ccgcagttac agtctgtagc tcaattgcct   840
acttttaacg ttatgaaag taacgcaatt agaaaccctc atttagttga cttcttgaat    900
aaccttagaa tttttacaga ttggtttagt gtcgacggc actattattg gggaggacat    960
cgagtgattt ccaaacgtgt aggaggaagg agataaatct tccctatata tggaagggag  1020
gcaaagcagg aacctccaag atccttact tttaatggac ctgtttttag gacgttatca   1080
aatcctaccc taagaccatt acaacaacct gcaccagctc ctccttttaa tttacgtggc  1140
ttggaaggtg taaaatttta tacacctaca aatacctta cgtatcgggg aagaggcccg   1200
cgtgattctt taactgaatt accgcctgga gatacaagtg tactacctcg cgaaggatat  1260
agtcaccggt tatgtcatgc aacatttatt caaagatctg gcacacccttt tttaacaaca  1320
ggcgtagtct tttcttggac acatcgtagt gctgatgaaa cgaatataat ttatccagat  1380
aagattactc aaattccact ggttaagtct tcaaacctga actctggcac ttccgttgtt  1440
tccggtccgg gtttcaccgg tggtgatatc attcgcacca acgttaatgg ctctgtgctg  1500
tccatgggcc tgaattttaa taacactagc ctgcaacgct accgtgtacg cgttcgctac  1560
gctgcttctc agaccatggt gctgcgtgtg acggttggcg gttctaccac tttcgaccag  1620
ggtttcccgt ccaccatgag cgcgaacgaa tctctgacct ctcagtcttt ccgtttcgca  1680
gaatttccgg ttggtatctc tgcgtctggc tctcagactg ctggcatctc catctccaat  1740
aacgcaggtc gtcagacttt ccattttgac aaaatcgaat tcattccgat caccgcaacc  1800
tttgaagcag aatatgacct ggaacgtgcg caagaataa                          1839

SEQ ID NO: 44          moltype = DNA  length = 1845
FEATURE                Location/Qualifiers
misc_feature           1..1845
                       note = Synthetic
source                 1..1845
                       mol_type = other DNA
                       organism = synthetic construct
SEQUENCE: 44
atgggccgcg gtagcatgga agtcaacaat caaaatcaat gcgtgccgta caattgcctg    60
aacaaccggg aaattgaaat tttaggcggt gaacggactc cagtggggaa cacgccaatt   120
gatatcagtc tgtccttgac gcaatttctg ttgtcggaat tcgtacctgg tgccggcttt   180
gtattgggc ttattgactt gatctggggg tttctggggc ctagcagtg ggacgcattt    240
ctgctgcaga tcgaacagct gattaaccag cgtatcgaag aattcgcgcg taaccaggca   300
atctcccgtc tggaaggtct gtccaacctg taccagatct acgacgagtc cttccgtgaa   360
tgggaagctg atccgaccaa cccggcactg cgcgaagaaa tgcgtatccga gttcaacgac  420
atgaactctg ctctgacgac ggccatccct ctgctggctg tgcagaatta tcaggtaccg   480
ctgctgtctg tgtacgtgca ggcggcgaac ctgcatctgt ccgtgttgcg cgacgttagc   540
gtgttcggtc agcgttgggg atttgatgtt gccacgatta tagccgtta caacgatctg    600
acacggttga ttggcgagta cacggactac gccgtgcgtt ggtataacac agggcttgaa   660
cgccttcgcg gttcgaactt ccaggattgg attcgttata tcgttttcg ccgcgagctg    720
acgttgaccg tgtggacat cgtctcggtc tttcagaatt atgacagtcg cctttatccg    780
atccagacga gctctcaatt gacgcgtgaa atttattccg atcttctgct ggccaacccc   840
agtggtgtgg gtagtttctc taatgtagat ttcgatagca ttctgatccg tcagcctcat   900
ctgatcgatt tcatgcgcgt tttaacgatt tacacgagtc gccataatgc ttcccggcaa   960
aacatctatt gggcgggcca tcaagtaacc gcagtagata cagccaaccg tacgattgtg  1020
tacccctgtca atgcagtgc agccaacttg aacctccgc ggacgttgcg gtttgagtcc    1080
cccgtcgtgg aaattcgctc taatccggtg tgggaccgcg aagtactggg catcgcaggc  1140
tcgtatgaat ctctttggtgt gaccagtgct tgttcatta caatcctggg ttttggctat  1200
acctatcgct cagggagcaa caccgaagtg acggcactcc cggatcatca ggtcaggcac  1260
attggttact tccgtcgctt taccaccacc ggggcgaccg ctcgtcagac cttgacaagc  1320
gcacctattg tgtcgtggac tcattcgagc gctgaaccgc caaaccgtat ctatcaaaac  1380
cgtattaccc agatcccagc cgttaaaggt aacttcctgt taacggagc tgtcatctca   1440
gggcctggat ttaccggtgg cgatcttgtc cgccttaacc gcaacaatga taatattcaa  1500
aatcgcggtt atattgaagt tccgatccag ttcgcctcga ctagcacgcg ttatcgcgta  1560
```

```
cgcgtccgtt acgccagcac taatgcgatt gaggtgaata ttaactgggg taatggcagt   1620
attttcaccg gaaccgcccc agcaaccgcg acgagcctgg ataacctgca gagcaatgat   1680
tttggttact tcgagagcac cacggccttt gccccttcgc tggggaacat tgtaggcgtg   1740
cgtaacttct ctgctaatgc cgatgtgatc attgatcgct tgagtttat ccccgtaacg    1800
gcaaccctgg aagcggagta tgatctgaaa cgcgcgaaaa aataa                   1845
```

```
SEQ ID NO: 45           moltype = DNA   length = 1839
FEATURE                 Location/Qualifiers
misc_feature            1..1839
                        note = Synthetic
source                  1..1839
                        mol_type = other DNA
                        organism = synthetic construct
SEQUENCE: 45
atgggccgcg gtagcatgga agtcaacaat caaaatcaat gcgtgccgta caattgcctg   60
aacaacccgg aaattgaaat tttaggcggt gaacggatct cagtggggaa cacgccaatt   120
gatatcagtc tgtccttgac gcaatttctg ttgtcggaat tcgtacctgg tgccggcttt   180
gtattggggc ttattgactt gatctggggg tttctggggc ctagccagtg ggacgcattt   240
ctgctgcaga tcgaacagct gattaaccag cgtatcgaag aattcgcgcg taaccaggca   300
atctcccgtc tggaaggtct gtccaacctg taccagatct acgcagagtc cttccgtgaa   360
tgggaagctg atccgaccaa cccggcactg cgcgaagaaa tgcgtatcca gttcaacgac   420
atgaactctg ctctgacgac ggccatccct ctgctgctg tgcagaatta tcaggtaccg   480
ctgctgtctg tgtacgtgca ggcggcgaac ctgcatctgt ccgtgttgcg cgacgttagc   540
gtgttcggtc agcgttgggg atttgatgtt gccacgatta atagccgtta caacgatctg   600
acacggttga ttggcgagta cacggactac gccgtgcgtt ggtataacac agggcttgac   660
cgccttcgcg gttcgaactt ccaggattgg attcgttata atcgtttttcg ccgcgagctg   720
acgttgaccg tgttggacat cgtgtcggtc tttcagaatt atgacagtcg cctttatccg   780
atccagacga gctctcaatt gacgcgtgaa atttattccg atcttctgct ggccaacccc   840
agtggtgtgg gtagtttctc taatgtagat ttcgatagca ttctgatccg tcagcctcat   900
ctgatcgatt tcatgcgcgt tttaacgatt tacacggatc gccataatgc ttcccggcac   960
aacatctatt gggcgggcca tcaagtaacc gcagtagata cagccaaccg tacgattgtg   1020
taccctgtca atggcagtgc agccaacttg aacctccgc ggacgttgcg gtttgagtcc   1080
cccgtcgtgg aaattcgctc taatccggtg tgggaccgcg gaagtactgg catcgcaggc   1140
tcgtatgaat tctttggtgt gaccagtgct tgttcatta caatcctggg ttttggctat   1200
acctatcgct cagggagcaa caccgaagtg acggcacttc cggatcatca ggtcagccac   1260
attggttact tccgtcgctt taccaccacc ggggcgaccg ctcgtcagac cttgacaagc   1320
gcacctattg tgtcgtggac tcattcgagc gctgaaccgc caaaccgtat ctatcaaaac   1380
cgtattaccc agatccact ggttaaggct ctgaacctgc actctggcgt taccgttgtt   1440
ggtggtccgg gtttcaccgg tggtgatatc ctgcgccgta cgaacaccgg cactttcggt   1500
gacatccgcc tgaatatcaa tgtaccactg agccaacgct accgtgtacg cattcgctac   1560
gcttccacta ccgacctgca gttcttcact cgtatcaatg gtaccaccgt taacatcggc   1620
aacttctctc gcaccatgaa ccgtggtgat aacctgaat accgctcttt ccgtaccgca   1680
ggttttctta cgccgtttaa cttcctgaac gcccagtcta ctttccggg gggcgcgcag   1740
tcttcagca accaggaagt ctacattgac cgtgtgaa tcgtgccggc ggaagttacc    1800
tttgaagcag aatatgacct ggaacgtgcg caaaaataa                          1839
```

```
SEQ ID NO: 46           moltype = DNA   length = 1839
FEATURE                 Location/Qualifiers
misc_feature            1..1839
                        note = Synthetic
source                  1..1839
                        mol_type = other DNA
                        organism = synthetic construct
SEQUENCE: 46
atgggccgcg gtagcatgga agtcaacaat caaaatcaat gcgtgccgta caattgcctg   60
aacaacccgg aaattgaaat tttaggcggt gaacggatct cagtggggaa cacgccaatt   120
gatatcagtc tgtccttgac gcaatttctg ttgtcggaat tcgtacctgg tgccggcttt   180
gtattggggc ttattgactt gatctggggg tttctgggc ctagccagtg ggacgcattt    240
ctgctgcaga tcgaacagct gattaaccag cgtatcgaag aattcgcgcg taaccaggca   300
atctcccgtc tggaaggtct gtccaacctg taccagatct acgcagagtc cttccgtgaa   360
tgggaagctg atccgaccaa cccggcactg cgcgaagaaa tgcgtatcca gttcaacgac   420
atgaactctg ctctgacgac ggccatccct ctgctggctg tgcagaatta tcaggtaccg   480
ctgctgtctg tgtacgtgca ggcggcgaac ctgcatctgt ccgtgttgcg cgacgttagc   540
gtgttcggtc agcgttgggg atttgatgtt gccacgatta atagccgtta caacgatctg   600
acacggttga ttggcgagta cacggactac gccgtgcgtt ggtataacac agggcttgac   660
cgccttcgcg gttcgaactt ccaggattgg attcgttata atcgtttttcg ccgcgagctg   720
acgttgaccg tgttggacat cgtgtcggtc tttcagaatt atgacagtcg cctttatccg   780
atccagacga gctctcaatt gacgcgtgaa atttattccg atcttctgct ggccaacccc   840
agtggtgtgg gtagtttctc taatgtagat ttcgatagca ttctgatccg tcagcctcat   900
ctgatcgatt tcatgcgcgt tttaacgatt tacacggatc gccataatgc ttcccggcac   960
aacatctatt gggcgggcca tcaagtaacc gcagtagata cagccaaccg tacgattgtg   1020
taccctgtca atggcagtgc agccaacttg aacctccgc ggacgttgcg gtttgagtcc   1080
cccgtcgtgg aaattcgctc taatccggtg tgggaccgcg gaagtactgg catcgcaggc   1140
tcgtatgaat tctttggtgt gaccagtgct tgttcatta caatcctggg ttttggctat   1200
acctatcgct cagggagcaa caccgaagtg acggcacttc cggatcatca ggtcagccac   1260
attggttact tccgtcgctt taccaccacc ggggcgaccg ctcgtcagac cttgacaagc   1320
gcacctattg tgtcgtggac tcattcgagc gcgaccgatc gcaacatcat ttacccggac   1380
gttataacc aaatcccgct ggtgaaggcg tttaacctga cctctggcac ttccgtagtg    1440
cgtggtccgg gttttcacggg tggcgatatt attcgtacta acgtgaacgg cagcgtcctg   1500
```

```
tccatgtccc tgaacttcag caacactact ctgcagcgct accgcgttcg cgttcgttac 1560
gccgcatctc agactatggt gatgtccgtc accgttggcg gttccaccac cggcaaccag 1620
ggtttcccat ctaccatgtc tgccaatggc gcgctgacct cccagagctt ccgtttcgca 1680
gaatttccgg taggcatctc tgcttctggt tctcagggtg cgtccatttc tatcagcaac 1740
aacgtaggcc gtcagatgtt ccatctggac cgcatcgaat ttctgccggt gacctccacc 1800
ttcgaagaag aatacgatct ggaacgtgcg caagaataa                         1839
```

```
SEQ ID NO: 47           moltype = DNA   length = 1839
FEATURE                 Location/Qualifiers
misc_feature            1..1839
                        note = Synthetic
source                  1..1839
                        mol_type = other DNA
                        organism = synthetic construct
SEQUENCE: 47
atgggccgcg gtagcatgga agtcaacaat caaaatcaat gcgtgccgta caattgcctg  60
aacaacccgg aaattgaaat tttaggcggt gaacggatct cagtggggaa cacgccaatt 120
gatatcagtc tgtccttgac gcaatttctg ttgtcggaat tcgtacctgg tgccggcttt 180
gtattggggc ttattgactt gatctggggg tttctggggc ctagccagtg ggacgcattt 240
ctgctgcaga tcgaacagct gattaaccag cgtatcgaag aattcgcgcg taaccaggca 300
atctcccgtc tggaaggtct gtccaacctg taccagatct acgcagagtc cttccgtgaa 360
tgggaagctg atccgaccaa cccggcactg cgcgaagaaa tgcgtatcca gttcaacgac 420
atgaactctg ctctgacgac ggccatccct ctgctggctg tgcagaatta tcaggtaccg 480
ctgctgtctg tgtacgtgca ggcggcgaac ctgcatctgt ccgtgttgcg cgacgttagc 540
gtgttcggtc agcgttgggg atttgatgtt gccacgatta tagccgttaa caacgatctg 600
acacggttga ttggcgagta cacggactac gccgtgcgtt ggtataacac agggcttgac 660
cgccttcgcg gttcgaactt ccaggattgg attcgttata atcgttttcg ccgcgagctg 720
acgttgaccg tgttggacat cgtgtcggtc tttcagaatt atgacagtcg cctttatccg 780
atccagacga gctctcaatt gacgcgtgaa atttattccg atcttctgct ggccaacccc 840
agtggtgtgg gtagtttctc taatgtagat ttcgatagca ttctgatccg tcagcctcat 900
ctgatcgatt tcatgcgcgt tttaacgatt tacacggatc gccataatgc ttcccggcac 960
aacatctatt gggcgggcca tcaagtaacc gcagtagata cagccaaccg tacgattgtg 1020
taccctgtca atggcagtgc agccaacttg aacctccgc ggacgttgcg gtttgagtcc 1080
ccgtcgtgg aaattcgctc taatccggtg tgggaccgcg gaagtactgg catcgcaggc 1140
tgtatgaat tctttggtgt gaccagtgct ttgttcatta caatcctggg ttttggctat 1200
acctatcgct cagggagcaa caccgaagtg acgcacttc cggatcatca ggtcagccac 1260
attggttact tccgtcgctt taccaccacc ggggcgaccg ctcgtcagac cttgacaagc 1320
gcacctattg tgtcgtggac tcattcgagc gctgaaccgc caaaccgtat ctatcaaaac 1380
cgtattaccc agatcccact ggtgaagcg tttaacctga cctctggcac ttccgtagtg 1440
cgtggtccgg gtttcacggg tggcgatatt attcgtacta acgtgaacgg cagcgtcctg 1500
tccatgtccc tgaacttcag caacactact ctgcagcgct accgcgttcg cgttcgttac 1560
gccgcatctc agactatggt gatgtccgtc accgttggcg gttccaccac cggcaaccag 1620
ggtttcccat ctaccatgtc tgccaatggc gcgctgacct cccagagctt ccgtttcgca 1680
gaatttccgg taggcatctc tgcttctggt tctcagggtg cgtccatttc tatcagcaac 1740
aacgtaggcc gtcagatgtt ccatctggac cgcatcgaat ttctgccggt gacctccacc 1800
ttcgaagaag aatacgatct ggaacgtgcg caagaataa                         1839
```

```
SEQ ID NO: 48           moltype = DNA   length = 1827
FEATURE                 Location/Qualifiers
misc_feature            1..1827
                        note = Synthetic
source                  1..1827
                        mol_type = other DNA
                        organism = synthetic construct
SEQUENCE: 48
atgggccgcg gtagcatgga agtcaacaat caaaatcaat gcgtgccgta caattgcctg  60
aacaacccgg aaattgaaat tttaggcggt gaacggatct cagtggggaa cacgccaatt 120
gatatcagtc tgtccttgac gcaatttctg ttgtcggaat tcgtacctgg tgccggcttt 180
gtattggggc ttattgactt gatctggggg tttctggggc ctagccagtg ggacgcattt 240
ctgctgcaga tcgaacagct gattaaccag cgtatcgaag aattcgcgcg taaccaggca 300
atctcccgtc tggaaggtct gtccaacctg taccagatct acgcagagtc cttccgtgaa 360
tgggaagctg atccgaccaa cccggcactg cgcgaagaaa tgcgtatcca gttcaacgac 420
atgaactctg ctctgacgac ggccatccct ctgctggctg tgcagaatta tcaggtaccg 480
ctgctgtctg tgtacgtgca ggcggcgaac ctgcatctgt ccgtgttgcg cgacgttagc 540
gtgttcggtc agcgttgggg atttgatgtt gccacgatta tagccgttaa caacgatctg 600
acacggttga ttggcgagta cacggactac gccgtgcgtt ggtataacac agggcttgac 660
cgccttcgcg gttcgaactt ccaggattgg attcgttata atcgttttcg ccgcgagctg 720
acgttgaccg tgttggacat cgtgtcggtc tttcagaatt atgacagtcg cctttatccg 780
atccagacga gctctcaatt gacgcgtgaa atttattccg atcttctgct ggccaacccc 840
agtggtgtgg gtagtttctc taatgtagat ttcgatagca ttctgatccg tcagcctcat 900
ctgatcgatt tcatgcgcgt tttaacgatt tacacggatc gccataatgc ttcccggcac 960
aacatctatt gggcgggcca tcaagtaacc gcagtagata cagccaaccg tacgattgtg 1020
taccctgtca atggcagtgc agccaacttg aacctccgc ggacgttgcg gtttgagtcc 1080
ccgtcgtgg aaattcgctc taatccggtg tgggaccgcg gaagtactgg catcgcaggc 1140
tgtatgaat tctttggtgt gaccagtgct ttgttcatta caatcctggg ttttggctat 1200
acctatcgct cagggagcaa caccgaagtg acgcacttc cggatcatca ggtcagccac 1260
attggttact tccgtcgctt taccaccacc ggggcgaccg ctcgtcagac cttgacaagc 1320
gcacctattg tgtcgtggac tcattcgagc gctgaaccgc caaaccgtat ctatcaaaac 1380
cgtattaccc agatcccatg ggttaaggca cacactctgg cgtccggcgc ctccgtgatt 1440
```

```
aaaggccctg gttttaccgg tggtgacatt ctgacgcgta actctatggg cgaactgggc   1500
actctgcgtg tcacgttcac tggtcgtctg ccgcagagct attacatccg tttccgctat   1560
gcatctgtcg caaaccgttc cggtaccttc cgctattctc agccgccgag ctacggcatc   1620
tccttcccaa aaaccatgga tgcgggtgaa ccgctgacct ctcgttcttt cgcacacacc   1680
acgctgttta ctcctattac gttttcccgt gctcaggagg agttcgatct gtacatccag   1740
tctggcgtat acatcgatcg tatcgagttc attccggtaa cggccacctt tgaagctgag   1800
tacgatctgg aacgtgcgca gaaataa                                       1827

SEQ ID NO: 49           moltype = DNA  length = 1839
FEATURE                 Location/Qualifiers
misc_feature            1..1839
                        note = Synthetic
source                  1..1839
                        mol_type = other DNA
                        organism = synthetic construct
SEQUENCE: 49
atgggccgcg gtagcatgga agtcaacaat caaaatcaat gcgtgccgta caattgcctg    60
aacaacccgg aaattgaaat tttaggcggt gaacggatct cagtggggaa cacgccaatt   120
gatatcagtc tgtccttgac gcaatttctg ttgtcggaat tcgtacctgg tgccggcttt   180
gtattggggc ttattgactt gatctggggg tttctggggc ctagccagtg ggacgcattt   240
ctgctgcaga tcgaacagct gattaaccag cgtatcgaag aattcgcgcg taaccaggca   300
atctcccgtc tggaaggtct gtccaacctg taccagatct acgcagagtc cttccgtgaa   360
tgggaagctg atccgaccaa cccggcactg cgcgaagaaa tgcgtatcca gttcaacgac   420
atgaactctg ctctgacgac ggccatccct ctgctggctg tgcagaatta tcaggtaccg   480
ctgctgtctg tgtacgtgca ggcggcgaac ctgcatctgt ccgtgttgcg cgacgttagc   540
gtgttcggtc agcgttgggg atttgatgtt gccacgatta atagccgtta caacgatctg   600
acacggttga ttggcgagta cacggactac gccgtgcgtt ggtataacac agggcttgac   660
cgccttcgcg gttcgaactt ccaggattgg attcgttata atcgttttcg ccgcgagctg   720
acgttgaccg tgttggacat cgtgtcggtc tttcagaatt atgacagtcg cctttatccg   780
atccagacga gctctcaatt gacgcgtgaa atttattccg atcttctgct ggccaacccc   840
agtggtgtgg gtagtttctc taatgtagat ttcgatagca ttctgatccg tcagcctcat   900
ctgatcgatt tcatgcgcgt tttaacgatt tacacggatc gccataatgc ttcccggcac   960
aacatctatt gggcgggcca tcaagtaacc gcagtagata cagccaaccg tacgattgtg  1020
taccctgtca atggcagtgc agccaacttg gaacctccgc ggacgttgcg gtttgagtcc  1080
cccgtcgtgg aaattcgctc taatccggtg tgggaccgcg aagtactgga tcgcaggc    1140
tcgtatgaat tctttggtgt gaccagtgct ttgttcatta caatcctggg ttttggctat  1200
acctatcgct cagggagcaa caccgaagtg acggcacttc cggatcatca ggtcagccac  1260
attggttact tccgtcgctt taccaccacc ggggcgaccg ctcgtcagac cttgacaagc  1320
gcacctattg tgtcgtggac tcattcgagc gccaccacaa ctaacaccat taacccgact  1380
gcaattatcc agattccact ggtgaaggcg ttcaatctgc atagcggggc aaccgtggtg  1440
cgcggcccgg gatttaccgg cggcgatatt ctgcgccgca ccaatacggg gacgtttgcc  1500
gatatgcgtg ttaacattac cggccgctg agtcagcgct accgcgtacg catccgctac   1560
gccagcacta ccgacctgca gttttttaca cgcattaatg tgacgtcggt gaatcagggc  1620
aatttccagc gtaccatgaa ccgtggcgat aatttagaga gcggcaactt ccggaccgca  1680
gggtttagca cgccgttttc cttttcaaac gcgcagagta cttcacgct tggcacacag   1740
gcttttcaa atcaggaggt gtacattgac cgcatcgagt ttgttccagc tgaagtaacc  1800
tttgaggccg aatctgattt ggaacgcgcc cagaagtaa                          1839

SEQ ID NO: 50           moltype = DNA  length = 1839
FEATURE                 Location/Qualifiers
misc_feature            1..1839
                        note = Synthetic
source                  1..1839
                        mol_type = other DNA
                        organism = synthetic construct
SEQUENCE: 50
atgggccgcg gtagcatgga agtcaacaat caaaatcaat gcgtgccgta caattgcctg    60
aacaacccgg aaattgaaat tttaggcggt gaacggatct cagtggggaa cacgccaatt   120
gatatcagtc tgtccttgac gcaatttctg ttgtcggaat tcgtacctgg tgccggcttt   180
gtattggggc ttattgactt gatctggggg tttctggggc ctagccagtg ggacgcattt   240
ctgctgcaga tcgaacagct gattaaccag cgtatcgaag aattcgcgcg taaccaggca   300
atctcccgtc tggaaggtct gtccaacctg taccagatct acgcagagtc cttccgtgaa   360
tgggaagctg atccgaccaa cccggcactg cgcgaagaaa tgcgtatcca gttcaacgac   420
atgaactctg ctctgacgac ggccatccct ctgctggctg tgcagaatta tcaggtaccg   480
ctgctgtctg tgtacgtgca ggcggcgaac ctgcatctgt ccgtgttgcg cgacgttagc   540
gtgttcggtc agcgttgggg atttgatgtt gccacgatta atagccgtta caacgatctg   600
acacggttga ttggcgagta cacggactac gccgtgcgtt ggtataacac agggcttgac   660
cgccttcgcg gttcgaactt ccaggattgg attcgttata atcgttttcg ccgcgagctg   720
acgttgaccg tgttggacat cgtgtcggtc tttcagaatt atgacagtcg cctttatccg   780
atccagacga gctctcaatt gacgcgtgaa atttattccg atcttctgct ggccaacccc   840
agtggtgtgg gtagtttctc taatgtagat ttcgatagca ttctgatccg tcagcctcat   900
ctgatcgatt tcatgcgcgt tttaacgatt tacacggatc gccataatgc ttcccggcac   960
aacatctatt gggcgggcca tcaagtaacc gcagtagata cagccaaccg tacgattgtg  1020
taccctgtca atggcagtgc agccaacttg gaacctccgc ggacgttgcg gtttgagtcc  1080
cccgtcgtgg aaattcgctc taatccggtg tgggaccgcg aagtactgga tcgcaggc    1140
tcgtatgaat tctttggtgt gaccagtgct ttgttcatta caatcctggg ttttggctat  1200
acctatcgct cagggagcaa caccgaagtg acggcacttc cggatcatca ggtcagccac  1260
attggttact tccgtcgctt taccaccacc ggggcgaccg ctcgtcagac cttgacaagc  1320
gcacctattg tgtcgtggac tcattcgagc gctgaaccgc aaaccgtat ctatcaaaac   1380
```

```
cgtattaccc agatcccact ggtgaaggcg ttcaatctgc atagcgggc aaccgtggtg   1440
cgcggcccgg gatttaccgg cggcgatatt ctgcgccgca ccaatacggg gacgtttgcc   1500
gatatgcgtg ttaacattac cggcccgctg agtcagcgct accgcgtacg catccgctac   1560
gccagcacta ccgacctgca gttttttaca cgcattaatg gtacgtcggt gaatcagggc   1620
aatttccagc gtaccatgaa ccgtggcgat aatttagaga gcgcaacctt ccggaccgca   1680
gggtttagca cgccgttttc cttttcaaac gcgcagagta ctttcacgct tggcacacag   1740
gcttttcaa atcaggaggt gtacattgac cgcatcgagt ttgttccagc tgaagtaacc   1800
tttgaggccg aatctgattt ggaacgcgcc cagaagtaa                         1839
```

```
SEQ ID NO: 51            moltype = DNA   length = 1845
FEATURE                  Location/Qualifiers
misc_feature             1..1845
                         note = Synthetic
source                   1..1845
                         mol_type = other DNA
                         organism = synthetic construct
SEQUENCE: 51
atgggccgcg gtagcatgga agtcaacaat caaaatcaat gcgtgccgta caattgcctg   60
aacaacccgg aaattgaaat tttaggcggt gaacggatct cagtgggaa cacgccaatt   120
gatatcagtc tgtccttgac gcaatttctg ttgtcggaat tcgtacctgg tgccggcttt   180
gtattggggc ttattgactt gatctggggg tttctggggc ctagccagtg ggacgcattt   240
ctgctgcaga tcgaacagct gattaaccag cgtatcgaag aattcgcgcg taaccaggca   300
atctcccgtc tggaaggtct gtccaacctg taccagatct acgcagagtc cttccgtgaa   360
tgggaagctg atccgaccaa cccggcactg cgcgaagaaa tgcgtatcca gttcaacgac   420
atgaactctg ctctgacgac ggccatccct ctgctggctg tgcagaatta tcaggtaccg   480
ctgctgtctg tgtacgtgca ggcggcgaac ctgcatctgt ccgtgttgcg cgacgttagc   540
gtgttcggtc agcgttgggg atttgatgtt gccacgatta atagccgtta caacgatctg   600
acacggttga ttggcgagta cacggactac gccgtgcgtt ggtataacac agggcttgac   660
cgccttcgcg gttcgaactt ccaggattgg attcgttata atcgttttcg ccgcgagctg   720
acgttgaccg tgttggacat cgtgtcggtc tttcagaatt atgacagtcg cctttatccg   780
atccagacga gctctcaatt gacgcgtgaa atttattccg atcttctgct ggccaacccc   840
agtggtgtgg gtagtttctc taatgtagat ttcgatagca ttctgatccg tcagcctcat   900
ctgatcgatt tcatgcgcgt tttaacgatt tacacggatc gccataatgc ttcccggcac   960
aacatctatt gggcgggcca tcaagtaacc gcagtagata cagccaaccg tacgattgtg   1020
taccctgtca atggcagtgc agccaacttg gaacctccgc ggacgttgcg gtttgagtcc   1080
cccgtcgtgg aaattcgctc taatccggtg tgggaccgcg gaagtactgg catcgcaggc   1140
tcgtatgaat tctttggtgt gaccagtgct ttgttcatta caatcctggg ttttggctat   1200
acctatcgct cagggagcaa caccgaagtg acggcactttc cggatcatca ggtcagccac   1260
attggttact tccgtcgctt taccaccacc ggggcgaccg ctcgtcagac cttgacaagc   1320
gcacctattg tgtcgtggac tcattcgagc gccgatcgca cgaacacgat tgccaccaac   1380
attatcaccc agatcccggc agtgaaaggc aactttctgt taacggcag cgtgatcagc   1440
ggtccaggtt ttaccggcgg tgacctggtg cgcctgaaca acagcggcaa caatatccaa   1500
aaccgtggtt atctggaagt cccgattcaa ttcatcagca gcgacacccg ttaccgcgtg   1560
cgtgttcgct acgcatccgt tacgccgatc caactgagcg ttaactgggg caattccaac   1620
attttcagca gcattgtccc tgctacgcg acctctctgg acaatttgca gagccgtgac   1680
ttcggctatt tcgaaagcac caacgctttc accagcgcta cgggcaatgt ggttggtgtt   1740
cgcaatttca gcgagaatgc gggcgtcatc attgaccgtt ttgagtttat cccggtgacc   1800
gcgaccttcg aagcggagta cgatctggag cgtgcgcagg aataa                  1845
```

```
SEQ ID NO: 52            moltype = DNA   length = 1845
FEATURE                  Location/Qualifiers
misc_feature             1..1845
                         note = Synthetic
source                   1..1845
                         mol_type = other DNA
                         organism = synthetic construct
SEQUENCE: 52
atgggccgcg gtagcatgga agtcaacaat caaaatcaat gcgtgccgta caattgcctg   60
aacaacccgg aaattgaaat tttaggcggt gaacggatct cagtgggaa cacgccaatt   120
gatatcagtc tgtccttgac gcaatttctg ttgtcggaat tcgtacctgg tgccggcttt   180
gtattggggc ttattgactt gatctggggg tttctggggc ctagccagtg ggacgcattt   240
ctgctgcaga tcgaacagct gattaaccag cgtatcgaag aattcgcgcg taaccaggca   300
atctcccgtc tggaaggtct gtccaacctg taccagatct acgcagagtc cttccgtgaa   360
tgggaagctg atccgaccaa cccggcactg cgcgaagaaa tgcgtatcca gttcaacgac   420
atgaactctg ctctgacgac ggccatccct ctgctggctg tgcagaatta tcaggtaccg   480
ctgctgtctg tgtacgtgca ggcggcgaac ctgcatctgt ccgtgttgcg cgacgttagc   540
gtgttcggtc agcgttgggg atttgatgtt gccacgatta atagccgtta caacgatctg   600
acacggttga ttggcgagta cacggactac gccgtgcgtt ggtataacac agggcttgac   660
cgccttcgcg gttcgaactt ccaggattgg attcgttata atcgttttcg ccgcgagctg   720
acgttgaccg tgttggacat cgtgtcggtc tttcagaatt atgacagtcg cctttatccg   780
atccagacga gctctcaatt gacgcgtgaa atttattccg atcttctgct ggccaacccc   840
agtggtgtgg gtagtttctc taatgtagat ttcgatagca ttctgatccg tcagcctcat   900
ctgatcgatt tcatgcgcgt tttaacgatt tacacggatc gccataatgc ttcccggcac   960
aacatctatt gggcgggcca tcaagtaacc gcagtagata cagccaaccg tacgattgtg   1020
taccctgtca atggcagtgc agccaacttg gaacctccgc ggacgttgcg gtttgagtcc   1080
cccgtcgtgg aaattcgctc taatccggtg tgggaccgcg gaagtactgg catcgcaggc   1140
tcgtatgaat tctttggtgt gaccagtgct ttgttcatta caatcctggg ttttggctat   1200
acctatcgct cagggagcaa caccgaagtg acggcactttc cggatcatca ggtcagccac   1260
attggttact tccgtcgctt taccaccacc ggggcgaccg ctcgtcagac cttgacaagc   1320
```

```
gcacctattg tgtcgtggac tcattcgagc gctgaaccgc caaaccgtat ctatcaaaac   1380
cgtattaccc agatcccagc agtgaaaggc aactttctgt ttaacggcag cgtgatcagc   1440
ggtccaggtt ttaccggcgg tgacctggtg cgcctgaaca acagcggcaa caatatccaa   1500
aaccgtggtt atctggaagt cccgattcaa ttcatcagca cgagcacccg ttaccgcgtc   1560
cgtgttcgct acgcatccgt tacgccgatc caactgagcg ttaactgggg caattccaac   1620
attttcagca gcattgtccc tgctacggcg acctctctgg acaatttgca gagccgtgac   1680
ttcggctatt tcgaaagcac caacgctttc accagcgcta cgggcaatgt ggttggtgtt   1740
cgcaatttca gcgagaatgc gggcgtcatc attgaccgtt ttgagtttat cccggtgacc   1800
gcgaccttcg aagcggagta cgatctggag cgtgcgcagg aataa               1845
```

SEQ ID NO: 53                moltype = DNA   length = 1845
FEATURE                  Location/Qualifiers
misc_feature          1..1845
                          note = Synthetic
source                   1..1845
                          mol_type = other DNA
                          organism = synthetic construct
SEQUENCE: 53

```
atgggccgcg gtagcatgga agtcaacaat caaaatcaat gcgtgccgta caattgcctg     60
aacaacccgg aaattgaaat tttaggcggt gaacggatct cagtggggaa cacgccaatt    120
gatatcagtc tgtccttgac gcaatttctg ttgtcggaat tcgtacctgg tgccggcttt    180
gtattggggc ttattgactt gatctggggg tttctgggcc tagccagtg ggacgccattt     240
ctgctgcaga tcgaacagct gattaaccag cgtatcgaag aattcgcgcg taaccaggca    300
atctcccgtc tggaaggtct gtccaacctg taccagatct acgcagagtc cttccgtgaa    360
tgggaagctg atccgaccaa cccggcactg cgcgaagaaa tgcgtatcca gttcaacgac    420
atgaactctg ctctgacgac ggccatccct ctgctgtctg tgcagaatta tcaggtaccg    480
ctgctgtctg tgtacgtgca ggcggcgaac ctgcatctgt ccgtgttgcg cgacgttagc    540
gtgttcggtc agcgttgggg atttgatgtt gccacgatta atagccgtta caacgatctg    600
acacggttga ttggcgagta cacggactac gccgtgcgtt ggtataacac agggcttgac    660
cgccttcgcg gttcgaactt ccaggattgg attcgttata atcgttttcg ccgcgagctg    720
acgttgaccg tgttggacat cgtgtcggtc tttcagaatt atgacagtcg cctttatccg    780
atccagacga gctctcaatt gacgcgtgaa atttattccg atcttctgct ggccaacccc    840
agtggtgtgg gtagtttctc taatgtagat ttcgatagca ttctgatccg tcagcctcat    900
ctgatcgatt tcatgcgcgt tttaacgatt tacacggatc gccataatgc ttcccggcac    960
aacatctatt gggcgggcca tcaagtaacc gcagtagata cagccaaccg tacgattgtg   1020
taccctgtca atggcagtgc agccaacttg aacctccgc ggacgttgcg gtttgagtcc    1080
cccgtcgtgg aaattcgctc taatccggtg tgggaccgcg aagtactgg catcgcaggc   1140
tcgtatgaat tctttggtgt gaccagtgct ttgttcatta caatcctggg ttttggctat   1200
acctatcgct cagggagcaa caccgaagtg acggcacttc cggatcatca ggtcagccac   1260
attggttact tccgtcgctt taccaccacc ggggcgaccg ctcgtcagac cttgacaagc   1320
gcacctattg tgtcgtggac tcattcgagc gctgaaccgc caaaccgtat ctatcaaaac   1380
cgtattaccc agatcccagc cgttaaaggt aacttcctgt ttaacggagc tgtcatctca   1440
gggcctggat ttaccggtgg cgacctggtg cgcctgaaca acagcggcaa caatatccaa   1500
aaccgtggtt atctggaagt cccgattcaa ttcatcagca cgagcacccg ttaccgcgtc   1560
cgtgttcgct acgcatccgt tacgccgatc caactgagcg ttaactgggg caattccaac   1620
attttcagca gcattgtccc tgctacggcg acctctctgg acaatttgca gagccgtgac   1680
ttcggctatt tcgaaagcac caacgctttc accagcgcta cgggcaatgt ggttggtgtt   1740
cgcaatttca gcgagaatgc gggcgtcatc attgaccgtt ttgagtttat cccggtgacc   1800
gcgaccttcg aagcggagta cgatctggag cgtgcgcagg aataa               1845
```

SEQ ID NO: 54                moltype = DNA   length = 1845
FEATURE                  Location/Qualifiers
misc_feature          1..1845
                          note = Synthetic
source                   1..1845
                          mol_type = other DNA
                          organism = synthetic construct
SEQUENCE: 54

```
atgggccgcg gtagcatgga agtcaacaat caaaatcaat gcgtgccgta caattgcctg     60
aacaacccgg aaattgaaat tttaggcggt gaacggatct cagtggggaa cacgccaatt    120
gatatcagtc tgtccttgac gcaatttctg ttgtcggaat tcgtacctgg tgccggcttt    180
gtattggggc ttattgactt gatctggggg tttctgggcc tagccagtg ggacgccattt     240
ctgctgcaga tcgaacagct gattaaccag cgtatcgaag aattcgcgcg taaccaggca    300
atctcccgtc tggaaggtct gtccaacctg taccagatct acgcagagtc cttccgtgaa    360
tgggaagctg atccgaccaa cccggcactg cgcgaagaaa tgcgtatcca gttcaacgac    420
atgaactctg ctctgacgac ggccatccct ctgctggctg tgcagaatta tcaggtaccg    480
ctgctgtctg tgtacgtgca ggcggcgaac ctgcatctgt ccgtgttgcg cgacgttagc    540
gtgttcggtc agcgttgggg atttgatgtt gccacgatta atagccgtta caacgatctg    600
acacggttga ttggcgagta cacggactac gccgtgcgtt ggtataacac agggcttgac    660
cgccttcgcg gttcgaactt ccaggattgg attcgttata atcgttttcg ccgcgagctg    720
acgttgaccg tgttggacat cgtgtcggtc tttcagaatt atgacagtcg cctttatccg    780
atccagacga gctctcaatt gacgcgtgaa atttattccg atcttctgct ggccaacccc    840
agtggtgtgg gtagtttctc taatgtagat ttcgatagca ttctgatccg tcagcctcat    900
ctgatcgatt tcatgcgcgt tttaacgatt tacacggatc gccataatgc ttcccggcac    960
aacatctatt gggcgggcca tcaagtaacc gcagtagata cagccaaccg tacgattgtg   1020
taccctgtca atggcagtgc agccaacttg aacctccgc ggacgttgcg gtttgagtcc    1080
cccgtcgtgg aaattcgctc taatccggtg tgggaccgcg aagtactgg catcgcaggc   1140
tcgtatgaat tctttggtgt gaccagtgct ttgttcatta caatcctggg ttttggctat   1200
acctatcgct cagggagcaa caccgaagtg acggcacttc cggatcatca ggtcagccac   1260
```

```
attggttact tccgtcgctt taccaccacc ggggcgaccg ctcgtcagac cttgacaagc   1320
gcacctattg tgtcgtggac tcattcgagc gctgaaccgc caaaccgtat ctatcaaaac   1380
cgtattaccc agatcccagc cgttaaaggt aacttcctgt ttaacggagc tgtcatctca   1440
gggcctggat ttaccggtgg cgatcttgtc cgccttaacc gcaacaatga taatattcaa   1500
aatcgcggtt atattgaagt tccgatccag ttcgcctcga ctagcacgcg ttatcgcgta   1560
cgcgtccgtt acgccagcac tacgccgatc caactgagcg ttaactgggg caattccaac   1620
attttcagca gcattgtccc tgctacggcg acctctctgg acaatttgca gagccgtgac   1680
ttcggctatt tcgaaagcac caacgctttc accagcgcta cgggcaatgt ggttggtgtt   1740
cgcaatttca gcgagaatgc gggcgtcatc attgaccgtt ttgagtttat cccggtgacc   1800
gcgaccttcg aagcggagta cgatctggag cgtgcgcagg aataa                  1845

SEQ ID NO: 55           moltype = DNA   length = 1839
FEATURE                 Location/Qualifiers
misc_feature            1..1839
                        note = Synthetic
source                  1..1839
                        mol_type = other DNA
                        organism = synthetic construct
SEQUENCE: 55
atgggccgcg gtagcatgga agtcaacaat caaaatcaat gcgtgccgta caattgcctg    60
aacaacccgg aaattgaaat tttaggcggt gaacggatct cagtggggaa cacgccaatt   120
gatatcagtc tgtccttgac gcaatttctg ttgtcggaat tcgtacctgg tgccggcttt   180
gtattgggcc ttattgactt gatctgggga tttctggggc ctagccagtg ggacgcattt   240
ctgctgcaga tcgaacagct gattaaccag cgtatcgaag aattcgcgcg taaccaggca   300
atctcccgtc tggaaggtct gtccaacctg taccagatct acgcagagtc cttccgtgaa   360
tgggaagctg atccgaccaa cccggcactg cgcgaagaaa tgcgtatccg gttcaacgac   420
atgaactctg ctctgacgac ggccatccct ctgctggctg tgcagaatta tcaggtaccg   480
ctgctgtctg tgtacgtgca ggcggcgaac ctgcatctgt ccgtgttgcg cgacgttagc   540
gtgttcggtc agcgttgggg atttgatgtt gccacgatta atagccgtta caacgatctg   600
acacggttga ttggcgagta cacggactac gccgtgcctg ggtataacac agggcttgac   660
cgccttcgcg gttcgaactt ccaggattgg attcgttata atcgtttctcg ccgcgagctg   720
acgttgaccg tgttggacat cgtgtcggtc tttcagaatt atgacagtcg cctttatccg   780
atccagacga gctctcaatt gacgcgtgaa atttattccg atcttctgct ggccaacccc   840
agtggtgtgg gtagtttctc taatgtagat ttcgatagca ttctgatccg tcagcctcat   900
ctgatcgatt tcatgcgcgt tttaacgatt acacggatc gccataatgc ttcccgcgcac   960
aacatctatt gggcgggcca tcaagtaacc gcagtagata cagccaaccg tacgattgtg  1020
taccctgtca atggcagtgc agccaacttg gaacctccgc ggacgttgcg gtttgagtcc  1080
cccgtcgtgg aaattcgctc taatccggtg tgggaccgcg gaagtactgg catcgcaggc  1140
tcgtatgaat tctttggtgt gaccagtgct ttgttcatta caatcctgag ttttggctat  1200
acctatcgct cagggagcaa caccgaagtg acggcacttc cggatcatca ggtcagccac  1260
attggttact tccgtcgctt taccaccacc ggggcgaccg ctcgtcagac cttgacaagc  1320
gcacctattg tgtcgtggac tcattcgagc gctgaaccgc caaaccgtat ctatcaaaac  1380
cgtattaccc agatcccact ggttaaggct cgtaacctgg actctggcgt taccgttgtt  1440
ggtggtccgg gtttcaccgg tggtgatatc ctgcgccgta cgaacaccgg cactttcggc  1500
gacatccgcc tgaatatcaa tgtaccactg agccaacgct accgtgtacg cattcgctac  1560
gcttccacta ccgacctgca gttcttcact cgtatcaatg gtaccaccgt taacatcggc  1620
aacttctctc gcaccatgaa ccgtggtgat aacctggaac actctcttt ccgtaccgca   1680
ggttttctca cgccgtttaa cttcctgaac gcccagtcta cttcacgct gggcgcgcag   1740
tctttcagca accaggaagt ctacattgac cgtgtggaat cgtgccggc ggaagttacc   1800
tttgaagcag aatatgacct ggaacgtgcg caaaaataa                         1839

SEQ ID NO: 56           moltype = DNA   length = 1830
FEATURE                 Location/Qualifiers
misc_feature            1..1830
                        note = Synthetic
source                  1..1830
                        mol_type = other DNA
                        organism = synthetic construct
SEQUENCE: 56
atgccctcaa atgaacatga ttatttgaaa gtttgtgatg atttaagtga aactaatatg    60
gagaggtttg acaaaaatga tgcactggag attggtatgt ctattgtatc tgaacttctt   120
ggcatgattc caggcggagc agccttacaa tttgtgttta tcaattgtg gtcgcgttta   180
ggtgattctg gatggagtgc attcatggaa catgttgaag aattaattga tactaaaata   240
gaagggtatg caaaaataa agccttatct gagttagcag gtatgcacag aaatcttgaa   300
acatatataa aattgcttaa tgaatgggaa aataatactg gaagttcaaa agcacaaggt   360
agagtagcta attatttga aagtcttgag caggcggttg aaagaggtat gcctcaattc   420
gcagttggta atttcgaaat accccttta actgtttatg tacaagctgc taaccttcat   480
ttattgttat taagagatgt ttcagtttat ggaaaacgct ggggatggtc agatcagaaa   540
attaagattt attatgcaga acaagttaag tatactcatg aatacaccaa tcattgttcg   600
acttggtata atagaggact agataaattg aaaaataagg ttcttcctta ccaagattgg   660
tacaactata atcgtttccg tagagaaatt actcttactg ttctagatat cgtcgctgta   720
ttcccacact atgatgtgaa agcatatcca attcaaacag ttggcaatt aacaagagaa   780
gtatatacag acccattaat taattcaat ccgcagttac agtctgtagc tcaattgcct   840
acttttaacg ttatgaaag taacgcaatt agaaaccctc atttagttga cttcttgaat   900
aaccttagaa tttttacaga ttggtttagt gtcggacggc actattattg ggaggacat   960
cgagtgattt ccaaacgtgt aggaggaagg gagataacct tccctatata tgaaggagg  1020
gcaaagcagg aacctccaag atcctttact tttaatggac ctgtttttag gacgttatca  1080
aatcctaccc taagaccatt acaacaaacct gcaccagctc ctcctttaa tttacgtggc  1140
ttggaaggtg taaaatttta tacacctaca aatacctta cgtatcgggg aagaggcccg  1200
```

```
cgtgattctt taactgaatt accgcctgga gatacaagtg tactacctcg cgaaggatat   1260
agtcaccggt tatgtcatgc aacatttatt caaagatctg gcacaccttt tttaacaaca   1320
ggcgtagtct tttcttggac acatcgtagt gctgatgaaa cgaatataat ttatccagat   1380
aagattactc aaattccatg ggtaaaggcg catacccttg aatcgggggc cactgttatt   1440
aagggtcctg gatttacagg aggggatatt cttactgttc ttactagtct tggttccttg   1500
ggcgctttac gagtaacttt tacggggcaa ttaccacaaa catataatat acgaatccga   1560
tatgcctcgg tgctaaataa atatggtaca ctccattttt cacagccacc tgcatatggg   1620
ctcacatttc caaaaactat ggatatagat gaaccattaa catctcgctc gtttgctttt   1680
acaactcttt ggacaccaat aaccttaca cgagcacaag aggaatttaa tctaacaata   1740
caatcaggtg tttatataga tagaattgaa tttgttccgg cagaagtaac atttgaggca   1800
gactatgact tggaaaaagc gcaaaagtaa                                    1830

SEQ ID NO: 57            moltype = AA   length = 627
FEATURE                  Location/Qualifiers
REGION                   1..627
                         note = Synthetic
source                   1..627
                         mol_type = protein
                         organism = synthetic construct
SEQUENCE: 57
MEIVNNQNQC VPYNCLNNPE NEILDIERSN STVATNIALE ISRLLASATP IGGILLGLFD    60
AIWGSIGPSQ WDLFLEQIEQ LINQRIEEFA RNQAISRLEG LSNLYQIYAE SFREWEADPT   120
NPALREEMRI QFNDMNSALT TAIPLLAVQN YQVPLLSVYV QAANLHLSVL RDVSVFGQAW   180
GFDIATINSR YNDLTRLIPI YTDYAVRWYN TGLDRLPRTG GLRNWARFNQ FRRELTISVL   240
DIISFFRNYD SRLYPIPTSS QLTREVYTDP VINITDYRVG PSFENIENSA IRSPHLMDFL   300
NNLTIDTDLI RGVHYWAGHR VTSHFTGSSQ VITTPQYGIT ANAEPRRTIA PSTFPGLNLF   360
YRTLSNPFFR RSENITPTLG INVVQGVGFI QPNNAEVLYR SRGTVDSLNE LPIDGENSLV   420
GYSHRLSHVT LTRSLYNTNI TSLPTFVWTH HSATNTNTIN PDIITQIPLV KGFRVWGGTS   480
VITGPGFTGG DILRRNTFGD FVSLQVNINS PITQRYRLRF RYASSRDARV IVLTGAASTG   540
VGGQVSVNMP LQKTMEIGEN LTSRTFRYTD FSNPFSFRAN PDIIGISEQP LFGAGSISSG   600
ELYIDKIEII LADATFEAES DLERAQK                                       627

SEQ ID NO: 58            moltype = AA   length = 627
FEATURE                  Location/Qualifiers
REGION                   1..627
                         note = Synthetic
source                   1..627
                         mol_type = protein
                         organism = synthetic construct
SEQUENCE: 58
MEIVNNQNQC VPYNCLNNPE NEILDIERSN STVATNIALE ISRLLASATP IGGILLGLFD    60
AIWGSIGPSQ WDLFLEQIEQ LINQRIEEFA RNQAISRLEG LSNLYQIYAE SFREWEADPT   120
NPALREEMRI QFNDMNSALT TAIPLFAVQN YQVPLLSVYV QAANLHLSVL RDVSVFGQAW   180
GFDIATINSR YNDLTRLIPI YTDYAVRWYN TGLDRLPRTG GLRNWARFNQ FRRELTISVL   240
DIISFFRNYD SRLYPIPTSS QLTREVYTDP VINITDYRVG PSFENIENSA IRSPHLMDFL   300
NNLTIDTDLI RGVHYWAGHR VTSHFTGSSQ VITTPQYGIT ANAEPRRTIA PSTFPGLNLF   360
YRTLSNPFFR RSENITPTLG INVVQGVGFI QPNNAEVLYR SRGTVDSLNE LPIDGENSLV   420
GYSHRLSHVT LTRSLYNTNI TSLPTFVWTH HSATNTNTIN PDIITQIPLV KGFRVWGGTS   480
VITGPGFTGG DILRRNTFGD FVSLQVNINS PITQRYRLRF RYASSRDARV IVLTGAASTG   540
VGGQVSVNMP LQKTMEIGEN LTSRTFRYTD FSNPFSFRAN PDIIGISEQP LFGAGSISSG   600
ELYIDKIEII LADATFEAES DLERAQK                                       627

SEQ ID NO: 59            moltype = AA   length = 627
FEATURE                  Location/Qualifiers
REGION                   1..627
                         note = Synthetic
source                   1..627
                         mol_type = protein
                         organism = synthetic construct
SEQUENCE: 59
MEIVNNQNQC VPYNCLNNPE NEILDIERSN STVATNIALE ISRLLASATP IGGILLGLFD    60
AIWGSIGPSQ WDLFLEQIEQ LIGQRIEEFA RNQAISRLEG LSNLYRIYTN AFKNWEADPT   120
NPVLREEMRI QFNDMNSAFT TAIPLFSVQG YEIPLLGVYV QAANLHLSVL RDVSVFGQAW   180
GFDIATINSR YNDLTRLIPI YTDYAVRWYN TGLDRLPRTG GLRNWARFNQ FRRELTISVL   240
DIISFFRNYD SRLYPIPTSS QLTREVYTDP VINITDYRVG PSFENIENSA IRSPHLMDFL   300
NNIIIDTDLI RGVHYWAGHR VTSHFTGSSQ VISSPQYGIT ANAEPSRTIA PSTFPGLNLF   360
YRTLSNPFFR RSENITPTLG INVVQGVGFI QPNNAEVLYR SRGTVDSLNE LPIDGENSLV   420
GYSHRLSHVT LTRSLYNTNI TSLPTFVWTH HSATNTNTIN PDIITQIPLV KGFRVWGGTS   480
VITGPGFTGG DILRRNTFGD FVSLQVNINS PITQRYRLRF RYASSRDARV IVLTGAASTG   540
VGGQVSVNMP LQKTMEIGEN LTSRTFRYTD FSNPFSFRAN PDIIGISEQP LFGAGSISSG   600
ELYIDKIEII LADATFEAES DLERAQK                                       627

SEQ ID NO: 60            moltype = AA   length = 627
FEATURE                  Location/Qualifiers
REGION                   1..627
                         note = Synthetic
source                   1..627
                         mol_type = protein
                         organism = synthetic construct
```

```
SEQUENCE: 60
MEIVNNQNQC VPYNCLNNPE NEILDIERSN STVATNIALE ISRLLASATP IGGILLGLFD    60
AIWGSIGPSQ WDLFLEQIEQ LIGQRIEEFA RNQAISRLEG LSNLYRIYTN AFKNWEADPT   120
NPVLREEMRI QFNDMNSAFT TAIPLFSVQG YEIPLLGVYV QAANLHLSVL RDVSVFGQAW   180
GFDIATINSR YNDLTRLIPI YTDYAVRWYN TGLDRLPRTG GLRNWARFNQ FRRELTISVL   240
DIISFFRNYD SRLYPIPTSS QLTREVYTDP VINITDYRVG PSFENIENSA IRSPHLMDFL   300
NNLTIDTDLI RGVHYWAGHR VTSHFTGSSQ VITTPQYGIT ANAEPRRTIA PSTFPGLNLF   360
YRTLSNPFFR RSDNIMPTLG INVVQGVGFI QPNNGEVLYR RRGTVDSLNE LPIDGENSLV   420
GYSHRLSHVT LTRSLYNTNI TSLPTFVWTH HSATNTNTNI PDIITQIPLV KGFRVWGGTS   480
VITGPGFTGG DILRRNTFGD FVSLQVNINS PITQRYRLRF RYASSRDARV IVLTGAASTG   540
VGGQVSVNMP LQKTMEIGEN LTSRTFRYTD FSNPFSFRAN PDIIGISEQP LFGAGSISSG   600
ELYIDKIEII LADATFEAES DLERAQK                                       627

SEQ ID NO: 61            moltype = AA   length = 627
FEATURE                  Location/Qualifiers
REGION                   1..627
                         note = Synthetic
source                   1..627
                         mol_type = protein
                         organism = synthetic construct
SEQUENCE: 61
MEIVNNQNQC VPYNCLNNPE NEILDIERSN STVATNIALE ISRLLASATP IGGILLGLFD    60
AIWGSIGPSQ WDLFLEQIEQ LIGQRIEEFA RNQAISRLQG LSNLYRIYTN AFKNWEVDPT   120
NPALREEMRI QFNDMNSALT TAIPLFSVQG YEIPLLSVYV QAANLHLSVL RDVSVFGQAW   180
GFDIATINSR YNDLTRLIPI YTDYAVRWYN TGLDRLPRTG GLRNWARFNQ FRRELTISVL   240
DIISFFRNYD SRLYPIPTSS QLTREVYTDP VINITDYRVG PSFENIENSA IRSPHLMDFL   300
NNLTIDTDLI RGVHYWAGHR VTSHFTGSSQ VITTPQYGIT ANAEPRRTIA PSTFPGLNLF   360
YRTLSNPFFR RSENITPTLG INVVQGVGFI QPNNAEVLYR SRGTVDSLNE LPIDGENSLV   420
GYSHRLSHVT LTRSLYNTNI TSLPTFVWTH HSATNTNTIN PDIITQIPLV KGFRVWGGTS   480
VITGPGFTGG DILRRNTFGD FVSLQVNINS PITQRYRLRF RYASSRDARV IVLTGAASTG   540
VGGQVSVNMP LQKTMEIGEN LTSRTFRYTD FSNPFSFRAN PDIIGISEQP LFGAGSISSG   600
ELYIDKIEII LADATFEAES DLERAQK                                       627

SEQ ID NO: 62            moltype = AA   length = 627
FEATURE                  Location/Qualifiers
REGION                   1..627
                         note = Synthetic
source                   1..627
                         mol_type = protein
                         organism = synthetic construct
SEQUENCE: 62
MEIVNNQNQC VPYNCLNNPE NEILDIERSN STVATNIALE ISRLLASATP IGGILLGLFD    60
AIWGSIGPSQ WDLFLEQIEQ LIGQRIEEFA RNQAISRLEG LSNLYRIYTN AFKNWEADPT   120
NPVLREEMRI QFNDMNSAFT TAIPLFSVQG YEIPLLGVYV QAANLHLSVL RDVSVFGQAW   180
GFDIATINSR YNDLTRLIPI YTDYAVRWYN TGLDRLPRTG GLRNWARFNQ FRRELTISVL   240
DIISFFRNYD SRLYPIPTSS QLTREVYTDP VINITDYRVG PSFENIENSA IRSPHLMDFL   300
NNLTIDTDLI RGVHYWAGHR VTSHFTGSSQ VITTPQYGIT ANAEPRRTIA PSTFPGLNLF   360
YRTLSNPFFR RSENITPTLG INVVQGVGFI QPNNAEVLYR SRGTVDSLNE LPIDGENSLV   420
GYSHRLSHVT LTRSLYNTNI TSLPTFVWTH HSATNTNTIN PDIITQIPLV KGFRVWGGTS   480
VITGPGFTGG DILRRNTFGD FVSLQVNINS PITQRYRLRF RYASSRDARV IVLTGAASTG   540
VGGQVSVNMP LQKTMEIGEN LTSRTFRYTD FSNPFSFRAN PDIIGISEQP LFGAGSISSG   600
ELYIDKIEII LADATFEAES DLERAQK                                       627

SEQ ID NO: 63            moltype = AA   length = 627
FEATURE                  Location/Qualifiers
REGION                   1..627
                         note = Synthetic
source                   1..627
                         mol_type = protein
                         organism = synthetic construct
SEQUENCE: 63
MEIVNNQNQC VPYNCLNNPE NEILDIERSN STVATNIALE ISRLLASATP IGGILLGLFD    60
AIWGSIGPSQ WDLFLEQIEQ LINQRIEEFA RNQAISRLEG LSNLYQIYAE AFREWEADPT   120
NPALTEEMRI QFNDMNSALT TAIPLFTVQN YQVPLLSVYV QAANLHLSVL RDVSVFGQAW   180
GFDIATINSR YNDLTRLIPI YTDYAVRWYN TGLDRLPRTG GLRNWARFNQ FRRELTISVL   240
DIISFFRNYD SRLYPIPTSS QLTREVYTDP VINITDYRVG PSFENIENSA IRSPHLMDFL   300
NNLTIDTDLI RGVHYWAGHR VTSHFTGSSQ VITTPQYGIT ANAEPRRTIA PSTFPGLNLF   360
YRTLSNPFFR RSENITPTLG INVVQGVGFI QPNNAEVLYR SRGTVDSLNE LPIDGENSLV   420
GYSHRLSHVT LTRSLYNTNI TSLPTFVWTH HSATNTNTIN PDIITQIPLV KGFRVWGGTS   480
VITGPGFTGG DILRRNTFGD FVSLQVNINS PITQRYRLRF RYASSRDARV IVLTGAASTG   540
VGGQVSVNMP LQKTMEIGEN LTSRTFRYTD FSNPFSFRAN PDIIGISEQP LFGAGSISSG   600
ELYIDKIEII LADATFEAES DLERAQK                                       627

SEQ ID NO: 64            moltype = AA   length = 627
FEATURE                  Location/Qualifiers
REGION                   1..627
                         note = Synthetic
source                   1..627
                         mol_type = protein
```

```
                        organism = synthetic construct
SEQUENCE: 64
MEIVNNQNQC VPYNCLNNPE NEILDIERSN STVATNIALE ISRLLASATP IGGILLGLFD    60
AIWGSIGPSQ WDLFLEQIEQ LIGQRIEEFA RNQAISRLEG LSNLYRIYTN AFKNWEADPT   120
NPVLREEMRI QFNDMNSAFT TAIPLFSVQG YEIPLLGVYV QAANLHLSVL RDVSVFGQAW   180
GFDIATINSR YNDLTRLIPI YTDYAVRWYN TGLDRLPRTG GLRNWARFNQ FRRELTISVL   240
DIISFFRNYD SRLYPIPTSS QLTREVYTDP VINITDYRVG PSFENIENSA IRSPHLMDFL   300
NNLTIDTDLI RGVHYWAGHR VTSHFTGSSQ VITTPQYGIT ANAEPRRTIA PSTFPGLNLF   360
YRTLSNPFFR RSENITPTLG INVVQGVGFI QPNNAEVLYR SRGTVDSLNE LPIDGENSLV   420
GYSHRLSHVT LTRSLYNTNI TSLPTFVWTH HSATNTNTIN PDIITQIPLV KGFRLGGGTS   480
VIKGPGFTGG DILRRNTFGD FVSLQVNINS PITQRYRLRF RYASSRDARV IVLTGAASTG   540
VGGQVSVNMP LQKTMEIGEN LTSRTFRYTD FSNPFSFRAN PDIIGISEQP LFGAGSISSG   600
ELYIDKIEII LADATFEAES DLERAQK                                      627

SEQ ID NO: 65            moltype = AA  length = 627
FEATURE                  Location/Qualifiers
REGION                   1..627
                         note = Synthetic
source                   1..627
                         mol_type = protein
                         organism = synthetic construct
SEQUENCE: 65
MEIVNNQNQC VPYNCLNNPE NEILDIERSN STVATNIALE ISRLLASATP IGGILLGLFD    60
AIWGSIGPSQ WDLFLEQIEQ LIGQRIEEFA RNQAISRLQG LSNLYRIYTN AFKNWEVDPT   120
NPALREEMRI QFNDMNSALT TAIPLFSVQG YEIPLLSVYV QAANLHLSVL RDVSVFGQAW   180
GFDIATINSR YNDLTRLIPI YTDYAVRWYN TGLDRLPRTG FRRELTISVL              240
DIISFFRNYD SRLYPIPTSS QLTREVYTDP VINITDYRVG PSFENIENSA IRSPHLMDFL   300
NNLTIDTDLI RGVHYWAGHR VTSHFTGSSQ VITTPQYGIT ANAEPRRTIA PSTFPGLNLF   360
YRTLSNPFFR RSENITPTLG INVVQGVGFI QPNNAEVLYR SRGTVDSLNE LPIDGENSLV   420
GYSHRLSHVT LTRSLYNTNI TSLPTFVWTH HSATNTNTIN PDIITQIPLV KGFRLGGGTS   480
VIKGPGFTGG DILRRNTFGD FVSLQVNINS PITQRYRLRF RYASSRDARV IVLTGAASTG   540
VGGQVSVNMP LQKTMEIGEN LTSRTFRYTD FSNPFSFRAN PDIIGISEQP LFGAGSISSG   600
ELYIDKIEII LADATFEAES DLERAQK                                      627

SEQ ID NO: 66            moltype = AA  length = 630
FEATURE                  Location/Qualifiers
REGION                   1..630
                         note = Synthetic
source                   1..630
                         mol_type = protein
                         organism = synthetic construct
SEQUENCE: 66
MEIVNNQNQC VPYNCLNNPE NEILDIERSN STVATNIALE ISRLLASATP IGGILLGLFD    60
AIWGSIGPSQ WDLFLEQIEQ LIGQRIEEFA RNQAISRLEG LSNLYRIYTN AFKNWEADPT   120
NPVLREEMRI QFNDMNSAFT TAIPLFSVQG YEIPLLGVYV QAANLHLSVL RDVSVFGQAW   180
GFDIATINSR YNDLTRLIPI YTDYAVRWYN TGLDRLPRTG GLRNWARFNQ FRRELTISVL   240
DIISFFRNYD SRLYPIPTSS QLTREVYTDP VINITDYRVG PSFENIENSA IRSPHLMDFL   300
TNIIIDTDLI RGVYYWAGHR INSRFTGTAF PHIITSPQYG ITANAEPRRT IAPGPFQGVP   360
SLLYRTLSDP FFRRSDNISP TLGINVVQGV GFLQPNNFES LYRRRGTVDS LNELPIDGEN   420
SLVGYSHRLS HVTLTRSLYN TNITSLPTFV WTHHSATNTN TINPDIITQI PLVKGFRVWG   480
GTSVITGPGF TGGDILRRNT FGDFVSLQVN INSPITQRYR LRFRYASSRD ARVIVLTGAA   540
STGVGGQVSV NMPLQKTMEI GENLTSRTFR YTDFSNPFSF RANPDIIGIS EQPLFGAGSI   600
SSGELYIDKI EIILADATFE AESDLERAQK                                   630

SEQ ID NO: 67            moltype = AA  length = 624
FEATURE                  Location/Qualifiers
REGION                   1..624
                         note = Synthetic
source                   1..624
                         mol_type = protein
                         organism = synthetic construct
SEQUENCE: 67
MEIVNNQNQC VPYNCLNNPE NEILDIERSN STVATNIALE ISRLLASATP IGGILLGLFD    60
AIWGSIGPSQ WDLFLEQIEQ LIGQRIEEFA RNQAISRLEG LSNLYRIYTN AFKNWEADPT   120
NPVLREEMRI QFNDMNSAFT TAIPLFSVQG YEIPLLGVYV QAANLHLSVL RDVSVFGQAW   180
GFDIATINSR YNDLTRLIPI YTDYAVRWYN TGLDRLPRTG GLRNWARFNQ FRRELTISVL   240
DIISFFRNYD SRLYPIPTSS QLTREVYTDP VINITDYRVG PSFENIENSA IRSPHLMDVL   300
NNLTIFTDWF SVGRNFYWGG HRVISNRIGG GNITSPIYGR EANQEPPRSF TFNGPVFRTL   360
SNPTFRPLQQ PWPAPPFNLR GVEGVEFSTP LNSFTYRGRG TVDSLNELPI DGENSLVGYS   420
HRLSHVTLTR SLYNTNITSL PTFVWTHHSA TNTNTINPDI ITQIPLVKGF RVWGGTSVIT   480
GPGFTGGDIL RRNTFGDFVS LQVNINSPIT QRYRLRFRYA SSRDARVIVL TGAASTGVGG   540
QVSVNMPLQK TMEIGENLTS RTFRYTDFSN PFSFRANPDI IGISEQPLFG AGSISSGELY   600
IDKIEIILAD ATFEAESDLE RAQK                                         624

SEQ ID NO: 68            moltype = AA  length = 615
FEATURE                  Location/Qualifiers
REGION                   1..615
                         note = Synthetic
source                   1..615
```

```
                        mol_type = protein
                        organism = synthetic construct
SEQUENCE: 68
MEIVNNQNQC VPYNCLNNPE NEILDIERSN STVATNIALE ISRLLASATP IGGILLGLFD    60
AIWGSIGPSQ WDLFLEQIEQ LIGQRIEEFA RNQAISRLEG LSNLYRIYTN APFKNWEADPT  120
NPVLREEMRI QFNDMNSAFT TAIPLFSVQG YEIPLLGVYV QAANLHLSVL RDVSVFGQAW   180
GFDIATINSR YNDLTRLIPI YTDYAVRWYN TGLDRLPRTG GLRNWARFNQ FRRELTISVL   240
DIISFFRNYD SRLYPIPTSS QLTREVYTDP VINITDYRVG PSFENIENSA IRSPHLMDFL   300
NNLTIDTDLI RGVHYWAGHR VTSHFTGSSQ VITTPQYGIT ANAEPRRTIA PSTFPGLNLF   360
YRTLSNPFFR RSENITPTLG INVVQGVGFI QPNNAEVLYR SRGTVDSLNE LPIDGENSLV   420
GYSHRLSHVT LTRSLYNTNI TSLPTFVWTH HSATNTNTIN PDIITQIPLV KAFNLSSGAA   480
VVRGPGFTGG DILRRKNTGT FGDIRVNINP PFAQRYRVRI RYASTTDLQF HTSINGKAIN   540
QGNFSATMNR GEDLDYKTFR TVGFTTPFSF SDVQSTFTIG AWNFSSGNEV YIDRIEFVPV   600
EVTYEAEYDF EKAQE                                                   615

SEQ ID NO: 69           moltype = AA  length = 615
FEATURE                 Location/Qualifiers
REGION                  1..615
                        note = Synthetic
source                  1..615
                        mol_type = protein
                        organism = synthetic construct
SEQUENCE: 69
MEIVNNQNQC VPYNCLNNPE NEILDIERSN STVATNIALE ISRLLASATP IGGILLGLFD    60
AIWGSIGPSQ WDLFLEQIEQ LIGQRIEEFA RNQAISRLEG LSNLYRIYTN AFKNWEADPT   120
NPVLREEMRI QFNDMNSAFT TAIPLFSVQG YEIPLLGVYV QAANLHLSVL RDVSVFGQAW   180
GFDIATINSR YNDLTRLIPI YTDYAVRWYN TGLDRLPRTG GLRNWARFNQ FRRELTISVL   240
DIISFFRNYD SRLYPIPTSS QLTREVYTDP VINITDYRVG PSFENIENSA IRSPHLMDFL   300
NNLTIDTDLI RGVHYWAGHR VTSHFTGSSQ VITTPQYGIT ANAEPRRTIA PSTFPGLNLF   360
YRTLSNPFFR RSENITPTLG INVVQGVGFI QPNNAEVLYR SRGTVDSLNE LPIDGENSLV   420
GYSHRLSHVT LTRSLYNTNI TSLPTFVWTH HSATNTNTIN PDIITQIPVV KAYELSSGAT   480
VVKGPGFTGG DVIRRTNTGG FGAIRVSVTG PLTQRYRIRF RYASTIDFDF PVTRGGTTIN   540
NFRFTRTMNR GQESRYESYR TVEFTTPFNF TQSQDIIRTS IQGLSGNGEV YLDRIEIIPV   600
NPTREAEEDL EAAKK                                                   615

SEQ ID NO: 70           moltype = AA  length = 617
FEATURE                 Location/Qualifiers
REGION                  1..617
                        note = Synthetic
source                  1..617
                        mol_type = protein
                        organism = synthetic construct
SEQUENCE: 70
MEIVNNQNQC VPYNCLNNPE NEILDIERSN STVATNIALE ISRLLASATP IGGILLGLFD    60
AIWGSIGPSQ WDLFLEQIEQ LIGQRIEEFA RNQAISRLEG LSNLYRIYTN AFKNWEADPT   120
NPVLREEMRI QFNDMNSAFT TAIPLFSVQG YEIPLLGVYV QAANLHLSVL RDVSVFGQAW   180
GFDIATINSR YNDLTRLIPI YTDYAVRWYN TGLDRLPRTG GLRNWARFNQ FRRELTISVL   240
DIISFFRNYD SRLYPIPTSS QLTREVYTDP VINITDYRVG PSFENIENSA IRSPHLMDFL   300
TNIIIDTDLI RGVYYWAGHR INSRFTGTAF PHIITSPQYG ITANAEPRRT IAPGPFQGVP   360
SLLYRTLSDP FFRRSDNISP TLGINVVQGV GFLQPNNFES LYRRRGTVDS LNELPIDGEN   420
SLVGYSHRLS HVTLTRSLYN TNITSLPTFV WTHHSATDRN IIYPDVINQI PLVKAFNLTS   480
GTSVVRGPGF TGGDIIRTNV NGSVLSMSLN FSNTTLQRYR VRVRYAASQT MVMSVTVGGS   540
TTGNQGFPST MSANGALTSQ SFRFAEFPVG ISASGSQGAS ISISNNVGRQ MFHLDRIEFL   600
PVTSTFEEEY DLERAQE                                                 617

SEQ ID NO: 71           moltype = AA  length = 618
FEATURE                 Location/Qualifiers
REGION                  1..618
                        note = Synthetic
source                  1..618
                        mol_type = protein
                        organism = synthetic construct
SEQUENCE: 71
MEIVNNQNQC VPYNCLNNPE NEILDIERSN STVATNIALE ISRLLASATP IGGILLGLFD    60
AIWGSIGPSQ WDLFLEQIEQ LIGQRIEEFA RNQAISRLEG LSNLYRIYTN AFKNWEADPT   120
NPVLREEMRI QFNDMNSAFT TAIPLFSVQG YEIPLLGVYV QAANLHLSVL RDVSVFGQAW   180
GFDIATINSR YNDLTRLIPI YTDYAVRWYN TGLDRLPRTG GLRNWARFNQ FRRELTISVL   240
DIISFFRNYD SRLYPIPTSS QLTREVYTDP VINITDYRVG PSFENIENSA IRSPHLMDFL   300
TNIIIDTDLI RGVYYWAGHR INSRFTGTAF PHIITSPQYG ITANAEPRRT IAPGPFQGVP   360
SLLYRTLSDP FFRRSDNISP TLGINVVQGV GFLQPNNFES LYRRRGTVDS LNELPIDGEN   420
SLVGYSHRLS HVTLTRSLYN TNITSLPTFV WTHHSAEFNN IIPSSQITQI PLTKSTNLGS   480
GTSVVKGPGF TGGDILRRTS PGQISTLRVN ITAPLSQRYR VRIRYASTTN LQFHTSIDGR   540
PINQGNFSAT MSSGGNLQSG SFRTVGFTTP FNFSNGSSVF TLSAHVFNSG NEVYIDRIEF   600
VPAEVTFEAE YDLERAQE                                                618

SEQ ID NO: 72           moltype = AA  length = 614
FEATURE                 Location/Qualifiers
REGION                  1..614
                        note = Synthetic
```

```
source                        1..614
                              mol_type = protein
                              organism = synthetic construct
SEQUENCE: 72
MEIVNNQNQC VPYNCLNNPE NEILDIERSN STVATNIALE ISRLLASATP IGGILLGLFD    60
AIWGSIGPSQ WDLFLEQIEQ LIGQRIEEFA RNQAISRLEG LSNLYRIYTN AFKNWEADPT   120
NPVLREEMRI QFNDMNSAFT TAIPLFSVQG YEIPLLGVYV QAANLHLSVL RDVSVFGQAW   180
GFDIATINSR YNDLTRLIPI YTDYAVRWYN TGLDRLPRTG GLRNWARFNQ FRRELTISVL   240
DIISFFRNYD SRLYPIPTSS QLTREVYTDP VINITDYRVG PSFENIENSA IRSPHLMDFL   300
NNLTIDTDLI RGVHYWAGHR VTSHFTGSSQ VITTPQYGIT ANAEPRRTIA PSTFPGLNLF   360
YRTLSNPFFR RSENITPTLG INVVQGVGFI QPNNAEVLYR SRGTVDSLNE LPIDGENSLV   420
GYSHRLSHVT LTRSLYNTNI TSLPTFVWTH HSATNTNTIN PDIITQIPLV KALNLHSGVT   480
VVGGPGFTGG DILRRTNTGT FGDIRLNINV PLSQRYRVRI RYASTTDLQF FTRINGTTVN   540
IGNFSRTMNR GDNLEYRSFR TAGFSTPFNF LNAQSTFTLG AQSFSNQEVY IDRVEFVPAE   600
VTFEAEYDLE RAQK                                                    614

SEQ ID NO: 73                 moltype = AA  length = 630
FEATURE                       Location/Qualifiers
REGION                        1..630
                              note = Synthetic
source                        1..630
                              mol_type = protein
                              organism = synthetic construct
SEQUENCE: 73
MEIVNNQNQC VPYNCLNNPE NEILDIERSN STVATNIALE ISRLLASATP IGGILLGLFD    60
AIWGSIGPSQ WDLFLEQIEQ LIGQRIEEFA RNQAISRLEG LSNLYRIYTN AFKNWEADPT   120
NPVLREEMRI QFNDMNSAFT TAIPLFSVQG YEIPLLGVYV QAANLHLSVL RDVSVFGQAW   180
GFDIATINSR YNDLTRLIPI YTDYAVRWYN TGLDRLPRTG GLRNWARFNQ FRRELTISVL   240
DIISFFRNYD SRLYPIPTSS QLTREVYTDP VINITDYRVG PSFENIENSA IRSPHLMDFL   300
TNIIIDTDLI RGVYYWAGHR INSRFTGTAF PHIITSPQYG ITANAEPRRT IAPGPFQGVP   360
SLLYRTLSNP FFRRSENITP TLGINVVQGV GFIQPNNAEV LYRSRGTVDS LNELPIDGEN   420
SLVGYSHRLS HVTLTRSLYN TNITSLPTFV WTHHSATNTN TINPDIITQI PLVKGFRVWG   480
GTSVITGPGF TGGDILRRNT FGDFVSLQVN INSPITQRYR LRFRYASSRD ARVIVLTGAA   540
STGVGGQVSV NMPLQKTMEI GENLTSRTFR YTDFSNPFSF RANPDIIGIS EQPLFGAGSI   600
SSGELYIDKI EIILADATFE AESDLERAQK                                   630

SEQ ID NO: 74                 moltype = AA  length = 630
FEATURE                       Location/Qualifiers
REGION                        1..630
                              note = Synthetic
source                        1..630
                              mol_type = protein
                              organism = synthetic construct
SEQUENCE: 74
MEIVNNQNQC VPYNCLNNPE NEILDIERSN STVATNIALE ISRLLASATP IGGILLGLFD    60
AIWGSIGPSQ WDLFLEQIEQ LIGQRIEEFA RNQAISRLEG LSNLYRIYTN AFKNWEADPT   120
NPVLREEMRI QFNDMNSAFT TAIPLFSVQG YEIPLLGVYV QAANLHLSVL RDVSVFGQAW   180
GFDIATINSR YNDLTRLIPI YTDYAVRWYN TGLDRLPRTG GLRNWARFNQ FRRELTISVL   240
DIISFFRNYD SRLYPIPTSS QLTREVYTDP VINITDYRVG PSFENIENSA IRSPHLMDFI   300
DRIVIYTNSV RSTPYWAGHE VISRRTGQGQ GNEIRFPLYG VAANAEPPVT IRPTGFTDEQ   360
RQWYRTLSNP FFRRSENITP TLGINVVQGV GFIQPNNAEV LYRSRGTVDS LNELPIDGEN   420
SLVGYSHRLS HVTLTRSLYN TNITSLPTFV WTHHSATNTN TINPDIITQI PLVKGFRVWG   480
GTSVITGPGF TGGDILRRNT FGDFVSLQVN INSPITQRYR LRFRYASSRD ARVIVLTGAA   540
STGVGGQVSV NMPLQKTMEI GENLTSRTFR YTDFSNPFSF RANPDIIGIS EQPLFGAGSI   600
SSGELYIDKI EIILADATFE AESDLERAQK                                   630

SEQ ID NO: 75                 moltype = AA  length = 630
FEATURE                       Location/Qualifiers
REGION                        1..630
                              note = Synthetic
source                        1..630
                              mol_type = protein
                              organism = synthetic construct
SEQUENCE: 75
MEIVNNQNQC VPYNCLNNPE NEILDIERSN STVATNIALE ISRLLASATP IGGILLGLFD    60
AIWGSIGPSQ WDLFLEQIEQ LIGQRIEEFA RNQAISRLEG LSNLYRIYTN AFKNWEADPT   120
NPVLREEMRI QFNDMNSAFT TAIPLFSVQG YEIPLLGVYV QAANLHLSVL RDVSVFGQAW   180
GFDIATINSR YNDLTRLIPI YTDYAVRWYN TGLDRLPRTG GLRNWARFNQ FRRELTISVL   240
DIISFFRNYD SRLYPIPTSS QLTREVYTDP VINITDYRVG PSFENIENSA IRSPHLMDFL   300
TNIIIDTDLI RGVYYWAGHR INSRFTGTAF PHIITSPQYG ITANAEPRRT IVPGPFQGVP   360
SLLYRTLSNP FFRRSENITP TLGINVVQGV GFIQPNNAEV LYRSRGTVDS LNELPIDGEN   420
SLVGYSHRLS HVTLTRSLYN TNITSLPTFV WTHHSATNTN TINPDIITQI PLVKGFRVWG   480
GTSVITGPGF TGGDILRRNT FGDFVSLQVN INSPITQRYR LRFRYASSRD ARVIVLTGAA   540
STGVGGQVSV NMPLQKTMEI GENLTSRTFR YTDFSNPFSF RANPDIIGIS EQPLFGAGSI   600
SSGELYIDKI EIILADATFE AESDLERAQK                                   630

SEQ ID NO: 76                 moltype = AA  length = 627
FEATURE                       Location/Qualifiers
REGION                        1..627
```

```
                        note = Synthetic
source                  1..627
                        mol_type = protein
                        organism = synthetic construct
SEQUENCE: 76
MEIVNNQNQC VPYNCLNNPE NEILDIERSN STVATNIALE ISRLLASATP IGGILLGLFD    60
AIWGSIGPSQ WDLFLEQIEQ LIGQRIEEFA RNQAISRLEG LSNLYRIYTN AFKNWEADPT   120
NPVLREEMRI QFNDMNSAFT TAIPLFSVQG YEIPLLGVYV QAANLHLSVL RDVSVFGQAW   180
GFDIATINSR YNDLTRLIPI YTDYAVRWYN TGLDRLPRTG GLRNWARFNQ FRRELTISVL   240
DIISFFRNYD SRLYPIPTSS QLTREVYTDP VINITDYRVG PSFENIENSA IRSPHLMDFL   300
NNIIIDTDLI RGVHYWAGHR VTSHFTGSSQ VISSPQYGIT ANAEPSRTIA PSTFPGLNLF   360
YRTLSNPFFR RSENITPTLG INVVQGVGFI QPNNAEVLYR SRGTVDSLNE LPIDGENSLV   420
GYSHRLSHVT LTRSLYNTNI TSLPTFVWTH HSATNTNTIN PDIITQIPLV KGFRVWGGTS   480
VITGPGFTGG DILRRNTFGD FVSLQVNINS PITQRYRLRF RYASSRDARV IVLTGAASTG   540
VGGQVSVNMP LQKTMEIGEN LTSRTFRYTD FSNPFSFRAN PDIIGISEQP LFGAGSISSG   600
ELYIDKIEII LADATFEAES DLERAQK                                      627

SEQ ID NO: 77           moltype = AA   length = 627
FEATURE                 Location/Qualifiers
REGION                  1..627
                        note = Synthetic
source                  1..627
                        mol_type = protein
                        organism = synthetic construct
SEQUENCE: 77
MEIVNNQNQC VPYNCLNNPE NEILDIERSN STVATNIALE ISRLLASATP IGGILLGLFD    60
AIWGSIGPSQ WDLFLEQIEQ LIGQRIEEFA RNQAISRLEG LSNLYRIYTN AFKNWEADPT   120
NPVLREEMRI QFNDMNSAFT TAIPLFSVQG YEIPLLGVYV QAANLHLSVL RDVSVFGQAW   180
GFDIATINSR YNDLTRLIPI YTDYAVRWYN TGLDRLPRTG GLRNWARFNQ FRRELTISVL   240
DIISFFRNYD SRLYPIPTSS QLTREVYTDP VINITDYRVG PSFENIENSA IRSPHLMDFL   300
NNLTIDTDLI RGVHYWAGHR VTSHFTGSSQ VITTPQYGIT ANAEPRRTIA PSTFPGLNLF   360
YRTLSNPFFR RSDNIMPTLG INVVQGVGFI QPNNGEVLYR RRGTVDSLNE LPIDGENSLV   420
GYSHRLSHVT LTRSLYNTNI TSLPTFVWTH HSATNTNTIN PDIITQIPLV KGFRVWGGTS   480
VITGPGFTGG DILRRNTFGD FVSLQVNINS PITQRYRLRF RYASSRDARV IVLTGAASTG   540
VGGQVSVNMP LQKTMEIGEN LTSRTFRYTD FSNPFSFRAN PDIIGISEQP LFGAGSISSG   600
ELYIDKIEII LADATFEAES DLERAQK                                      627

SEQ ID NO: 78           moltype = AA   length = 627
FEATURE                 Location/Qualifiers
REGION                  1..627
                        note = Synthetic
source                  1..627
                        mol_type = protein
                        organism = synthetic construct
SEQUENCE: 78
MEIVNNQNQC VPYNCLNNPE NEILDIERSN STVATNIALE ISRLLASATP IGGILLGLFD    60
AIWGSIGPSQ WDLFLEQIEQ LIGQRIEEFA RNQAISRLEG LSNLYRIYTN AFKNWEADPT   120
NPVLREEMRI QFNDMNSAFT TAIPLFSVQG YEIPLLGVYV QAANLHLSVL RDVSVFGQAW   180
GFDIATINSR YNDLTRLIPI YTDYAVRWYN TGLDRLPRTG GLRNWARFNQ FRRELTISVL   240
DIISFFRNYD SRLYPIPTSS QLTREVYTDP VINITDYRVG PSFENIENSA IRSPHLMDFL   300
NNLTIDTDLI RGVHYWAGHR VTSHFTGSSQ VITTPQYGIT ANAEPRRTIA PSTFPGLNLF   360
YRTLSNPFFR RSDNISPTLG INVVQGVGFL QPNNFESLYR RRGTVDSLNE LPIDGENSLV   420
GYSHRLSHVT LTRSLYNTNI TSLPTFVWTH HSATNTNTIN PDIITQIPLV KGFRVWGGTS   480
VITGPGFTGG DILRRNTFGD FVSLQVNINS PITQRYRLRF RYASSRDARV IVLTGAASTG   540
VGGQVSVNMP LQKTMEIGEN LTSRTFRYTD FSNPFSFRAN PDIIGISEQP LFGAGSISSG   600
ELYIDKIEII LADATFEAES DLERAQK                                      627

SEQ ID NO: 79           moltype = AA   length = 627
FEATURE                 Location/Qualifiers
REGION                  1..627
                        note = Synthetic
source                  1..627
                        mol_type = protein
                        organism = synthetic construct
SEQUENCE: 79
MEIVNNQNQC VPYNCLNNPE NEILDIERSN STVATNIALE ISRLLASATP IGGILLGLFD    60
AIWGSIGPSQ WDLFLEQIEQ LISQRIEEFA RNQAISRLEG LSNLYKVYVR AFSDWEKDPT   120
NPVLREEMRI QFNDMNSAFT TAIPLFSVQG YEIPLLGVYV QAANLHLSVL RDVSVFGQAW   180
GFDIATINSR YNDLTRLIPI YTDYAVRWYN TGLDRLPRTG GLRNWARFNQ FRRELTISVL   240
DIISFFRNYD SRLYPIPTSS QLTREVYTDP VINITDYRVG PSFENIENSA IRSPHLMDFL   300
NNLTIDTDLI RGVHYWAGHR VTSHFTGSSQ VITTPQYGIT ANAEPRRTIA PSTFPGLNLF   360
YRTLSNPFFR RSENITPTLG INVVQGVGFI QPNNAEVLYR SRGTVDSLNE LPIDGENSLV   420
GYSHRLSHVT LTRSLYNTNI TSLPTFVWTH HSATNTNTIN PDIITQIPLV KGFRVWGGTS   480
VITGPGFTGG DILRRNTFGD FVSLQVNINS PITQRYRLRF RYASSRDARV IVLTGAASTG   540
VGGQVSVNMP LQKTMEIGEN LTSRTFRYTD FSNPFSFRAN PDIIGISEQP LFGAGSISSG   600
ELYIDKIEII LADATFEAES DLERAQK                                      627

SEQ ID NO: 80           moltype = AA   length = 627
FEATURE                 Location/Qualifiers
```

```
REGION                       1..627
                             note = Synthetic
source                       1..627
                             mol_type = protein
                             organism = synthetic construct
SEQUENCE: 80
MEIVNNQNQC VPYNCLNNPE NEILDIERSN STVATNIALE ISRLLASATP IGGILLGLFD   60
AIWGSIGPSQ WDLFLEQIEQ LIGQRIEEFA RNQAISRLEG LSNLYRIYTN AFKNWEADPT  120
NPVLREEMRI QFNDMNSAFT TAIPLFSVQG YQVPLLSVYV QAANLHLSVL RDVSVFGQAW  180
GFDIATINSR YNDLTRLIPI YTDYAVRWYN TGLDRLPRTG GLRNWARFNQ FRRELTISVL  240
DIISFFRNYD SRLYPIPTSS QLTREVYTDP VINITDYRVG PSFENIENSA IRSPHLMDFL  300
NNLTIDTDLI RGVHYWAGHR VTSHFTGSSQ VITTPQYGIT ANAEPRRTIA PSTFPGLNLF  360
YRTLSNPFFR RSENITPTLG INVVQGVGFI QPNNAEVLYR SRGTVDSLNE LPIDGENSLV  420
GYSHRLSHVT LTRSLYNTNI TSLPTFVWTH HSATNTNTIN PDIITQIPLV KGFRVWGGTS  480
VITGPGFTGG DILRRNTFGD FVSLQVNINS PITQRYRLRF RYASSRDARV IVLTGAASTG  540
VGGQVSVNMP LQKTMEIGEN LTSRTFRYTD FSNPFSFRAN PDIIGISEQP LFGAGSISSG  600
ELYIDKIEII LADATFEAES DLERAQK                                      627

SEQ ID NO: 81                moltype = AA  length = 627
FEATURE                      Location/Qualifiers
REGION                       1..627
                             note = Synthetic
source                       1..627
                             mol_type = protein
                             organism = synthetic construct
SEQUENCE: 81
MEIVNNQNQC VPYNCLNNPE NEILDIERSN STVATNIALE ISRLLASATP IGGILLGLFD   60
AIWGSIGPSQ WDLFLEQIEQ LIGQRIEEFA RNQAISRLEG LSNLYRIYTN AFKNWEADPT  120
NPALTEEMRI QFNDMNSALT TAIPLFSVQG YEIPLLGVYV QAANLHLSVL RDVSVFGQAW  180
GFDIATINSR YNDLTRLIPI YTDYAVRWYN TGLDRLPRTG GLRNWARFNQ FRRELTISVL  240
DIISFFRNYD SRLYPIPTSS QLTREVYTDP VINITDYRVG PSFENIENSA IRSPHLMDFL  300
NNLTIDTDLI RGVHYWAGHR VTSHFTGSSQ VITTPQYGIT ANAEPRRTIA PSTFPGLNLF  360
YRTLSNPFFR RSENITPTLG INVVQGVGFI QPNNAEVLYR SRGTVDSLNE LPIDGENSLV  420
GYSHRLSHVT LTRSLYNTNI TSLPTFVWTH HSATNTNTIN PDIITQIPLV KGFRVWGGTS  480
VITGPGFTGG DILRRNTFGD FVSLQVNINS PITQRYRLRF RYASSRDARV IVLTGAASTG  540
VGGQVSVNMP LQKTMEIGEN LTSRTFRYTD FSNPFSFRAN PDIIGISEQP LFGAGSISSG  600
ELYIDKIEII LADATFEAES DLERAQK                                      627

SEQ ID NO: 82                moltype = AA  length = 627
FEATURE                      Location/Qualifiers
REGION                       1..627
                             note = Synthetic
source                       1..627
                             mol_type = protein
                             organism = synthetic construct
SEQUENCE: 82
MEIVNNQNQC VPYNCLNNPE NEILDIERSN STVATNIALE ISRLLASATP IGGILLGLFD   60
AIWGSIGPSQ WDLFLEQIEQ LIGQRIEEFA RNQAISRLEG LSNLYRIYTN AFKNWEADPT  120
NPVLREEMRI QFNDMNSAFT TAIPLFSVQG YQVPLLSVYV QAVNLHLSVL RDVSVFGQAW  180
GFDIATINSR YNDLTRLIPI YTDYAVRWYN TGLDRLPRTG GLRNWARFNQ FRRELTISVL  240
DIISFFRNYD SRLYPIPTSS QLTREVYTDP VINITDYRVG PSFENIENSA IRSPHLMDFL  300
NNLTIDTDLI RGVHYWAGHR VTSHFTGSSQ VITTPQYGIT ANAEPRRTIA PSTFPGLNLF  360
YRTLSNPFFR RSENITPTLG INVVQGVGFI QPNNAEVLYR SRGTVDSLNE LPIDGENSLV  420
GYSHRLSHVT LTRSLYNTNI TSLPTFVWTH HSATNTNTIN PDIITQIPLV KGFRVWGGTS  480
VITGPGFTGG DILRRNTFGD FVSLQVNINS PITQRYRLRF RYASSRDARV IVLTGAASTG  540
VGGQVSVNMP LQKTMEIGEN LTSRTFRYTD FSNPFSFRAN PDIIGISEQP LFGAGSISSG  600
ELYIDKIEII LADATFEAES DLERAQK                                      627

SEQ ID NO: 83                moltype = AA  length = 627
FEATURE                      Location/Qualifiers
REGION                       1..627
                             note = Synthetic
source                       1..627
                             mol_type = protein
                             organism = synthetic construct
SEQUENCE: 83
MEIVNNQNQC VPYNCLNNPE NEILDIERSN STVATNIALE ISRLLASATP IGGILLGLFD   60
AIWGSIGPSQ WDLFLEQIEQ LIGQRIEEFA RNQAISRLEG LSNLYRIYTN AFKNWEADPT  120
NPVLREEMRI QFNDMNSAFT TAIPLFSVQG YEVALLSVYV QAANLHLSVL RDVSVYGQAW  180
GFDIATINSR YNDLTRLIPI YTDYAVRWYN TGLDRLPRTG GLRNWARFNQ FRRELTISVL  240
DIISFFRNYD SRLYPIPTSS QLTREVYTDP VINITDYRVG PSFENIENSA IRSPHLMDFL  300
NNLTIDTDLI RGVHYWAGHR VTSHFTGSSQ VITTPQYGIT ANAEPRRTIA PSTFPGLNLF  360
YRTLSNPFFR RSENITPTLG INVVQGVGFI QPNNAEVLYR SRGTVDSLNE LPIDGENSLV  420
GYSHRLSHVT LTRSLYNTNI TSLPTFVWTH HSATNTNTIN PDIITQIPLV KGFRVWGGTS  480
VITGPGFTGG DILRRNTFGD FVSLQVNINS PITQRYRLRF RYASSRDARV IVLTGAASTG  540
VGGQVSVNMP LQKTMEIGEN LTSRTFRYTD FSNPFSFRAN PDIIGISEQP LFGAGSISSG  600
ELYIDKIEII LADATFEAES DLERAQK                                      627

SEQ ID NO: 84                moltype = AA  length = 627
```

```
FEATURE              Location/Qualifiers
REGION               1..627
                     note = Synthetic
source               1..627
                     mol_type = protein
                     organism = synthetic construct
SEQUENCE: 84
MEIVNNQNQC VPYNCLNNPE NEILDIERSN STVATNIALE ISRLLASATP IGGILLGLFD   60
AIWGSIGPSQ WDLFLEQIEQ LIGQRIEEFA RNQAISLYRIYTN APKNWEADPT          120
NPVLREEMRI QFNDMNSAFT TAIPLFSVQG YEIPLLSVYV QAANLHLSIL RDVSVFGQAW  180
GFDIATINSR YNDLTRLIPI YTDYAVRWYN TGLDRLPRTG GLRNWARFNQ FRRELTISVL  240
DIISFFRNYD SRLYPIPTSS QLTREVYTDP VINITDYRVG PSFENIENSA IRSPHLMDFL  300
NNLTIDTDLI RGVHYWAGHR VTSHFTGSSQ VITTPQYGIT ANAEPRRTIA PSTFPGLNLF  360
YRTLSNPFFR RSENITPTLG INVVQGVGFI QPNNAEVLYR SRGTVDSLNE LPIDGENSLV  420
GYSHRLSHVT LTRSLYNTNI TSLPTFVWTH HSATNTNTIN PDIITQIPLV KGFRVWGGTS  480
VITGPGFTGG DILRRNTFGD FVSLQVNINS PITQRYRLRF RYASSRDARV IVLTGAASTG  540
VGGQVSVNMP LQKTMEIGEN LTSRTFRYTD FSNPFSFRAN PDIIGISEQP LFGAGSISSG  600
ELYIDKIEII LADATFEAES DLERAQK                                      627

SEQ ID NO: 85        moltype = AA  length = 627
FEATURE              Location/Qualifiers
REGION               1..627
                     note = Synthetic
source               1..627
                     mol_type = protein
                     organism = synthetic construct
SEQUENCE: 85
MEIVNNQNQC VPYNCLNNPE NEILDIERSN STVATNIALE ISRLLASATP IGGILLGLFD   60
AIWGSIGPSQ WDLFLEQIEQ LIGQRIEEFA RNQAISRLEG LSNLYRIYTN AFKNWEADPT  120
NPVLREEMRI QFNDMNSAFT TAIPLFSVQG YEIPLLSVYV QAANLHLSVL RDVSVFGQAW  180
GFDIATINSR YNDLTRLIPI YTDYAVRWYN TGLDRLPRTG GLRNWARFNQ FRRELTISVL  240
DIISFFRNYD SRLYPIPTSS QLTREVYTDP VINITDYRVG PSFENIENSA IRSPHLMDFL  300
NNLTIDTDLI RGVHYWAGHR VTSHFTGSSQ VITTPQYGIT ANAEPRRTIA PSTFPGLNLF  360
YRTLSNPFFR RSENITPTLG INVVQGVGFI QPNNAEVLYR SRGTVDSLNE LPIDGENSLV  420
GYSHRLSHVT LTRSLYNTNI TSLPTFVWTH HSATNTNTIN PDIITQIPLV KGFRVWGGTS  480
VITGPGFTGG DILRRNTFGD FVSLQVNINS PITQRYRLRF RYASSRDARV IVLTGAASTG  540
VGGQVSVNMP LQKTMEIGEN LTSRTFRYTD FSNPFSFRAN PDIIGISEQP LFGAGSISSG  600
ELYIDKIEII LADATFEAES DLERAQK                                      627

SEQ ID NO: 86        moltype = AA  length = 627
FEATURE              Location/Qualifiers
REGION               1..627
                     note = Synthetic
source               1..627
                     mol_type = protein
                     organism = synthetic construct
SEQUENCE: 86
MEIVNNQNQC VPYNCLNNPE NEILDIERSN STVATNIALE ISRLLASATP IGGILLGLFD   60
AIWGSIGPSQ WDLFLEQIEQ LIGQRIEEFA RNQAISRLEG LSNLYRIYTN AFKNWEADPT  120
NPVLREEMRI QFNDMNSAFT TAIPLFSVQG YEIPLLTVYV QAANLHLSLL RDAVYFGQAW  180
GFDIATINSR YNDLTRLIPI YTDYAVRWYN TGLDRLPRTG GLRNWARFNQ FRRELTISVL  240
DIISFFRNYD SRLYPIPTSS QLTREVYTDP VINITDYRVG PSFENIENSA IRSPHLMDFL  300
NNLTIDTDLI RGVHYWAGHR VTSHFTGSSQ VITTPQYGIT ANAEPRRTIA PSTFPGLNLF  360
YRTLSNPFFR RSENITPTLG INVVQGVGFI QPNNAEVLYR SRGTVDSLNE LPIDGENSLV  420
GYSHRLSHVT LTRSLYNTNI TSLPTFVWTH HSATNTNTIN PDIITQIPLV KGFRVWGGTS  480
VITGPGFTGG DILRRNTFGD FVSLQVNINS PITQRYRLRF RYASSRDARV IVLTGAASTG  540
VGGQVSVNMP LQKTMEIGEN LTSRTFRYTD FSNPFSFRAN PDIIGISEQP LFGAGSISSG  600
ELYIDKIEII LADATFEAES DLERAQK                                      627

SEQ ID NO: 87        moltype = AA  length = 609
FEATURE              Location/Qualifiers
REGION               1..609
                     note = Synthetic
source               1..609
                     mol_type = protein
                     organism = synthetic construct
SEQUENCE: 87
MPINNQKQCI PYNCLSNPEE VLLDGERILP DIDPLEVSLS LLQFLLNNFV PGGGFISGLV   60
DKIWGALRPS EWDLFLAQIE QLINERIAEF ARNAAIANLE GLGNNFNIYV EAFKEWEEDP  120
NNPETRTRVI DRFRILDGLL ERDIPSFRIS GFEVPLLSVY AQAANLHLAL LRDSVIFGER  180
WGLTTKNVND IYNRQIREIH EYSNHCVDTY NTELERLGFR SIAQWRIYNQ FRRELTLTVL  240
DIVALFPNYD SRLYPIQTFS QLTREIVTSP VSEFYYGVIN SGNIIGTLTE QQIRRPHLMD  300
FFNSMIMYTS DNRREHYWSG LEMTAYFTGF AGAQVSFPLV GTRGESAPPL TVRSVNDGIY  360
RILSAPFYSA PFLGTIVLGS RGEKFDFALN NISPPPSTIY RHPGTVDSLV SIPPQDNSVP  420
PHRGSSHRLS HVTMRASSPI FHWTHRSATT TNTINPNAII QIPLVKAFNL HSGATVVRGP  480
GFTGGDILRR TNTGTFADMR VNITGPLSQR YRVRIRYAST TDLQFFTRIN GTSVNQGNFQ  540
RTMNRGDNLE SGNFRTAGFS TPFSFSNAQS TFTLGTQAFS NQEVYIDRIE FVPAEVTFEA  600
ESDLERAQK                                                          609
```

```
SEQ ID NO: 88              moltype = AA   length = 610
FEATURE                    Location/Qualifiers
REGION                     1..610
                           note = Synthetic
source                     1..610
                           mol_type = protein
                           organism = synthetic construct
SEQUENCE: 88
MPINNQNQCI PYNCLSNPEE VFLDGERILP DIDPLEVSLS LLQFLLNNFV PGGGFISGLL   60
DKIWGALRPS DWELFLEQIE QLINERIAEF ARNAAIANLE GLGNNFNIYV EAFKEWEEDP  120
NNPETRTRVI DRFRILDGLL ERDIPSFRIS GFEVPLLSVY AQAANLHLAL LRDSVVFGER  180
WGLTTTNVND IYNRQVNRIG EYSKHCVDTY KTELERLGFR SIAQWRIYNQ FRRELTLTVL  240
DIVAVFPNYD SRLYPIRTIS QLTREIYTSP VSEFYYGVIN SNNIIGTLTE QQIRRPHLMD  300
FFNSMIMYTS DNRREHYWSG LEMTATNTEG HQRSFPLAGT IGNSAPPVTV RNNGEGIYRI  360
LSEPFYSAPF LGTSVLGSRG EEFAFASNTT TSLPSTIYRN RGTVDSLVSI PPQDYSVPPH  420
RGYSHLLSHV TMRNSSPIFH WIHRSATPRN TIDPDSITQI PAVKGAYIFN SPVITGPGHT  480
GGDIIRFNPN TQNNIRIPFQ SNAVQRYRIR MRYAAEADCI LESGVNIVTG AGVTFRPIPI  540
KATMTPGSPL TYYSFQYADL NINLTAPIRP NNFVSIRRSN QPGNLYIDRI EFIPIDPIRE  600
AEHDLERAQK                                                        610

SEQ ID NO: 89              moltype = AA   length = 608
FEATURE                    Location/Qualifiers
REGION                     1..608
                           note = Synthetic
source                     1..608
                           mol_type = protein
                           organism = synthetic construct
SEQUENCE: 89
MPINNQNQCI PYNCLSNPEE VFLDGERILP DIDPLEVSLS LLQFLLNNFV PGGGFISGLL   60
DKIWGALRPS DWELFLEQIE QLINERIAEF ARNAAIANLE GLGNNFNIYV EAFKEWEEDP  120
NNPETRTRVI DRFRILDGLL ERDIPSFRIS GFEVPLLSVY AQAANLHLAL LRDSVVFGER  180
WGLTTTNVND IYNRQVNRIG EYSKHCVDTY KTELERLGFR SIAQWRIYNQ FRRELTLTVL  240
DIVAVFPNYD SRLYPIRTIS QLTREIYTSP VSEFYYGVIN SNNIIGTLTE QQIRRPHLMD  300
FFNSMIMYTS DNRREHYWSG LEMTATNTEG HQRSFPLAGT IGNSAPPVTV RNNGEGIYRI  360
LSEPFYSAPF LGTSVLGSRG EEFAFASNTT TSLPSTIYRN RGTVDSLVSI PPQDYSVPPH  420
RGYSHLLSHV TMRNSSPIFH WIHRSATPRN TIDPDSITQI PLVKAHTLQS GTTVVRGPGF  480
TGGDILRRTS GGPFAYTIVN INGQLPQRYR ARIRYASTTN LRIYVTVAGE RIFAGQFNKT  540
MDTGDPLTFQ SFSYATINTA FTFPMSQSSF TVGADTFSSG NEVYIDRFEL IPVTATFEAE  600
YDLERAQK                                                          608

SEQ ID NO: 90              moltype = AA   length = 610
FEATURE                    Location/Qualifiers
REGION                     1..610
                           note = Synthetic
source                     1..610
                           mol_type = protein
                           organism = synthetic construct
SEQUENCE: 90
MPINNQNQCI PYNCLSNPEE VFLDGERILP DIDPLEVSLS LLQFLLNNFV PGGGFISGLL   60
DKIWGALRPS DWELFLEQIE QLINQRIEEF ARNQAISRLE GLSNLYQIYA ESFREWEADP  120
NNPETRTRVI DRFRILDGLL ERDIPSFRIS GFEVPLLSVY AQAANLHLAL LRDSVVFGER  180
WGLTTTNVND IYNRQVNRIG EYSKHCVDTY KTELERLGFR SIAQWRIYNQ FRRELTLTVL  240
DIVAVFPNYD SRLYPIRTIS QLTREIYTSP VSEFYYGVIN SNNIIGTLTE QQIRRPHLMD  300
FFNSMIMYTS DNRREHYWSG LEMTATNTEG HQRSFPLAGT IGNSAPPVTV RNNGEGIYRI  360
LSEPFYSAPF LGTSVLGSRG EEFAFASNTT TSLPSTIYRN RGTVDSLVSI PPQDYSVPPH  420
RGYSHLLSHV TMRNSSPIFH WIHRSATPRN TIDPDSITQI PAVKGAYIFN SPVITGPGHT  480
GGDIIRFNPN TQNNIRIPFQ SNAVQRYRIR MRYAAEADCI LESGVNIVTG AGVTFRPIPI  540
KATMTPGSPL TYYSFQYADL NINLTAPIRP NNFVSIRRSN QPGNLYIDRI EFIPIDPIRE  600
AEHDLERAQK                                                        610

SEQ ID NO: 91              moltype = AA   length = 610
FEATURE                    Location/Qualifiers
REGION                     1..610
                           note = Synthetic
source                     1..610
                           mol_type = protein
                           organism = synthetic construct
SEQUENCE: 91
MPINNQNQCI PYNCLSNPEE VFLDGERILP DIDPLEVSLS LLQFLLNNFV PGGGFISGLL   60
DKIWGALRPS DWELFLEQIE QLIDRRIERT VRAKAIAELE GLGRSYQLYG EAFKEWEKDP  120
NNPETRTRVI DRFRILDGLL ERDIPSFRIS GFEVPLLSVY AQAANLHLAL LRDSVVFGER  180
WGLTTTNVND IYNRQVNRIG EYSKHCVDTY KTELERLGFR SIAQWRIYNQ FRRELTLTVL  240
DIVAVFPNYD SRLYPIRTIS QLTREIYTSP VSEFYYGVIN SNNIIGTLTE QQIRRPHLMD  300
FFNSMIMYTS DNRREHYWSG LEMTATNTEG HQRSFPLAGT IGNSAPPVTV RNNGEGIYRI  360
LSEPFYSAPF LGTSVLGSRG EEFAFASNTT TSLPSTIYRN RGTVDSLVSI PPQDYSVPPH  420
RGYSHLLSHV TMRNSSPIFH WIHRSATPRN TIDPDSITQI PAVKGAYIFN SPVITGPGHT  480
GGDIIRFNPN TQNNIRIPFQ SNAVQRYRIR MRYAAEADCI LESGVNIVTG AGVTFRPIPI  540
KATMTPGSPL TYYSFQYADL NINLTAPIRP NNFVSIRRSN QPGNLYIDRI EFIPIDPIRE  600
AEHDLERAQK                                                        610
```

```
SEQ ID NO: 92            moltype = AA  length = 610
FEATURE                  Location/Qualifiers
REGION                   1..610
                         note = Synthetic
source                   1..610
                         mol_type = protein
                         organism = synthetic construct
SEQUENCE: 92
MPINNQNQCI PYNCLSNPEE VFLDGERILP DIDPLEVSLS LLQFLLNNFV PGGGFISGLL    60
DKIWGALRPS DWELFLEQIE QLINERIAEF ARNAAIANLE GLGNNFNIYV EAFKEWEEDP   120
NNPETRTRVI DRFRILDGLL ERDIPSFRIS GFEVQLLSVF AQAANLHLSL LRDVVFFGER   180
WGLTTTNVND IYNRQVNRIG EYSKHCVDTY KTELERLGFR SIAQWRIYNQ FRRELTLTVL   240
DIVAVFPNYD SRLYPIRTIS QLTREIYTSP VSEFYYGVIN SNNIIGTLTE QQIRRPHLMD   300
FFNSMIMYTS DNRREHYWSG LEMTATNTEG HQRSFPLAGT IGNSAPPVTV RNNGEGIYRI   360
LSEPFYSAPF LGTSVLGSRG EEFAFASNTT TSLPSTIYRN RGTVDSLVSI PPQDYSVPPH   420
RGYSHLLSHV TMRNSSPIFH WIHRSATPRN TIDDPSITQI PAVKGAYIFN SPVITGPGHT   480
GGDIIRFNPN TQNNIRIPFQ SNAVQRYRIR MRYAAEADCI LESGVNIVTG AGVTFRPIPI   540
KATMTPGSPL TYYSFQYADL NINLTAPIRP NNFVSIRRSN QPGNLYIDRI EFIPIDPIRE   600
AEHDLERAQK                                                         610

SEQ ID NO: 93            moltype = AA  length = 610
FEATURE                  Location/Qualifiers
REGION                   1..610
                         note = Synthetic
source                   1..610
                         mol_type = protein
                         organism = synthetic construct
SEQUENCE: 93
MPINNQNQCI PYNCLSNPEE VFLDGERILP DIDPLEVSLS LLQFLLNNFV PGGGFISGLL    60
DKIWGALRPS DWELFLEQIE QLINERIAEF ARNAAIANLE GLGNNFNIYV EAFKEWEEDP   120
NNPETRTRVI DRFRILDGLL ERDIPSFRIS GFQVPFLSVY VQAANLHLSV LRDVSVFGER   180
WGLTTTNVND IYNRQVNRIG EYSKHCVDTY KTELERLGFR SIAQWRIYNQ FRRELTLTVL   240
DIVAVFPNYD SRLYPIRTIS QLTREIYTSP VSEFYYGVIN SNNIIGTLTE QQIRRPHLMD   300
FFNSMIMYTS DNRREHYWSG LEMTATNTEG HQRSFPLAGT IGNSAPPVTV RNNGEGIYRI   360
LSEPFYSAPF LGTSVLGSRG EEFAFASNTT TSLPSTIYRN RGTVDSLVSI PPQDYSVPPH   420
RGYSHLLSHV TMRNSSPIFH WIHRSATPRN TIDDPSITQI PAVKGAYIFN SPVITGPGHT   480
GGDIIRFNPN TQNNIRIPFQ SNAVQRYRIR MRYAAEADCI LESGVNIVTG AGVTFRPIPI   540
KATMTPGSPL TYYSFQYADL NINLTAPIRP NNFVSIRRSN QPGNLYIDRI EFIPIDPIRE   600
AEHDLERAQK                                                         610

SEQ ID NO: 94            moltype = AA  length = 610
FEATURE                  Location/Qualifiers
REGION                   1..610
                         note = Synthetic
source                   1..610
                         mol_type = protein
                         organism = synthetic construct
SEQUENCE: 94
MPINNQNQCI PYNCLSNPEE VFLDGERILP DIDPLEVSLS LLQFLLNNFV PGGGFISGLL    60
DKIWGALRPS DWELFLEQIE QLINERIAEF ARNAAIANLE GLGNNFNIYV EAFKEWEEDP   120
NNPETRTRVI DRFRILDGLL ERDIPSFRIS GFEVPLLLVY TQAANLHLAL LRDSVVFGER   180
WGLTTTNVND IYNRQVNRIG EYSKHCVDTY KTELERLGFR SIAQWRIYNQ FRRELTLTVL   240
DIVAVFPNYD SRLYPIRTIS QLTREIYTSP VSEFYYGVIN SNNIIGTLTE QQIRRPHLMD   300
FFNSMIMYTS DNRREHYWSG LEMTATNTEG HQRSFPLAGT IGNSAPPVTV RNNGEGIYRI   360
LSEPFYSAPF LGTSVLGSRG EEFAFASNTT TSLPSTIYRN RGTVDSLVSI PPQDYSVPPH   420
RGYSHLLSHV TMRNSSPIFH WIHRSATPRN TIDDPSITQI PAVKGAYIFN SPVITGPGHT   480
GGDIIRFNPN TQNNIRIPFQ SNAVQRYRIR MRYAAEADCI LESGVNIVTG AGVTFRPIPI   540
KATMTPGSPL TYYSFQYADL NINLTAPIRP NNFVSIRRSN QPGNLYIDRI EFIPIDPIRE   600
AEHDLERAQK                                                         610

SEQ ID NO: 95            moltype = AA  length = 610
FEATURE                  Location/Qualifiers
REGION                   1..610
                         note = Synthetic
source                   1..610
                         mol_type = protein
                         organism = synthetic construct
SEQUENCE: 95
MPINNQNQCI PYNCLSNPEE VFLDGERILP DIDPLEVSLS LLQFLLNNFV PGGGFISGLL    60
DKIWGALRPS DWELFLEQIE QLINERIAEF ARNAAIANLE GLGNNFNIYV EAFKEWEEDP   120
NNPETRTRVI DRFRILDGLL ERDIPSFRIS GFEVPLLSVY TQAANLHLAL LRDSVIFGER   180
WGLTTTNVND IYNRQVNRIG EYSKHCVDTY KTELERLGFR SIAQWRIYNQ FRRELTLTVL   240
DIVAVFPNYD SRLYPIRTIS QLTREIYTSP VSEFYYGVIN SNNIIGTLTE QQIRRPHLMD   300
FFNSMIMYTS DNRREHYWSG LEMTATNTEG HQRSFPLAGT IGNSAPPVTV RNNGEGIYRI   360
LSEPFYSAPF LGTSVLGSRG EEFAFASNTT TSLPSTIYRN RGTVDSLVSI PPQDYSVPPH   420
RGYSHLLSHV TMRNSSPIFH WIHRSATPRN TIDDPSITQI PAVKGAYIFN SPVITGPGHT   480
GGDIIRFNPN TQNNIRIPFQ SNAVQRYRIR MRYAAEADCI LESGVNIVTG AGVTFRPIPI   540
KATMTPGSPL TYYSFQYADL NINLTAPIRP NNFVSIRRSN QPGNLYIDRI EFIPIDPIRE   600
```

```
AEHDLERAQK                                                                   610

SEQ ID NO: 97              moltype = AA  length = 612
FEATURE                    Location/Qualifiers
REGION                     1..612
                           note = Synthetic
source                     1..612
                           mol_type = protein
                           organism = synthetic construct
SEQUENCE: 96
MPSNEHDYLK VCDDLSETNM ERFDKNDALE IGMSIVSELL GMIPGGAALQ FVFNQLWSRL    60
GDSGWSAFME HVEELIDTKI EGYAKNKALS ELAGMHRNLE TYIKLLNEWE NNTGSSKAQG   120
RVANYFESLE QAVERGMPQF AVGNFEIPLL TVYVQAANLH LLLLRDVSVY GKRWGWSDQK   180
IKIYYEKQVK YTHEYTNHCS TWYNRGLDKL KNKGSSYQDW YNYNRFRREI TLTVLDIVAV   240
FPHYDVKAYP IQTVGQLTRE VYTDPLINFN PQLQSVAQLP TFNVMESNAI RNPHLVDFLN   300
NLRIFTDWFS VGRHYYWGGH RVISKRVGGR EITFPIYGRE AKQEPPRSFT FNGPVFRTLS   360
NPTLRPLQQP APAPPFNLRG LEGVKFYTPT NTFTYRGRGP RDSLTELPPG DTSVLPREGY   420
SHRLCHATFV QRSGTPFLTT GPVFSWTHRS ATDRNIIYPD VINQIPLVKA FNLTSGTSVV   480
RGPGFTGGDI IRTNVNGSVL SMSLNFSNTT LQRYRVRVRY AASQTMVMSV TVGGSTTGNQ   540
GFPSTMSANG ALTSQSFRFA EFPVGISASG SQGASISISN NVGRQMFHLD RIEFLPVTST   600
FEEEYDLERA QE                                                      612

SEQ ID NO: 97              moltype = AA  length = 612
FEATURE                    Location/Qualifiers
REGION                     1..612
                           note = Synthetic
source                     1..612
                           mol_type = protein
                           organism = synthetic construct
SEQUENCE: 97
MPSNEHDYLK VCDDLSETNM ERFDKNDALE IGMSIVSELL GMIPGGAALQ FVFNQLWSRL    60
GDSGWSAFME HVEELIDTKI EGYAKNKALS ELAGMHRNLE TYIKLLNEWE NNTGSSKAQG   120
RVANYFESLE QAVERGMPQF AVGNFEIPLL TVYVQAANLH LLLLRDVSVY GKRWGWSDQK   180
IKIYYEKQVK YTHEYTNHCS TWYNRGLDKL KNKGSSYQDW YNYNRFRREI TLTVLDIVAV   240
FPHYDVKAYP IQTVGQLTRE VYTDPLINFN PQLQSVAQLP TFNVMESNAI RNPHLVDFLN   300
NLRIFTDWFS VGRHYYWGGH RVISKRVGGR EITFPIYGRE AKQEPPRSFT FNGPVFRTLS   360
NPTLRPLQQP APAPPFNLRG LEGVKFYTPT NTFTYRGRGP RDSLTELPPG DTSVLPREGY   420
SHRLCHATFI QRSGTPFLTT GVVFSWTHRS ATDRNIIYPD VINQIPLVKA FNLTSGTSVV   480
RGPGFTGGDI IRTNVNGSVL SMSLNFSNTT LQRYRVRVRY AASQTMVMSV TVGGSTTGNQ   540
GFPSTMSANG ALTSQSFRFA EFPVGISASG SQGASISISN NVGRQMFHLD RIEFLPVTST   600
FEEEYDLERA QE                                                      612

SEQ ID NO: 98              moltype = AA  length = 608
FEATURE                    Location/Qualifiers
REGION                     1..608
                           note = Synthetic
source                     1..608
                           mol_type = protein
                           organism = synthetic construct
SEQUENCE: 98
MPSNEHDYLK VCDDLSETNM ERFDKNDALE IGMSIVSELL GMIPGGAALQ FVFNQLWSRL    60
GDSGWSAFME HVEELIDTKI EGYAKNKALS ELAGMHRNLE TYIKLLNEWE NNTGSSKAQG   120
RVANYFESLE QAVERGMPQF AVGNFEIPLL TVYVQAANLH LLLLRDVSVY GKRWGWSDQK   180
IKIYYEKQVK YTHEYTNHCS TWYNRGLDKL KNKGSSYQDW YNYNRFRREI TLTVLDIVAV   240
FPHYDVKAYP IQTVGQLTRE VYTDPLINFN PQLQSVAQLP TFNVMESNAI RNPHLVDFLN   300
NLRIFTDWFS VGRHYYWGGH RVISKRVGGR EITFPIYGRE AKQEPPRSFT FNGPVFRTLS   360
NPTLRPLQQP APAPPFNLRG LEGVKFYTPT NTFTYRGRGP RDSLTELPPG DTSVLPREGY   420
SHRLCHATFI QRSGTPFLTT GVVFSWTHRS ASPTNEVSPS RITQIPWVKA HTLASGASVI   480
KGPGFTGGDI LTRNSMGELG TLRVTFTGRL PQSYYIRFRY ASVANRSGTF RYSQPPSYGI   540
SFPKTMDAGE PLTSRSFAHT TLFTPITFSR AQEEFDLYIQ SGVYIDRIEF IPVTATFEAE   600
YDLERAQK                                                           608

SEQ ID NO: 99              moltype = AA  length = 612
FEATURE                    Location/Qualifiers
REGION                     1..612
                           note = Synthetic
source                     1..612
                           mol_type = protein
                           organism = synthetic construct
SEQUENCE: 99
MPSNEHDYLK VCDDLSETNM ERFDKNDALE IGMSIVSELL GMIPGGAALQ FVFNQLWSRL    60
GDSGWSAFME HVEELIDTKI EGYAKNKALS ELAGMHRNLE TYIKLLNEWE NNTGSSKAQG   120
RVANYFESLE QAVERGMPQF AVGNFEIPLL TVYVQAANLH LLLLRDVSVY GKRWGWSDQK   180
IKIYYEKQVK YTHEYTNHCS TWYNRGLDKL KNKGSSYQDW YNYNRFRREI TLTVLDIVAV   240
FPHYDVKAYP IQTVGQLTRE VYTDPLINFN PQLQSVAQLP TFNVMESNAI RNPHLVDFLN   300
NLRIFTDWFS VGRHYYWGGH RVISKRVGGR EITFPIYGRE AKQEPPRSFT FNGPVFRTLS   360
NPTLRPLQQP APAPPFNLRG LEGVKFYTPT NTFTYRGRGP RDSLTELPPG DTSVLPREGY   420
SHRLCHATFI QRSGTPFLTT GVVFSWTHRS ADETNIIYPD KITQIPLVKS FNLNSGTSVV   480
SGPGFTGGDI IRTNVNGSVL SMGLNFNNTS LQRYRVRVRY AASQTMVLRV TVGGSTTFDQ   540
```

```
GFPSTMSANE SLTSQSFRFA EFPVGISASG SQTAGISISN NAGRQTFHFD KIEFIPITAT  600
FEAEYDLERA QE                                                     612

SEQ ID NO: 100           moltype = AA  length = 614
FEATURE                  Location/Qualifiers
REGION                   1..614
                         note = Synthetic
source                   1..614
                         mol_type = protein
                         organism = synthetic construct
SEQUENCE: 100
MGRGSMEVNN QNQCVPYNCL NNPEIEILGG ERISVGNTPI DISLSLTQFL LSEFVPGAGF  60
VLGLIDLIWG FLGPSQWDAF LLQIEQLINQ RIEEFARNQA ISRLEGLSNL YQIYAESFRE  120
WEADPTNPAL REEMRIQFND MNSALTTAIP LLAVQNYQVP LLSVYVQAAN LHLSVLRDVS  180
VFGQRWGFDV ATINSRYNDL TRLIGEYTDY AVRWYNTGLD RLRGSNFQDW IRYNRFRREL  240
TLTVLDIVSV FQNYDSRLYP IQTSSQLTRE IYSDLLLANP SGVGSFSNVD FDSILIRQPH  300
LIDFMRVLTI YTDRHNASRH NIYWAGHQVT AVDTANRTIV YPVNGSAANL EPPRTLRFES  360
PVVEIRSNPV WDRGSTGIAG SYEFFGVTSA LFITILGFGY TYRSGSNTEV TALPDHQVSH  420
IGYFRRFTTT GATARQTLTS APIVSWTHSS AEPPNRIYQN RITQIPAVKG NPLFNGAVIS  480
GPGFTGGDLV RLNRNNDNIQ NRGYIEVPIQ FASTSTRYRV RVRYASTNAI EVNINWGNGS  540
IFTGTAPATA TSLDNLQSND FGYFESTTAF APSLGNIVGV RNFSANADVI IDRFEFIPVT  600
ATLEAEYDLE RAEK                                                   614

SEQ ID NO: 101           moltype = AA  length = 612
FEATURE                  Location/Qualifiers
REGION                   1..612
                         note = Synthetic
source                   1..612
                         mol_type = protein
                         organism = synthetic construct
SEQUENCE: 101
MGRGSMEVNN QNQCVPYNCL NNPEIEILGG ERISVGNTPI DISLSLTQFL LSEFVPGAGF  60
VLGLIDLIWG FLGPSQWDAF LLQIEQLINQ RIEEFARNQA ISRLEGLSNL YQIYAESFRE  120
WEADPTNPAL REEMRIQFND MNSALTTAIP LLAVQNYQVP LLSVYVQAAN LHLSVLRDVS  180
VFGQRWGFDV ATINSRYNDL TRLIGEYTDY AVRWYNTGLD RLRGSNFQDW IRYNRFRREL  240
TLTVLDIVSV FQNYDSRLYP IQTSSQLTRE IYSDLLLANP SGVGSFSNVD FDSILIRQPH  300
LIDFMRVLTI YTDRHNASRH NIYWAGHQVT AVDTANRTIV YPVNGSAANL EPPRTLRFES  360
PVVEIRSNPV WDRGSTGIAG SYEFFGVTSA LFITILGFGY TYRSGSNTEV TALPDHQVSH  420
IGYFRRFTTT GATARQTLTS APIVSWTHSS AEPPNRIYQN RITQIPLVKA LNLHSGVTVV  480
GGPGFTGGDI LRRTNTGTFG DIRLNINVPL SQRYRVRIRY ASTTDLQFFT RINGTTVNIG  540
NFSRTMNRGD NLEYRSFRTA GFSTPFNFLN AQSTFTLGAQ SFSNQEVYID RVEFVPAEVT  600
FEAEYDLERA QK                                                     612

SEQ ID NO: 102           moltype = AA  length = 612
FEATURE                  Location/Qualifiers
REGION                   1..612
                         note = Synthetic
source                   1..612
                         mol_type = protein
                         organism = synthetic construct
SEQUENCE: 102
MGRGSMEVNN QNQCVPYNCL NNPEIEILGG ERISVGNTPI DISLSLTQFL LSEFVPGAGF  60
VLGLIDLIWG FLGPSQWDAF LLQIEQLINQ RIEEFARNQA ISRLEGLSNL YQIYAESFRE  120
WEADPTNPAL REEMRIQFND MNSALTTAIP LLAVQNYQVP LLSVYVQAAN LHLSVLRDVS  180
VFGQRWGFDV ATINSRYNDL TRLIGEYTDY AVRWYNTGLD RLRGSNFQDW IRYNRFRREL  240
TLTVLDIVSV FQNYDSRLYP IQTSSQLTRE IYSDLLLANP SGVGSFSNVD FDSILIRQPH  300
LIDFMRVLTI YTDRHNASRH NIYWAGHQVT AVDTANRTIV YPVNGSAANL EPPRTLRFES  360
PVVEIRSNPV WDRGSTGIAG SYEFFGVTSA LFITILGFGY TYRSGSNTEV TALPDHQVSH  420
IGYFRRFTTT GATARQTLTS APIVSWTHSS ATDRNIIYPD VINQIPLVKA FNLTSGTSVV  480
RGPGFTGGDI IRTNVNGSVL SMSLNFSNTT LQRYRVRVRY AASQTMVMSV TVGGSTTGNQ  540
GFPSTMSANG ALTSQSFRFA EFPVGISASG SQGASISISN NVGRQMFHLD RIEFLPVTST  600
FEEEYDLERA QE                                                     612

SEQ ID NO: 103           moltype = AA  length = 612
FEATURE                  Location/Qualifiers
REGION                   1..612
                         note = Synthetic
source                   1..612
                         mol_type = protein
                         organism = synthetic construct
SEQUENCE: 103
MGRGSMEVNN QNQCVPYNCL NNPEIEILGG ERISVGNTPI DISLSLTQFL LSEFVPGAGF  60
VLGLIDLIWG FLGPSQWDAF LLQIEQLINQ RIEEFARNQA ISRLEGLSNL YQIYAESFRE  120
WEADPTNPAL REEMRIQFND MNSALTTAIP LLAVQNYQVP LLSVYVQAAN LHLSVLRDVS  180
VFGQRWGFDV ATINSRYNDL TRLIGEYTDY AVRWYNTGLD RLRGSNFQDW IRYNRFRREL  240
TLTVLDIVSV FQNYDSRLYP IQTSSQLTRE IYSDLLLANP SGVGSFSNVD FDSILIRQPH  300
LIDFMRVLTI YTDRHNASRH NIYWAGHQVT AVDTANRTIV YPVNGSAANL EPPRTLRFES  360
PVVEIRSNPV WDRGSTGIAG SYEFFGVTSA LFITILGFGY TYRSGSNTEV TALPDHQVSH  420
IGYFRRFTTT GATARQTLTS APIVSWTHSS AEPPNRIYQN RITQIPLVKA FNLTSGTSVV  480
```

```
RGPGFTGGDI IRTNVNGSVL SMSLNFSNTT LQRYRVRVRY AASQTMVMSV TVGGSTTGNQ    540
GFPSTMSANG ALTSQSFRFA EFPVGISASG SQGASISISN NVGRQMFHLD RIEFLPVTST    600
FEEEYDLERA QE                                                       612

SEQ ID NO: 104           moltype = AA   length = 608
FEATURE                  Location/Qualifiers
REGION                   1..608
                         note = Synthetic
source                   1..608
                         mol_type = protein
                         organism = synthetic construct
SEQUENCE: 104
MGRGSMEVNN QNQCVPYNCL NNPEIEILGG ERISVGNTPI DISLSLTQFL LSEFVPGAGF    60
VLGLIDLIWG FLGPSQWDAF LLQIEQLINQ RIEEFARNQA ISRLEGLSNL YQIYAESFRE    120
WEADPTNPAL REEMRIQFND MNSALTTAIP LLAVQNYQVP LLSVYVQAAN LHLSVLRDVS    180
VFGQRWGFDV ATINSRYNDL TRLIGEYTDY AVRWYNTGLD RLRGSNFQDW IRYNRFRREL    240
TLTVLDIVSV FQNYDSRLYP IQTSSQLTRE IYSDLLLANP SGVGSFSNVD FDSILIRQPH    300
LIDFMRVLTI YTDRHNASRH NIYWAGHQVT AVDTANRTIV YPVNGSAANL FDSILIRFES    360
PVVEIRSNPV WDRGSTGIAG SYEFFGVTSA LFITILGFGY TYRSGSNTEV TALPDHQVSH    420
IGYFRRFTTT GATARQTLTS APIVSWTHSS AEPPNRIYQN RITQIPWVKA HTLASGASVI    480
KGPGFTGGDI LTRNSMGELG TLRVTFTGRL PQSYYIRFRY ASVANRSGTF RYSQPPSYGI    540
SFPKTMDAGE PLTSRSFAHT TLFTPITFSR AQEEFDLYIQ SGVYIDRIEF IPVTATFEAE    600
YDLERAQK                                                            608

SEQ ID NO: 105           moltype = AA   length = 612
FEATURE                  Location/Qualifiers
REGION                   1..612
                         note = Synthetic
source                   1..612
                         mol_type = protein
                         organism = synthetic construct
SEQUENCE: 105
MGRGSMEVNN QNQCVPYNCL NNPEIEILGG ERISVGNTPI DISLSLTQFL LSEFVPGAGF    60
VLGLIDLIWG FLGPSQWDAF LLQIEQLINQ RIEEFARNQA ISRLEGLSNL YQIYAESFRE    120
WEADPTNPAL REEMRIQFND MNSALTTAIP LLAVQNYQVP LLSVYVQAAN LHLSVLRDVS    180
VFGQRWGFDV ATINSRYNDL TRLIGEYTDY AVRWYNTGLD RLRGSNFQDW IRYNRFRREL    240
TLTVLDIVSV FQNYDSRLYP IQTSSQLTRE IYSDLLLANP SGVGSFSNVD FDSILIRQPH    300
LIDFMRVLTI YTDRHNASRH NIYWAGHQVT AVDTANRTIV YPVNGSAANL EPPRTLRFES    360
PVVEIRSNPV WDRGSTGIAG SYEFFGVTSA LFITILGFGY TYRSGSNTEV TALPDHQVSH    420
IGYFRRFTTT GATARQTLTS APIVSWTHSS ATTTNTINPN AIIQIPLVKA FNLHSGATVV    480
RGPGFTGGDI LRRTNTGTFA DMRVNITGPL SQRYRVRIRY ASTTDLQFFT RINGTSVNQG    540
NFQRTMNRGD NLESGNFRTA GFSTPFSFSN AQSTFTLGTQ AFSNQEVYID RIEFVPAEVT    600
FEAESDLERA QK                                                       612

SEQ ID NO: 106           moltype = AA   length = 612
FEATURE                  Location/Qualifiers
REGION                   1..612
                         note = Synthetic
source                   1..612
                         mol_type = protein
                         organism = synthetic construct
SEQUENCE: 106
MGRGSMEVNN QNQCVPYNCL NNPEIEILGG ERISVGNTPI DISLSLTQFL LSEFVPGAGF    60
VLGLIDLIWG FLGPSQWDAF LLQIEQLINQ RIEEFARNQA ISRLEGLSNL YQIYAESFRE    120
WEADPTNPAL REEMRIQFND MNSALTTAIP LLAVQNYQVP LLSVYVQAAN LHLSVLRDVS    180
VFGQRWGFDV ATINSRYNDL TRLIGEYTDY AVRWYNTGLD RLRGSNFQDW IRYNRFRREL    240
TLTVLDIVSV FQNYDSRLYP IQTSSQLTRE IYSDLLLANP SGVGSFSNVD FDSILIRQPH    300
LIDFMRVLTI YTDRHNASRH NIYWAGHQVT AVDTANRTIV YPVNGSAANL EPPRTLRFES    360
PVVEIRSNPV WDRGSTGIAG SYEFFGVTSA LFITILGFGY TYRSGSNTEV TALPDHQVSH    420
IGYFRRFTTT GATARQTLTS APIVSWTHSS AEPPNRIYQN RITQIPLVKA FNLHSGATVV    480
RGPGFTGGDI LRRTNTGTFA DMRVNITGPL SQRYRVRIRY ASTTDLQFFT RINGTSVNQG    540
NFQRTMNRGD NLESGNFRTA GFSTPFSFSN AQSTFTLGTQ AFSNQEVYID RIEFVPAEVT    600
FEAESDLERA QK                                                       612

SEQ ID NO: 107           moltype = AA   length = 614
FEATURE                  Location/Qualifiers
REGION                   1..614
                         note = Synthetic
source                   1..614
                         mol_type = protein
                         organism = synthetic construct
SEQUENCE: 107
MGRGSMEVNN QNQCVPYNCL NNPEIEILGG ERISVGNTPI DISLSLTQFL LSEFVPGAGF    60
VLGLIDLIWG FLGPSQWDAF LLQIEQLINQ RIEEFARNQA ISRLEGLSNL YQIYAESFRE    120
WEADPTNPAL REEMRIQFND MNSALTTAIP LLAVQNYQVP LLSVYVQAAN LHLSVLRDVS    180
VFGQRWGFDV ATINSRYNDL TRLIGEYTDY AVRWYNTGLD RLRGSNFQDW IRYNRFRREL    240
TLTVLDIVSV FQNYDSRLYP IQTSSQLTRE IYSDLLLANP SGVGSFSNVD FDSILIRQPH    300
LIDFMRVLTI YTDRHNASRH NIYWAGHQVT AVDTANRTIV YPVNGSAANL EPPRTLRFES    360
PVVEIRSNPV WDRGSTGIAG SYEFFGVTSA LFITILGFGY TYRSGSNTEV TALPDHQVSH    420
```

-continued

```
IGYFRRFTTT GATARQTLTS APIVSWTHSS ADRTNTIATN IITQIPAVKG NFLFNGSVIS    480
GPGFTGGDLV RLNNSGNNIQ NRGYLEVPIQ FISTSTRYRV RVRYASVTPI QLSVNWGNSN    540
IFSSIVPATA TSLDNLQSRD FGYFESTNAF TSATGNVVGV RNFSENAGVI IDRFEFIPVT    600
ATFEAEYDLE RAQE                                                     614

SEQ ID NO: 108         moltype = AA   length = 614
FEATURE                Location/Qualifiers
REGION                 1..614
                       note = Synthetic
source                 1..614
                       mol_type = protein
                       organism = synthetic construct
SEQUENCE: 108
MGRGSMEVNN QNQCVPYNCL NNPEIEILGG ERISVGNTPI DISLSLTQFL LSEFVPGAGF    60
VLGLIDLIWG FLGPSQWDAF LLQIEQLINQ RIEEFARNQA ISRLEGLSNL YQIYAESFRE   120
WEADPTNPAL REEMRIQFND MNSALTTAIP LLAVQNYQVP LLSVYVQAAN LHLSVLRDVS   180
VFGQRWGFDV ATINSRYNDL TRLIGEYTDY AVRWYNTGLD RLRGSNFQDW IRYNRFRREL   240
TLTVLDIVSV FQNYDSRLYP IQTSSQLTRE IYSDLLLANP SGVGSFSNVD FDSILIRQPH   300
LIDFMRVLTI YTDRHNASRH NIYWAGHQVT AVDTANRTIV YPVNGSAANL EPPRTLRFES   360
PVVEIRSNPV WDRGSTGIAG SYEFFGVTSA LFITILGFGY TYRSGSNTEV TALPDHQVSH   420
IGYFRRFTTT GATARQTLTS APIVSWTHSS AEPPNRIYQN RITQIPAVKG NFLFNGSVIS   480
GPGFTGGDLV RLNNSGNNIQ NRGYLEVPIQ FISTSTRYRV RVRYASVTPI QLSVNWGNSN   540
IFSSIVPATA TSLDNLQSRD FGYFESTNAF TSATGNVVGV RNFSENAGVI IDRFEFIPVT   600
ATFEAEYDLE RAQE                                                    614

SEQ ID NO: 109         moltype = AA   length = 614
FEATURE                Location/Qualifiers
REGION                 1..614
                       note = Synthetic
source                 1..614
                       mol_type = protein
                       organism = synthetic construct
SEQUENCE: 109
MGRGSMEVNN QNQCVPYNCL NNPEIEILGG ERISVGNTPI DISLSLTQFL LSEFVPGAGF    60
VLGLIDLIWG FLGPSQWDAF LLQIEQLINQ RIEEFARNQA ISRLEGLSNL YQIYAESFRE   120
WEADPTNPAL REEMRIQFND MNSALTTAIP LLAVQNYQVP LLSVYVQAAN LHLSVLRDVS   180
VFGQRWGFDV ATINSRYNDL TRLIGEYTDY AVRWYNTGLD RLRGSNFQDW IRYNRFRREL   240
TLTVLDIVSV FQNYDSRLYP IQTSSQLTRE IYSDLLLANP SGVGSFSNVD FDSILIRQPH   300
LIDFMRVLTI YTDRHNASRH NIYWAGHQVT AVDTANRTIV YPVNGSAANL EPPRTLRFES   360
PVVEIRSNPV WDRGSTGIAG SYEFFGVTSA LFITILGFGY TYRSGSNTEV TALPDHQVSH   420
IGYFRRFTTT GATARQTLTS APIVSWTHSS AEPPNRIYQN RITQIPAVKG NFLFNGAVIS   480
GPGFTGGDLV RLNNSGNNIQ NRGYLEVPIQ FISTSTRYRV RVRYASVTPI QLSVNWGNSN   540
IFSSIVPATA TSLDNLQSRD FGYFESTNAF TSATGNVVGV RNFSENAGVI IDRFEFIPVT   600
ATFEAEYDLE RAQE                                                    614

SEQ ID NO: 110         moltype = AA   length = 614
FEATURE                Location/Qualifiers
REGION                 1..614
                       note = Synthetic
source                 1..614
                       mol_type = protein
                       organism = synthetic construct
SEQUENCE: 110
MGRGSMEVNN QNQCVPYNCL NNPEIEILGG ERISVGNTPI DISLSLTQFL LSEFVPGAGF    60
VLGLIDLIWG FLGPSQWDAF LLQIEQLINQ RIEEFARNQA ISRLEGLSNL YQIYAESFRE   120
WEADPTNPAL REEMRIQFND MNSALTTAIP LLAVQNYQVP LLSVYVQAAN LHLSVLRDVS   180
VFGQRWGFDV ATINSRYNDL TRLIGEYTDY AVRWYNTGLD RLRGSNFQDW IRYNRFRREL   240
TLTVLDIVSV FQNYDSRLYP IQTSSQLTRE IYSDLLLANP SGVGSFSNVD FDSILIRQPH   300
LIDFMRVLTI YTDRHNASRH NIYWAGHQVT AVDTANRTIV YPVNGSAANL EPPRTLRFES   360
PVVEIRSNPV WDRGSTGIAG SYEFFGVTSA LFITILGFGY TYRSGSNTEV TALPDHQVSH   420
IGYFRRFTTT GATARQTLTS APIVSWTHSS AEPPNRIYQN RITQIPAVKG NFLFNGAVIS   480
GPGFTGGDLV RLNRNNDNIQ NRGYIEVPIQ FASTSTRYRV RVRYASTTPI QLSVNWGNSN   540
IFSSIVPATA TSLDNLQSRD FGYFESTNAF TSATGNVVGV RNFSENAGVI IDRFEFIPVT   600
ATFEAEYDLE RAQE                                                    614

SEQ ID NO: 111         moltype = AA   length = 612
FEATURE                Location/Qualifiers
REGION                 1..612
                       note = Synthetic
source                 1..612
                       mol_type = protein
                       organism = synthetic construct
SEQUENCE: 111
MGRGSMEVNN QNQCVPYNCL NNPEIEILGG ERISVGNTPI DISLSLTQFL LSEFVPGAGF    60
VLGLIDLIWG FLGPSQWDAF LLQIEQLINQ RIEEFARNQA ISRLEGLSNL YQIYAESFRE   120
WEADPTNPAL REEMRIQFND MNSALTTAIP LLAVQNYQVP LLSVYVQAAN LHLSVLRDVS   180
VFGQRWGFDV ATINSRYNDL TRLIGEYTDY AVRWYNTGLD RLRGSNFQDW IRYNRFRREL   240
TLTVLDIVSV FQNYDSRLYP IQTSSQLTRE IYSDLLLANP SGVGSFSNVD FDSILIRQPH   300
LIDFMRVLTI YTDRHNASRH NIYWAGHQVT AVDTANRTIV YPVNGSAANL EPPRTLRFES   360
```

```
PVVEIRSNPV WDRGSTGIAG SYEFFGVTSA LFITILGFGY TYRSGSNTEV TALPDHQVSH    420
IGYFRRFTTT GATARQTLTS APIVSWTHSS AEPPNRIYQN RITQIPLVKA LNLHSGVTVV    480
GGPGFTGGDI LRRTNTGTFG DIRLNINVPL SQRYRVRIRY ASTTDLQFFT RINGTTVNIG    540
NFSRTMNRGD NLEYRSFRTA GFSTPFNFLN AQSTFTLGAQ SFSNQEVYID RVEFVPAEVT    600
FEAEYDLERA QK                                                       612

SEQ ID NO: 112            moltype = AA   length = 609
FEATURE                   Location/Qualifiers
REGION                    1..609
                          note = Synthetic
source                    1..609
                          mol_type = protein
                          organism = synthetic construct
SEQUENCE: 112
MPSNEHDYLK VCDDLSETNM ERFDKNDALE IGMSIVSELL GMIPGGAALQ FVFNQLWSRL     60
GDSGWSAFME HVEELIDTKI EGYAKNKALS ELAGMHRNLE TYIKLLNEWE NNTGSSKAQG    120
RVANYFESLE QAVERGMPQF AVGNFEIPLL TVYVQAANLH LLLLRDVSVY GKRWGWSDQK    180
IKIYYEKQVK YTHEYTNHCS TWYNRGLDKL KNKGSSYQDW YNYNRFRREI TLTVLDIVAV    240
FPHYDVKAYP IQTVGQLTRE VYTDPLINFN PQLQSVAQLP TFNVMESNAI RNPHLVDFLN    300
NLRIFTDWFS VGRHYYWGGH RVISKRVGGR EITFPIYGRE AKQEPPRSFT FNGPVFRTLS    360
NPTLRPLQQP APAPPFNLRG LEGVKFYTPT NTFTYRGRGP RDSLTELPPG DTSVLPREGY    420
SHRLCHATFI QRSGTPFLTT GVVFSWTHRS ADETNIIYPD KITQIPWVKA HTLESGATVI    480
KGPGFTGGDI LTVLTSLGSL GALRVTFTGQ LPQTYNIRIR YASVLNKYGT LHFSQPPAYG    540
LTFPKTMDID EPLTSRSFAF TTLWTPITFT RAQEEFNLTI QSGVYIDRIE FVPAEVTFEA    600
DYDLEKAQK                                                           609

SEQ ID NO: 113            moltype = DNA   length = 840
FEATURE                   Location/Qualifiers
misc_feature              1..840
                          note = Synthetic
source                    1..840
                          mol_type = other DNA
                          organism = synthetic construct
SEQUENCE: 113
gggatcgagg gaaggatttc agaattaggc atggaaatcg ttaataacca gaaccagtgc     60
gttccgtaca actgtctgaa caaccctgaa aacgaaatcc tggatatcga acgttccaac    120
tccacggtgg ccaccaacat cgctctggaa atttcccgcc tgctggcaag cgccactcca    180
attggtggta ttctgctggg cctgttcgac gccatttggg ttctatcgg cccgtctcaa    240
tgggacctgt ttctggaaca gatcgaacag ctgattaacc aacgtatcga agaattcgcg    300
cgtaaccagg caatctcccg tctggaaggt ctgtccaacc tgtaccagat ctacgcagag    360
tccttccgtg aatgggaagc tgatccgacc aacccggcac tgcgcgaaga aatgcgtatc    420
cagttcaacg acatgaactc tgctctgacg acggccatcc tctgctggc tgtgcagaat    480
tatcaggtac cgctgctgtc tgtgtacgtg caggcggcga acctgcatct gtccgtactg    540
cgtgacgtgt ctgttttcgg ccaggcgtgg ggtttcgaca ttgccactat caactctcgt    600
tacaatgacc tgacccgtct gatcccgatc tatacggact acgctgttcg ttggtacaac    660
actggtctga tcgtctgcc acgtaccggc ggtctgcgca attgggctcg tttcaaccag    720
ttccgtcgtg agctgactat ctctgtgctg gacatcatta gcttcttccg caactatgac    780
tctcgcctgt atccaatccc aaccagcagc cagctgacgc gtgaagtgta tactgaccct    840

SEQ ID NO: 114            moltype = DNA   length = 840
FEATURE                   Location/Qualifiers
misc_feature              1..840
                          note = Synthetic
source                    1..840
                          mol_type = other DNA
                          organism = synthetic construct
SEQUENCE: 114
gggatcgagg gaaggatttc agaattaggc atggaaatcg ttaataacca gaaccagtgc     60
gttccgtaca actgtctgaa caaccctgaa aacgaaatcc tggatatcga acgttccaac    120
tccacggtgg ccaccaacat cgctctggaa atttcccgcc tgctggcaag cgccactcca    180
attggtggta ttctgctggg cctgttcgac gccatttggg ttctatcgg cccgtctcaa    240
tgggacctgt ttctggaaca gatcgaacag ctgattaacc aacgtatcga agaattcgcg    300
cgtaaccagg caatttcacg cctggaaggt ctgagtaacc tttaccagat ttatgctgaa    360
tcgttccggg aatgggaagc agaccctacc aacccggcac ttcgtgagga aatgcgcatc    420
cagttcaatg atatgaatag cgcgctgaca actgctatcc cacttttcgc cgttcagaat    480
tatcaagtgc cgctgctgtc tgtttacgtc caggccgcga acctgcatct gtccgtactg    540
cgtgacgtgt ctgttttcgg ccaggcgtgg ggtttcgaca ttgccactat caactctcgt    600
tacaatgacc tgacccgtct gatcccgatc tatacggact acgctgttcg ttggtacaac    660
actggtctga tcgtctgcc acgtaccggc ggtctgcgca attgggctcg tttcaaccag    720
ttccgtcgtg agctgactat ctctgtgctg gacatcatta gcttcttccg caactatgac    780
tctcgcctgt atccaatccc aaccagcagc cagctgacgc gtgaagtgta tactgaccct    840

SEQ ID NO: 115            moltype = DNA   length = 840
FEATURE                   Location/Qualifiers
misc_feature              1..840
                          note = Synthetic
source                    1..840
                          mol_type = other DNA
                          organism = synthetic construct
```

```
SEQUENCE: 115
gggatcgagg gaaggatttc agaattaggc atggaaatcg ttaataacca gaaccagtgc    60
gttccgtaca actgtctgaa caaccctgaa aacgaaatcc tggatatcga acgttccaac   120
tccacggtgg ccaccaacat cgctctggaa atttcccgcc tgctggcaag cgccactcca   180
attggtggta ttctgctggg cctgttcgac gccatttggg gttctatcgg cccgtctcaa   240
tgggacctgt ttctggaaca gatcgaacag ctgatcggca agcgtatcga agaattcgca   300
cgcaatcagg ccatttctcg tctgcaaggc ctgtctaacc tgtatcgcat ctacaccaat   360
gctttcaaaa attgggaagt agacccgact aatccggctc tgcgcgaaga aatgcgcatt   420
cagtttaacg atatgaactc cgcgctgacg actgcaattc cgctgttctc tgttcagggt   480
tacgaaatcc cgctgctgtc tgtctacgtt caggccgcga acctgcatct gtccgtactg   540
cgtgacgtgt ctgttttcgg ccaggcgtgg ggtttcgaca ttgccactat caactctcgt   600
tacaatgacc tgacccgtct gatcccgatc tatacggact acgctgttcg ttggtacaac   660
actggtctgg atcgtctgcc acgtaccggc ggtctgcgca attgggctcg tttcaaccag   720
ttccgtcgtg agctgactat ctctgtgctg gacatcatta gcttcttccg caactatgac   780
tctcgcctgt atccaatccc aaccagcagc cagctgacgc gtgaagtgta tactgaccct   840

SEQ ID NO: 116           moltype = DNA   length = 840
FEATURE                  Location/Qualifiers
misc_feature             1..840
                         note = Synthetic
source                   1..840
                         mol_type = other DNA
                         organism = synthetic construct
SEQUENCE: 116
gggatcgagg gaaggatttc agaattaggc atggaaatcg ttaataacca gaaccagtgc    60
gttccgtaca actgtctgaa caaccctgaa aacgaaatcc tggatatcga acgttccaac   120
tccacggtgg ccaccaacat cgctctggaa atttcccgcc tgctggcaag cgccactcca   180
attggtggta ttctgctggg cctgttcgac gccatttggg gttctatcgg cccgtctcaa   240
tgggacctgt ttctggaaca gatcgaacag ctgattggcc aacgtatcga agaattcgcg   300
cgtaaccagg caatttcacg cctggaaggt ctgagtaacc tttaccggat ttatactaac   360
gcgttcaaga attgggaagc agaccctacc aacctggaac ttaaagagga aatgcgcacc   420
cagttcaatg atatgaatag cgcgtttaca actgctatcc cacttttctc cgttcggggt   480
tatgaactgc cgctgctgtc tgtttacgtc caggccgcga acctgcatct gtccgtactg   540
cgtgacgtgt ctgttttcgg ccaggcgtgg ggtttcgaca ttgccactat caactctcgt   600
tacaatgacc tgacccgtct gatcccgatc tatacggact acgctgttcg ttggtacaac   660
actggtctgg atcgtctgcc acgtaccggc ggtctgcgca attgggctcg tttcaaccag   720
ttccgtcgtg agctgactat ctctgtgctg gacatcatta gcttcttccg caactatgac   780
tctcgcctgt atccaatccc aaccagcagc cagctgacgc gtgaagtgta tactgaccct   840

SEQ ID NO: 117           moltype = DNA   length = 840
FEATURE                  Location/Qualifiers
misc_feature             1..840
                         note = Synthetic
source                   1..840
                         mol_type = other DNA
                         organism = synthetic construct
SEQUENCE: 117
gggatcgagg gaaggatttc agaattaggc atggaaatcg ttaataacca gaaccagtgc    60
gttccgtaca actgtctgaa caaccctgaa aacgaaatcc tggatatcga acgttccaac   120
tccacggtgg ccaccaacat cgctctggaa atttcccgcc tgctggcaag cgccactcca   180
attggtggta ttctgctggg cctgttcgac gccatttggg gttctatcgg cccgtctcaa   240
tgggacctgt ttctggaaca gatcgaacag ctgattggcc aacgtatcga agaattcgcg   300
cgtaaccagg caatttcacg cctggaaggt ctgagtaacc tttaccggat ttatactaac   360
gcgttcaaga actgggaagc agaccctacc aacccggtac ttcgtgagga aatgcgcatc   420
cagttcaatg atatgaatag cgcgtttaca actgctatcc cacttttctc cgttcagggt   480
tatgaaattc cgctgctggg tgtttacgtc caggccgcga acctgcatct gtccgtactg   540
cgtgacgtgt ctgttttcgg ccaggcgtgg ggtttcgaca ttgccactat caactctcgt   600
tacaatgacc tgacccgtct gatcccgatc tatacggact acgctgttcg ttggtacaac   660
actggtctgg atcgtctgcc acgtaccggc ggtctgcgca attgggctcg tttcaaccag   720
ttccgtcgtg agctgactat ctctgtgctg gacatcatta gcttcttccg caactatgac   780
tctcgcctgt atccaatccc aaccagcagc cagctgacgc gtgaagtgta tactgaccct   840

SEQ ID NO: 118           moltype = DNA   length = 840
FEATURE                  Location/Qualifiers
misc_feature             1..840
                         note = Synthetic
source                   1..840
                         mol_type = other DNA
                         organism = synthetic construct
SEQUENCE: 118
gggatcgagg gaaggatttc agaattaggc atggaaatcg ttaataacca gaaccagtgc    60
gttccgtaca actgtctgaa caaccctgaa aacgaaatcc tggatatcga acgttccaac   120
tccacggtgg ccaccaacat cgctctggaa atttcccgcc tgctggcaag cgccactcca   180
attggtggta ttctgctggg cctgttcgac gccatttggg gttctatcgg cccgtctcaa   240
tgggacctgt ttctggaaca gatcgaacag ctgattgacc aaaaaatcgg agaattcgcg   300
cgtaaccagg caatttcacg cctggaagaa attagtagcc tttacgggat ttatactgaa   360
gcgttccggg aatgggaagc agaccctacc aacccggcac ttaaagagga aatgcgcacc   420
cagttcaatg atatgaatag cattctggta actgctatcc cacttttctc cgttcagaat   480
tatcaagtgc cgtttctgtc tgtttacgtc caggccgcga acctgcatct gtccgtactg   540
```

```
cgtgacgtgt ctgttttcgg ccaggcgtgg ggtttcgaca ttgccactat caactctcgt    600
tacaatgacc tgacccgtct gatcccgatc tatacggact acgctgttcg ttggtacaac    660
actggtctgg atcgtctgcc acgtaccggc ggtctgcgca attgggctcg tttcaaccag    720
ttccgtcgtg agctgactat ctctgtgctg gacatcatta gcttcttccg caactatgac    780
tctcgcctgt atccaatccc aaccagcagc cagctgacgc gtgaagtgta tactgaccct    840

SEQ ID NO: 119         moltype = DNA   length = 840
FEATURE                Location/Qualifiers
misc_feature           1..840
                       note = Synthetic
source                 1..840
                       mol_type = other DNA
                       organism = synthetic construct
SEQUENCE: 119
gggatcgagg gaaggatttc agaattaggc atggaaatcg ttaataacca gaaccagtgc     60
gttccgtaca actgtctgaa caaccctgaa acgaaatcc tggatatcga acgttccaac    120
tccacggtgg ccaccaacat cgctctggaa atttcccgcc tgctggcaag cgccactcca    180
attggtggta ttctgctggg cctgttcgac gccatttggg gttctatcgg cccgtctcaa    240
tgggacctgt ttctggaaca gatcgaacag ctgattaacc aacgtatcga agaattcgcg    300
cgtaaccagg caatttcacg cctggaaggt ctgagtaacc tttaccagat ttatgctgaa    360
gcgttccggg aatgggaagc agaccctacc aacccggcac ttactgagga aatgcgcatc    420
cagttcaatg atatgaatag cgcgctgaca actgctatcc acttttcac cgttcagaat    480
tatcaagtgc cgctgctgtc tgtttacgtc caggccgcga acctgcatct gtccgtactg    540
cgtgacgtgt ctgttttcgg ccaggcgtgg ggtttcgaca ttgccactat caactctcgt    600
tacaatgacc tgacccgtct gatcccgatc tatacggact acgctgttcg ttggtacaac    660
actggtctgg atcgtctgcc acgtaccggc ggtctgcgca attgggctcg tttcaaccag    720
ttccgtcgtg agctgactat ctctgtgctg gacatcatta gcttcttccg caactatgac    780
tctcgcctgt atccaatccc aaccagcagc cagctgacgc gtgaagtgta tactgaccct    840

SEQ ID NO: 120         moltype = DNA   length = 840
FEATURE                Location/Qualifiers
misc_feature           1..840
                       note = Synthetic
source                 1..840
                       mol_type = other DNA
                       organism = synthetic construct
SEQUENCE: 120
gggatcgagg gaaggatttc agaattaggc atggaaatcg ttaataacca gaaccagtgc     60
gttccgtaca actgtctgaa caaccctgaa aacgaaatcc tggatatcga acgttccaac    120
tccacggtgg ccaccaacat cgctctggaa atttcccgcc tgctggcaag cgccactcca    180
attggtggta ttctgctggg cctgttcgac gccatttggg gttctatcgg cccgtctcaa    240
tgggacctgt ttctggaaca gatcgaacag ctgattagcc aacgtatcga agaattcgcg    300
cgtaaccagg caatttcacg cctggaaggt ctgagtaacc tttaccagat ttatgctgaa    360
gcgttccgtg aatgggaagc agaccctacc aacccggcac ttcgtgagga aatgcgcatc    420
cagttcaatg atatgaatag cgcgctgaca actgctatcc acttttcac cgttcagaat    480
tatcaagtgc cgctgctgtc tgtttacgtc caggccgcga acctgcatct gtccgtactg    540
cgtgacgtgt ctgttttcgg ccaggcgtgg ggtttcgaca ttgccactat caactctcgt    600
tacaatgacc tgacccgtct gatcccgatc tatacggact acgctgttcg ttggtacaac    660
actggtctgg atcgtctgcc acgtaccggc ggtctgcgca attgggctcg tttcaaccag    720
ttccgtcgtg agctgactat ctctgtgctg gacatcatta gcttcttccg caactatgac    780
tctcgcctgt atccaatccc aaccagcagc cagctgacgc gtgaagtgta tactgaccct    840

SEQ ID NO: 121         moltype = DNA   length = 840
FEATURE                Location/Qualifiers
misc_feature           1..840
                       note = Synthetic
source                 1..840
                       mol_type = other DNA
                       organism = synthetic construct
SEQUENCE: 121
gggatcgagg gaaggatttc agaattaggc atggaaatcg ttaataacca gaaccagtgc     60
gttccgtaca actgtctgaa caaccctgaa aacgaaatcc tggatatcga acgttccaac    120
tccacggtgg ccaccaacat cgctctggaa atttcccgcc tgctggcaag cgccactcca    180
attggtggta ttctgctggg cctgttcgac gccatttggg gttctatcgg cccgtctcaa    240
tgggacctgt ttctggaaca gatcgaacag ctgattaacc aacgtatcgc agaagccgtg    300
cgtaacacgg caatttcaaga actggaaggt atggctcgcg tttaccggac ttatgctaca    360
gcgttcgcgg aatgggaaaa agcccctgac gacccggaac ttcgtgaggc actgcgcacc    420
cagttcactg ctacggaaac ctatatttca ggtcgtatct cagttttgaa aattcagact    480
tttgaagtgc agctgctgtc tgttttcgcc caggccgcga acctgcatct gtccgtactg    540
cgtgacgtgt ctgttttcgg ccaggcgtgg ggtttcgaca ttgccactat caactctcgt    600
tacaatgacc tgacccgtct gatcccgatc tatacggact acgctgttcg ttggtacaac    660
actggtctgg atcgtctgcc acgtaccggc ggtctgcgca attgggctcg tttcaaccag    720
ttccgtcgtg agctgactat ctctgtgctg gacatcatta gcttcttccg caactatgac    780
tctcgcctgt atccaatccc aaccagcagc cagctgacgc gtgaagtgta tactgaccct    840

SEQ ID NO: 122         moltype = DNA   length = 840
FEATURE                Location/Qualifiers
misc_feature           1..840
                       note = Synthetic
```

```
source                    1..840
                          mol_type = other DNA
                          organism = synthetic construct
SEQUENCE: 122
gggatcgagg gaaggatttc agaattaggc atgccaaaag ttaataacaa gaaccagtgc    60
cttccgtaca actgtctgaa caaccctgaa aacgaaatcc tggatatcga acgttccaac   120
tccacggtgg ccaccaacat cgctctggaa atttcccgcc tgctggcaag cgccactcca   180
attggtggta ttctgctggg cctgttcgac gccatttggg ttctatcgg cccgtctcaa   240
tgggacctgt ctctggaaca gattgaactg ctgatcgacc agaaaatcga agagtttgct   300
cgtaaccagg ccatcagccg tctggaagaa atttcttccc tgtacggtat ctacacggaa   360
gcatttcgtg aatgggaagc cgacccaacc aacccggcac tgaaggaaga aatgcgtacg   420
cagttcaacg acatgaactc tattctggtg actgccattc cgctgttttc tgtgcagaac   480
tatcaagtgc ctttcctgag cgtgtacgtg caagcggcca acctgcacct gtccgtactg   540
cgtgacgtgc ctgttttcgg ccaggcgtgg ggtttcgaa ttgccactat caactctcgt   600
tacaatgacc tgacccgtct gatcccgatc tatacggact acgctgttcg ttggtacaac   660
actggtctgg atcgtctgcc acgtaccggc ggtctgcgca ttgggctcg tttcaaccag   720
ttccgtcgtg agctgactat ctctgtgctg gacatcatta gcttcttccg caactatgac   780
tctcgcctgt atccaatccc aaccagcagc cagctgacgg tgaagtgta tactgaccct   840

SEQ ID NO: 123           moltype = DNA   length = 882
FEATURE                  Location/Qualifiers
misc_feature             1..882
                         note = Synthetic
source                   1..882
                         mol_type = other DNA
                         organism = synthetic construct
SEQUENCE: 123
gggatcgagg gaaggatttc agaattaggc atggaaatca ttaataacca gaaccagtgc    60
attccgtaca actgtctgaa caaccctgaa gtcgaaatcc tgggtatcga acgttccaac   120
tccacggtgg tcgaagacat ctctctggga ctttcccgcc tgctggtaag cgccattcca   180
cttggtgatt ttctgctgag cctgttcgac gtcatttggg gtgctatcgg ccggtctgaa   240
tgggacattt ttctggaaca gattgaactg ctgatcggcc agcggatcga agagtttgct   300
cgtaaccagg ccatcagccg tctggaaggc ctttctaacc tgtaccgtat ctacacgaac   360
gcatttaaaa actgggaagc cgacccaacc aacccggtac tgcgggaaga aatgcgtatt   420
cagttcaacg acatgaactc tgcttttacg actgccattc cgctgttttc tgtgcagggc   480
tatgaaattc ctttgctggg cgtggaaccg catcggtacc aggcgaacaa aattaaaatat   540
ccgctgaaaa ttaaaaaata tgccattctg agtgtcgagt ctgctgaacg catggcgttt   600
tttatgagca cttccgttag cgacgaactt cagcttttcg cgcaggaaat tcagtcgctt   660
ctttcgacca acattcttcg tgggttcgcc cgtgatgtgg gttttgtgca acgtaccagc   720
aaatatcagg ctaaggatct ggtggcgctt tgtgtctgga tgaaccagaa tgtggcgact   780
acctctctga cgcagctttg tagctgcttg gaagcctcta ccgaagtcct gatttcaccc   840
gaaggcctta accagctgac gcgtgaagtg tatactgacc ct                      882

SEQ ID NO: 124           moltype = DNA   length = 837
FEATURE                  Location/Qualifiers
misc_feature             1..837
                         note = Synthetic
source                   1..837
                         mol_type = other DNA
                         organism = synthetic construct
SEQUENCE: 124
gggatcgagg gaaggatttc agaattaggc atggacaata taaccgaa ccagtgcatt      60
ccgtacaact gtctgagcaa ccctgaactt gaaatcctgg aaatcgaacg ttccaacaac   120
acggtggtcg aagacatcac tctgggactt tcccgcctgc tggtaagcgc cattccactt   180
ggtgatttta ttctgggcct gttcgacgtc atttgggcg ctcttggccg gtctgaatgg   240
gacattttc tggaacagat tgaactgctg atcggccagc ggatcgaaga gtttgctcgt   300
aaccaggcca tcagcgtct ggaaggcctt tctaacctgt accgtatcta cacgaacgca   360
tttaagatt gggaagccga cccaaccaac ctggaactga aggaagaaat gcgtacgcag   420
ttcaacgaca tgaactctgc ttttacgact gccattccgc tgttttctgt gcggggctat   480
gaactgcctt tgctgagcgt gtacgtgcaa gcggccaact gcacctgtc cgtactgcgt   540
gacgtgtctg ttttcggcca gcggtgggt ttcgacgttg ccactgtcaa ccgtcgttac   600
gatgacctga ccactaacat cggggactat acggactacg ctcttagttg gtacaacact   660
ggtctgaatc gtctgccacg taacgacggt ctgcgcggtt gggctcgttt caaccggttc   720
cgtcgtgagc tgactatctc tgtgctggac atcattagct tcttccagaa ctatgactct   780
cgcctgtatc caatcccaac catcagccag ctgacgcgtg aagtgtatac tgaccct     837

SEQ ID NO: 125           moltype = AA   length = 280
FEATURE                  Location/Qualifiers
REGION                   1..280
                         note = Synthetic
source                   1..280
                         mol_type = protein
                         organism = synthetic construct
SEQUENCE: 125
GIEGRISELG MEIVNNQNQC VPYNCLNNPE NEILDIERSN STVATNIALE ISRLLASATP    60
IGGILLGLFD AIWGSIGPSQ WDLFLEQIEQ LINQRIEEFA RNQAISRLEG LSNLYQIYAE   120
SFREWEADPT NPALREEMRI QFNDMNSALT TAIPLLAVQN YQVPLLSVYV QAANLHLSVL   180
RDVSVFGQAW GFDIATINSR YNDLTRLIPI YTDYAVRWYN TGLDRLPRTG GLRNWARFNQ   240
FRRELTISVL DIISFFRNYD SRLYPIPTSS QLTREVYTDP                         280
```

```
SEQ ID NO: 126          moltype = AA   length = 280
FEATURE                 Location/Qualifiers
REGION                  1..280
                        note = Synthetic
source                  1..280
                        mol_type = protein
                        organism = synthetic construct
SEQUENCE: 126
GIEGRISELG MEIVNNQNQC VPYNCLNNPE NEILDIERSN STVATNIALE ISRLLASATP   60
IGGILLGLFD AIWGSIGPSQ WDLFLEQIEQ LINQRIEEFA RNQAISRLEG LSNLYQIYAE  120
SFREWEADPT NPALREEMRI QFNDMNSALT TAIPLFAVQN YQVPLLSVYV QAANLHLSVL  180
RDVSVFGQAW GFDIATINSR YNDLTRLIPI YTDYAVRWYN TGLDRLPRTG GLRNWARFNQ  240
FRRELTISVL DIISFFRNYD SRLYPIPTSS QLTREVYTDP                        280

SEQ ID NO: 127          moltype = AA   length = 280
FEATURE                 Location/Qualifiers
REGION                  1..280
                        note = Synthetic
source                  1..280
                        mol_type = protein
                        organism = synthetic construct
SEQUENCE: 127
GIEGRISELG MEIVNNQNQC VPYNCLNNPE NEILDIERSN STVATNIALE ISRLLASATP   60
IGGILLGLFD AIWGSIGPSQ WDLFLEQIEQ LIGQRIEEFA RNQAISRLQG LSNLYRIYTN  120
AFKNWEVDPT NPALREEMRI QFNDMNSALT TAIPLFSVQN YEIPLLSVYV QAANLHLSVL  180
RDVSVFGQAW GFDIATINSR YNDLTRLIPI YTDYAVRWYN TGLDRLPRTG GLRNWARFNQ  240
FRRELTISVL DIISFFRNYD SRLYPIPTSS QLTREVYTDP                        280

SEQ ID NO: 128          moltype = AA   length = 280
FEATURE                 Location/Qualifiers
REGION                  1..280
                        note = Synthetic
source                  1..280
                        mol_type = protein
                        organism = synthetic construct
SEQUENCE: 128
GIEGRISELG MEIVNNQNQC VPYNCLNNPE NEILDIERSN STVATNIALE ISRLLASATP   60
IGGILLGLFD AIWGSIGPSQ WDLFLEQIEQ LIGQRIEEFA RNQAISRLEG LSNLYRIYTN  120
AFKDWEADPT NLELKEEMRT QFNDMNSAFT TAIPLFSVRG YELPLLSVYV QAANLHLSVL  180
RDVSVFGQAW GFDIATINSR YNDLTRLIPI YTDYAVRWYN TGLDRLPRTG GLRNWARFNQ  240
FRRELTISVL DIISFFRNYD SRLYPIPTSS QLTREVYTDP                        280

SEQ ID NO: 129          moltype = AA   length = 280
FEATURE                 Location/Qualifiers
REGION                  1..280
                        note = Synthetic
source                  1..280
                        mol_type = protein
                        organism = synthetic construct
SEQUENCE: 129
GIEGRISELG MEIVNNQNQC VPYNCLNNPE NEILDIERSN STVATNIALE ISRLLASATP   60
IGGILLGLFD AIWGSIGPSQ WDLFLEQIEQ LIGQRIEEFA RNQAISRLEG LSNLYRIYTN  120
AFKNWEADPT NPVLREEMRI QFNDMNSAFT TAIPLFSVQG YEIPLLGVYV QAANLHLSVL  180
RDVSVFGQAW GFDIATINSR YNDLTRLIPI YTDYAVRWYN TGLDRLPRTG GLRNWARFNQ  240
FRRELTISVL DIISFFRNYD SRLYPIPTSS QLTREVYTDP                        280

SEQ ID NO: 130          moltype = AA   length = 280
FEATURE                 Location/Qualifiers
REGION                  1..280
                        note = Synthetic
source                  1..280
                        mol_type = protein
                        organism = synthetic construct
SEQUENCE: 130
GIEGRISELG MEIVNNQNQC VPYNCLNNPE NEILDIERSN STVATNIALE ISRLLASATP   60
IGGILLGLFD AIWGSIGPSQ WDLFLEQIEQ LIDQKIGEFA RNQAISRLEE ISSLYGIYTE  120
AFREWEADPT NPALKEEMRT QFNDMNSILV TAIPLFSVYV YQVPFLSVYV QAANLHLSVL  180
RDVSVFGQAW GFDIATINSR YNDLTRLIPI YTDYAVRWYN TGLDRLPRTG GLRNWARFNQ  240
FRRELTISVL DIISFFRNYD SRLYPIPTSS QLTREVYTDP                        280

SEQ ID NO: 131          moltype = AA   length = 280
FEATURE                 Location/Qualifiers
REGION                  1..280
                        note = Synthetic
source                  1..280
                        mol_type = protein
                        organism = synthetic construct
SEQUENCE: 131
```

```
GIEGRISELG MEIVNNQNQC VPYNCLNNPE NEILDIERSN STVATNIALE ISRLLASATP    60
IGGILLGLFD AIWGSIGPSQ WDLFLEQIEQ LIDQKIGEFA RNQAISRLEE ISSLYGIYTE   120
AFREWEADPT NPALKEEMRT QFNDMNSILV TAIPLFSVQN YQVPFLSVYV QAANLHLSVL   180
RDVSVFGQAW GFDIATINSR YNDLTRLIPI YTDYAVRWYN TGLDRLPRTG GLRNWARFNQ   240
FRRELTISVL DIISFFRNYD SRLYPIPTSS QLTREVYTDP                        280

SEQ ID NO: 132          moltype = AA   length = 280
FEATURE                 Location/Qualifiers
REGION                  1..280
                        note = Synthetic
source                  1..280
                        mol_type = protein
                        organism = synthetic construct
SEQUENCE: 132
GIEGRISELG MEIVNNQNQC VPYNCLNNPE NEILDIERSN STVATNIALE ISRLLASATP    60
IGGILLGLFD AIWGSIGPSQ WDLFLEQIEQ LISQRIEEFA RNQAISRLEG LSNLYQIYAE   120
AFREWEADPT NPALREEMRI QFNDMNSALT TAIPLFTVQN YQVPLLSVYV QAANLHLSVL   180
RDVSVFGQAW GFDIATINSR YNDLTRLIPI YTDYAVRWYN TGLDRLPRTG GLRNWARFNQ   240
FRRELTISVL DIISFFRNYD SRLYPIPTSS QLTREVYTDP                        280

SEQ ID NO: 133          moltype = AA   length = 280
FEATURE                 Location/Qualifiers
REGION                  1..280
                        note = Synthetic
source                  1..280
                        mol_type = protein
                        organism = synthetic construct
SEQUENCE: 133
GIEGRISELG MEIVNNQNQC VPYNCLNNPE NEILDIERSN STVATNIALE ISRLLASATP    60
IGGILLGLFD AIWGSIGPSQ WDLFLEQIEQ LINQRIAEAV RNTAIQELEG MARVYRTYAT   120
AFAEWEKAPD DPELREALRT QFTATETYIS GRISVLKIQT FEVQLLSVFA QAANLHLSVL   180
RDVSVFGQAW GFDIATINSR YNDLTRLIPI YTDYAVRWYN TGLDRLPRTG GLRNWARFNQ   240
FRRELTISVL DIISFFRNYD SRLYPIPTSS QLTREVYTDP                        280

SEQ ID NO: 134          moltype = AA   length = 280
FEATURE                 Location/Qualifiers
REGION                  1..280
                        note = Synthetic
source                  1..280
                        mol_type = protein
                        organism = synthetic construct
SEQUENCE: 134
GIEGRISELG MPKVNNKNQC LPYNCLNNPE NEILDIERSN STVATNIALE ISRLLASATP    60
IGGILLGLFD AIWGSIGPSQ WDLSLEQIEL LIDQKIGEFA RNQAISRLEE ISSLYGIYTE   120
AFREWEADPT NPALKEEMRT QFNDMNSILV TAIPLFSVQN YQVPFLSVYV QAANLHLSVL   180
RDVSVFGQAW GFDIATINSR YNDLTRLIPI YTDYAVRWYN TGLDRLPRTG GLRNWARFNQ   240
FRRELTISVL DIISFFRNYD SRLYPIPTSS QLTREVYTDP                        280

SEQ ID NO: 135          moltype = AA   length = 294
FEATURE                 Location/Qualifiers
REGION                  1..294
                        note = Synthetic
source                  1..294
                        mol_type = protein
                        organism = synthetic construct
SEQUENCE: 135
GIEGRISELG MEIINNQNQC IPYNCLNNPE VEILGIERSN STVVEDISLG LSRLLVSAIP    60
LGDFLLSLFD VIWGAIGRSE WDIFLEQIEL LIGQRIEEFA RNQAISRLEG LSNLYRIYTN   120
AFKNWEADPT NPVLREEMRI QFNDMNSAFT TAIPLFSVQG YEIPLLGVEP HRYQANKIKY   180
PLKIKKYAIL SVESAERMAF FMSTSVSDEL QLFAQEIQSL LSSNILRGFA RDVGFVQRTS   240
KYQAKDLVAL CVWMNQNVAT TSLTQLCSCL EASTEVLISP EGLNQLTREV YTDP         294

SEQ ID NO: 136          moltype = AA   length = 279
FEATURE                 Location/Qualifiers
REGION                  1..279
                        note = Synthetic
source                  1..279
                        mol_type = protein
                        organism = synthetic construct
SEQUENCE: 136
GIEGRISELG MDNNQNQCI PYNCLSNPEL EILEIERSNN TVVEDITLGL SRLLVSAIPL     60
GDFILGLFDV IWGALGRSEW DIFLEQIELL IGQRIEEFAR NQAISRLEGL SNLYRIYTNA   120
FKDWEADPTN LELEEMRTQ FNDMNSAFTT AIPLFSVRGY ELPLLSVYVQ AANLHLSVLR    180
DVSVFGQRWG FDVATVNRRY DDLTTNIGDY TDYALSWYNT GLNRLPRNDG LRGWARFNRF   240
RRELTISVLD IISFFQNYDS RLYPIPTISQ LTREVYTDP                         279

SEQ ID NO: 137          moltype = DNA   length = 273
FEATURE                 Location/Qualifiers
source                  1..273
```

```
                        mol_type = other DNA
                        organism = Bacillus thuringiensis
SEQUENCE: 137
cagatcgaac agctgattaa ccaacgtatc gaagaattcg cgcgtaacca ggcaatttca   60
cgcctggaag gtctgagtaa cctttaccag atttatgctg aatcgttccg ggaatgggaa  120
gcagacccta ccaacccggc acttcgtgag gaaatgcgca tccagttcaa tgatatgaat  180
agcgcgctga caactgctat cccacttttc gccgttcaga attatcaagt gccgctgctg  240
tctgtttacg tccaggccgc gaacctgcat ctg                               273

SEQ ID NO: 138          moltype = DNA   length = 273
FEATURE                 Location/Qualifiers
source                  1..273
                        mol_type = other DNA
                        organism = Bacillus thuringiensis
SEQUENCE: 138
cagatcgaac agctgattaa ccaacgtatc gaagaattcg cgcgtaacca ggcaatttca   60
cgcctggaag gtctgagtaa cctttaccag atttatgctg aatcgttccg ggaatgggaa  120
gcagacccta ccaacccggc acttcgtgag gaaatgcgca tccagttcaa tgatatgaat  180
agcgcgctga caactgctat cccacttttc gccgttcaga attatcaagt gccgctgctg  240
tctgtttacg tccaggccgc gaacctgcat ctg                               273

SEQ ID NO: 139          moltype = DNA   length = 273
FEATURE                 Location/Qualifiers
source                  1..273
                        mol_type = other DNA
                        organism = Bacillus thuringiensis
SEQUENCE: 139
cagatcgagc aactgattaa ccagcgtatc gaagaattcg cgcgtaacca ggcaatctcc   60
cgtctggaag gtctgtccaa cctgtaccag atctacgcag agtccttccg tgaatgggaa  120
gctgatccga ccaacccggc actgcgcgaa gaaatgcgta tccagttcaa cgacatgaac  180
tctgctctga cgacggccat ccctctgctg gctgtgcaga attatcaggt accgctgctg  240
tctgtgtacg tgcaggcggc taacctgcac ctg                               273

SEQ ID NO: 140          moltype = DNA   length = 273
FEATURE                 Location/Qualifiers
source                  1..273
                        mol_type = other DNA
                        organism = Bacillus thuringiensis
SEQUENCE: 140
cagatcgagc aactgattaa ccagcgtatc gaagaattcg cgcgtaacca ggcaatctcc   60
cgtctggaag gtctgtccaa cctgtaccag atctacgcag agtccttccg tgaatgggaa  120
gctgatccga ccaacccggc actgcgcgaa gaaatgcgta tccagttcaa cgacatgaac  180
tctgctctga cgacggccat ccctctgctg gctgtgcaga attatcaggt accgctgctg  240
tctgtgtacg tgcaggcggc taacctgcac ctg                               273

SEQ ID NO: 141          moltype = DNA   length = 273
FEATURE                 Location/Qualifiers
source                  1..273
                        mol_type = other DNA
                        organism = Bacillus thuringiensis
SEQUENCE: 141
cagatcgaac agctgattag ccaacgtatc gaagaattcg cgcgtaacca ggcaatttca   60
cgcctggaag gtctgagtaa cctttacaaa gtttatgttc gggcgttcag cgattgggaa  120
aaagacccta ccaacccggc acttcgtgag gaaatgcgca tccagttcaa tgatatgaat  180
agcgcgctga ttactgctat cccacttttc gccgttcaga attatgaagt ggcgctgctg  240
tctgtttacg tccaggccgc gaacctgcat ctg                               273

SEQ ID NO: 142          moltype = DNA   length = 273
FEATURE                 Location/Qualifiers
source                  1..273
                        mol_type = other DNA
                        organism = Bacillus thuringiensis
SEQUENCE: 142
cagatcgaac agctgattag ccaacgtatc gaagaattcg cgcgtaacca ggcaatttca   60
cgcctggaag gtctgagtaa caactacgaa atttatactg aaacgttccg ggcatgggaa  120
aaagaccta gcaacccggc acttcgtgag gaaatgcgca cccagttcaa tgttatgaat  180
agcgcgctga ttgctgctat cccactttta cgcgttcgta attatgaagt ggcgctgctg  240
tctgtttacg tccaggccgc gaacctgcat ctg                               273

SEQ ID NO: 143          moltype = DNA   length = 273
FEATURE                 Location/Qualifiers
source                  1..273
                        mol_type = other DNA
                        organism = Bacillus thuringiensis
SEQUENCE: 143
cagatcgaac agctgattga ccaaaaaatc gaagaattcg cgcgtaacca ggcaatttca   60
cgcctggaag gtattagtag cctttacggt atttatactg aagcgttccg ggaatgggaa  120
gcagacccta ccaacccggc acttaaagag gaaatgcgca cccagttcaa tgatatgaat  180
agcattctgg taactgctat cccacttttc agcgttcaga attatcaagt gccgtttctg  240
```

```
tctgtttacg tccaggccgc gaacctgcat ctg                                    273

SEQ ID NO: 144          moltype = DNA   length = 273
FEATURE                 Location/Qualifiers
source                  1..273
                        mol_type = other DNA
                        organism = Bacillus thuringiensis
SEQUENCE: 144
cagatcgagc tgctgatcgg ccagcgtatc gaagaattcg cacgcaatca ggccatttct        60
cgtctgcaag gcctgtctaa cctgtatcgc atctcaccca atgctttcaa aaattgggaa       120
gtagacccga ctaatccggc tctgcgcgaa gaaatgcgca ttcagtttaa cgatatgaac       180
tccgcgctga cgactgcaat tccgctgttc tctgttcagg ttacgaaat cccgctgctg        240
tctgtctacg ttcaggccgc gaacctgcac ctg                                    273

SEQ ID NO: 145          moltype = DNA   length = 273
FEATURE                 Location/Qualifiers
source                  1..273
                        mol_type = other DNA
                        organism = Bacillus thuringiensis
SEQUENCE: 145
cagatcgaac agctgattaa ccaacgtatc gccgaagccg tgcgtaacac cgcaattcaa        60
gaactggaag gtatggctcg cgtctaccgt acttatgtca cagcgttcgc agaatgggaa       120
aaagccctg acgacccgga acttcgtgag gcccttcgca cccagttcac tgctacgaa        180
acctatatta gcggtcgtat ctcagtttta aaaattcaga cttttgaagt gcagctgctg       240
tctgttttcg cccaggccgc gaacctgcat ctg                                    273

SEQ ID NO: 146          moltype = DNA   length = 273
FEATURE                 Location/Qualifiers
source                  1..273
                        mol_type = other DNA
                        organism = Bacillus thuringiensis
SEQUENCE: 146
cagatcgaac agctgattaa cgaacgtatc gccgaattcg cgcgtaacgc cgcaattgca        60
aacctggaag gtctgggtaa caacttcaat atttatgttg aagcgttcaa agaatgggaa       120
gaagacccta acaacccgga aacccgtacg cgcgttatcg accgtttccg tattctggat       180
ggcctgctgg aacgtgatat cccatctttc cgcattctg gttttgaagt gccgctgctg        240
tctgtttacg cccaggccgc gaacctgcat ctg                                    273

SEQ ID NO: 147          moltype = DNA   length = 273
FEATURE                 Location/Qualifiers
source                  1..273
                        mol_type = other DNA
                        organism = Bacillus thuringiensis
SEQUENCE: 147
cagatcgaac agctgattaa cgaacgtatc gccgcatacg cgcgtagcgc cgcaatttca        60
aacctggaag gtctgggtaa caacttcaat atttatgttg aagcgttcaa agaatgggaa       120
gcagaccctg acaaccccggt aacccgtacg cgcgttgtcg accgtttccg tattctggat       180
ggcctgctgg aacgtgatat cccatctttc cgcattgctg gttttgaagt gccgctgctg       240
tctgtttacg cccaggccgc gaacctgcat ctg                                    273

SEQ ID NO: 148          moltype = DNA   length = 273
FEATURE                 Location/Qualifiers
source                  1..273
                        mol_type = other DNA
                        organism = Bacillus thuringiensis
SEQUENCE: 148
cagatcgaac agctgattga ccaacgtatc gaagcacacg tgcgtaacca ggcaatttca        60
cgcctggaag gtctgggtga cagctacgaa gtttatattg aatcgttacg ggaatgggaa       120
gcaagcccta caacgagag ccttcagcag gacgttcgca accgtttcag taatacggat        180
aacgcgctga ttactgctat cccaattta cgcgaacagg ttttgaaat ccgctgctg          240
actgtttacg tccaggccgc gaacctgcat ctg                                    273

SEQ ID NO: 149          moltype = DNA   length = 273
FEATURE                 Location/Qualifiers
source                  1..273
                        mol_type = other DNA
                        organism = Bacillus thuringiensis
SEQUENCE: 149
cagatcgaac agctgattaa cgaacgtatc accacagtcg agcgtaaccg cgcaattcaa        60
accctgagcg gtctgagtag cagctacgaa gtttatattg aagcgttacg ggaatgggaa       120
aacaaccctg acaacccggc aagccaggag cgcgttcgca cccgtttccg tactacggat       180
gacgcgctga ttactgctat cccaaattta gccattcctg attttgaaat tgcgacgctg       240
tctgtttacg tccaggccgc gaacctgcat ctg                                    273

SEQ ID NO: 150          moltype = DNA   length = 273
FEATURE                 Location/Qualifiers
source                  1..273
                        mol_type = other DNA
                        organism = Bacillus thuringiensis
```

```
SEQUENCE: 150
cagattgagc gcttgatcga ccagcgcatt gaggcaacag ttcgtgcgaa agcgattacg    60
gagctggagg gcctgggccg gaattaccag atctacgctg aagcccttcaa agagtgggaa  120
agcgaccccg acaacgaagc ggcaaaatca cgcgtgattg atcgtttccg catcctggac  180
ggattgattg aagccaacat tcctagtttc cgtattattg ggtttgaggt gccgctgctg  240
tccgtttacg tgcaggctgc gaacctgcat ttg                                273

SEQ ID NO: 151           moltype = DNA   length = 273
FEATURE                  Location/Qualifiers
source                   1..273
                         mol_type = other DNA
                         organism = Bacillus thuringiensis
SEQUENCE: 151
cagattgagc agttgatcga ccagcgcatt gaggcaacag ttcgtgcgaa agcgattgcc    60
gagctggagg gcctgggccg gagttttcag ctgtacgttg aagcccttcaa agagtgggaa  120
gaaaccccgg acaacaccgc ggcacgctca cgcgtgaccg agcgtttccg catcattgac  180
gcacagattg aagccaacat tcctagtttc cgtattcctg ggtttgaggt gccgctgctg  240
tccgtttacg cgcaggctgc gaacctgcat ttg                                273

SEQ ID NO: 152           moltype = DNA   length = 273
FEATURE                  Location/Qualifiers
source                   1..273
                         mol_type = other DNA
                         organism = Bacillus thuringiensis
SEQUENCE: 152
cagattgagc agttgatcga ccgtcgcatt gaggcaacag ttcgtgcgaa agcgattgcc    60
gagctggagg gcctgggccg gagttaccag ctgtacggtg aagcccttcaa agagtgggaa  120
aaaaccccgg acaacaccgc ggcacgctca cgcgtgaccg agcgtttccg catcattgac  180
gcacagattg aagccaacat tcctagtttc cgtgtatccg ggtttgaggt gccgctgctg  240
tccgtttaca cgcaggctgc gaacctgcat ttg                                273

SEQ ID NO: 153           moltype = DNA   length = 273
FEATURE                  Location/Qualifiers
source                   1..273
                         mol_type = other DNA
                         organism = Bacillus thuringiensis
SEQUENCE: 153
cagattgagc agttgatcga ccgtcgcatt gagcgtacag ttcgtgcgaa agcgattgcc    60
gagctggagg gcctgggccg gagttaccag ctgtacggtg aagcccttcaa agagtgggaa  120
aaaaccccgg acaacaccgc ggcacgctca cgcgtgaccg agcgtttccg catcattgac  180
gcacagattg aagccaacat tcctagtttc cgtgtatccg ggtttgaggt gccgctgctg  240
ctggtttaca cgcaggctgc gaacctgcat ttg                                273

SEQ ID NO: 154           moltype = DNA   length = 273
FEATURE                  Location/Qualifiers
source                   1..273
                         mol_type = other DNA
                         organism = Bacillus thuringiensis
SEQUENCE: 154
cagatcgaac agctgattaa ccaacgtatc accgaattcg cgcgtggcca ggcaattcaa    60
cgcctggtag gttttggtcg cagctacgat gaatatattt tagcgttaaa agaatgggaa  120
aacgaccctg acaacccggc aagcaaagag cgcgttcgca cccgtttccg tactacggat  180
gacgcgctgt taactggtgt cccacttatg gccattcctg gttttgaact ggcgacgctg  240
tctgtttacg cccagtccgc gaacctgcat ctg                                273

SEQ ID NO: 155           moltype = DNA   length = 273
FEATURE                  Location/Qualifiers
source                   1..273
                         mol_type = other DNA
                         organism = Bacillus thuringiensis
SEQUENCE: 155
cagattgaac agctgatccg tcaggaaatc accgagctgg aacgtaaccg tgccactgca    60
atcctgaccg gcctgtcttc ctcctacaac ctgtacgtag aagcactgcg tgaatgggaa  120
aatgacccaa ataacccggc atctcaagaa cgcgttcgta cgcgtttccg tctgaccgac  180
gatgcgatcg tgactggtct gccgactctg gctattcgta acctggaggt ggtgaacctg  240
agcgtgtaca cgcaagcggc caacctgcac ctg                                273

SEQ ID NO: 156           moltype = DNA   length = 273
FEATURE                  Location/Qualifiers
source                   1..273
                         mol_type = other DNA
                         organism = Bacillus thuringiensis
SEQUENCE: 156
cagatcgaac agctgatcga ccaacgtatc gagactgtgg aacgcaaccg tgcgattcaa    60
accctgatcg gtctgagcaa ttcttatgat gtcaacatcg aagcgctgaa ggaatgggaa  120
aacaacccgg ataacagcgc gtcccaggaa cgtgttcgta accgcttccg cactacggac  180
gatgccctga tcacttctat tccgctgctg gcgatcccga acttcgagat tgcgactctg  240
tccgtgtatg ttcaggcagc gaacctgcat ctg                                273
```

| SEQ ID NO: 157 | moltype = DNA   length = 276 |
|---|---|
| FEATURE | Location/Qualifiers |
| source | 1..276 |
| | mol_type = other DNA |
| | organism = Bacillus thuringiensis |

SEQUENCE: 157
```
catgttgaac agatcgttcg tcagcagcag atcacggaca gcgtacgtga cactgcaatt    60
gcacgtctgg aaggtctggg tcgcggctat cgttcttatc agcaggcgct ggaaacctgg   120
ctggacaacc gtaacgacgc acgcagccgt tccatcattc gcgaacgtta tatcgcccctg  180
gaactggaca ttactacggc tatcccactg ttctccattc gcaacgagga agtgccgctg   240
ctgatggttt acgcccaggc cgcgaacctg catctg                             276
```

| SEQ ID NO: 158 | moltype = DNA   length = 273 |
|---|---|
| FEATURE | Location/Qualifiers |
| source | 1..273 |
| | mol_type = other DNA |
| | organism = Bacillus thuringiensis |

SEQUENCE: 158
```
cacgtggaag aactggtagc tcagaagatc tccacctatg cacgcaacaa agcgctgagc    60
gatctgaaag gcctgggcga tgctctggca gtctaccacg aatctctgga aagctggatc   120
gaaaccgta acaacacccg tgctcgttct gtcgtgaaaa accaatacat cgcgctgaa    180
ctgatgttcg ttcagaatct gccgtctttc gcagtctccg gcgaggaagt tccgctgctg   240
ccgatctatc gtcaggctgc taacctgcac ctg                                273
```

| SEQ ID NO: 159 | moltype = AA   length = 91 |
|---|---|
| FEATURE | Location/Qualifiers |
| source | 1..91 |
| | mol_type = protein |
| | organism = Bacillus thuringiensis |

SEQUENCE: 159
```
QIEQLINQRI EEFARNQAIS RLEGLSNLYQ IYAESFREWE ADPTNPALRE EMRIQFNDMN    60
SALTTAIPLF AVQNYQVPLL SVYVQAANLH L                                   91
```

| SEQ ID NO: 160 | moltype = AA   length = 91 |
|---|---|
| FEATURE | Location/Qualifiers |
| source | 1..91 |
| | mol_type = protein |
| | organism = Bacillus thuringiensis |

SEQUENCE: 160
```
QIEQLINQRI EEFARNQAIS RLEGLSNLYQ IYAESFREWE ADPTNPALRE EMRIQFNDMN    60
SALTTAIPLF AVQNYQVPLL SVYVQAANLH L                                   91
```

| SEQ ID NO: 161 | moltype = AA   length = 91 |
|---|---|
| FEATURE | Location/Qualifiers |
| source | 1..91 |
| | mol_type = protein |
| | organism = Bacillus thuringiensis |

SEQUENCE: 161
```
QIEQLINQRI EEFARNQAIS RLEGLSNLYQ IYAESFREWE ADPTNPALRE EMRIQFNDMN    60
SALTTAIPLL AVQNYQVPLL SVYVQAANLH L                                   91
```

| SEQ ID NO: 162 | moltype = AA   length = 91 |
|---|---|
| FEATURE | Location/Qualifiers |
| source | 1..91 |
| | mol_type = protein |
| | organism = Bacillus thuringiensis |

SEQUENCE: 162
```
QIEQLINQRI EEFARNQAIS RLEGLSNLYQ IYAESFREWE ADPTNPALRE EMRIQFNDMN    60
SALTTAIPLL AVQNYQVPLL SVYVQAANLH L                                   91
```

| SEQ ID NO: 163 | moltype = AA   length = 91 |
|---|---|
| FEATURE | Location/Qualifiers |
| source | 1..91 |
| | mol_type = protein |
| | organism = Bacillus thuringiensis |

SEQUENCE: 163
```
QIEQLISQRI EEFARNQAIS RLEGLSNLYK VYVRAFSDWE KDPTNPALRE EMRIQFNDMN    60
SALITAIPLF RVQNYEVALL SVYVQAANLH L                                   91
```

| SEQ ID NO: 164 | moltype = AA   length = 91 |
|---|---|
| FEATURE | Location/Qualifiers |
| source | 1..91 |
| | mol_type = protein |
| | organism = Bacillus thuringiensis |

SEQUENCE: 164
```
QIEQLISQRI EEFARNQAIS RLEGLSNNYE IYTETFRAWE KDPSNPALRE EMRTQFNVMN    60
SALIAAIPLL RVRNYEVALL SVYVQAANLH L                                   91
```

| SEQ ID NO: 165 | moltype = AA   length = 91 |
|---|---|

```
FEATURE                 Location/Qualifiers
source                  1..91
                        mol_type = protein
                        organism = Bacillus thuringiensis
SEQUENCE: 165
QIEQLIDQKI EEFARNQAIS RLEGISSLYG IYTEAFREWE ADPTNPALKE EMRTQFNDMN   60
SILVTAIPLF SVQNYQVPFL SVYVQAANLH L                                 91

SEQ ID NO: 166          moltype = AA  length = 91
FEATURE                 Location/Qualifiers
source                  1..91
                        mol_type = protein
                        organism = Bacillus thuringiensis
SEQUENCE: 166
QIELLIGQRI EEFARNQAIS RLQGLSNLYR IYTNAFKNWE VDPTNPALRE EMRIQFNDMN   60
SALTTAIPLF SVQGYEIPLL SVYVQAANLH L                                 91

SEQ ID NO: 167          moltype = AA  length = 91
FEATURE                 Location/Qualifiers
source                  1..91
                        mol_type = protein
                        organism = Bacillus thuringiensis
SEQUENCE: 167
QIEQLINQRI AEAVRNTAIQ ELEGMARVYR TYATAFAEWE KAPDDPELRE ALRTQFTATE   60
TYISGRISVL KIQTFEVQLL SVFAQAANLH L                                 91

SEQ ID NO: 168          moltype = AA  length = 91
FEATURE                 Location/Qualifiers
source                  1..91
                        mol_type = protein
                        organism = Bacillus thuringiensis
SEQUENCE: 168
QIEQLINERI AEFARNAAIA NLEGLGNNFN IYVEAFKEWE EDPNNPETRT RVIDRFRILD   60
GLLERDIPSF RISGFEVPLL SVYAQAANLH L                                 91

SEQ ID NO: 169          moltype = AA  length = 91
FEATURE                 Location/Qualifiers
source                  1..91
                        mol_type = protein
                        organism = Bacillus thuringiensis
SEQUENCE: 169
QIEQLINERI AAYARSAAIS NLEGLGNNFN IYVEAFKEWE ADPDNPVTRT RVVDRFRILD   60
GLLERDIPSF RIAGFEVPLL SVYAQAANLH L                                 91

SEQ ID NO: 170          moltype = AA  length = 91
FEATURE                 Location/Qualifiers
source                  1..91
                        mol_type = protein
                        organism = Bacillus thuringiensis
SEQUENCE: 170
QIEQLIDQRI EAHVRNQAIS RLEGLGDSYE VYIESLREWE ASPNNESLQQ DVRNRFSNTD   60
NALITAIPIL REQGFEIPLL TVYVQAANLH L                                 91

SEQ ID NO: 171          moltype = AA  length = 91
FEATURE                 Location/Qualifiers
source                  1..91
                        mol_type = protein
                        organism = Bacillus thuringiensis
SEQUENCE: 171
QIEQLINERI TTVERNRAIQ TLSGLSSSYE VYIEALREWE NNPDNPASQE RVRTRFRTTD   60
DALITAIPNL AIPDFEIATL SVYVQAANLH L                                 91

SEQ ID NO: 172          moltype = AA  length = 91
FEATURE                 Location/Qualifiers
source                  1..91
                        mol_type = protein
                        organism = Bacillus thuringiensis
SEQUENCE: 172
QIERLIDQRI EATVRAKAIT ELEGLGRNYQ IYAEAFKEWE SDPDNEAAKS RVIDRFRILD   60
GLIEANIPSF RIIGFEVPLL SVYVQAANLH L                                 91

SEQ ID NO: 173          moltype = AA  length = 91
FEATURE                 Location/Qualifiers
source                  1..91
                        mol_type = protein
                        organism = Bacillus thuringiensis
SEQUENCE: 173
QIEQLIDQRI EATVRAKAIA ELEGLGRSFQ LYVEAFKEWE ETPDNTAARS RVTERFRIID   60
AQIEANIPSF RIPGFEVPLL SVYAQAANLH L                                 91
```

```
SEQ ID NO: 174           moltype = AA   length = 91
FEATURE                  Location/Qualifiers
source                   1..91
                         mol_type = protein
                         organism = Bacillus thuringiensis
SEQUENCE: 174
QIEQLIDRRI EATVRAKAIA ELEGLGRSYQ LYGEAFKEWE KTPDNTAARS RVTERFRIID    60
AQIEANIPSF RVSGFEVPLL SVYTQAANLH L                                   91

SEQ ID NO: 175           moltype = AA   length = 91
FEATURE                  Location/Qualifiers
source                   1..91
                         mol_type = protein
                         organism = Bacillus thuringiensis
SEQUENCE: 175
QIEQLIDRRI ERTVRAKAIA ELEGLGRSYQ LYGEAFKEWE KTPDNTAARS RVTERFRIID    60
AQIEANIPSF RVSGFEVPLL LVYTQAANLH L                                   91

SEQ ID NO: 176           moltype = AA   length = 91
FEATURE                  Location/Qualifiers
source                   1..91
                         mol_type = protein
                         organism = Bacillus thuringiensis
SEQUENCE: 176
QIEQLINQRI TEFARGQAIQ RLVGFGRSYD EYILALKEWE NDPDNPASKE RVRTRFRTTD    60
DALLTGVPLM AIPGFELATL SVYAQSANLH L                                   91

SEQ ID NO: 177           moltype = AA   length = 91
FEATURE                  Location/Qualifiers
source                   1..91
                         mol_type = protein
                         organism = Bacillus thuringiensis
SEQUENCE: 177
QIEQLIRQEI TELERNRATA ILTGLSSSYN LYVEALREWE NDPNNPASQE RVRTRFRLTD    60
DAIVTGLPTL AIRNLEVVNL SVYTQAANLH L                                   91

SEQ ID NO: 178           moltype = AA   length = 91
FEATURE                  Location/Qualifiers
source                   1..91
                         mol_type = protein
                         organism = Bacillus thuringiensis
SEQUENCE: 178
QIEQLIDQRI ETVERNRAIQ TLIGLSNSYD VNIEALKEWE NNPDNSASQE RVRNRFRTTD    60
DALITSIPLL AIPNFEIATL SVYVQAANLH L                                   91

SEQ ID NO: 179           moltype = AA   length = 92
FEATURE                  Location/Qualifiers
source                   1..92
                         mol_type = protein
                         organism = Bacillus thuringiensis
SEQUENCE: 179
HVEQIVRQQQ ITDSVRDTAI ARLEGLGRGY RSYQQALETW LDNRNDARSR SIIRERYIAL    60
ELDITTAIPL FSIRNEEVPL LMVYAQAANL HL                                  92

SEQ ID NO: 180           moltype = AA   length = 91
FEATURE                  Location/Qualifiers
source                   1..91
                         mol_type = protein
                         organism = Bacillus thuringiensis
SEQUENCE: 180
HVEELVAQKI STYARNKALS DLKGLGDALA VYHESLESWI ENRNNTRARS VVKNQYIALE    60
LMFVQNLPSF AVSGEEVPLL PIYRQAANLH L                                   91

SEQ ID NO: 181           moltype = DNA   length = 1845
FEATURE                  Location/Qualifiers
source                   1..1845
                         mol_type = other DNA
                         organism = Bacillus thuringiensis
SEQUENCE: 181
atgggccgcg gtagcatgga agtcaacaat caaaatcaat gcgtgccgta caattgcctg    60
aacaacccgg aaattgaaat tttaggcggt gaacggatct cagtggggaa cacgccaatt   120
gatatcagtc tgtccttgac gcaatttctg ttgtcggaat cgtacctgg tgccggcttt    180
gtattgggc ttattgactt gatctggggg tttctgggc ctagccagtg ggacgcattt     240
ctgctgcaga tcgaacagct gatttcacag cgtattgagg agtttgctcg caaccaagcg   300
attagccgct tggaaggatt gtcaaacctg tatcgcattt acgcggaagc cttccgcgca   360
tgggaagccg atcccacaaa cctggctttg cgcgaagaaa tgcgcacaca attcaacgat   420
atgaactctg ccctggtgac agccattccg ttgttctcag tgcagaatta tcaggtgcca   480
cttctgagcg tgtatgtgca agcggcgaac ctgcatctgt ccgtgttgcg cgacgttagc   540
```

```
gtgttcggtc agcgttgggg atttgatgtt gccacgatta atagccgtta caacgatctg    600
acacggttga ttggcgagta cacggactac gccgtgcgtt ggtataacac agggcttgac    660
cgccttcgcg gttcgaactt ccaggattgg attcgttata atcgttttcg ccgcgagctg    720
acgttgaccg tgttggacat cgtgtcggtc tttcagaatt atgacagtcg cctttatccg    780
atccagacga gctctcaatt gacgcgtgaa atttattccg atcttctgct ggccaacccg    840
agtggtgtgg gtagtttctc taatgtagat ttcgatagca ttctgatccg tcagcctcat    900
ctgatcgatt tcatgcgcgt tttaacgatt tacacggatc gccataatgc ttcccggcac    960
aacatctatt gggcgggcca tcaagtaacc gcagtagata cagccaaccg tacgattgtg   1020
taccctgtca atggcagtgc agccaacttg gaacctccgc ggacgttgcg gtttgagtcg   1080
cccgtcgtgg aaattcgctc taatccggtg tgggaccgcg gaagtactgc catcgcaggc   1140
tcgtatgaat tctttggtgt gaccagtgct ttgttcatta caatcctggg ttttggctat   1200
acctatcgct cagggagcaa caccgaagtg acggcacttc cggatcatca ggtcagccac   1260
attggttact tccgtcgctt taccaccacc ggggcgaccg ctcgtcagac cttgacaagc   1320
gcacctattg tgtcgtggac tcattcgagc gctgaaccgc caaaccgtat ctatcaaaac   1380
cgtattaccc agatcccagc cgttaaaggt aacttcctgt ttaacggagc tgtcatctca   1440
gggcctggat ttaccggtgg cgatcttgtc cgccttaacc gcaacaatga taatattcaa   1500
aatcgcggtt atattgaagt tccgatccag ttcgcctcga ctagcacgcg ttatcgcgta   1560
cgcgtccgtt acgccagcac taatgcgatt gaggtgaata ttaactgggg taatggcagt   1620
attttcaccg gaaccgcccc agcaaccgcg acgagcctgg ataacctgca gagcaatgat   1680
tttggttact tcgagagcac cacggccttt gcccccttcgc tggggaacat tgtaggcgtg   1740
cgtaacttct ctgctaatgc cgatgtgatc attgatcgct ttgagtttat ccccgtaacg   1800
gcaaccctgg aagcggagta tgatctggaa cgcgcgaaaa aataa                   1845
```

SEQ ID NO: 182             moltype = DNA  length = 2040
FEATURE                    Location/Qualifiers
source                     1..2040
                           mol_type = other DNA
                           organism = Bacillus thuringiensis

SEQUENCE: 182

```
atgccccgaa ataatcaaaa tgattatgaa gttattgacg cttccaattg tggttgtgcg     60
tcaggtgatg ttgtgaaata tcctttgaca aatgatccga atgccggatt acaaaatatc    120
aattataaag agtacttaca aatgtcagat gagaactaca ctgattccta tataaatcct    180
agtttgtcta ttagtgggaa atctgtaata caagttggaa ttaacattgt agggaggttg    240
ttgagctttt ttggattccc atttgctaat caagtggtcg ctgtctatag ctacctttta    300
aacacccttat ggcaaataa tgatactgaa gtatgggaat cttttatgac acaagtagaa    360
gaacttgttg atcaaaaaat atcagaagcg gtagtaggga ccgcattgga tcatttatct    420
ggattaaact ataattatga attatatgta gaggctttgg aagagtggct ggaaagacca    480
aatgccgcaa gagccaacct agttttttaat agatttacta cactagatag tctatttacg    540
caatttatgc caagttttgg ctctggtcct gggagtaata gtgatgcaga ttcattactt    600
tcagtatatg cacaagcagc aaaccttcat ttgttattct aaaagatgc agacatttat    660
ggagctagat gggggctgaa tcaaactcaa atagatcaat accataatcg tcaacaaacc    720
cttactcgga attatacaaa tcattgtgtt actacgttta tgatggatt agagaaaata    780
agaaacacaa gcgctgagag ttggtttaaa tacaatcaat actgtagaga gatgacatta    840
atggcaatgg atttagtggc attatttccg tattataatg tacgagaata ctcaatggca    900
gtaaatcctc aacttacacg agaggtgtat acagatccaa ttgcatttga tccatcagaa    960
caaccgaata ctcaattgtg tcgaaaatgg tatactgccc gctttgtaca gaataacgtt   1020
aatttttctc agttagaaaa tgcattcatt cgttcaccac atctcttcga aagattacat   1080
tctctggaaa ttaatttttat aaatggagct aattggtggt ggcataaggt aaggaaccaa   1140
cttttaaata attcattaat actcgaaaga gattacggta catctactgt taattctcct   1200
acgactcaac ttaccgtgaa tacttcaaat gctgatatat accaagtacg ttctcgtgca   1260
gaaaatccga ctgcagctgc aggtacttac tattcagtta gaggtgttga gttttattta   1320
agctcaggcg ttaagaggga gttttctgga actacagtcg ctcctttggc ttgccaagaa   1380
ttgcgaaatt caattgatga gttaccaagt ttagaaccaa atgagcctat catcagaaat   1440
tatagtcata gattatctca tattacttgg taccaattta gtggccgcca aagtggaaat   1500
ccgactacta ataatggga tataccttact tatgtctgga cacatcgcga tgtggacttt   1560
aataatacaa ttactcccaa tagaattact caaatacctt ggataaaggc atctgaaata   1620
gctgcgaata ctactgtcgt aaaaggccca ggatttacag gaggggatat acttcgaagc   1680
acgatccctg gtacagttgg aacgattagg gctaatgtta tggccccatt aacacaacaa   1740
tatcgtataa gattacgtta tcgtcgaca acaaaattttg ttgttaattt attttgttaac   1800
aattcagcta gtggttttac tctcccaagt acaatggttc aaaatgagtc tttaacatac   1860
gaatcgttta taccgaagaa ggtgacaaga actattagat tttcacagtc agacactaca   1920
ctgagattgg gtatatttc gtttgaccct ggtcaagaag tgtatgtaga taacttgaa   1980
atcgttccaa ttaatccagc tcgtgaggcg aagaggatt tagaagcagc gaaaaaataa   2040
```

SEQ ID NO: 183             moltype = DNA  length = 1845
FEATURE                    Location/Qualifiers
source                     1..1845
                           mol_type = other DNA
                           organism = Bacillus thuringiensis

SEQUENCE: 183

```
atgccgaata tattcaaaaa tcaatgcgta cctataatt gtctaagcac ccctgagaaa     60
atactattag atgaggaaag aattgagact ggaatacat caatcgatct ttctttgtcg    120
cttgtgagcc ttctttagg tgaattcgtc cctggtgcgt catttgtact aggtctaatt    180
gatataatat ggggattgc aggtccctct caatgggacg cattctggt acagattgaa    240
cagttaattg acgaaagaat aggtcagttc gcaggaatc aagcaattc tagattgaa    300
gggctaagca atctctatca aatatacgca aagattttta cacagtggga agcagatccc    360
gataatccag cattaagaga agagatgcgt actcaattca atgatatgaa cagtgctctt    420
acaaccgcta ttcctctttt ggcagttcaa aactatcaaa ttcctctttt atcagtatat    480
gttcaagctg caaatttaca tttatcagtt ttgagagatg tttcagtgtt tggacaaagt    540
```

-continued

```
tggggatttg atgcggcgac tattaatagc cgttataatg atttaactag gcttattagc  600
agctatacag atcatgtagt aagatggtat gatacaggat tagaccgttt gcgaggctct  660
acttaccaag actggtttag atacaaccga tttagaagag aattaacatt gactgcatta  720
gatatcgttg ctcttttccc aaactatgat atcaaaatgt atccaatcca acccgttagc  780
caactaacaa gggaagttta tacggaccca ttaattaatt tcaatccgca gttacagtct  840
gtagctcaat tgcctacttt taacgttatg gaaagtaacg caattagaaa ccctcattta  900
gttgacttct tgaataacct tagaattttt acagattggt ttagtgtcgg acggcactat  960
tattggggag gacatcgagt gatttccaaa cgtgtaggag gaagggagat aaccttccct  1020
atatatggaa gggaggcaaa gcaggaacct ccaagatcct ttacttttaa tggacctgtt  1080
tttaggacgt tatcaaatcc taccctaaga ccattacaac aacctgcacc agctcctcct  1140
tttaatttac gtggcttgga aggtgtaaaa ttttatacac ctacaaatac ctttacgtat  1200
cggggaagag gcccgcgtga ttctttaact gaattaccgc ctggagatac aagtgtacta  1260
cctcgcgaag gatatagtca ccggttatgt catgcaacat ttattcaaag atctggcaca  1320
cctttttaa caacaggcgt agtcttttct tggacacatc gtagtgctga tgaaacgaat  1380
ataatttatc cagataagat tactcaaatt ccatgggtaa aggcgcatac ccttgaatcg  1440
ggggccactg ttattaaggg tcctggattt acaggagggg atattcttac tgttcttact  1500
agtcttggtt ccttgggcgc tttacgagta actttacgg ggcaattacc acaaacatat  1560
aatatacgaa tccgatatgc ctcggtgcta aataaatatg gtacactcca tttttcacag  1620
ccacctgcat atgggctcac atttccaaaa actatggata tagatgaacc attaacatct  1680
cgctcgtttg cttttacaac tctttggaca ccaataacct ttacacgagc acaagaggaa  1740
tttaatctaa caatacaatc aggtgtttat atagatagaa ttgaatttgt tccggcagaa  1800
gtaacatttg aggcagacta tgacttggaa aaagcgcaaa agtaa                 1845

SEQ ID NO: 184         moltype = DNA  length = 1854
FEATURE                Location/Qualifiers
source                 1..1854
                       mol_type = other DNA
                       organism = Bacillus thuringiensis
SEQUENCE: 184
atggataata ataatcaaaa tcaatgcata ccttacaatt gtttaagtaa tcctgaatta  60
gagatattag agattgaaag atcaaataat accgtagtag aagacatcac cttggggctg  120
agtcgtctgc tcgtttccgc aattccacta ggggatttta tacttggctt gtttgatgta  180
atatgggggg ctttaggtcg ttcagagtgg gatatatttt tagagcaaat tgagctattg  240
atcggccaaa gaatagagga atttgctagg aatcaggcaa tttctagatt agaagggcta  300
agcaatcttt atcgaattta cacaaatgct tttaaagact gggaagcaga tcctactaat  360
ctagaattaa aagaagagat gcgtactcaa tttaatgaca tgaacagtgc ttttacaaca  420
gctattcctc tttttcagt tcgaggttat gaacttcctc ttttatcagt atatgttcaa  480
gctgcaaatt tacatttatc agttttaaga gatgtttcag tgtttggaca acgttgggga  540
tttgacgtag caacagtcaa tcgtcgttat gatgatttaa ctacgaatat aggcgactac  600
acagattatg ctttaagctg gtataatacg ggattaaacc gtttaccacg taatgatggg  660
ctgcgaggat gggcaagatt taataggttt agaagagagt taacaatatc agtattagat  720
attatttctt ttttccaaaa ttacgattct agattatatc caattccaac aatctcccaa  780
ttaacgcggg aagtatatac agatccggta attaatataa ctgattatag agttacccca  840
agtttcgaga gtattgaaaa ctcagccatt agaagccccc atcttatgga tttcttaact  900
aatataatta ttgacactga tttaataaga ggtgtttact attgggcagg acatcgtata  960
aattctcgct ttaccgggac cgcttttcca catataataa catctcctca atatggaata  1020
actgcaaacg cagaaccaag acgtacaata gtgcctggtc cttttcaagg tgtgccttcc  1080
ctactttata gaacactatc agacccttc ttccgaagat cagacaatat tagtccaacc  1140
ttagggataa atgtagtaca gggggtaggg ttcttacaac caaataattt tgaatctcta  1200
tatagaagga gagggacagt agattctctc gatgagttgc caattgatgg tgaaaatcca  1260
ttagttggat atagtcatcg attaagtcac gttacattaa ccaggtcatt atttaatact  1320
aatataacta gcctgccaac atttgtttgg acacatcaca gtgctactga tacaaataca  1380
attgctccag atgtcattac ccaaataccg ttagtaaagg cttttaatct tcattcaggt  1440
gccacggttg ctagagggcc aggatttaca ggtggggata tccttcgaag aacgaatgtt  1500
ggtaactttg gagatatgcg tgtaaatatt actgcaccac tatcacaaag atatcgagta  1560
aggattcgtt atgcttctac tacaaattta cgattccata catcaattaa cggaagagct  1620
attaatcagg cggattttcc agctactatg aatagtgggg gtaatttaca gtccggaagc  1680
ttcaggattg caggttttac tactccattt accttttcag atgcactaag cacattcaca  1740
ataggtgctt ttggcttctc ttcaggtaac gaagtttata tagatcgaat tgaatttgtt  1800
ccggcagaag taacctttga ggcagaatat gatctagaaa gagcacaaaa gtaa        1854

SEQ ID NO: 185         moltype = DNA  length = 2004
FEATURE                Location/Qualifiers
source                 1..2004
                       mol_type = other DNA
                       organism = Bacillus thuringiensis
SEQUENCE: 185
atggagataa taaataatca gaatcaatgc attccttaca attgtttaaa taatcctgaa  60
gtagagatat tagggattga aaggtcaaat agtaccgtag tagaagacat cagcttgggg  120
cttagccgtc tgttagtttc cgcaatccca cttggggatt ttttacttag cttgtttgat  180
gtaatatggg gggctatagg tcgttcagaa tgggatatat ttttagagca gattgagcta  240
ttgatcggcc aaagaataga ggaattcgct aggaaccagg caatttctag attagaaggg  300
ctaagcaatc tttaccgaat ttacacaaat gcttttaaaa actgggaagc agatcctact  360
aatccagtat taagagaaga gatgcgtatt caatttaatg acatgaacag tgcttttaca  420
acagctattc ctcttttttc agttcaaggt tatgaaattc ctcttttagg ggtagaacca  480
catcgctatc aagctaacaa aataaaatac cccctaaaaa taaaaaaata cgctattctt  540
tctgtagaat cagcggaaag gatggcgttt tttatgtcta cttctgtatc tgatgaatta  600
caactcttcg ctcaggaaat tcagagctta ttatcttcaa atatcttaag aggttttgct  660
agagatgttg gttttgtaca gcgaaccagt aagtaccaag ccaaagattt agtcgcttta  720
```

-continued

```
tgtgtatgga tgaaccaaaa tgtcgctacg acgtctttaa ctcag

```
aatgggcaa gggcagcctt agtttctcag cgatttaaca atttagatag cctatttaca  540
caatttatgc ctagctttgg ctctggtcct ggaagtcgaa attatgcaac tatattactt  600
ccagtatatg cacaagcagc aaaccttcat ttgttattat taaaagatgt agacatttat  660
ggagctagat gggggctgaa tcaaactcaa atagatctat tccattctcg tcaacaaggg  720
cttactcaga cttatacaaa tcattgtgtt actgcgtata atgatggatt agcggaatta  780
agaggcacaa gcgttgagag ttggctcaaa tatcatcaat accgtaggga aatgacagta  840
acggcaatgg atttagtggc attattccca tactataatg ttcgacaata tccaaatggg  900
gcaaatccac aacttacacg tgaggtatat acagatccaa tcgtatttaa tccgcctaag  960
cctccaagtg gcgctttctg cgaaagtttt tatactatcc gagcggcacg agaacgttta 1020
acttttcgc aacttgaaaa tgcaataatt cgtccaccgc gcttgtttga aaggtttcaa 1080
gcattaggga tttatacaca cgaggcgaga ctgaatcaaa atagtgctcc aatgaactat 1140
tggattggac attttataag aaatactcgt ttgggtgact caacaacaat tacttcaaat 1200
tatgaacaa ccaataatcg tttaactaat ttcactcctc ctactaacag tgatgtttat 1260
caaattaatt caatctcaag taatttagcc gctatttag gcactatatt tgggttact 1320
aacgcagcat tccatcatgg atcaggaaat atttggtcgt atgtcggaca aaataacgcc 1380
cttgcacaat gtcatcaaaa ctataattca atagaagaat taccaaacca aagcgatgaa 1440
cctacagtta gaagttatag ccatagatta tctcatatca cctctttta tttcaatgta 1500
cagcttaata atcctgtact ctctactggc aatatgcctg tatatgtgtg gacacatcgc 1560
ggtgtggacc ttaataacac gattacttca gatagaatta ctcaattacc attggtaaag 1620
gcatctgaac ttgttgcagg tactactgtc gtgaaaggac caggattcac aggaggagat 1680
atacttcgaa gaacgagcaa tggtaatttt ggaacaataa gagtaatggt tagttcacca 1740
ttaacacaac aatatcgcct aagagttcgt tatgcctcaa caggaaattt cagcatagtg 1800
gtaagacgtg gaagcactac tgtaggtaat attagagtcc caagtacaat gaacagggga 1860
gcggaattca ggtacgaatc ctttgacacg agagagtta ctactactgg tccgcagaat 1920
ccgccttta catttacaca aactcaagag agtctaacag tggctgcaga aggtgttagc 1980
accggtagtg aatattttat agatcgaatt gaaatcatcc ctgtaaatcc gacacgagaa 2040
gcggaagagg atttagaagc agcgaagaaa gcggtggcgt aa                    2082

SEQ ID NO: 188          moltype = DNA   length = 2124
FEATURE                 Location/Qualifiers
source                  1..2124
                        mol_type = other DNA
                        organism = Bacillus thuringiensis
SEQUENCE: 188
atgaatcgaa ataatcaaaa tgaatatgaa gttattgatg cccccccattg tgggtgtccg   60
tcagaggatg ttgtaaaata tcctttgaca gatgattcga atgctggatt gcaaaatatg  120
aattataaag agtatttgaa tatgtctgag ggagattatg ctgattcaat tagatatcct  180
ttagccaata atccatattc atctgcttta aatttaaatt cttgtcaaaa tagtagtatt  240
ctcaactgga ttaacatatt aggaaatgca gcaaaagaag ccatatctat tgggacaaca  300
ataatctcta ttattacaac acctcctctc actggattaa tttcaataac ttatgatctt  360
ataagtaaag tgctaggagg tagtagtggc ccatccatat cagatttgtc tatatgtgac  420
ttattatcta ttattgattt acggataagt caaagtgttt tgaatgatgg gattgctgat  480
tttaacggtt ctataatcat atataggaac tatttggaag cattagatag ctggaataag  540
aataatactc ctgctgctgc tgaagaggtc cgtgctcgtt ttagagccgc tgacacagaa  600
tttgataaa ttttaacacg aggctcttta acaaatggtg gctcgttagc tagacaagat  660
ggccaaatat tattattacc ttctttgca agtgctgcat atttccattt atcactattg  720
agagatgctg ctaggtatgg ggctaattgg gggctattca atgctcacac tcttataaat  780
tatcagtcaa aattagtaga acttattgaa tcatatacta attattgtgt acattgtgtat  840
aatcaaggtc ttaaccaact aaggcaacga ggtaatagtg ctacagcttg gttagaattt  900
catagatatc gtagagagat gacattgatg gtattagata tagtagcatc atttttcaagt  960
cttgatatta ctagatatcc gatagaaaca gattttcagt tgagtagggt cattatacca 1020
gatccaatcg gttttgtaaa tcgtggtaat cttaggctgg aaagctggtt cagctctgtt 1080
aataacgcta cttttttcagg gctagaaagt gcaataccta atcctagcca gtcttggttt 1140
ttaaatagta tgattatatc tactggttca cttacattgc cagttagccc aaatactgat 1200
agagcgaggg tgtggtatgg gggcgagat cgagttttctc ctgctagttc acaatttatt 1260
actgaacaaa tgtctgggca acagacggct gataccaaa atatttagg gcgaaatata 1320
tttgaaatag attctcaagc atgtaattta aataatacca cttatggagt aataggggct 1380
ttattttatc atgatgctag tcagggttct caaagatctt tatatgaagg ttttattaga 1440
acaacaggga tagataatcc tgttgttcag aaatattaaca cttatttccc tggagaaaat 1500
tcagatatcc caactccaca agactatact catatattaa gtagaacaat aaatttaaca 1560
gggggactta gacaagtagc atctggtcgt cgttcttctc tagtaatgta tggttggaca 1620
cataagagcc tgactcttaa caataccatt aatccagata gaattacaca gataccgttg 1680
acaaagctag atagccgggg ttcaaatatt tcttatgtga acgatccagg atttataggc 1740
ggaaatctac tcagaatgac ggccaatggt acacttggga cattaagggc aaattttccca 1800
cttaacatta gatcacattt tcgcattaga gtccgttatg ctgctacaag aaatattcga 1860
ttgagtgtaa atggaagttt cggtactatt tctcaggaat ttcctagtac aatgagattg 1920
ggagaggatt taagatacgg ttcctttgct ataagagagt ttagtacatc tgttagaccc 1980
actgcaagtc ctgacgtaat ccgattgaca gtagagccaa ttttctctgg gcaacagatt 2040
tatgtagaca gaattgagtt cgtcccagtt attcccacaa gagaagcgga agagaattta 2100
gacgcagcga agaaagcggt ggcg                                        2124

SEQ ID NO: 189          moltype = DNA   length = 1971
FEATURE                 Location/Qualifiers
source                  1..1971
                        mol_type = other DNA
                        organism = Bacillus thuringiensis
SEQUENCE: 189
atgccatcta agaatcaaaa tatgtatcaa gtttgtctca gcaatacgac agttgataaa   60
aactttacaa attcactaga aaacaacaca aatatggaat tacaaaatat taattatgaa  120
```

```
gattgtttga gaatgtctga gtatgaaggt atagagccgt tgttagtgt atcaacaatt    180
caaacaggta ttggtattgc gggtaaaata cttggtaccc taggcgttcc ttttgcagga   240
caagtagcta gtctttatag ttttatctta ggtgagctat ggcctaaggg gaaaagccaa   300
tgggaaatct ttatgaaaca tgtagaagag attattaatc aaaaaatatc aacttatgca   360
agaagtaaag cacttacaga cttgaaagga ttaggagatg cctttagctgt ctaccatgaa   420
tcgctggaaa gttgggttgg aaatcgtaat aacacaaggg ctaggagtgt tgtcaagagc   480
caatatatcg cattagaatt gatgttcgtt cagaaactac cttcttttgc agtgtctgga   540
gaggaggtaa cattattacc gatatatgcc caagctgcaa atttacattt gttgctatta   600
cgagatgcgt ctatttttgg aaaagagtgg ggattatcat cttcagaaat ttcaacattt   660
tataaccgtc aagtcgaacg agcaggagat tattccgacc attgtgtgaa atggtatagc   720
acaggtctaa ataacttgag gggtacaaat gccgaaagtt gggtacgata taatcaattc   780
cgtagagaca tgactttaat ggtactagat ttagtggcac tatttccaag ctatgataca   840
caaatgtatc caattaaaac tacagcccaa cttacaagag aagtatatac agacgcaatt   900
gggacaatac atccgcatcc aagttttaca agtacgactt ggtataataa taatgcacct   960
tcgctctctg ccatagaggc tgcggttatc cgaagcccgc atctacttga ttttccagaa  1020
caacttacaa tttacagcac attaagtcga tggagtaaca ctcagtatat gaatatatgg  1080
gtaggtcata gacttgaatc tcgaacaata ggagggtcat aaatacctc gacacaagga  1140
tctaccaata cttctattaa tcctgtaaga ttacagttta cggctcgaga cgtttatagg  1200
actgaatcat tggcagggct aaatatattt ttaactcaac ctgttaatgg ggtaccttgg  1260
gttagattta attggagaaa tccctgaat tctcttagag gtagccttct ctatactata  1320
gggtatactg gagttgggac gcaattacaa gattcagaaa ctgaattacc accagaaaca  1380
acagaacgac caaattatga atcttacagt catagattat ctcatatagg actcattca  1440
tcatctcatg tgagagcatt ggtatattct tggacgcacc gtagtgcaga tcgtacaaat  1500
acaattggac caaatagaat tacacaaata ccattggtaa aagcacttaa ccttcattca  1560
ggtgctactg ttgttagagg gccaggattt acaggtgggg atatccttcg tagaacgaat  1620
actggtacat ttggagatat acgttaaat attaatgtgc cattatccca agatatcgc   1680
gtaaggattc gttatgcttc tactacagat ttcaattt tcacgagaat taatggaacc    1740
actgttaata ttgctaattt ctcaagaact atgaataggg gggataattt agaatctaga  1800
agttttagaa ctgcaggatt tagtactcct ttttaatttt taaatgccca aagcacattc  1860
acattgggtg ctcagagttt ttcaaaatcag gaagtttata tagataggat tgaatttgtt  1920
ccggtagaag taacatatga ggcagaatat gattttgaaa aagcgcaaga g           1971

SEQ ID NO: 190         moltype = DNA   length = 1986
FEATURE                Location/Qualifiers
source                 1..1986
                       mol_type = other DNA
                       organism = Bacillus thuringiensis
SEQUENCE: 190
atgccactaa agaatcaaga taagcatcaa agttttccta gcaatgcgaa agtagataaa    60
atctctacgg attcactaaa aaatgaaaca gatatagaat tacaaaacat taatcatgaa   120
gattgtttga aaatgtctga gtatgaaaat gtagagccgt tgttagtgc atcaacaatt   180
caaacaggta ttggtattgc gggtaaaata cttggtaccc taggcgttcc ttttgcagga   240
caagtagcta gtctttatag ttttatctta ggtgagctat ggcctaaggg gaaaatccaa   300
tgggaaatct ttatgaaaca tgtagaagag attattaatc aaaaaatatc aacttatgca   360
agaaataaag cacttacaga cttgaaagga ttaggagatg cctttagctg ctaccatgat   420
tcgcttgaaa gttgggttgg aaatcgtaat aacacaaggg ctaggagtgt tgtcaagagc   480
caatatatcg cattagaatt gatgttcgtt cagaaactac cttcttttgc agtgtctgga   540
gaggaggtac cattattacc gatatatgcc caagctgcaa atttacattt gttgctatta   600
agagatgcat ctatttttgg aaaagagtgg ggattatcat cttcagaaat ttcaacattt   660
tataaccgtc aagtcgaacg agcaggagat tattccgacc attgtgtgaa atggtatagc   720
acaggtctaa ataacttgag gggtacaaat gccgaaagtt gggtacgata taatcaattc   780
cgtagagaca tgactttaat ggtactagat ttagtggcac tatttccaag ctatgataca   840
caaatgtatc caattaaaac tacagcccaa cttacaagag aagtatatac agacgcaatt   900
gggacagtac atccgcatcc aagttttaca agtacgactt ggtataataa taatgcacct   960
tcgttctctg ccatagaggc tgcggctatc cgaagcccgc atctacttga ttttctagaa  1020
caacttacaa ttttttagcgc ttcatcacga tggagtaata ctaggcacat gacttattgg  1080
cgggggcaca cgattcaatc tcggccaata ggaggcggat aaatacctc aacgcatggg   1140
gctaccaata cttctattaa tcctgtaaca ttacggttcg catcacgaga cgtttatagg  1200
actgaatctt atgcaggagt gcttctatgg ggaatttacc ttgaacctat tcatggtgtc  1260
cctactgtta ggtttaattt tacgaaccct cagaatattt ctgatagagg taccgctaac  1320
tatagtcaac cttatgagtc acctgggctt caattaaaag attcagaaac tgaattacca  1380
ccagaaacaa cagaacgacc aaattatgaa tcttacagtc acaggttatc tcatataggt  1440
ataatttac aatccagggt gaatgtaccg gtatattctt ggacgcatcg tagtgcagat   1500
cgtacgaata cgattggacc aaatagaatc acccaaatcc caatggtaaa agcatccgaa  1560
cttcctcaag gtaccactgt tgttagagga ccaggattta ctggtgggga tattcttcga  1620
agaacgaata ctggtggatt tggaccgata agagtaactg ttaacggacc attaacacaa  1680
agatatcgta taggattccg ctatgcttca actgtagatt tgatttcttt tgtatccgt   1740
ggaggtacta ctgtaaataa ttttagattc ctacgtacaa tgaacagtgg agacgaacta  1800
aaatacggaa attttgtgag acgtgcttttt actacaccctt ttacttttac acaaattcaa  1860
gatataattc gaacgtctat tcaaggcctt agtggaaatg gggaagtgta tagataaaa   1920
attgaaatta ttccagttac tgcaaccttc gaagcagaat atgatttaga aagagcgcaa  1980
gagtaa                                                              1986

SEQ ID NO: 191         moltype = DNA   length = 1845
FEATURE                Location/Qualifiers
source                 1..1845
                       mol_type = other DNA
                       organism = Bacillus thuringiensis
SEQUENCE: 191
```

-continued

```
atgccgaata atattcaaaa tcaatgcgta ccttataatt gtctaagcac ccctgagaaa  60
atactattag atgaggaaag aattgagact gggaatacat caatcgatct ttctttgtcg  120
cttgtgagcc ttcttttagg tgaattcgtc cctggtgcgt catttgtact aggtctaatt  180
gatataatat ggggatttgc aggtccctct caatgggacg catttctggt acagattgaa  240
cagttaattg acgaaagaat aggtcagttc gcaaggaatc aagcaatttc tagattagaa  300
gggctaagca atctctatca aatatacgca gaagatttta cacagtggga agcagatccc  360
gataatccag cattaagaga agagatgcgt actcaattca atgatatgaa cagtgctctt  420
acaaccgcta ttcctctttt ggcagttcaa aactatcaaa ttcctctttt atcagtatat  480
gttcaagctg caaatttaca tttatcagtt ttgagagatg tttcagtgtt tggacaaagt  540
tggggatttg atgcggcgac tattaatagc cgttataatg atttaactag gcttattagc  600
agctatacag atcatgtagt aagatggtat gatacaggat tagaccgttt gcgaggctct  660
acttaccaag actggtttag atacaaccga tttagaagag aattaacatt gactgcatta  720
gatatcgttg ctcttttccc aaactatgat atcaaaatgt atccaatcca acccgttagc  780
caactaacaa gggaagttta tacggaccca ttaattaatt tcaatccgca gttacagtct  840
gtagctcaat tgcctacttt taacgttatg gaaagtaacg caattagaaa ccctcattta  900
gttgacttct tgaataacct tagaattttt acagattggt ttagtgtcgg acggcactat  960
tattggggag gacatcgagt gatttccaaa cgtgtaggag gaagggagat aaccttccct  1020
atatatggaa gggaggcaaa gcaggaacct ccaagatcct ttacttttaa tggacctgtt  1080
tttaggacgt tatcaaatcc taccctaaga ccattacaac aacctgcacc agctcctcct  1140
tttaatttac gtggcttgga aggtgtaaaa ttttatacac ctacaaatac ctttacgtat  1200
cggggaagag gcccgcgtga ttctttaact gaattaccgc ctggagatac aagtgtacta  1260
cctcgcgaag gatatagtca ccggttatgt catgcaacat ttattcaaag atctggcaca  1320
cctttttttaa caacaggcgt agtcttttct tggacacatc gtagtgctga tgaaacgaat  1380
ataatttatc cagataagat tactcaaatt ccatgggtaa aggcgcatac ccttgaatcg  1440
ggggccactg ttattaaggg tcctggattt acaggagggg atattcttac tgttcttact  1500
agtcttggtt ccttgggcgc tttacgagta acttttacgg ggcaattacc acaaacatat  1560
aatatacgaa tccgatatgc ctcggtgcta aataaatatg gtacactcca tttttcacag  1620
ccacctgcat atgggctcac atttccaaaa actatggata tagatgaacc attaacatct  1680
cgctcgtttg cttttacaac tctttggaca ccaataacct ttacacgagc acaagaggaa  1740
tttaatctaa caatacaatc aggtgtttat atagatagaa ttgaatttgt tccggcagaa  1800
gtaacatttg aggcagacta tgacttggaa aaagcgcaaa agtaa                  1845

SEQ ID NO: 192         moltype = DNA  length = 1848
FEATURE                Location/Qualifiers
source                 1..1848
                       mol_type = other DNA
                       organism = Bacillus thuringiensis
SEQUENCE: 192
atgccgaaag tgaataataa aaatcaatgt ctgccttata attgtttaaa taatcctgaa  60
aatgagatat tagatattga aaggtcaaat agtactgtag caacaaacat cgccttggag  120
attagtcgtc tgctcgcttc cgcaactcca ataggggggga ttttattagg attgtttgat  180
gcaatatggg ggtctatagg cccttcacaa tgggatttat ctttagagca aattgagcta  240
ttgattgacc aaaaaatagg ggaattcgct agaaaccagg caatttctag attagaagag  300
ataagcagtc tgtacggaat ttatacagaa gcttttagag agtgggaagc agatcctact  360
aatccagcat taaaagaaga gatgcgtact caatttaatg acatgaacag tattcttgta  420
acagctattc ctcttttttc agttcaaaat tatcaagtcc catttttatc agtatatgtt  480
caagctgcaa atttgcattt atcggttttg agagatgttt cagtgtttgg gcaggcttgg  540
ggatttgata tagcaacaat aaatagtcgt tataatgatc tgactagact tattcctata  600
tatacagatt atgctgtacg ctggtacaat acgggattag atcgcttacc acgaactggt  660
gggctgcgaa actgggcaag atttaatcag tttagaagag agttaacaat atcagtatta  720
gatattattt ctttttttcag aaattacgat tctaggttat atccaattcc aacaagctcc  780
caattaacgc gggaagtata tacagatccg gtaattaata taactgacta tagagttggc  840
cccagcttcg agaatattga gaactcagcc attagaagcc cccaccttat ggacttctta  900
aataatttga ccattgatac ggatttgatt agaggtgttc actattgggc agggcatcgt  960
gtaacttctc attttacagg tagttctcaa gtgataacaa cccctcaata tgggataacc  1020
gcaaatgcgg aaccaagacg aactattgct cctagtactt ttccaggtct taacctattt  1080
tatagaacat tatcaaatcc tttttccga agatcagaaa atattacttc taccttaggg  1140
ataaatgtag tacagggagt agggttcatt caaccaaata atgctgaagt tctatataga  1200
agtaggggga cagtagattc tcttaatgag ttaccaattg atggtgagaa ttcattagtt  1260
ggatatagtc atcgattaag tcatgttaca ctaaccaggt cgttatataa tactaatata  1320
attagcctgc caacatttgt ttggacacat cacagtgcta ctaatacaaa tacaattaat  1380
ccagatatta ttacacaaat acctttagtg aaaggattta gacttggtgg tggcacctct  1440
gtcattaaag gaccaggatt tacaggaggg gatatccttc gaagaaatac cattggtgag  1500
tttgtgtctt tacaagtcaa tattaactca ccaattaccc aaagataccg tttaagattt  1560
cgttatgctt ccagtaggga tgcacgaatt actgtagcga taggaggaca aattagagta  1620
gatatgaccc ttgaaaaaac catggaaatt ggggagagct taacatctag aacatttagc  1680
tataccaatt ttagtaatcc tttttcattt agggctaatc cagatataat tagaatagct  1740
gaagaacttc ctattcgtgg tggtgagctt tgtatagata aaattgaact tattctagca  1800
gatgcaacat ttgaagaaga atatgatttg gaaagagcac agaagtaa               1848

SEQ ID NO: 193         moltype = DNA  length = 1848
FEATURE                Location/Qualifiers
source                 1..1848
                       mol_type = other DNA
                       organism = Bacillus thuringiensis
SEQUENCE: 193
atggataata ataatcaaaa tcaatgcata ccttacaatt gtttaagtaa tcctgaatta  60
gagatattag agattgaaag atcaaataat accgtagtag aagacatcac cttggggctg  120
agtcgtctgc tcgtttccgc aattccacta ggggatttta tacttggcct gtttgatgta  180
```

```
atatgggggg ctttaggtcg ttcagagtgg gatatatttt tagagcaaat tgagctattg    240
atcggccaaa gaatagagga atttgctagg aatcaggcaa tttctagatt agaagggcta    300
agcaatcttt atcgaattta cacaaatgct tttaaagact gggaagcaga tcctactaat    360
ctagaattaa aagaagagat gcgtactcaa tttaatgaca tgaacagtgc ttttacaaca    420
gctattcctc tttttttcagt tcgaggttat gaacttcctc ttttatcagt atatgttcaa    480
gctgcaaatt tacatttatc agttttaaga gatgtttcag tgtttggaca acgttgggga    540
tttgacgtag caacagtcaa tcgtcgttat gatgatttaa ctacgaatat aggcgactac    600
acagattatg ctttaagctg gtataatacg ggattaaacc gtctaccacg taatgatggg    660
ctgcgaggat gggcaagatt taataggttt agaagagatt taacaatatc agtattagat    720
attatttctt ttttccaaaa ttacgattct agattatatc caattccaac aatctcccaa    780
ttaacgcggg aagtatatac agatccggta attaatataa ctgattatag agttacccca    840
agtttcgaga gtattgaaaa ctcagcaatt agaagccccc atcttatgga tttcttaact    900
aatataatta ttgacactga tttaataaga ggtgtttact attgggcagg acatcgtata    960
aattctcgct ttaccgggac cgcttttcca catataataa catctcctca atatggaata   1020
actgcaaacg cagaaccaag acgtacaata gcgcctggtc cttttcaagg tgccttccct   1080
acttatagaa cactatcaga cccttttcttc gaagatcag acaatattag tccaaccttaa   1140
gggataaatg tagtacaggg ggtagggttc ttacaaccaa ataattttga atctctatat   1200
agaaggagag ggacagtaga ttctctcgat gagttgccaa ttgatggtga aaatccatta   1260
gttggatata gtcatcgatt aagtcacgtt acattaacca ggtcattatt taatactaat   1320
ataactagcc tgccaacatt tgtttggaca catcacagtg ctactgatac aaatacaatt   1380
gctccagatg tcattaccca aataccgtta gtaaaggctt tcaatcttca ttcaggtgcc   1440
acggttgcta gagggccagg attacaggt ggggatatcc ttcgaagaac gaatgttggt   1500
aactttggag atatgcgtgt aaatattact gcaccactat cacaaagata tcgagtaagg   1560
attcgttatg cttctactac aaatttacga ttccatacat caattaacgg aagagctatt   1620
aatcaggcgg attttccagc tactatgaat agtgggggta atttacagtc cggaagcttc   1680
aggattgcag gttttactac tccatttacc ttttcagatg cactaagcac attcacaata   1740
ggtgctttg gcttctcttc aggtaacgaa gtttatatag atcgaattga atttgttccg   1800
gcagaagtaa cctttgaggc agaatatgat ctagaaagag cacaaaag              1848

SEQ ID NO: 194        moltype = DNA   length = 2049
FEATURE               Location/Qualifiers
source                1..2049
                      mol_type = other DNA
                      organism = Bacillus thuringiensis
SEQUENCE: 194
atgcctcgaa ataatcaaaa tgaatatgaa gttattgatg ccccacattg tgggtgtccg     60
gcagatgatg ttgtaaaata tcctttgaca gatgatccga atgctggatt gcaaaatatg    120
aactataagg aatatttaca aacgtatggt ggagactata cagatcctct tattaatcct    180
aacttatctg ttagtggaaa agatgtaata caagttgaa ttaattgt agggagatta      240
ctaagctttt ttggattccc ctttctagt caatggtta ctgtatatac ctatctttta      300
aacagcttgt ggccggatga cgagaattct gtatgggacg cttttatgga gagagtagaa    360
gaacttattg atcaaaaaat ctcagaagca gtaaaggta gggcattgga tgacctaact    420
ggattacaat ataattataa tttatatgta gaagcattga atgagtggct gaatagacca    480
aatggcgcaa gggcatcctt agtttctcag cgatttaaca ttttagatag cctatttaca    540
caatttatgc caagctttgg ctctggtcct ggaagtcaaa attatgcaac tatattactt    600
ccagtatatg cacaagcagc aaaccttcat ttgttattat taaagatgc agacattat      660
ggagctagat ggggctgaa tcaaactcaa acatatctcg tccattctcg tcaacaaagc     720
cttactcaga cttatacaaa tcattgtgtt actgcgtata atgatggatt agcggaatta     780
agaggcacaa gcgttgcgag ttggctcaaa tatcatcaat accgtaggga aatgacagta     840
acggcaatgc atttagtggc attattccca tactataatg ttagacaata tccaaatggg     900
gcaaatccac aacttacacg tgaggtatat acagatccaa tcgtatttaa tccgcctgag     960
cgtccaagtg gcgcttctg cgaaagtttt tatactatcc gagcggctcg agaacgttta    1020
acttttttcgc aacttgaaca tgcaataatt cgtccgccgc gcttgtttga aaggtttcaa   1080
gctttaggga tttatacagg cgaggcgcga ctgaatgcaa atagtgctcc aatgaactat    1140
tggattggac atttttataag aaatacacgt ttaggtgact caacaacaat tactacaaat   1200
tatgcaacaa ccaataatcg tttaactaac ttcagtatgc cttctgatgt ttatcaaatc    1260
aattcaacct caagtaattt agccgctatt ttaggcactt tatatggggt tactagagca   1320
caattccatt ttggatcagg aagttttccg acgtatgtcg gacaaaatag cgttcttcca   1380
caatgtcatc aaaactataa ttcaatagaa gaattaccaa accaaagcga tgaacctaca   1440
gttagaagtt atagccatag attatctcat atcacctctt ttaatttcaa tgtacagctt   1500
aataatcctt taatttctgc gggcaatatg cctgtatatg tgtggacaca tcgcagtgtg   1560
gaccttacta acaggatttc ttcagataga attactcaaa taccagtggt aaaggcatat   1620
gagctaagta gtggtgctac tgtcgtgaaa ggtccaggat tcacaggagg agatgtaatc   1680
cgaagaacaa atactggtgg gttcggagca ataagggtgt tggtcactgg accgctaaca   1740
caacgatatc gcataaggtt ccgttatgct tcgacaatga tttttgattt ctttgtaaca   1800
cgtgggagaa ctactataaa taattttaga tttacacgta caatgaacag gggacaggaa   1860
tcaagatatg aatcctatcg tactgtagag tttacaactc cttttaactt tacacaaagt   1920
caagatataa ttcgaacatc tatccaggga cttagtggaa atgggaagt ataccttgat    1980
agaattgaaa tcatccctgt aaatccgaca cgagaagcag aagaggatct agaagatgca   2040
aagaaataa                                                          2049

SEQ ID NO: 195        moltype = DNA   length = 2010
FEATURE               Location/Qualifiers
source                1..2010
                      mol_type = other DNA
                      organism = Bacillus thuringiensis
SEQUENCE: 195
atgcctcgaa ataatcaaaa tgaatatgaa attattgacg cttccacttg tggttgttcg     60
tcagatgatg ttgttcaata ccctttggca agagatccga atgctgtatt ccaaaatatg    120
```

```
cattataaag attatttgca aacgtatgat ggagactata caggttctct tataaatcct    180
aacttatcta ttaatcctag agatgtactg caaactggaa ttaatattgt gggaagatta    240
ctaggatttc taggtgttcc atttgctggt cagttagtta ctttctatac ctttctttta    300
aatcaactgt ggccaacaaa tgataatgca gtatgggaag cttttatggc acaaatagaa    360
gagcttatta atcaaagaat atccgaagca gtagtacgga cagcagcgga tcatttaacg    420
ggattacacg ataattatga gttatatgta gaggcattgg aggaatggct ggaaagaccg    480
aatgctgcta gaactaatct acttttaat  agatttacca ccctagatag tcttttaca     540
caatttatgc caagctttgg tactggacct ggaagtcaaa actacgcagt tccattactt    600
acagtatacg cacaagcagc gaaccttcat ttgttattat taaaggatgc tgaaatatat    660
ggagcaagat ggggactgaa ccaaaatcag attaactcat tccatacgcg ccaacaagaa    720
cgtactcaat attatacaaa tcattgcgta acgacgtata ataccggttt agatagatta    780
agaggcacaa atactgaaag ttggttaaat tatcatcgtt tccgtagaga gatgacatta    840
atggcaatgg atttagtagc gctattccca tattataatg tacgacaata tccaaatgga    900
gcaaatcctc agcttacacg tgaaatatat acggatccaa ttgtatttaa tccaccagct    960
aatgtgggat tatgtagacg ttggggcaat aacccatata atagattttc tgaactagaa   1020
aacgctttta tccgcccgcc acatctttt  gatagattga ataccttaac aattagtaga   1080
aatagatttg acgttgggtc aaactttata gaaccgtggt ctggacatac gttacgccgt   1140
agttattcga ataattcgac agtatatgaa gatagttatg gccaaattac agccacaaga   1200
acaacaatta atctgccggc taatggaact ggccgagtag aatcaacagc agtagatttt   1260
cgtagcgcgc ttgtggggat atacggtgtt aatagagctt cttttattcc aggtggtgtg   1320
tttagtggca cgactcagcc ctctactgga ggatgtagag atttgtatga ttcaagtgat   1380
gaattaccac cagacgaaag tactggaagt tttgcccata gactatctca tgttacctt    1440
ttaagtttta caactaatca ggccggatcc atagccaatt caggacgcgt ccctacttat   1500
gtctggaccc atcgcgatgt ggactttaat aatacaatta accccaatag aattactcaa   1560
ataccagtgg taaaggcata tgagctaagt agtggtgcta ctgtcgtgaa aggtccagga   1620
ttcacaggag gagatgtaat ccgaagaaca aatattggtg ggttcggagc aataagggtg   1680
tcggtcactg gaccgctaac acaacgatat cgcataaggt tccgttatgc ttcgacaata   1740
gattttgatt tctttgtaac acgtggagga actactataa ataatttag  atttacacgt   1800
acaatgaaca ggggacagga atcaagatat gaatcctatc gtactgtgga gtttacaact   1860
cctttaact  ttacacaaag tcaagatata attcgaacat ctatccaggg acttagtgga   1920
aatggggaag tataccttga tagaattgaa atcatccctg taaatccaac acgagaagcg   1980
gaagaggatc tagaagcagc aaagaaataa                                    2010

SEQ ID NO: 196       moltype = DNA  length = 1845
FEATURE              Location/Qualifiers
source               1..1845
                     mol_type = other DNA
                     organism = Bacillus thuringiensis
SEQUENCE: 196
atgccaaata ggagggaatt tatgaataac gaaacacaaa atcaatgcat cccttataat     60
tgtttaagta accctgaagt ggagatatta ggaggagaca gaagtgctgg tattctgcca    120
atacaaatct ctctatcgtt aacgcgtttc cttgctggcg aatttatccc aggagtggga    180
gttgcacttg ggttatttga tttaatatgg ggatttataa gtccttctga ttgggatcaa    240
tttcttgtac ggattgaaca attaattgat caaagaatag aagaattaga aagaactaga    300
gcactctctg cattacaagg actagcgaat agttatgggg tgtatgttga agcgcttaga    360
gcgtgggagg ctgatcctaa taatgaagca ttaaaggaag atgtgcgtac tcgatttact    420
agtattgatg gtgatttaat agcagagatt cctagattta gacttagagg ttatgaggtt    480
cctctgttat cggtatatgt tcaagcaact aatttacatt tatctatgtt aagagattcc    540
gtaagtcttg ggctgcggtg gggatttgat attgccacga ttaataatca ttataacaga    600
ttaattaata atattcgtga gtatacagat tatagtgtga gcacatacaa tataggatta    660
gaacgcttaa ggggaactcg tgttcaagat tgggtaaagt ttaatcagtt taggagggaa    720
ctaacactta ctgtgttaga tattgtttct cttttccaa  actatgatgt cagaacatat    780
ccaattcaaa cagtatcaca attaactaga gaaatttata caaatcctgt atttgaaaat    840
tcaccagtta atattaatct tgttaatggc tttaatagag ttgagtacgg agtccgacaa    900
cctcatctta tggatcacct catgaatgta tctatttctg aagaagatta tagaggggac    960
accttttggg gaggtcactc tattgcctcc gtagatacgg tggtaatct  tgtcggtttc   1020
ccgtttatg  gtaatttcga tagatttcgt tttcaaacaa tcaacgctca acaatttcct   1080
cttttagaa  cgttatcaga tcctgtttat aacctcagta catctggagg gagaaacaga   1140
ctatttgctc ttgaagggat aggatttcaa caggctgtaa cgggaaccac acgagctttt   1200
aggagagtcg gaacaataga ttctcttatt gaaataccac ctcaagatga aagtgaagta   1260
ccttggaatg gctatagtca tgtattaaat catattacat ttataaattg gccagctgtt   1320
ttcctacaag gggaaagaat agcttctcca atgttttctt ggacacatcg tagtgcagat   1380
cgtatcaata gaattattcc agatgttatc aatcaaattc cagctgttaa aggcagctct   1440
attattaatg gaactgtaat ttcaggacca ggatttactg gaggagattt agttagatta   1500
gaaaataatg catacttga  aattccagtg caattccaaa caacatctac aaattatcga   1560
gttcgtgtac gttatgcctc cacctctcaa gcatctataa gtgtagtttt tggaaatata   1620
gatcatccta gtaccatacc agccacagct gaatcattag acaatctaca atataacgat   1680
tttgattatt ttgatgttat tggtactttc ttaccttcat taggcggtag tttagctttt    1740
agaactttaa gttcgaatgc aaatgtggta atagatagat tcgaatttat cccagttact   1800
gcaacatttg aggcagaata tgatttagaa aaagcgcaag agtaa                   1845

SEQ ID NO: 197       moltype = DNA  length = 1866
FEATURE              Location/Qualifiers
source               1..1866
                     mol_type = other DNA
                     organism = Bacillus thuringiensis
SEQUENCE: 197
atgccgataa tgaataatca gaattattgc attcctata  attgtttgaa taatcctgca     60
ctcgaaatat tagaagaaga aagaatatca gttggtaata caccaatcga tatttccctg    120
```

```
tcgcttacgc agtttctttt gagtgaattt gtcccaggtg cggggtttgt attaggttta   180
tttgatttaa tatggggatt tgtaggcccc tctcaatggg atgcatttct tgtgcaaatt   240
gaacagttaa ttaaccaaag aatagaggaa ttcgctagga accaagcaat ttctagatta   300
gaagggctaa gcaatcttta ccgaatttac tcagaagctt ttagaaatg ggaagcagat    360
cctactaatc cagcgttaag agaagaaatg cgtattcaat tcaatgacat gaacagtgct   420
cttgtaacag ctcttcctct tttttcagtt caaaattatc aagttcctct tttatcagta   480
tatgttcaag ctgcaaattt acatttatcg gttttgagag atgtgtcagt gtttggacaa   540
cgttggggat tgatgtagc gacaatcaat agtcgttata atgatttaac taggaatatt    600
ggcgaatata cagattatgc tgtacgctgg tacaatacgg gattagaacg tgtatgggga   660
ccggattcca gagattgggt aagatataat caatttagaa gagaactaac actaactgta   720
ttagatatta tttctctatt tccgaactat gatagtagaa cgtatccaat tcgaacagtt   780
gcccaattaa caagagaaat ttatacaaac ccagtattag aaaatttga tggtaatttt    840
cgtggaatgg ctcagagaat agaacagaat attaggcaac cacatcttat ggatatcctt   900
aatacaataa ccatttatac tgatgtgcat agaggcttta attattggtc aggacatcaa   960
ataacagctt ctcctgtcgg ttttgcgggg ccagaaatta cttttcctag atatggaacc  1020
atgggaaatg cagctccacc cgtacttgtc tcattaatag gtttggggat ttttagaaca  1080
ttatcatcac ctctttacag aagacttata cttggttcag gcccaaataa tcaggaactg  1140
tttgtccttg atggaacgga attttctttt gcctccctca cgaccaatct accttctact  1200
atatacagac aaaggggaac ggtcgattca ctagatgtaa taccgccaca ggataatagt  1260
gtgccagctc gtgcgggatt tagtcatcga ttaagtcatg ttacaatgct gagccaagca  1320
gctggagcag tttacacctt gagagctcca acgtttctt ggcagcatcg cagtgctgaa   1380
ttcagtaacc aaattccctc atcacaaatt acacaaatac ctttaacaaa gtctattaat  1440
cttggctctg ggaccactgt cgttaaaggg ccaggattta caggaggaga tattcttcga  1500
agaacttcat ctggcgaaat ttcaacttta agagtaacta ttactgcacc attatcacaa  1560
agatatcgcg taaggattcg ttatgcttct actacaaatt tacaattcaa tacagtaatt  1620
aacggaagat ccattaatca ggcgaatttt ccagcaacta tggataatgg ggaaaattta  1680
caattcgaaa acttcagaac tgtaggttat actactcctt ttagcttttc agatgcatca  1740
agtatatttta cattaactgc tcggaacttc tcttcaggta acgaagttta tatagatcga  1800
attgaatttg ttccagcaga tgcaacatta gaggcagaat atgatttaga aagagcgcaa  1860
aagtaa                                                             1866

SEQ ID NO: 198          moltype = DNA  length = 1971
FEATURE                 Location/Qualifiers
source                  1..1971
                        mol_type = other DNA
                        organism = Bacillus thuringiensis
SEQUENCE: 198
atgccttcaa ataggaaaaa tgagaatgaa attataaatg ccttatcgat tccagctgta    60
tcgaatcatt ccgcacaaat ggatctatcg ctagatgctc gtattgagga ttctttgtgt   120
atagccgagg ggaataatat caatccactt gttagcgcat caacagtcca acgggtata    180
aacatagctg gtagaatatt gggcgtatta ggtgtgccgt ttgctggaca actagctagt   240
ttttatagtt ttccttgttgg ggaattatgg cctagtggca gagatccttg gaaattttc   300
ctggaacatg tagaacaact tataagacaa caagtaacag aaaatactag gaatacgtct   360
attgctcgat tagaaggtct aggaagaggc tatagatctt accagcaggc tcttgaaact   420
tggttagata accgaaatga tgcaagatca agaagcatta ttcttgagcg ctatgttgct   480
ttagaacttg acattactac tgctataccg cttttcagaa tacgaaatga agaagttcca   540
ttattaatgg tatatgctca agctgcaaat ttacacctat tattattgag agacgcatcc   600
ctttttggta gtgaatgggg gatggcatct tccgatgtta accaatatta ccaagaacaa   660
atcaggtata cagaggaata ttctaaccat tgcgtacaat ggtataatac agggctaaat   720
aacttaagag ggacaaatgc tgaaagttgg ctgcggtata tcaattccg tagagaccta    780
acgttagggg tattagattt agtagcccta ttcccaagct atgatactcg cacttatcca   840
atcaatacga gtgctcagtt aacaagagaa atttatacag atccaattgg gagaacaaat   900
gcaccttcag gatttgcaag tacgaattgg tttaataata atgcaccatc gttttctgcc   960
atagaggctg ccatttttcag gcctccgcat ctacttgatt ttccagaaca acttacaatt  1020
tacagtgcat caagccgttg gagtagcact caacatatga attattgggt gggacatagg  1080
cttaacttcc gcccaatagg agggacatta aatacctcaa cacaaggact tactaataat  1140
acttcaatta atcctgtaac attacagttt acgtctcgtg acgtttatag aacagaatca  1200
aatgcaggga caaatatact atttactact cctgtgaatg gagtaccttg gctagattt   1260
aattttataa accctcagaa tatttatgaa agaggcgcca ctacctacag tcaaccgtat  1320
cagggagttg ggattcaatt atttgattca gaaactgaat taccaccaga aacaacagaa  1380
cgaccaaatt atgaatcata tagtcataga ttatctcata taggactaat catagggaac   1440
actttgagag caccagtcta ttcttggacg catcgtagtg caactaatac aaatacaatt  1500
aatccagata ttattacaca aataccttta gtgaaaggat ttagacttgg tggtggcacc  1560
tctgtcatta aaggaccagg atttacagga ggggatatcc ttcgaagaaa taccattggt  1620
gagtttgtgt ctttacaagt caatattaac tcaccaatta cccaaagata ccgtttaaga  1680
tttcgttatg cttccagtag ggatgcacga attactgtag cgataggagg acaaattaga  1740
gtagatatga ccttgaaaaa acgatgaaa attggggaga gcttaacatc tagaacacttt  1800
agctatacca attttagtaa tcctttttca tttagggcta atccagatat aattagaata  1860
gctgaagaac ttcctattcg tggtggtgag ctttatatag ataaaattga acttattcta  1920
gcagaggtaa catttgaggc agaatatgat ttagaaagag cacaaagta a             1971

SEQ ID NO: 199          moltype = DNA  length = 1650
FEATURE                 Location/Qualifiers
source                  1..1650
                        mol_type = other DNA
                        organism = Bacillus thuringiensis
SEQUENCE: 199
atgccgata caatcatcct gcagacaatt gcggcaaaca tcggtagtag cttgatgcct     60
atgggaaacc cacaaaattt ataccttatat tcttactatg gaattaagct catcccattt   120
```

```
ttaggttcaa tcctgctttt agctgtactt ggaattagtt tgttatttat atttactcaa    180
aaacttcaaa aaacagattt gaaaatagaa ctacctgtta ttaccgtgaa aaatcgaaaa    240
aaagctaccg tctggatttt gatacttatc actatcattg catctatttt tggaaaagag    300
tggggattat catcttcaga aatttcaaca ttttataacc gtcaagtcga acgagcagga    360
gattattccg accattgtgt gaaatggtat agcacaggtc taaataactt gaggggtaca    420
aatgccgaaa gttgggtacg atataatcaa ttccgtagag acatgacttt aatggtacta    480
gatttagtgg cactatttcc aagctatgat acacaaatgt atccaattaa aactacagcc    540
caacttacaa gagaagtata tacagacgca attgggacag tacatccgca tccaagtttt    600
acaagtacga cttggtataa taataatgca ccttcgttct ctgccataga ggctgctgtt    660
gttcgaaacc cgcatctact cgattttcta gaacaagtta caatttacag cttattaagt    720
cgatggagta acactcagta tatgaatatg tggggaggac ataaactaga attccgaaca    780
ataggaggaa cgttaaatat ctcaacacaa ggatctacta atacttctat taatcctgta    840
acattaccgt tcacttctcg agacgtctat aggactgaat cattggcagg gctgaatcta    900
tctttaactc aacctgttaa tggagtacct aggggttgatt ttcattggaa attcgtcaca    960
catccgatcg catctgataa tttctattat ccagggtatg ctggaattgg gacgcaatta   1020
caggattcag aaaatgaatt accacctgaa gcaacaggac agccaaatta tgaatcttat   1080
agtcatagat tatctcatat aggactcatt tcagcatcac atgtgaaagc attggtatat   1140
tcttggacgc atcgtagtgc agatcgtaca aatacaattg agccaaatag cattacacaa   1200
ataccattag taaaagcttt caatctgtct tcaggtgccg ctgtagtgag aggaccagga   1260
tttacaggtg gggatatcct tcgaagaacg aatactggta cacttgggga tatacgagta   1320
aatattaatc caccatttgc acaaagatat cgcgtgagga ttcgctatgc ttctaccaca   1380
gatttacaat tccatacgtc aattaacggt aaagtatta tcaaggtaa tttttcagca   1440
actatgaata gaggagagga cttagactat aaaaccttta gaactgtagg ctttaccact   1500
ccatttagct tttagatgt acaaagtaca ttcacaatag gtgcttggaa cttctcttca   1560
ggtaacgaag tttatataga tagaattgaa tttgttccgg tagaagtaac atatgaggca   1620
gaatatgatt ttgaaaaagc gcaagagtaa                                    1650

SEQ ID NO: 200           moltype = DNA  length = 1956
FEATURE                  Location/Qualifiers
source                   1..1956
                         mol_type = other DNA
                         organism = Bacillus thuringiensis
SEQUENCE: 200
atgccaccaa ataaccagga taatcatgaa accttatcca acaaagtgac agtcgaaaaa     60
ccttttacag attcactaaa aaatgaaaca actaaaaata gtaattatga agattgtttg    120
aaaatgtcta gacatgaaag cgtagagccg tttgttagtg tatcaacaat tcaaacggga    180
attggtattg ctggtaaaat ccttggtagc ctaggcgttc cttttgctgg gcaagtagct    240
agcctttata gtttattct aggtgagctt tggcctaagg ggaaaagtca atgggaaatc    300
tttatggaag atgtagaaaa acttgttgat caaaaaatat cgatttacgc aagaaacaaa    360
gcacttgcag atttaaaagg attaggagat gctctggctg tctaccatga atcccttgaa    420
agttggattg aaaatcgtaa taacagaaga gctagaagtg ttgttaaaga ccaatatatc    480
gctttggaac ttatgtttgt tcagagactt ccttcttttg cagtatctgg agaagaggtg    540
ccgctattac caatttatgc tcaagctgca aatttacact tattgctatt aagagatgca    600
tcaattttttg gagaagaatg gggtttttca acttcagaaa tttcaacatt ttataaccga    660
caatctagtc ggacgataga atattctgac tattgctcag gatggtataa tacaggacta    720
aatcgcttga gaggtgcaaa tgctgaaagt tgggtacgat ataatcaatt ccgtagagac    780
atgactttaa tggtactaga tctagtagca ctattcccaa gctatgacac tcgcacttat    840
ccaattaaaa ctagtgccca acttacaaga gaagtctata cagatccaaa cggtattgta    900
gcaggaggca ataataattg gtttagaaat ggggcttcgt tttccactat agaaaacgca    960
attattcgac aacctcacct atatgatttt ctaacgaacc ttacaattta cacgagaata   1020
agtcgagcaa accctgctta tatgaatttg tgggcaggge atagaattac ttctaataga   1080
ataggttcta gtaatagtag tgaattggtg tatggggcta taactaatcc agttagtact   1140
actaacttat catttgtcaa tcgggatgtt taccgaactg aatcattagc tggtgggctt   1200
ggcactctga atggaatact ttatggttta actagagttg attttgatat gatatttcgt   1260
aaccgtcctg atatagtaac tggattattt tatcatccgg gacacgcggg cattgcaacc   1320
caagtaaaag attcagaaac agaattacca cctgaaacga cagaacagcc aaattataga   1380
gcatttagtc atctactaag tcatatttca atgggtccaa cgactcaaga cgtacctcca   1440
gtatattctt ggacacacca gagtgcagac cgttcaaata caatcgattc ggataggata   1500
acacaaatac cattggtaaa ggcgcataccc ctttcaatcg gtaccactgt agtaaaaggg   1560
ccagggttta caggagggga tatcctccgt cgaacaagtg gaggaccatt tgcttttagt   1620
aatgttaatc tagattttaa cttgtcacaa aggtatcgtg ctagaattcg ttatgcctct   1680
actactgact taagaattta cgtaacggtt gcaggcgaac gaatttatgc tggtaaattt   1740
aataaaacca tgaaaaaagg tgacccatta acattccaat catttagtta cgcaactatt   1800
aatacagctt ttacattccc agaaagatcg agcagcttga ctgtaggtgc tgatacgttc   1860
gattcaggta atgaagttta tgtagataga tttgaattaa tcccggatac tgtaacattt   1920
gaggcagagt ctgatttaga aaaagcgcaa aagtaa                             1956

SEQ ID NO: 201           moltype = DNA  length = 1977
FEATURE                  Location/Qualifiers
source                   1..1977
                         mol_type = other DNA
                         organism = Bacillus thuringiensis
SEQUENCE: 201
atgccactaa agaatcaaga taagcatcaa agttttttcta gcaatgcgaa agtagataaa     60
atcgctacgg attcactaaa aaatgaaaca gatatagaat tgaaaaatat gaataatgaa    120
gattatttga aatgtctga gcatgagagt ttgatccgt ttgttagtgc atcaacaatt    180
caaacgggta ttggaattgc tggtaaaatc cttggtactc taggtgttcc cttttgctggg    240
caaatagcta gcctctatag ttttatccta ggcgagcttt ggccaaaggg gaaaagtcag    300
tgggaaatct ttatggaaca tgtagaagag cttattgcac aaaaaaaatc aacttacgca    360
```

```
agaaacaaag cactcacaga tttaaaaggt ttaggagatg ctttggctgt ttaccatgag    420
tcacttgaaa gttggattaa aaatcgcaat aacacaaggg ctagaagtgt tgttaagagc    480
caatatatct ctctagaact tatgtttgtt cagaagctgc cttcctttgc ggtatctggg    540
gaagaagttc ctctattacc aatatacgcc caagctgcaa atctcactt gttgctatta     600
agagatgcat ctattttttgg aaaagagtgg ggattatcat cttcagaaat ttcaacattt   660
tataaccgtc aagccgaaag aacgagtgac tattccgacc attgtgtgaa atggtatagt    720
acaggtctaa ataacttgag gggtaaaaat gccgaaagct gggttcgcta taatcaattt    780
cgtaaagata tgatattaat ggtactagat ttagtggcac tattcccaag ttatgataca    840
catatgtatc caattaaaac tacagcccaa cttactagag aagtatatac aaacgcaatt    900
gggacagtac atccgcatcc aagttttgca agtacgactt ggtataataa taatgcacct    960
tcgtttttctg ccatagaggc tgccgttatc cgaagcccgc acctactcga ttttctagaa  1020
caagttacaa tttacagctt attaagtcgg tggagtaaca ctcagtatat gaatatgtgg   1080
ggagggcata gacttgaatt ccgaacaata ggaggagcat taaatacctc aacacaagga   1140
tctactaata cttctattaa tcctgtaaca ttaccgttca cgtctcgaga cgtctatagg   1200
actgaatcat tggcagggct gaatctattt ttaactcaac ctgttaatgg agtacctagg   1260
gttgattttc attggaaatt cgtcacacat ccgatcgcat ctgataattt ctattatcca   1320
gggtatgctg gaattgggac gcaattacaa gattcagaaa ctgaattacc acctgaaaca   1380
acaggacagc caaattatga atcatatagt catagattat ctcatataag actcatttca   1440
gcatcacatg tgaaagcatt ggtatattct tggacgcatc gtagtgcaga tcgtacaaat   1500
acaattgagc caaatagcat tacacaaata ccattagtaa aagcattcaa tcttccttca   1560
ggtgccgctg ttgttagagg accaggattt acaggtgggg atatccttcg aagaacaaat   1620
actggtacat ttggggatat acgagtaaat attaatccac catttgcaaa aggtatcgc    1680
gtaaggattc gttatgcttc tactacagat gtacaattcc atacgtcaat taacggtaaa   1740
gctattaatc aagtaatttt ttcagcaact atgaatagag gagaggactt agactataaa   1800
acctttagaa ctgtaggatt tactactcca tttagctttt cggatgtaca aagtacattc   1860
acaataggtg cttggaactt ctcttcaggt aacgaagttt atatagatag aattgaattt   1920
gttccggtag aagtaacata tgaggcagag catgattttg aaaaagcgca agagtaa      1977

SEQ ID NO: 202          moltype = DNA   length = 1830
FEATURE                 Location/Qualifiers
source                  1..1830
                        mol_type = other DNA
                        organism = Bacillus thuringiensis
SEQUENCE: 202
atgccctcaa atgaacatga ttatttgaaa gtttgtgatg atttaagtga aactaatatg     60
gagaggtttg acaaaaatga tgcactggag attggtatgt ctattgtatc tgaacttctt    120
ggcatgattc caggcggagc agccttacaa tttgtgttta atcaattgtg gtcgcgttta    180
ggtgattctg gatggagtgc attcatgaaa catgttgaag aattaattga tactaaaata    240
gaagggtatg caaaaaataa agccttatct gagttagcag gtatgcacag aaatcttgaa    300
acatatataa aattgcttaa tgaatgggaa aataatactg gaagttcaaa agcacaaggt    360
agagtagcta attatttga aagtcttgag caggcggttg aaagaggtat gcctcaattc     420
gcagttggta atttcgaaat acccctttta actgtttatg tacaagctgc taaccttcat    480
ttattgttat taagagatgt ttcagtttat ggaaaacgct gggatggtc agatcagaaa    540
attaagattt attatgagaa acaagttaag tatactcatg aatacaccaa tcattgttcg   600
acttggtata atagaggact agataaattg aaaaataagg gttcttctta ccaagattgg    660
tacaactata atcgtttccg tagagaaatt actcttactg ttctagatat cgtcgctgta   720
ttcccacact atgatgtgaa agcttatcca attcaaacag ttggccaatt aacaaagggaa   780
gtttatacag accctttaat taatttttat ccgcaactag attctgtatc tcaattcct    840
actttagtg atatggaaaa tgcaacaatt agaaccccac atctgatgga gttttaaga    900
atgctaacaa tctatacaga ttggtatagt gtgggaagaa actattattg gggaggacat    960
cgagtgactt cttaccgtgt aggaggagaa aatataacct cccctttata tggaagtgag   1020
gcaaatcaag agctgcctag acaactgtat ttttatgggc cggttttag aacattatca    1080
aatcctactt taagatactt acagcaacct cgcgccagctc cgccgtttgc tttacgtcgc   1140
ttagaaggag tagaatttca caccactaca ggtactgata tgtatcgtga aagaggatcg   1200
gtagattctt ttaatgagct accgcctttt aatccagttg gactacctcg taatgcatat   1260
agtcaccgtt tatgtcatgc aacgtttgtc cgtaaatctg ggaccccta tctaataacc   1320
ggtactgtct tttctggac acatcgtagt gctgaagaaa ccaatacaat tgattcaat    1380
agaatcacgc aaaattccatt ggtgaaagca tatcaaatta gctcgggcac tactgtgagg  1440
agaggtccag gattcacagg aggcgatata cttcgaagaa ctggtcccgg tacattggg   1500
gatataaaac taaatatcaa ttcaccatta tctcaaagat atcgcgtagg gattcgttat   1560
gcttctacta ctgatttaca attttttcacg aatattaatg gaactaccat taatatgggt 1620
aatttcccaa aaaccgtgaa taattcgagt tctgaaggct atagaactgt atcatttagt   1680
actccatttta gcttttcaaa tgcacaaagt atatttagat tagtataca agcttttttct 1740
ggagtccacg agattcacgt tgatagaatt gaatttgtcc cggcagaggt aacatttgag   1800
gcagagtatg atttagaaag ggcgcaaaag                                   1830

SEQ ID NO: 203          moltype = DNA   length = 1866
FEATURE                 Location/Qualifiers
source                  1..1866
                        mol_type = other DNA
                        organism = Bacillus thuringiensis
SEQUENCE: 203
atggcttata ataataatca aaatcaatgc ataccttata attgtttgaa taatcccgaa     60
atcgaaatat tagaaggcgg aagaatatca gttggtaata ccccaattga tatttctctt    120
tcgcttactc agtttctttt gagtgaattt gtcccaggtg cggggtttgt attaggatta    180
attgatttaa tatggggatt tgtaggtcct tcccaatggg acgcatttct tgctcaagtg    240
gaacagttaa ttaaccaaag aatagcagaa gctgtaagaa atacagcaat tcaggaatta    300
gagggaatgg cacgggttta tagaacctat gctactgctt ttgctgagtg ggaaaaagct    360
cctgatgacc cagagctaag agaagcacta cgtacacaat ttacagcaac tgagacttat    420
```

```
ataagtggaa gaatatccgt tttaaaaatt caaacttttg aagtacagct gttatcagtg   480
tttgcccaag ctgcaaattt acatttatct ttattaagag acgttgtgtt ttttgggcaa   540
agatggggtt tttcaacgac aaccgtaaat aattactaca atgatttaac agaagggatt   600
agtacctata cagattatgc tgtacgctgg tacaatacgg gattagaacg tgtatgggga   660
ccggattcta gagattgggt aaggtataat caatttgaga gagaattaac actaactgta   720
ttagatatcg ttgctctgtt cccgaattat gatagtagaa gatatccaat tcgaacagtt   780
tcccaattaa caagagaaat ttatacaaac ccagtattag aaaattttga tggtagtttt   840
cgaggctcgg ctcagggcat agaaagaagt attaggagtc cacatttgat ggatatactt   900
aacagtataa ccatctatac ggatgctcat aggggttatt attattggtc agggcatcaa   960
ataatggctt ctcctgtcgg tttttcgggg ccagaattca cgtttccgct atatggaacc  1020
atgggaaatg cagctccaca acaacgtatt gttgcccaac taggtcaggg cgtgtataga  1080
acattatcct ctacttttta tagaagacct tttaatatag gatataataa tcaacaacta  1140
tctgttcttg acgggacaga atttgcttat ggaacctcct caaatttgcc atccgctgta  1200
tacagaaaaa gcgaacggt agattcgctg gatgaaatac caccacagaa taacaacgtg  1260
ccacctaggc aaggatttag tcatcgatta agccatgttt caatgtttcg ttcaggctct  1320
agtagtagtg taagtataat aagagctcct atgttctctt ggatacatcg tagtgctgaa  1380
tttaataata taattgcatc ggatagtatt actcaaatcc ctgcagtgaa gggaaacttt  1440
cttttaatg gttctgtaat ttcaggacca ggatttactg gtggggactt agttagatta  1500
aatagtagtg gaaataacat tcagaataga gggtatattg aagttccaat tcacttccca  1560
tcgacatcta ccagatatcg agttcgtgta cggtatgctt ctgtaacccc gattcacctc  1620
aacgttaatt ggggtaattc atccattttt tccaatacag taccagctac agctacgtca  1680
ttagataatc tacaatcaag tgattttggt tattttgaga ggccaatgc ttttacatct  1740
tcattaggta atatagtagg tgttagaaat tttagtggga ctgcaggagt gataatagac  1800
agatttgaat ttattccagt tactgcaaca ctcgaggctg aatataatct ggagagagcg  1860
cagaag                                                             1866

SEQ ID NO: 204         moltype = DNA  length = 1839
FEATURE                Location/Qualifiers
source                 1..1839
                       mol_type = other DNA
                       organism = Bacillus thuringiensis
SEQUENCE: 204
atggagagaa ataatcagaa tcaatgcatt cctataatt gttaaaataa tcttgagagt    60
gagatattag atattgaaag tttaagtagt agaagtagag aacaagtagc ggaaatcagc   120
ttggggctca cgcgctttct tttggagtca ctgctccctg gtgcgagttt tggatttgat   180
ttatttgata tcgtttgggg agttattggt cctgatcaat ggagcctatt tcttgcgcag   240
attgaacaat taattgatca acgaatagaa acacatgtaa gaaatcaagc gatcagtaga   300
ttagagggc ttggagatag ttatgaagtg tatattgagg cgcttagaga atgggaggcg   360
tctcctaata atgaatcctt acagcaagat gtgcgcaatc gatttagtaa taccgataat   420
gccttaataa acgcgatacc tattttgaga gagcagggct ttgaaattcc tcttttaacg   480
acttatgttc aggctgccaa tttgcattta tctttattaa gagatgctgt atattttgga   540
cagagatggg gacttgacac agctacggtt aacaatcatt ataatcggtt aattaatctt   600
attaacgctt actccgaatca ttgtgctcaa tggttcaata tggctctaaa taatttttgg   660
gttgtatcaa gtaggtattt ggatttccaa agagaggtaa caatatctgt tttagatatc   720
gttgctcttt tcccgaatta tgacattcgg acatatccaa tccaacact aagtcaatta   780
acaagagaaa tttatacatc tccagttgct gaacctggtg caagtcttaa tgtggattta   840
cggaatatat tgagagaacc tcacctaatg gattttttaa ctcgcctcgt tatttatacc   900
ggtgtgcaga gtggtattta ccattgggca ggacatgaaa tatcttctag gactacaggt   960
aatttgtcga gtaatataca atttccgcta tatggaatag ccgcaagtgc agataggcca  1020
gttaattga caattcacta ttctgaaact atttatagaa cattatcagc tcctatctat  1080
tcaatatctg gtgggatttc tcctaataga acgagagtta tggaggagt aaggttctta  1140
attgcgagag ataataatat gaattccttg ccatttttat atagaaaga gggttctcta  1200
gattcttta ccgagttacc acctgaagat gagaatgcac cacttatat gggtatagt  1260
catcggttat gccatgctag atttgctagg tcatctgtag tagctgaacc aagtaatttc  1320
gcaaggcttc cagtatttc ttggacacat cgtagtgcg gccctactaa tgaagtaagt  1380
tcatctagaa taacacaaat ccccatggta aaagcacata cccttgattc gggagcctct  1440
gttattaagg gccctggatt tacaggaggg gacattctta ctaggcctaa ctttggtacc  1500
ttgggagctt taggagtaac tttacaggg cgattatcac aaagatacaa tataagaatc  1560
cgatatgctt ctgtagcaaa tcggagtggt acatttagct attcactgcc accttcgtat  1620
ggaatttcat ttccaaaaac tatggacgca ggtgaaccat taacacctcg ttcgttcgct  1680
cttacaacgc tcttcactcc aataacctt tcgcgagcgc aagaagaatt taatctattc  1740
atccagcagg gtgtttatat agacagaata gaatttgttc cagttgatga aacatttgaa  1800
gcagaatatg atttagaaag agcacaaaag taaggatcc                         1839

SEQ ID NO: 205         moltype = DNA  length = 1977
FEATURE                Location/Qualifiers
source                 1..1977
                       mol_type = other DNA
                       organism = Bacillus thuringiensis
SEQUENCE: 205
atgccatcta agaatcaaaa tatgtatcaa gtttgtcta gcaatacgac agttgataaa    60
aactttacaa attcactaga aaacaacaca atatgaat tacaaaatat taattatgaa   120
gattgtttga gaatgtctga gtatgaaggt atagagccgt ttgttagtgt atcaacaatt   180
caaacaggta ttggtattgc gggtaaaata cttggtaccc taggcgttcc ttttgcagga   240
caagtagcta gtctttatag ttttatctta ggtgagctat ggcctaaggg gaaaagccaa   300
tgggaaatct ttatgaaca tgtagaagag attattaatc aaaaaatatc aacttatgca   360
agaagtaaag cacttacaga cttgaaagga ttaggagatg ccttagctgt ctaccatgaa   420
tcgctggaaa gttgggttgg aaatcgtaat aacacaaggg ctaggagtgt tgtcaagagc   480
caatatatcg cattagaatt gatgttcgtt cagaaactac cttctttttgc agtgtctgga   540
```

```
gaggaggtaa cattattacc gatatatgcc caagctgcaa atttacattt gttgctatta    600
cgagatgcgt ctatttttgg aaaagagtgg ggattatcat cttcagaaat ttcaacattt    660
tataaccgtc aagtcgaacg agcaggagat tattccgacc attgtgtgaa atggtatagc    720
acaggtctaa ataacttgag gggtacaaat gccgaaagtt gggtacgata taatcaattc    780
cgtagagaca tgactttaat ggtactagat ttagtgcgac tatttccaag ctatgataca    840
caaatgtatc caattaaaac tacagcccaa cttacaagag aagtatatac agacgcaatt    900
gggacaatac atccgcatcc aagttttaca agtacgactt ggtataataa taatgcacct    960
tcgttctctg ccatagaggc tgctgttgtt cgaaacccgc atctactcga ttttctagaa   1020
caagttacaa tttacagctt attaagtcga tggagtaaca ctcagtatat gaatatgtgt   1080
ggaggacata aactagaatt ccgaacaata ggaggaacgt taaatacctc aacacaagga   1140
tctactaata ctgctattaa tcctgtaaca ttaccgttca cttcacgaga cgtctatagg   1200
actgaatcat tggcagggct gaatctattt ttaactcaac ctgttaatgg agtacctagg   1260
gttgattttc attggaaatt cgtcacacat ccgatcgcat ctgataattt ctattatcca   1320
gggtatgctg gaattgggac gcaattacag gattcagaaa atgaattacc atctgaagca   1380
acaggacagc caaattatga atcttatagt catagattat ctcatatagg actcatttca   1440
gcatcacatg tgaaagcatt ggtatattct tggacacatc gtagtgcaga tcgtacaaat   1500
acaattgagc caaatagcat tacacaaata ccattagtaa aagcgttcaa tctgtcttca   1560
ggtgccgctg tagtgagagg accaggattt acaggtgggp atatccttcg aagaacgaat   1620
actggtacat ttggggatat acgagtaaat attaatccac catttgcaca aagatatcgc   1680
gtgaggattc gctatgcttc tactacagat ttacaattcc atacgtcaat taacggtaaa   1740
gctattaatc aaggtaattt ttcagcaact atgaatagag gagaggactt agactataaa   1800
acctttagaa ctgtaggctt taccactcca tttagctttt cagatgtaca aagtacattc   1860
acaataggtg cttggaactt ctcttcaggt aacgaagttt atatagatag aattgaattt   1920
gttccggtag aagtaactta tgaggcagaa tatgattttg aaaaagcgca agagtaa     1977

SEQ ID NO: 206          moltype = DNA   length = 2056
FEATURE                 Location/Qualifiers
source                  1..2056
                        mol_type = other DNA
                        organism = Bacillus thuringiensis
SEQUENCE: 206
atggaggaa aagggatgaa tcgaaataat caaaatgaat atgaagttat ttatgctgcc     60
acttgtgggt gcccgtcaga tgatgttgta aatacccctt ggcaagtga tccaaatgcc    120
tcgttacaaa atatcaatta taaagattat ttgaaaattt gacaaggaga ctatatagat    180
tcgtatataa atcctggcaa tgttagaact tgactacaaa ctggaattga tattgtagca    240
ttgctagtag ggactttagg tggaccggtt ggtggcatac ttactggttt gctttccact    300
cttttttggtt ttctctggcc atctaatgat caagcagtat gggaagcatt tatagaacaa    360
atggaagaac tgattgaaca acggatatca gaccaagtag taaggactgc actggatgat    420
ttaacgggaa ttcaaaatta ttacaatcaa tatttattag cattggagga gtgggaagaa    480
ggaccaaaca gtgtaagagc taatctagtt ttgcagagat ttgaaaacct acatgcgcta    540
tttgtaagta atatgcccag ctttggcagt ggtcctggaa gtcaaagatt tgaggcacaa    600
ttgctgatag tttatgcaca agcagcaaat cttcatttgt tattattaag agatgctgaa    660
atatatggag caagatgggg acttcgtgaa tctcaaattg aattatattt tgatgagcta    720
caaaataata ctcgtgatta taccaatcat tgtgtgaacg cgtataataa cgggttagag    780
aaggtacgag gaacaaacgc tgcaagttgg ttgaagtacc atcaattccg tcgagaggcg    840
accttgacgg cgatggattt ggtggcgcta tttccatatt ataacttacg acaatacccac    900
atagcagtaa atccccagct cacgcgtgag tgtatatacag atccattagg tgttccgttt    960
gaagaatcga atccatttcc agaaatcaga tgttcaagat ggcaagaaac ttctgccatg   1020
acttttcga atttggaaaa tgcaatagtt cgtccaccac atttatttga tataataaga   1080
aatttaagga tttatactgg tacttttagg ttcaataaca ataaccttat tgaagggtgg   1140
attgacatt ctgtaactaa taatcgcctg gaaatttcaa cagaattcac aagcaattac   1200
ggtatcacta cacctattat aaacagttat aattttgcta atcgtgatgt ttatcaaatt   1260
aatacaagat caaatacttc gttgattgca tttcaaaacg caccttttatt tggaatcact   1320
agggctcaat ttcagccagg tgggacctat tcagtaaatc aacgaacttc tttgttatgt   1380
gagcaaaatt ataattcaac tgatgagtta ccgagtctag acccgqgatga acctatcagt   1440
agaagttata gtcatagatt atcacatatt acctcttatt tgcatcgtgt acttactatt   1500
gatggtatta atatatattc aggtaatctt cctacttatg tttggacgca tcgagatgtg   1560
gaccttacta atacaattac cgctgacaga attacacact taccattaat aaaatcaaat   1620
gtacaacgca gtggccgccc tgtaaaagga ccaggattta caggaggaga tgtacttcga   1680
atatcatcaa gtgatgctga tatatcaata ataggagtat ggctggttgc accactaaca   1740
caacaatatc gtataagagc gcgttatgct tcaaatgtag atgttactat ccgtttcata   1800
agacacaaca cccaaagtgt tataggaagc gctagcttat caagtacaat gaatagcgga   1860
gaggagtcaa gatatgaagc gtatcgtact gtagaggtaa ttagtaattt tagattaaat   1920
agcagttcag aacagatccg aatagttact caaggacttc gtgcaaatgg acaattgtat   1980
cttgatagcc ttgaatttat ccctgtaaat ccaacacgag aagcagaaga ggatttagaa   2040
gcggcgaaga aataag                                                  2056

SEQ ID NO: 207          moltype = DNA   length = 1956
FEATURE                 Location/Qualifiers
source                  1..1956
                        mol_type = other DNA
                        organism = Bacillus thuringiensis
SEQUENCE: 207
atgccaccaa ataaccagga taatcatgaa acctatccaa caaagtgac agtcgaaaaa      60
ccttttacag attcactaaa aaatgaaaca actaaaaata gtaattatga agattgtttg    120
aaaatgtcta gacatgaaag cgtagagccg tttgttagtg tatcaacaat tcaaacggga    180
attggtattg ctggtaaaat ccttggtagc ctaggcgttc ctttttgctgg gcaagtagct    240
agcctttata gttttattct aggtgagctt tggcctaagg ggaaaagtca atgggaaatc    300
tttatggaag atgtagaaaa acttgttgat caaaaaatat cgatttacgc aagaaacaaa    360
```

```
gcacttgcag atttaaaagg attaggagat gctctggctg tctaccatga atcccttgaa  420
agttggattg aaaatcgtaa taacagaaga gctagaagtg ttgttaaaga ccaatatatc  480
gctttggaac ttatgtttgt tcagagactt ccttcttttg cagtatctgg agaagaggtg  540
ccgctattac caatttatgc tcaagctgca aatttacact tattgctatt aagagatgca  600
tcaatttttg gagaagaatg ggtttttca acttcagaaa tttcaacatt ttataaccgc  660
caatctagtc ggacgataga atattctgac tattgctcag gatggtataa tacaggacta  720
aatcgcttga gaggtgcaaa tgctgaaagt tgggtacgat ataatcaatt ccgtagagac  780
atgactttaa tggtactaga tctagtagca ctattcccaa gctatgacac tcgcacttat  840
ccaattaaaa ctagtgccca acttacaaga gaagtctata cagatccaaa cggtattgta  900
gcaggaggca ataataattg gtttagaaat ggggcttcgt tttccactat agaaaacgca  960
attattcgac aacctcacct atatgatttt ctaacgaacc ttacaattta cacgagaata  1020
agtcgagcaa accctgctta tatgaatttg tgggcagggc atagaattac ttctaataga  1080
ataggttcta gtaatagtag tgaattggtg tatggggcta taactaatcc agttagtact  1140
actaacttat catttgtcaa tcgggatgtt taccgaactg aatcattagc tggtgggctt  1200
ggcactctga atggaatact ttatggttta actagagttg attttgatat gatatttcgt  1260
aaccgtcctg atatagtaac tggattattt tatcatccgg gacacgcggg cattgcaacc  1320
caagtaaaag attcagaaac agaattacca cctgaaacga cagaacagcc aaattataga  1380
gcatttagtc atctactaag tcatatttca atgggtccaa cgactcaaga cgtacctcca  1440
gtatattctt ggacacacca gagtgcagac cgttcaaata caatcgattc ggataggata  1500
acacaaatac cattggtaaa ggcgcatacc cttcaatcgg gtaccactgt agtaaaaggg  1560
ccagggttta caggagggga tatcctccgt cgaacaagtg gaggaccatt tgcttttagt  1620
aatgttaatc tagattttaa cttgtcacaa aggtatcgtg ctagaattcg ttatgcctct  1680
actactgact taagaattta cgtaacggtt gcaggcgaac gaatttatgc tggtaaattt  1740
aataaaacca tgaaaaaagg tgacccatta acattccaat catttagtta cgcaactatt  1800
aatacagctt ttacattccc agaaagatcg agcagcttga ctgtaggtgc tgatacgttc  1860
gattcaggta atgaagttta tgtagataga tttgaattaa tcccggatac tgtaacattt  1920
gaggcagagt ctgatttaga aaaagcgcaa aagtaa                            1956
```

```
SEQ ID NO: 208         moltype = DNA  length = 2055
FEATURE                Location/Qualifiers
source                 1..2055
                       mol_type = other DNA
                       organism = Bacillus thuringiensis
SEQUENCE: 208
atgcctcgaa ataatcaaaa tgaatatgaa gttattgatg ccccacattg tgggtgtccg  60
gcagatgatg ttgtaaaata tcctttgaca gatgatccga atgctggatt gcaaaatatg  120
aactataagg aatatttaca aacgtatggt ggagactata cagatcctct tattaatcct  180
aacttatctg ttagtggaaa agatgtaata caagttggaa ttaatattgt agggagatta  240
cttagctttt ttggattccc cttttctagt caatgggtta ctgtatatac ctatctttta  300
aacagcttgt ggccggatga cgagaattct gtatgggacg cttttatgga gagagtagaa  360
gaacttattg atcaaaaaat ctcagaagca gtaaagggta gggcattgga tgacctaact  420
ggattacaat ataattataa tttatatgta gaagcattag atgagtggct gaatagacca  480
aatggcgcaa gggcatcctt agtttctcag cgatttaaca ttttagatag cctatttaca  540
caatttatgc ctagctttgg ctctggtcct ggaagtcaaa attatgcaac tatattactt  600
ccagtatatg cacaagcagc aaaccttcat ttgttattat taaaagatgc agacatttat  660
ggagctagat gggggctgaa tcaaactcaa atagatcaat tccattctcg tcaacaaagc  720
cttactcaga cttatacaaa tcattgtgtt actgcgtata atgatggatt agcggaatta  780
agaggcacaa gcgttgcgag ttggctcaaa tatcatcaat accgtaggga aatgacagta  840
acggcaatgg atttagtggc attattccca tactataatg ttagacaata tccaaatggg  900
gcaaatccac aacttacacg tgaggtatat acagatccaa tcgtatttaa tccgcctgag  960
cgtccaagtg gcgctttctg cgaaagtttt tatactatcc gagcggcacg agaacgttta  1020
actttttcgc aacttgaaca tgcaataatt cgtccgccgc gcttgtttga aaggtttcaa  1080
gcattaggga tttatacagg cgaggcgcga ctgaatgcaa atagtgctcc aatgaactat  1140
tggattggac attttataag aaatacacgt ttaggtgact caacaacaat tactacaaat  1200
tatggaacaa ccaataatcg tttaactaac ttcagtatgc cttctgatgt ttatcaaatc  1260
aattcaacct caagtaattt agccgctatt tttaggcactt tatatggggt tactagagca  1320
caattccatt ttggatcagg aagtttttcg acgtatgtcg gacaaaatag cgttcttcca  1380
caatgtcatc aaaactataa ttcaatagaa gaattaccaa accaaagcga tgaacctaca  1440
gttagaagtt atagccatag attatctcat atcacctctt ttaatttcaa tgtacagctt  1500
aataatcctt taatttctgc gggcaatatg cctgtatatg tgtggacaca tcgcagtgtg  1560
gaccttacta acaggatttc ttcagataga attactcaaa taccagtggt aaaggcatat  1620
gagctaagta gtggtgctac tgtcgtgaaa ggtccaggat tcacaggagg agatgtaatc  1680
cgaagaacaa atactggtgg gttcggagca ataagggtgt tggtcactgg accgctaaca  1740
caacgatatc gcataaggtt ccgttatgct tcgacaatag attttgattt ctttgtaaca  1800
cgtggaggaa ctactataaa taattttaga tttacacgta caatgaacag gggacaggaa  1860
tcaagatatg aatcctatcg tactgtagag tttacaactc cttttaactt tacacaaagt  1920
caagatataa ttcgaacatc tatccaggga cttagtggaa atggggaagt ataccttgat  1980
agaattgaaa tcatccctgt aaatccaacg cgagaggcgg aagaggattt agaagcggcg  2040
aagaaataag gatcc                                                   2055
```

```
SEQ ID NO: 209         moltype = DNA  length = 2046
FEATURE                Location/Qualifiers
source                 1..2046
                       mol_type = other DNA
                       organism = Bacillus thuringiensis
SEQUENCE: 209
atgccccgaa ataatcaaaa tgattatgaa gttattgacg cttccaattg tggttgtgcg  60
tcaggtgatg ttgtgaaata tcctttgaca aatgatccga atgccggatt acaaaatatc  120
aattataaag agtacttaca aatgtcagat gagaactaca ctgattccta tataaatcct  180
```

```
agtttgtcta ttagtgggaa atctgtaata caagttggaa ttaacattgt agggaggttg    240
ttgagctttt ttggattccc atttgctaat caagtggtcg ctgtctatag ctaccttta    300
aacaccttat ggccaaataa tgatactgaa gtatgggaat cttttatggc acaagtagaa    360
gaacttgttg atcaaaaaat atcagaagcg gtagtaggga ccgcattgga tcatttatct    420
ggattaaact ataattatga attatatgta gaggcttttgg aagagtggct ggaaagacca    480
aatgccgcaa gagccaacct agttttaat agatttacta cactagatag tctatttacg    540
caatttatgc caagttttgg ctctggtcct gggagtaata ggtatgcaga ttcattactt    600
tcagtatatg cacaagcagc aaaccttcat ttgttattct aaaagatgc agacatttat    660
ggagctagat gggggctgaa tcaaactcaa atagatcaat accataatcg tcaacaaacc    720
cttactcgga attatacaaa tcattgtgtt actacgttta atgatggatt agagaaaata    780
agaaacacaa gcgctgagag ttggtttaaa tacaatcaat atcgtagaga gatgacatta    840
atggcaatgg atttagtggc attatttccg tattataatg tacgagaata ctcaatggca    900
gtaaatcctc aacttacacg agaggtgtat acagatccaa ttgcatttga tccatcagaa    960
caaccgaata ctcaattgtg tcgaaaatgg tatactgccc gctttgtaca gaataacgtt   1020
aattttctc agttagaaaa tgcattcatt cgttccaccac atctcttcga aagattacat   1080
tctctggaaa ttaattttat aaatggagct aattggtggt ggcataaggt aaggaaccaa   1140
cttttaaata attcattaat actcgaaaga gattacggta catctactgt taattctcct   1200
acgactcaac ttaccgtgaa tacttcaaat gctgatatat accaagtacg ttctcgtgca   1260
gaaaatccga ctgcagctgc aggtacttac tattcagtta gaggtgttga gttttattta   1320
agctcaggcg ttaagaggga gttttctgga actacagtcg ctcccttggc ttgccaagaa   1380
ttgcgaaatt caattgatga gttaccaagt ttagaaccaa atgagcctat catcagaaat   1440
tatagtcata gattatctca tattacttgg taccaattta gtggccgcca aagtggaaat   1500
ccgactacta ataatgggga tatacctact tatgtctgga cacatcgcga tgtggacttt   1560
aataatacaa ttactcccaa tagaattact caaataccat ggataaaggc atctgaaata   1620
gctgcgaata ctactgtcgt aaaaggccca ggatttacag gagggatat acttcgaagc   1680
acgatccctg gtacagttgg aacgattagg gctaatgtta tggccccatt aacacaacaa   1740
tatcgtataa gattacgtta tgcgtcgaca acaaattttg ttgttaattt atttgttaac   1800
aattcagcta gtggttttac tctcccaagt acaatggttc aaaatgagtc tttaacatac   1860
gaatcgttta ataccgaaga ggtgacaaga actattgat tttcacagtc agacactaca   1920
ctgagattgg gtatattttc gtttgaccct ggtcaagaag tgtatgtaga taaacttgaa   1980
atcgttccaa ttaatccagc tcgtgaggcg gaagaggatt tagaagcagc gaaaaataa   2040
ggatcc                                                              2046

SEQ ID NO: 210          moltype = DNA  length = 1956
FEATURE                 Location/Qualifiers
source                  1..1956
                        mol_type = other DNA
                        organism = Bacillus thuringiensis
SEQUENCE: 210
atgccaccaa ataaccagaa taatcatcaa accttatcta gcaatatgac agttaataaa     60
acttctacag attcactaaa aaatgaaaca actatggaat tgaaaaatag taattataaa    120
gattgtttaa aaatgtcaga acatgaaagt atagaaccgt tgttagtgt atcaacaatt    180
caaacgggaa ttggtattgc tggtaaaatc cttggtagct taggcgttcc tttttctggg    240
caagtagctca gcctctatag tttatatcta ggtgagcttt ggcctaaggg gaaaagccaa    300
tgggaaatct ttatggaaca tgtggaagag cttgttgccc aaaaaatatc gacttacgca    360
agaaacaaag cacttgcaga tttaaaagga ttaggagatg ctctagctgt ctaccatgaa    420
tcccttgaaa gctggattaa agatcgcaat aacacaagag ttagaagtgt tgttaaaac    480
caatatatta atttggaact tatgtttgtt cagaaacttc cttcctttgc agtttctgga    540
gaagaggtgc cgctattacc aatctatgcc caagctgcaa atttacactt gttgctatta    600
agagatgcat ctacttttgg aaaagagtgg ggttttcaa cttcagaaat ttcaacattt    660
tataaaactc aatctagtcg cacgagagaa tattctgact actgttcaga atggtataat    720
acgggactaa atcgcttaaa agggacaaat gccgcaagtt gggtacggta taatcaattc    780
cgtagagata tgacttaat ggtactagat ctagtagcac tattcccatg ctatgataca    840
catatgtatc ccattccaac tagcgtccaa cttacgcgag aagtgtatac agatccaaac    900
ggtgcagtag gagtaaacaa tactggttgg tttcaaaatg gggcttcgtt ttccgctata    960
gaaaacgcaa ttattcgaca acctcaccta tatgatttta taacaaacct tacaattacc   1020
acgagaagaa gtcaagtagg cactgcaatt ctgaatttgt gggcagggca taaaattaat   1080
tttaataga taggttctag taatagtagc gaattggtgt atggagctag tactaaccg   1140
gttagtacta atagcttatc atttgtcaat caggatgttt ttcgaactat atcattactc   1200
ggcataaatg gctctgtgag cggactaact tatggcttaa ctcgcgttga ttttgatata   1260
agaaatcgta actttactaa tataatcagt tcagtaacgt ataattctgg gcatcaaaat   1320
attggaacac aaacaaggga ttcagaaact gaattaccac cagaaacgac agaacagcca   1380
aattatgaag ctaatagtca tctactaagc catatttcaa tgtctccaac gactgcagca   1440
acacctccag tatattcttg gacacaccat aatgcagatc ggcgaatac aatcagttcg   1500
gataggataa cacaaatacc attagtaaag gcacataccc ttcaatcggg taccactgta   1560
gtaaagggc cagggtttac aggaggggat atcctccgtc gaacaagtgg aggaccattt   1620
gcttttagta atgttaatct agattttaac ttgtcacaaa ggtatcgtgc tagaattcgt   1680
tatgcctcta ctactaactt gagaatttac ataacggttg caggcgaacg aattttagct   1740
ggtcaattta ataaaactat ggaaaaaggt gacccattaa gcttccaatc tttttagttaa   1800
gcaactatta atacagcctt tacattccca acgagatcga gcagtttgac tgtaggtgct   1860
gatacgttcg attcaggtaa tgaagtgtat gtagatagat ttgaattaat cccggatact   1920
tcaaaatttg aggcagagtc cgatttagaa aagcg                              1956

SEQ ID NO: 211          moltype = DNA  length = 1884
FEATURE                 Location/Qualifiers
source                  1..1884
                        mol_type = other DNA
                        organism = Bacillus thuringiensis
SEQUENCE: 211
```

```
atgcctctat cgctagatgc tcgtattgag gattctttgt gtatagccga ggggaatagt   60
atcaatccac ttgttagcgc ctcaacagtc caaacgggta ttaacatagc tggtagaata  120
ctaggtgtat taggcgtacc gtttgctgga caactagcta gttttatag ttttcttgtc  180
ggtgaattat ggccccgcgg cagagatcag tgggaaattt tcttagaaca tgtcgaacaa  240
cttataaatc aacaaataac agaaaatgct aggaatacgg cacttgctcg attacaaggt  300
ttaggagatt cctttagagc ctatcaacag tcacttgaag attggctaga aaaccgtgat  360
gatgcaagaa cgagaagtgt tctttatacc caatatatag ctttagaact tgattttctt  420
aatgcaatgc cgcttttcgc aattagaaac caagaagttc cattattgat ggtatatgct  480
caagctgcaa atttacacct attattattg agagatgcct ctcttttttgg tagtaaattt  540
gggcttacat cgcaggaaat tcaacgctat tatgagcgcc aagtggaacg aacgagagat  600
tattccgact attgcgtaga atggtataat acaggtctaa atagcttgag agggacaaat  660
gccgcaagtt gggtacggta taatcaattc cgtagagatc taacgttagg agtattagat  720
ctagtggcgc tattcccaag ctatgacact cgcacttatc caataaatac gagtgctcag  780
ttaacaaggg aagtttatac agacgcaatt gggactgtac atccgagtca agcttttgca  840
agtacgactt ggtataataa taatgcacct tcgctctctg ccatagaggc tgcggttatc  900
cgaagcccgc atctacttga ttttccagaa caacttacaa tttacagcac attaagtcga  960
tggagtaaca ctcagtatat gaatatatgg gtaggtcata gacttgaatc tcgaacaata 1020
ggagggtcat taaatacctc gacacaagga tctaccaata cttctattaa tcctgtaaga 1080
ttacagttta cggctcgaga cgtttatagg actgaatcat tggcagggct aaatatattt 1140
ttaactcaac ctgttaatgg ggtaccttgg gttagattta attggagaaa tccccctgaat 1200
tctcttagag gtagccttct ctatactata gggtatactg gagttgggac gcaattacaa 1260
gattcagaaa ctgaattacc accagaaaca acagaacgac aaaattatga atcttacagt 1320
catagattat ctcatatagg actcatttca tcatctcatg tgagagcatt ggtatattct 1380
tggacgcacc gtagtgcaga tcgtacaaat acaattggac caaatagaat tacacaaata 1440
ccattggtaa aagcacttaa ccttcattca ggtgctactg ttgttagagg gccaggatttt 1500
acaggtgggg atatccttcg tagaacgaat actggtacat ttggagatat acgttttaaat 1560
attaatgtgc cattatccca aagatatcgc gtaaggattc gttatgcttc tactacagat 1620
ttacaatttt tcacgagaat taatggaacc actgttaata ttggtaattt ctcaagaact 1680
atgaataggg gggataattt agaatctaga agttttagag ctgcaggatt tagtactcct 1740
tttaattttt caaatgccca aagcacattc acattgggtg ctcagagttt ttcaaatcag 1800
gaagtttata tagatagagt cgaatttgtt ccggcagagg taaccttcga agcagaatat 1860
gatttagaaa gagcgcaaga gtaa                                         1884

SEQ ID NO: 212         moltype = DNA  length = 1968
FEATURE                Location/Qualifiers
source                 1..1968
                       mol_type = other DNA
                       organism = Bacillus thuringiensis
SEQUENCE: 212
atgccaccaa agaatcaaaa taagtatcaa agtttatcga aaaatgcgac agttgataaa   60
atctctacgg attcactaaa aaatgaaaca gatagagaat tgaaaaatat ttataatgaa  120
gattgtttga gaatgtctga gcatgaaagt atggagccgt tgttagtgc atcaacaatt  180
caaacgggta ttggtattgc tggtaaaatc cttggtaacc taggcgttcc ttttgctgga  240
caagtagcta gcctctatag ttttatccta gatgagcttt ggcccaaagg gaaaagccaa  300
tgggaaatct ttatggaaca tgtagaagag cttattgctc aaaaaatatc gacttacgcc  360
agaaacaaag cacttgcaga tttaaaagga ttaggggatg ctttggctgt ctaccatgag  420
tcgctgaaa gttggattaa aaatcgcaat aacacaagg ccagaagtgt tgttaagaac  480
caatacatcg ctttagaact tatgtttgtg caagcgttgc cttctttttgc agtgtctgga  540
gaggaagtac cactattacc aatatatgct caagctgcaa atttacactt gttgctatta  600
agagatgcgt ctatttttgg aaaagagtgg ggattatccg actcagaaat ttccacattt  660
tataatcgcc aatctggaag gtcgagggaa tattctgacc actgcgtaaa atggtataat  720
acaggcctaa atcgcttgag gggaacaaat gccgaaagtt gggtacgtta taatcaattc  780
cgcagagaca tgacttttaat ggtactagat ttagtcgcac tattcccaag ctatgataca  840
catatgtatc caattaaaac tacagcccaa cttacaagag aagtttatac aaatccaatt  900
ggtgtcgtag gaggagtttc ttggtttgaa aacgccgctc ctttcgccgc tatagaaaac  960
gcagttattc gacaacctca tctatacgat tttatgactg accttaccat ttacacgaga 1020
ctaagtcgag cactccctcg ttatatgaat ttgtgggcgg gcatagaat caatttttaat 1080
acaattcgtg gttctactag tcgcgaaatg gtgtatggag ctattactaa tccagttagt 1140
actactcccc tttcattttgt caatcaagat attttataga ctcaatcaat agctggagta 1200
cttctcaatc tttcaagcag attttacggc gtacctagaa ttgattttga tataagaaat 1260
cgtaactatc ctaatataat caatagacta acttataatc ctggatacgc agaaattgca 1320
actcaagtaa aagattcaga aactgaatta ccgcctgaaa caacagaaca gccaaaattat 1380
gaagctgcta gtcatctgct atgtcatatt ggaatgcctc caacggggtc cggaactggt 1440
tcagcaactc ctccagtata ttcttggaca caccggggtc cgggtcgtac gaatatcatt 1500
aattcggata gtattacaca aatcccatta gtaaaggcta ataaccttca ttcaggcgct 1560
actgtcgtca agggcccagg atttacagga ggagacatac tccgaagaac tagcgcgggt 1620
acatttgtgg atttaccagt taatcttatt agttggcaat tatcacaaag ttatcgcgta 1680
aggatacgtt atgccttcta cacggattta caatttcata cgtcaattaa cgggagagca 1740
attaatcagg ggaatttttc agcaactatg aatagaggag atgccttaga atctagaacc 1800
tttagaactg tagggtttac tactcctttt aacttttcag atgcgcaaag tacattcaca 1860
ataagtgctt ggaacttctc ttcaagtaac gaagtttata tagatagaat tgaatttgtt 1920
ccagcagaag taacattaga ggcagaaagt ttagaaagag cgcaaaaaa            1968

SEQ ID NO: 213         moltype = DNA  length = 1977
FEATURE                Location/Qualifiers
source                 1..1977
                       mol_type = other DNA
                       organism = Bacillus thuringiensis
SEQUENCE: 213
```

```
atgaattctt atcaaaataa gaatgaatat gaaatactgg atgcttcaga aaatactgta    60
aatgcgttaa acagatatcc tttcgcaaat aatccgtatt cttccatttt tagttcttgt   120
ccacgcagtg ggcctggtaa ttggattaat atactaggaa atgcagttag cgaagcagta   180
tctatttcgc aagatataat atctcttctt acacagcctt ctatctctgg gataaattca   240
atggcattta gtcttttaag tagaatgata ggtagtaatg gaaggtctat atcggagtta   300
tctatgtgtg acttactagc tattattgat ttgcgggtaa atcagagtgt tttggatgac   360
ggagttgctg attttaacgg ctcgttagtt atatacagaa actatttaga ggctttacaa   420
aggtggaaca ataatcccaa tcccgctaat gccgaagagg ttcgtactcg ttttaggaa    480
tctgatacaa tattcgatct cattttaaca caagggtctt taacgaatgg cggttcatta   540
gccagaaata atgctcaaat attattattg ccttcttttg caaatgctgc atactttcat   600
ttactgctat aagagatgc taatgtatat gggaataatt ggggtttatt tggggttaca    660
cctaatataa attatgaatc gaaattacta aaccttatta gattatatac caattattgc   720
acacattggt ataatcaagg actaaatgaa ctaagaaatc gaggttccaa tgctacagct   780
tggttggaat ttcatagatt tcgtagagat atgacattga tggtattgga tatagtatca   840
tcattttcaa gtcttgatat tactagatat ccaagagcaa cagattttca attgagtagg   900
ataatttata cagatccaat tggttttgta aatcgtagtg accctagcgc accaagaacc   960
tggtttagtt ttcacaatca agctaatttt tcagcgttag aaagtggaat acctagtcct  1020
tcattctcac aattcttaga tagtatgcgt atatctactg gcccgcttag ttacctgct   1080
tctcctaata tccatagagc acgggtatgg tatggtaatc aaaataactt taatggatct  1140
agtagccaaa cttttgggga aataacaaat gataatcaaa ccatttcggg tttaaatatt  1200
ttcagaatag attcacaggc tgttaatcta ataatactac gtttggagt tagtagagct   1260
gaatttatc atgatgctag tcaaggctct caaagatcca tatatcaagg atttgttgat  1320
acaggtgggg ctagtaccgc tgtagcccag aatattcaaa cattttttccc gggagaaat   1380
tcgagtatac caactccaca agattatact catatattaa gtaggtcaac aaattttaaca  1440
ggaggacttc gacaagtagc atctggacgt cgttcttctt tagtattaca cggttggaca  1500
cataaaagtc tgagtcgtca aaatagagtt gaaccaaata gattactca agtgccggcct  1560
gttaaagcaa gttctccttc gaattgtact gtaattgcag gacctggatt tacaggtggg  1620
gatttagtca gaatgagttc aaactgtagc gtaagttaca attttacacc agctgatcag  1680
caagttgtaa tacgtctacg ttatgcttgt caagggacac cttcattaag gataacgttt  1740
ggtaatggtt ctagccaaat aattccgctt gtttctacaa cttcatcaat aaataatctt  1800
caatatgaaa atttagttt tgcttctggt ccaaatagcg ttaacttttt atcagctggt   1860
acttcaataa ctattcaaaa tatcagtaca aattctaacg tagtgctaga tagaattgaa  1920
attgtgccag aacaacctat tcctattatt ccaggggact atcaaattgt aacagct     1977

SEQ ID NO: 214          moltype = AA  length = 614
FEATURE                 Location/Qualifiers
source                  1..614
                        mol_type = protein
                        organism = Bacillus thuringiensis
SEQUENCE: 214
MGRGSMEVNN QNQCVPYNCL NNPEIEILGG ERISVGNTPI DISLSLTQFL LSEFVPGAGF    60
VLGLIDLIWG FLGPSQWDAF LLQIEQLISQ RIEEFARNQA ISRLEGLSNL YRIYAEAFRA   120
WEADPTNLAL REEMRTQFND MNSALVTAIP LFSVQNYQVP LLSVYVQAAN LHLSVLRDVS   180
VFGQRWGFDV ATINSRYNDL TRLIGEYTDY AVRWYNTGLD RLRGSNFQDW IRYNRFRREL   240
TLTVLDIVSV FQNYDSRLYP IQTSSQLTRE IYSDLLLANP SGVGSFSNVD FDSILIRQPH   300
LIDFMRVLTI YTDRHNASRH NIYWAGHQVT AVDTANRTIV YPVNGSAANL EPPRTLRFES   360
PVVEIRSNPV WDRGSTGIAG SYEFFGVTSA LFITILGFYI TYRSGSNTEV TALPDHQVSL   420
IGYFRRFTTT GATARQTLTS APIVSWTHSS AEPPNRIYQN RITQIPAVKG NFLFNGAVIS   480
GPGFTGDLV RLNRNNDNIQ NRGYIEVPIQ FASTSTRYRV RVRYASTNAI EVNINWGNGS   540
IFTGTAPATA TSLDNLQSND FGYFESTTAF APSLGNIVGV RNFSANADVI IDRFEFIPVT   600
ATLEAEYDLE RAEK                                                    614

SEQ ID NO: 215          moltype = AA  length = 679
FEATURE                 Location/Qualifiers
source                  1..679
                        mol_type = protein
                        organism = Bacillus thuringiensis
SEQUENCE: 215
MPRNNQNDYE VIDASNCGCA SGDVVKYPLT NDPNAGLQNI NYKEYLQMSD ENYTDSYINP    60
SLSISGKSVI QVGINIVGRL LSFFGFPFAN QVVAVYSYLL NTLWPNNDTE VWESFMAQVE   120
ELVDQKISEA VVGTALDHLS GLNYNYELYV EALEEWLERP NAARANLVFN RFTTLDSLFT   180
QFMPSFGSGP GSNRYADSLL SVYAQAANLH LLFLKDADIY GARWGLNQTQ IDQYHNRQQT   240
LTRNYTNHCV TTFNDGLEKI RNTSAESWFK YNQYRREMTL MAMDLVALFP YYNVREYSMA   300
VNPQLTREVY TDPIAFDPSE QPNTQLCRKW YTARFVQNNV NFSQLENAFI RSPHLFERLH   360
SLEINFINGA NWWWHKVRNQ LLNNSLILER DYGTSTVNSP TTQLTVNTSN ADIYQVRSRA   420
ENPTAAAGTY YSVRGVEFYL SSGVKREFSG TTVAPLACQE LRNSIDELPS LEPNEPIIRN   480
YSHRLSHITW YQFSGRQSGN PTTNNGDIPT YVWTHRDVDF NNTITPNRIT QIPWIKASEI   540
AANTTVVKGP GFTGGDILRS TIPGTVGTIR ANVMAPLTQQ YRIRLRYAST TNFVVNLFVN   600
NSASGFTLPS TMVQNESLTY ESFNTEEVTR TIRFSQSDTT LRLGIFSFDP GQEVYVDKLE   660
IVPINPAREA EEDLEAAKK                                               679

SEQ ID NO: 216          moltype = AA  length = 614
FEATURE                 Location/Qualifiers
source                  1..614
                        mol_type = protein
                        organism = Bacillus thuringiensis
SEQUENCE: 216
MPNNIQNQCV PYNCLSTPEK ILLDEERIET GNTSIDLSLS LVSLLLGEFV PGASFVLGLI    60
DIIWGFAGPS QWDAFLVQIE QLIDERIGQF ARNQAISRLE GLSNLYQIYA EDFTQWEADP   120
```

```
DNPALREEMR TQFNDMNSAL TTAIPLLAVQ NYQIPLLSVY VQAANLHLSV LRDVSVFGQS    180
WGFDAATINS RYNDLTRLIS SYTDHVVRWY DTGLDRLRGS TYQDWFRYNR FRRELTLTAL    240
DIVALFPNYD IKMYPIQPVS QLTREVYTDP LINFNPQLQS VAQLPTFNVM ESNAIRNPHL    300
VDFLNNLRIF TDWFSVGRHY YWGGHRVISK RVGGREITFP IYGREAKQEP PRSFTFNGPV    360
FRTLSNPTLR PLQQPAPAPP FNLRGLEGVK FYTPTNTFTY RGRGPRDSLT ELPPGDTSVL    420
PREGYSHRLC HATFIQRSGT PFLTTGVVFS WTHRSADETN IIYPDKITQI PWVKAHTLES    480
GATVIKGPGF TGGDILTVLT SLGSLGALRV TFTGQLPQTY NIRIRYASVL NKYGTLHFSQ    540
PPAYGLTFPK TMDIDEPLTS RSFAFTTLWT PITFTRAQEE FNLTIQSGVY IDRIEFVPAE    600
VTFEADYDLE KAQK                                                    614

SEQ ID NO: 217          moltype = AA  length = 617
FEATURE                 Location/Qualifiers
source                  1..617
                        mol_type = protein
                        organism = Bacillus thuringiensis
SEQUENCE: 217
MDNNNQNQCI PYNCLSNPEL EILEIERSNN TVVEDITLGL SRLLVSAIPL GDFILGLFDV     60
IWGALGRSEW DIFLEQIELL IGQRIEEFAR NQAISRLEGL SNLYRIYTNA FKDWEADPTN    120
LELKEEMRTQ FNDMNSAFTT AIPLFSVRGY ELPLLSVYVQ AANLHLSVLR DVSVFGQRWG    180
FDVATVNRRY DDLTTNIGDY TDYALSWYNT GLNRLPRNDG LRGWARFNRF RRELTISVLD    240
IISFFQNYDS RLYPIPTISQ LTREVYTDPV INITDYRVTP SFESIENSAI RSPHLMDFLT    300
NIIIDTDLIR GVYYWAGHRI NSRFTGTAFP HIITSPQYGI TANAEPRRTI VPGPFQGVPS    360
LLYRTLSDPF FRRSDNISPT LGINVVQGVG FLQPNNFESL YRRRGTVDSL DELPIDGENP    420
LVGYSHRLSH VTLTRSLFNT NITSLPTFVW THHSATDTNT IAPDVITQIP LVKAFNLHSG    480
ATVARGPGFT GGDILRRTNV GNFGDMRVNI TAPLSQRYRV RIRYASTTNL RFHTSINGRA    540
INQADFPATM NSGGNLQSGS FRIAGFTTPF TFSDALSTFT IGAFGFSSGN EVYIDRIEFV    600
PAEVTFEAEY DLERAQK                                                 617

SEQ ID NO: 218          moltype = AA  length = 667
FEATURE                 Location/Qualifiers
source                  1..667
                        mol_type = protein
                        organism = Bacillus thuringiensis
SEQUENCE: 218
MEIINNQNQC IPYNCLNNPE VEILGIERSN STVVEDISLG LSRLLVSAIP LGDFLLSLFD     60
VIWGAIGRSE WDIFLEQIEL LIGQRIEEFA RNQAISRLEG LSNLYRIYTN AFKNWEADPT    120
NPVLREEMRI QFNDMNSAFT TAIPLFSVQG YEIPLLGVEP HRYQANKIKY PLKIKKYAIL    180
SVESAERMAF FMSTSVSDEL QLFAQEIQSL LSSNILRGFA RDVGFVQRTS KYQAKDLVAL    240
CVWMNQNVAT TSLTQLCSCL EASTEVLISP EGLNQRFNKA AVQFLQHILA ELLNQKLASS    300
MPISSPYTSI FKRIRILDST AFQLPDVFSS VYPGAGGCSH TAGIKIQLEY DLLSGQFLHI    360
HTGPGKQHDR TYGTLCAPTV TANDLCIRDL GYFHLKDLQY IQDKEAYYIS RIKSNTRIYQ    420
KNPNPDYFQD GRIKKGTEYI QIDMETLMNS LQPGQTYEIA DAYVGMIDKV PARVIVHRLT    480
KQQQQKRLQD QAVREKKKGM KYSPRSKRLS GINVYMTNTP TDIVPMGQVH DWYSLRWQIE    540
ILFKTWKSFF HIHHCKKIKP ERLECHLYGQ LIAILLCSSI MFQMRQLLLI KKKRELSEYK    600
AIYMIKDYFL LLFQTIQKNT QELSKVLLRL FNLLQQNGRK SHRYEKKTVF DILGVVYNCT    660
MSDNQAA                                                            667

SEQ ID NO: 219          moltype = AA  length = 693
FEATURE                 Location/Qualifiers
source                  1..693
                        mol_type = protein
                        organism = Bacillus thuringiensis
SEQUENCE: 219
MPRNNQNEYE VIDASTCGCP SDDVVKYPLT DDPNAGLQNM NYKEYLQMYG GDYTDPLINP     60
NLPVSGKDVI QVGINIVGRL LSFFGFPFSS QWVAVYTHLL NSLWPDDENS VWDAFMKRVE    120
ELIDQKIAEA VHGLALDHLT GLQHNYNLYV EALDEWLNRP NGARAALVSQ RFNNLDSLFT    180
QFMPSFGSGP GSRNYATILL PVYAQAANLH LLLLKDVDIY GARWGLNQTQ IDLFHSRQQG    240
LTQTYTNHCV TAYNDGLAEL RGTSVESWLK YHQYRREMTV TAMDLVALFP YYNVRQYPNG    300
ANPQLTREVY TDPIVFNPPK PPSGAFCESF YTIRAARERL TFSQLENAII RPPRLFERFQ    360
ALGIYTHEAR LNQNSAPMNY WIGHFIRNTR LGDSTTITSN YGTTNNRLTN FTPPTNSDVY    420
QINSISSNLA AILGTIFGVT NAAPHHGSGN IWSYVGQNNV LAQCHQNYNS IEEELPNQSDE   480
PTVRSYSHRL SHITSFNFNV QLNNPVLSTG NMPVYWTHR GVDLNNTITS DRITQLPLVK    540
ASELVAGTTV VKGPGFTGGD ILRRTSNGNF GTIRVMVSSP LTQQYRLRVR YASTGNFSIV    600
VRRGSTTVGN IRVPSTMNRG AEFRYESFDT REFTTTGPQN PPFTFTQTQE SLTVAAEGVS    660
TGSEYFIDRI EIIPVNPTRE AEEDLEAAKK AVA                                693

SEQ ID NO: 220          moltype = AA  length = 693
FEATURE                 Location/Qualifiers
source                  1..693
                        mol_type = protein
                        organism = Bacillus thuringiensis
SEQUENCE: 220
MPRNNQNEYE VIDASTCGCP SDDVVKYPLT DDPNAGLQNM NYKEYLQMYG GDYTDPLINP     60
NLPVSGKDVI QVGINIVGRL LSFFGFPFSS QWVAVYTHLL NSLWPDDENS VWDAFMKRVE    120
ELIDQKIAEA VHGLALDHLT GLQHNYNLYV EALDEWLNRP NGARAALVSQ RFNNLDSLFT    180
QFMPSFGSGP GSRNYATILL PVYAQAANLH LLLLKDVDIY GARWGLNQTQ IDLFHSRQQG    240
LTQTYTNHCV TAYNDGLAEL RGTSVESWLK YHQYRREMTV TAMDLVALFP YYNVRQYPNG    300
ANPQLTREVY TDPIVFNPPK PPSGAFCESF YTIRAARERL TFSQLENAII RPPRLFERFQ    360
ALGIYTHEAR LNQNSAPMNY WIGHFIRNTR LGDSTTITSN YGTTNNRLTN FTPPTNSDVY    420
```

```
QINSISSNLA AILGTIFGVT NAAFHHGSGN IWSYVGQNNV LAQCHQNYNS IEELPNQSDE   480
PTVRSYSHRL SHITSFNFNV QLNNPVLSTG NMPVYVWTHR GVDLNNTITS DRITQLPLVK   540
ASELVAGTTV VKGPGFTGGD ILRRTSNGNF GTIRVMVSSP LTQQYRLRVR YASTGNFSIV   600
VRRGSTTVGN IRVPSTMNRG AEFRYESFDT REFTTTGPQN PPFTFTQTQE SLTVAAEGVS   660
TGSEYFIDRI EIIPVNPTRE AEEDLEAAKK AVA                                693

SEQ ID NO: 221             moltype = AA  length = 708
FEATURE                    Location/Qualifiers
source                     1..708
                           mol_type = protein
                           organism = Bacillus thuringiensis
SEQUENCE: 221
MNRNNQNEYE VIDAPHCGCP SEDVVKYPLT DDSNAGLQNM NYKEYLNMSE GDYADSIRYP    60
LANNPYSSAL NLNSCQNSSI LNWINILGNA AKEAISIGTT IISIITTPSL TGLISITYDL   120
ISKVLGGSSG PSISDLSICD LLSIIDLRIS QSVLNDGIAD FNGSIIIYRN YLEALDSWNK   180
NNTPAAAEEV RARFRAADTE FDRILTRGSL TNGGSLARQD GQILLLPSFA SAAYFHLSLL   240
RDAARYGANW GLFNATPLIN YQSKLVELIE SYTNYCVHWY NQGLNQLRQR GNSATAWLEF   300
HRYRREMTLM VLDIVASFSS LDITRYPIET DFQLSRVIYT DPIGFVNRGN LRLESWFSSV   360
NNATFSGLES AIPNPSQSWF LNSMIISTGS LTLPVSPNTD RARVWYGGRD RVSPASSQFI   420
TEQMSGQQTA DTQNILGRNI FRIDSQACNL NNTTYGVNRA LFYHDASQGS QRSLYEGFIR   480
TTGIDNPVVQ NINTYFPGEN SDIPTPQDYT HILSRTINLT GGLRQVASGR RSSLVMYGWT   540
HKSLTLNNTI NPDRITQIPL TKLDSRGSNI SYVNDPGFIG LQNLLRMTANG TLGTLRANFP   600
LNIRSHFRIR VRYAATRNIR LSVNGSFGTI SQEFPSTMRL GEDLRYGSFA IREFSTSVRP   660
TASPDVIRLT VEPIFSGQQI YVDRIEFVPV IPTREAEENL DAAKKAVA                708

SEQ ID NO: 222             moltype = AA  length = 657
FEATURE                    Location/Qualifiers
source                     1..657
                           mol_type = protein
                           organism = Bacillus thuringiensis
SEQUENCE: 222
MPSKNQMYQ SLSSNTTVDK NFTNSLENNT NMELQNINYE DCLRMSEYEG IEPFVSVSTI     60
QTGIGIAGKI LGTLGVPFAG QVASLYSFIL GELWPKGKSQ WEIFMEHVEE IINQKISTYA   120
RSKALTDLKG LGDALAVYHE SLESWVGNRN NTRARSVVKS QYIALELMFV QKLPSFAVSG   180
EEVTLLPIYA QAANLHLLLL RDASIFGKEW GLSSSEISTF YNRQVERAGD YSDHCVKWYS   240
TGLNNLRGTN AESWRYNQF RRDMTLMVLD LVALFPSYDT QMYPIKTTAQ LTREVYTDAI    300
GTIHPHPSFT STTWYNNNAP SLSAIEAAVI RSPHLLDFPE QLTIYSTLSR WSNTQYMNIW   360
VGHRLESRTI GGSLNTSTQG STNTSINPVR LQFTARDVYR TESLAGLNIF LTQPVNGVPW   420
VRFNWRNPLN SLRGSLLYTI GYTGVGTQLQ DSETELPPET TERPNYESYS HRLSHIGLIS   480
SSHVRALVYS WTHRSADRTN TIGPNRITQI PLVKALNLHS GATVVRGPGF TGGDILRRTN   540
TGTFGDIRLN INVPLSQRYR VRIRYASTTD LQFFTRINGT TVNIANFSRT MNRGDNLESR   600
SFRTAGFSTP FNFSNAQSTF TLGAQSFSNQ EVYIDRIEFV PVEVTYEAEY DFEKAQE      657

SEQ ID NO: 223             moltype = AA  length = 661
FEATURE                    Location/Qualifiers
source                     1..661
                           mol_type = protein
                           organism = Bacillus thuringiensis
SEQUENCE: 223
MPLKNQDKHQ SFSSNAKVDK ISTDSLKNET DIELQNINHE DCLKMSEYEN VEPFVSASTI    60
QTGIGIAGKI LGTLGVPFAG QVASLYSFIL GELWPKGKNQ WEIFMEHVEE IINQKISTYA   120
RNKALTDLKG LGDALAVYHD SLESWVGNRN NTRARSVVKS QYIALELMFV QKLPSFAVSG   180
EEVPLLPIYA QAANLHLLLL RDASIFGKEW GLSSSEISTF YNRQVERAGD YSDHCVKWYS   240
TGLNNLRGTN AESWRYNQF RRDMTLMVLD LVALFPSYDT QMYPIKTTAQ LTREVYTDAI    300
GTVHPHPSFT STTWYNNNAP SFSAIEAAAI RSPHLLDFPE QLTIFSASSR WSNTRHMTYW   360
RGHTIQSRPI GGGLNTSTHG ATNTSINPVT LRFASRDVYR TESYAGVLLW GIYLEPIHGV   420
PTVRFNFTNP QNISDRGTAN YSQPYESPGL QLKDSETELP PETTERPNYE SYSHRLSHIG   480
IILQSRVNVP VYSWTHRSAD RTNTIGPNRI TQIPMVKASE LPQGTTVVRG PGFTGGDILR   540
RTNTGGFGPI RVTVNGPLTQ RYRIGFRYAS TVDFDFFVSR GGTTVNNRF LRTMNSGDEL    600
KYGNFVRRAF TTPFTFTQIQ DIIRTSIQGL SGNGEVYIDK IEIIIPVTATF EAEYDLERAQ   660
E                                                                  661

SEQ ID NO: 224             moltype = AA  length = 614
FEATURE                    Location/Qualifiers
source                     1..614
                           mol_type = protein
                           organism = Bacillus thuringiensis
SEQUENCE: 224
MPNNIQNQCV PYNCLSTPEK ILLDEERIET GNTSIDLSLS LVSLLLGEFV PGASFVLGLI    60
DIIWGFAGPS QWDAFLVQIE QLIDERIGQF ARNQAISRLE GLSNLYQIYA EDFTQWEADP   120
DNPALREEMR TQFNDMNSAL TTAIPLLAVQ NYQIPLLSVY VQAANLHLSV LRDVSVFGQS   180
WGFDAATINS RYNDLTRLIS SYTDHVVRWY DTGLDRLRGS TYQDWFRYNR FRRELTLTAL   240
DIVALFPNYD IKMYPIQPVS QLTREVYTDP LINFNPQLQS VAQLPTFNVN ESNAIRNPHL   300
VDFLNNLRIF TDWFSVGRHY YWGGHRVISK RVGGREITFP IYGREAKQEP PRSFTFNGPV   360
FRTLSNPTLR PLQQPAPAPP FNLRGLEGVK FYTPTNTFTY RGRGPRDSLT ELPPGDTSVL   420
PREGYSHRLC HATFIQRSGT PFLTTGVVFS WTHRSADETN IIYPDKITQI PWVKAHTLES   480
GATVIKGPGF TGGDILTVLT SLGSLGALRV TFTGQLPQTY NIRIRYASVL NKYGTLHFSQ   540
PPAYGLTFPK TMDIDEPLTS RSFAFTTLWT PITFTRAQEE FNLTIQSGVY IDRIEFVPAE   600
VTFEADYDLE KAQK                                                    614
```

```
SEQ ID NO: 225            moltype = AA  length = 615
FEATURE                   Location/Qualifiers
source                    1..615
                          mol_type = protein
                          organism = Bacillus thuringiensis
SEQUENCE: 225
MPKVNNKNQC LPYNCLNNPE NEILDIERSN STVATNIALE ISRLLASATP IGGILLGLFD    60
AIWGSIGPSQ WDLSLEQIEL LIDQKIGEFA RNQAISRLEE ISSLYGIYTE AFREWEADPT   120
NPALKEEMRT QFNDMNSILV TAIPLFSVQN YQVPFLSVYV QAANLHLSVL RDVSVFGQAW   180
GFDIATINSR YNDLTRLIPI YTDYAVRWYN TGLDRLPRTG GLRNWARFNQ FRRELTISVL   240
DIISFFRNYD SRLYPIPTSS QLTREVYTDP VINITDYRVG PSFENIENSA IRSPHLMDFL   300
NNLTIDTDLI RGVHYWAGHR VTSHFTGSSQ VITTPQYGIT ANAEPRRTIA PSTFPGLNLF   360
YRTLSNPFFR RSENITSTLG INVVQGVGFI QPNNAEVLYR SRGTVDSLNE LPIDGENSLV   420
GYSHRLSHVT LTRSLYNTNI ISLPTFVWTH HSATNTNTIN PDIITQIPLV KGFRLGGGTS   480
VIKGPGFTGG DILRRNTIGE FVSLQVNINS PITQRYRLRF RYASSRDARI TVAIGGQIRV   540
DMTLEKTMEI GESLTSRTFS YTNFSNPFSF RANPDIIRIA EELPIRGGEL CIDKIELILA   600
DATFEEEYDL ERAQK                                                   615

SEQ ID NO: 226            moltype = AA  length = 616
FEATURE                   Location/Qualifiers
source                    1..616
                          mol_type = protein
                          organism = Bacillus thuringiensis
SEQUENCE: 226
MDNNNQNQCI PYNCLSNPEL EILEIERSNN TVVEDITLGL SRLLVSAIPL GDFILGLFDV    60
IWGALGRSEW DIFLEQIELL IGQRIEEFAR NQAISRLEGL SNLYRIYTNA FKDWEADPTN   120
LELKEEMRTQ FNDMNSAFTT AIPLFSVRGY ELPLLSVYVQ AANLHLSVLR DVSVFGQRWG   180
FDVATVNRRY DDLTTNIGDY TDYALSWYNT GLNRLPRNDG LRGWARFNRF RRELTISVLD   240
IISFFQNYDS RLYPIPTISQ LTREVYTDPV INITDYRVTP SFESIENSAI RSPHLMDFLT   300
NIIIDTDLIR GVYYWAGHRI NSRFTGTAFP HIITSPQYGI TANAEPRRTI APGPFQGAFP   360
TYRTLSDPFF RRSDNISPTL GINVVQGVGF LQPNNFESLY RRRGTVDSLD ELPIDGENPL   420
VGYSHRLSHV TLTRSLFNTN ITSLPTFVWT HHSATDTNTI APDVITQIPL VKAFNLHSGA   480
TVARGPGFTG GDILRRTNVG NFGDMRVNIT APLSQRYRVR IRYASTTNLR PHTSINGRAI   540
NQADFPATMN SGGNLQSGSF RIAGFTTPFT FSDALSTFTI GAFGFSSGNE VYIDRIEFVP   600
AEVTFEAEYD LERAQK                                                  616

SEQ ID NO: 227            moltype = AA  length = 682
FEATURE                   Location/Qualifiers
source                    1..682
                          mol_type = protein
                          organism = Bacillus thuringiensis
SEQUENCE: 227
MPRNQNEYE VIDAPHCGCP ADDVVKYPLT DDPNAGLQNM NYKEYLQTYG GDYTDPLINP    60
NLSVSGKDVI QVGINIVGRL LSFFGFPFSS QWVTVYTYLL NSLWPDDENS VWDAFMERVE   120
ELIDQKISEA VKGRALDDLT GLQYNYNLYV EALDEWLNRP NGARASLVSQ RFNILDSLFT   180
QFMPSFGSGP GSQNYATILL PVYAQAANLH LLLLKDADIY GARWGLNQTQ IDQFHSRQQS   240
LTQTYTNHCV TAYNDGLAEL RGTSVASWLK YHQYRREMTV TAMDLVALFP YYNVRQYPNG   300
ANPQLTREVY TDPIVFNPPE RPSGAFCESF YTIRAARERL TFSQLEHAII RPPRLFERFQ   360
ALGIYTGEAR LNANSAPMNY WIGHFIRNTR LGDSTTITTN YGTTNNRLTN FSMPSDVYQI   420
NSTSSNLAAI LGTLYGVTRA QFHFGSGSFS TYVGQNSVLP QCHQNYNSIE RLPNQSDEPT   480
VRSYSHRLSH ITSFNFNVQL NNPLISAGNM PVYVWTHRSV DLTNRISSDR ITQIPVVKAY   540
ELSSGATVVK GPGFTGGDVI RRTNTGGFGA IRVLVTGPLT QRYRIRFRYA STIDFDFFVT   600
RGGTTINNFR FTRTMNRGQE SRYESYRTVE FTTPFNFTQS QDIIRTSIQG LSGNGEVYLD   660
RIEIIPVNPT REAEEDLEDA KK                                           682

SEQ ID NO: 228            moltype = AA  length = 669
FEATURE                   Location/Qualifiers
source                    1..669
                          mol_type = protein
                          organism = Bacillus thuringiensis
SEQUENCE: 228
MPRNNQNEYE IIDASTCGCS SDDVVQYPLA RDPNAVFQNM HYKDYLQTYD GDYTGSLINP    60
NLSINPRDVL QTGINIVGRL LGFLGVPFAG QLVTFYTFLL NQLWPTDNDA VWEAFMAQIE   120
ELINQRISEA VVGTAADHLT GLHDNYELYV EALEEWLERP NAARTNLLFN RFTTLDSLFT   180
QFMPSFGTGP GSQNYAVPLL TVYAQAANLH LLLLKDAEIY GARWGLNQNQ INSFHTRQQE   240
RTQYYTNHCV TTYNTGLDRL RGTNTESWLN YHRFRREMTL MAMDLVALFP YYNVRQYPNG   300
ANPQLTREIY TDPIVFNPPA NVGLCRRWGN NPYNRFSELE NAFIRPPHLF DRLNTLTISR   360
NRFDVGSNFI EPWSGHTLRR SYSNNSTVYE DSYGQITATR TTINLPANGT GRVESTAVDF   420
RSALVGIYGV NRASFIPGGV FSGTTQPSTG GCRDLYDSSD ELPPDESTGS FAHRLSHVTF   480
LSFTTNQAGS IANSGRVPTY VWTHRDVDFN NTINPNRITQ IPVVKAYELS SGATVVKGPG   540
FTGGDVIRRT NIGGFGAIRV SVTGPLTQRY RIRFRYASTI DFDFFVTRGG TTINNFRFTR   600
TMNRGQESRY ESYRTVEFTT PFNFTQSQDI IRTSIQGLSG NGEVYLDRIE IIPVNPTREA   660
EEDLEAAKK                                                          669

SEQ ID NO: 229            moltype = AA  length = 614
FEATURE                   Location/Qualifiers
source                    1..614
                          mol_type = protein
```

```
                        organism = Bacillus thuringiensis
SEQUENCE: 229
MPNRREFMNN ETQNQCIPYN CLSNPEVEIL GGDRSAGILP IQISLSLTRF LAGEFIPGVG    60
VALGLFDLIW GFISPSDWDQ FLVRIEQLID QRIEELERTR ALSALQGLAN SYGVYVEALR   120
AWEADPNNEA LKEDVRTRFT SIDGDLIAEI PRFFLRGYEV PLLSVYVQAT NLHLSMLRDS   180
VSLGLRWGFD IATINNHYNR LINNIREYTD YSVSTYNIGL ERLRGTRVQD WVKFNQFRRE   240
LTLTVLDIVS LFPNYDVRTY PIQTVSQLTR EIYTNPVFEN SPVNINLVNG FNRVEYGVRQ   300
PHLMDHLMNV SISEEDYRGD TFWGGHSIAS VDTGGNLVGF PFYGNFDRFR FQTINAQQFP   360
LFRTLSDPVY NLSTSGGRNR LFALEGIGFQ QAVTGTTRAF RRVGTIDSLI EIPPQDESEV   420
PWNGYSHVLN HITFINWPAV FLQGERIASP MFSWTHRSAD RINRIIPDVI NQIPAVKGSS   480
IINGTVISGP GFTGGDLVRL ENNAYLEIPV QFQTTSTNYR VRVRYASTSQ ASISVVFGNI   540
DHPSTIPATA ESLDNLQYND FDYFDVIGTF LPSLGGSLAF RTLSSNANVV IDRFEFIPVT   600
ATFEAEYDLE KAQE                                                    614

SEQ ID NO: 230          moltype = AA  length = 621
FEATURE                 Location/Qualifiers
source                  1..621
                        mol_type = protein
                        organism = Bacillus thuringiensis
SEQUENCE: 230
MPIMNNQNYC IPYNCLNNPA LEILEEERIS VGNTPIDISL SLTQFLLSEF VPGAGFVLGL    60
FDLIWGFVGP SQWDAFLVQI EQLINQRIEE FARNQAISRL EGLSNLYRIY SEAFREWEAD   120
PTNPALREEM RIQFNDMNSA LVTALPLFSV QNYQVPLLSV YVQAANLHLS VLRDVSVFGQ   180
RWGFDVATIN SRYNDLTRNI GEYTDYAVRW YNTGLERVWG PDSRDWVRYN QFRRELTLTV   240
LDIISLFPNY DSRTYPIRTV AQLTREIYTN PVLENFDGNF RGMAQRIEQN IRQPHLMDIL   300
NTITIYTDVH RGFNYWSGHQ ITASPVGFAG PEITFPRYGT MGNAAPPVLV SLIGLGFRT    360
LSSPLYRRLI LGSGPNNQEL FVLDGTEFSF ASLTTNLPST IYRQRGTVDS LDVIPPQDNS   420
VPARAGFSHR LSHVTMLSQA AGAVYTLRAP TFSWQHRSAE FSNQIPSSQI TQIPLTKSIN   480
LGSGTTVVKG PGFTGGDILR RTSSGEISTL RVTITAPLSQ RYRVRIRYAS TTNLQFNTVI   540
NGRSINQANF PATMDNGENL QFENFRTVGY TTPFSFSDAS SIFTLTARNF SSGNEVYIDR   600
IEFVPADATL EAEYDLERAQ K                                            621

SEQ ID NO: 231          moltype = AA  length = 656
FEATURE                 Location/Qualifiers
source                  1..656
                        mol_type = protein
                        organism = Bacillus thuringiensis
SEQUENCE: 231
MPSNRKNENE IINALSIPAV SNHSAQMDLS LDARIEDSLC IAEGNNINPL VSASTVQTGI    60
NIAGRILGVL GVPFAGOLAS FYSFLVGELW PSGRDPWEIF LEHVEQLIRQ QVTENTRNTA   120
IARLEGLGRG YRSYQQALET WLDNRNDARS RSIILERYVA LELDITTAIP LFRIRNEEVP   180
LLMVYAQAAN LHLLLLRDAS LFGSEWGMAS SDVNQYYQEQ IRYTEEYSNH CVQWYNTGLN   240
NLRGTNAESW LRYNQFRRDL TLGVLDLVAL FPSYDTRTYP INTSAQLTRE IYTDPIGRTN   300
APSGFASTNW FNNNAPSFSA IEAAIFRPPH LLDFPEQLTI YSASSRWSST QHMNYWVGHR   360
LNFRPIGGTL NTSTQGLTNN TSINPVTLQF TSRDVYRTES NAGTNILFTT PVNGVPWARF   420
NFINPQNIYE RGATTYSQPY QGVGIQLFDS ETELPPETTE RPNYESYSHR LSHIGLIIGN   480
TLRAPVYSWT HRSATNTNTI NPDIITQIPL VKGFRLGGGT SVIKGPGFTG GDILRRNTIG   540
EFVSLQVNIN SPITQRYRLR FRYASSRDAR ITVAIGGQIR VDMTLEKTME IGESLTSRTF   600
SYTNFSNPFS FRANPDIIRI AEELPIRGGE LYIDKIELIL AEVTFEAEYD LERAQK       656

SEQ ID NO: 232          moltype = AA  length = 549
FEATURE                 Location/Qualifiers
source                  1..549
                        mol_type = protein
                        organism = Bacillus thuringiensis
SEQUENCE: 232
MPDTIILQTI AANIGSSLMP MGNPQNLYLY SYYGIKLIPF LGSILLLAVL GISLLFIFTQ    60
KLQKTDLKIE LPVITVKNRK KATVWILILI TIIASIFGKE WGLSSSEIST FYNRQVERAG   120
DYSDHCVKWY STGLNNLRGT NAESWVRYNQ FRRDMTLMVL DLVALFPSYD TQMYPIKTTA   180
QLTREVYTDA IGTVHPHPSF TSTTWYNNNA PSFSAIEAAV VRNPHLLDFL EQVTIYSLLS   240
RWSNTQYMNM WGGHKLEFRT IGGTLNISTQ GSTNTSINPV TLPFTSRDVY RTESLAGLNL   300
SLTQPVNGVP RVDFHWKFVT HPIASDNFYY PGYAGIGTQL QDSENELPPE ATGQPNYESY   360
SHRLSHIGLI SASHVKALVY SWTHRSADRT NTIEPNSITQ IPLVKAFNLS SGAAVVRGPG   420
FTGGDILRRT NTGTLGDIRV NINPPFAQRY RVRIRYASTT DLQFHTSING KAINQGNFSA   480
TMNRGEDLDY KTFRTVGFTT PFSFLDVQST FTIGAWNFSS GNEVYIDRIE FVPVEVTYEA   540
EYDFEKAQE                                                          549

SEQ ID NO: 233          moltype = AA  length = 651
FEATURE                 Location/Qualifiers
source                  1..651
                        mol_type = protein
                        organism = Bacillus thuringiensis
SEQUENCE: 233
MPPNNQDNHE TLSNKVTVEK PFTDSLKNET TKNSNYEDCL KMSRHESVEP FVSVSTIQTG    60
IGIAGKILGS LGVPFAGQVA SLYSFILGEL WPKGKSQWEI FMEDVEKLVD QKISIYARNK   120
ALADLKGLGD ALAVYHESLE SWIENRNNRR ARSVVKDQYI ALELMFVQRL PSFAVSGEEV   180
PLLPIYAQAA NLHLLLLRDA SIFGEEWGFS TSEISTFYNR QSSRTIEYSD YCSGWYNTGL   240
NRLRGANAES WVRYNQFRRD MTLMVLDLVA LFPSYDTRTY PIKTSAQLTR EVYTDPNGIV   300
AGGNNWFRN GASFSTIENA IIRQPHLYDF LTNLTIYTRI SRANPAYMNL WAGHRITSNR   360
```

```
IGSSNSSELV YGAITNPVST TNLSFVNRDV YRTESLAGGL GTLNGILYGL TRVDFDMIFR    420
NRPDIVTGLF YHPGHAGIAT QVKDSETELP PETTEQPNYR AFSHLLSHIS MGPTTQDVPP    480
VYSWTHQSAD RSNTIDSDRI TQIPLVKAHT LQSGTTVVKG PGFTGGDILR RTSGGPFAFS    540
NVNLDFNLSQ RYRARIRYAS TTDLRIYVTV AGERIYAGKF NKTMKKGDPL TFQSFSYATI    600
NTAFTFPERS SSLTVGADTF DSGNEVYVDR FELIPDTVTF EAESDLEKAQ K             651

SEQ ID NO: 234           moltype = AA  length = 658
FEATURE                  Location/Qualifiers
source                   1..658
                         mol_type = protein
                         organism = Bacillus thuringiensis
SEQUENCE: 234
MPLKNQDKHQ SFSSNAKVDK IATDSLKNET DIELKNMNNE DYLRMSEHES IDPFVSASTI    60
QTGIGIAGKI LGTLGVPFAG QIASLYSFIL GELWPKGKSQ WEIFMEHVEE LIAQKISTYA    120
RNKALTDLKG LGDALAVYHE SLESWIKNRN NTRARSVVKS QYISLELMFV QKLPSFAVSG    180
EEVPLLPIYA QAANLHLLLL RDASIFGKEW GLSSSEISTF YNRQAERTSD YSDHCVKWYS    240
TGLNNLRGKN AESWVRYNQF RKDMILMVLD LVALFPSYDT HMYPIKTTAQ LTREVYTNAI    300
GTVHPHPSFA STTWYNNNAP SFSAIEAAVI RSPHLLDFLE QVTIYSLLSR WSNTQYMNMW    360
GGHRLEFRTI GGALNTSTQG STNTSINPVT LPFTSRDVYR TESLAGLNLF LTQPVNGVPR    420
VDFHWKFVTH PIASDNFYYP GYAGIGTQLQ DSETELPPET TGQPNYESYS HRLSHIGLIS    480
ASHVKALVYS WTHRSADRTN TIEPNSITQI PLVKAFNLPS GAAVVRGPGF TGGDILRRTN    540
TGTFGDIRVN INPPFAQRYR VRIRYASTTD VQFHTSINGK AINQGNFSAT MNRGEDLDYK    600
TFRTVGFTTP FSFSDVQSTF TIGAWNFSSG NEVYIDRIEF VPVEVTYEAE HDFEKAQE     658

SEQ ID NO: 235           moltype = AA  length = 610
FEATURE                  Location/Qualifiers
source                   1..610
                         mol_type = protein
                         organism = Bacillus thuringiensis
SEQUENCE: 235
MPSNEHDYLK VCDDLSETNM ERFDKNDALE IGMSIVSELL GMIPGGAALQ FVFNQLWSRL    60
GDSGWSAFME HVEELIDTKI EGYAKNKALS ELAGMHRNLE TYIKLLNEWE NNTGSSKAQG    120
RVANYFESLE QAVERGMPQF AVGNFEIPLL TVYVQAANLH LLLLRDVSVY GKRWGWSDQK    180
IKIYYEKQVK YTHEYTNHCS TWYNRGLDKL KNKGSSYQDW YNYNRFRREI TLTVLDIVAV    240
FPHYDVKAYP IQTVGQLTRE VYTDPLINFN PQLDSVSQLP TFSDMENATI RTPHLMEFLR    300
MLTIYTDWYS VGRNYYWGGH RVTSYRVGGE NITSPLYGSE ANQELPRQLY FYGPVFRTLS    360
NPTLRYLQQP APAPPFALRR LEGVEFHTTT GTDMYRERGS VDSFNELPPF NPVGLPRNAY    420
SHRLCHATFV RKSGTPYLIT GTVFSWTHRS AEETNTIGNI RITQIPLVKA YQISSGTTVR    480
RGPGFTGGDI LRRTGPGTFG DIKLNINSPL SQRYRVRIRY ASTTDLQFFT NINGTTINMG    540
NFPKTVNNSS SEGYRTVSFS TPFSFSNAQS IFRLGIQAFS GVHEIHVDRI EFVPAEVTFE    600
AEYDLERAQK                                                          610

SEQ ID NO: 236           moltype = AA  length = 622
FEATURE                  Location/Qualifiers
source                   1..622
                         mol_type = protein
                         organism = Bacillus thuringiensis
SEQUENCE: 236
MAYNNNQNQC IPYNCLNNPE IEILEGGRIS VGNTPIDISL SLTQFLLSEF VPGAGFVLGL    60
IDLIWGFVGP SQWDAFLAQV EQLINQRIAE AVRNTAIQEL EGMARVYRTY ATAFAEWEKA    120
PDDPELREAL RTQFTATETY ISGRISVLKI QTFEVQLLSV FAQAANLHLS LLRDVVFFGQ    180
RWGFSTTTVN NYYNDLTEGI STYTDYAVRV YNTGLERVWG PDSRDWVRYN QFRRELTLTV    240
LDIVALFPNY DSRRYPIRTV SQLTREIYTN PVLENFDGSF RGSAQGIERS IRSPHLMDIL    300
NSITIYTDAH RGYYYWSGHQ IMASPVGFSG PEFTFPLYGT MGNAAPQQRI VAQLGQGVYR    360
TLSSTFYRRP FNIGINNQQL SVLDGTEFAY GTSSNLPSAV RYRKSGTVDSL DEIPPQNNNV    420
PPRQGFSHRL SHVSMFRSGS SSSVSIIRAP MFSWIHRSAE FNNIIASDSI TQIPAVKGNF    480
LFNGSVISGP GFTGGDLVRL NSSGNNIQNR GYIEVPIHFP STSTRYRVRV RYASVTPIHL    540
NVNWGNSSIF SNTVPATATS LDNLQSSDFG YFESANAFTS SLGNIVGVRN FSGTAGVIID    600
RFEFIPVTAT LEAEYNLERA QK                                            622

SEQ ID NO: 237           moltype = AA  length = 609
FEATURE                  Location/Qualifiers
source                   1..609
                         mol_type = protein
                         organism = Bacillus thuringiensis
SEQUENCE: 237
MPRNNQNQCI PYNCLNNLES EILDIESLSS RSREQVAEIS LGLTRFLLES LLPGASFGFG    60
LFDIVWGVIG PDQWSLFLAQ IEQLIDQRIE THVRNQAISR LEGLGDSYEV YIEALREWEA    120
SPNNESLQQD VRNRFSNTDN ALINAIPILR EQGFEIPLLT TYVQAANLHL SLLRDAVYFG    180
QRWGLDTATV NNHYNRLINL INAYSDHCAQ WFNRALNNFG VVSSRYLDFQ REVTISVLDI    240
VALFPNYDIR TYPIPTLSQL TREIYTSPVA EPGASLNVDL RNILREPHLM DFLTRLVIYT    300
GVQSGIYHWA GHEISSRTTG NLSSNIQFPL YGIAASADRP VNLTIHYSET IYRTLSAPIY    360
SISGGISPNR TRVVEGVRFL IARDNNMNSL PFLYRKEGSL SDFTELPPED ENAPPYIGYS    420
HRLCHARFAR SSVVAEPSNF ARLPVFSWTH RSAGPTNEVS SSRITQIPWV KAHTLDSGAS    480
VIKGPGFTGG DILTRPNFGT LGALGVTFTG RLSQRYNIRI RYASVANRSG TFSYSLPPSY    540
GISFPKTMDA GEPLTPRSFA LTTLFTPITF RSRAQEEFNLF IQQGVYIDRI EFVPVDETFE    600
AEYDLERAQ                                                           609

SEQ ID NO: 238           moltype = AA  length = 719
```

-continued

FEATURE Location/Qualifiers
source 1..719
mol_type = protein
organism = Bacillus thuringiensis
SEQUENCE: 238
MPSKNQNMYQ SLSSNTTVDK NFTNSLENNT NMELQNINYE DCLRMSEYEG IEPFVSVSTI 60
QTGIGIAGKI LGTLGVPFAG QVASLYSFIL GELWPKGKSQ WEIFMEHVEE IINQKISTYA 120
RSKALTDLKG LGDALAVYHE SLESWVGNRN NTRARSVVKS QYIALELMFV QKLPSFAVSG 180
EEVTLLPIYA QAANLHLLLL RDASIFGKEW GLSSSEISTF YNRQVERAGD YSDHCVKWYS 240
TGLNNLRGTN AESWVRYNQF RRDMTLMVLD LVALFPSYDT QMYPIKTTAQ LTREVYTDAI 300
GTIHPHPSFT STTWYNNNAP SFSAIEAAVV RNPHLLDFLE QVTIYSLLSR WSNTQYMNMW 360
GGHKLEFRTI GGTLNTSTQG STNTAINPVT LPFTSRDVYR TESLAGLNLF LTQPVNGVPR 420
VDFHWKFVTH PIASDNFYYP GYAGIGTQLQ DSENELPSEA TGQPNYESYS HRLSHIGLIS 480
ASHVKALVYS WTHRSADRTN TIEPNSITQI PLVKAFNLSS GAAVVRGPGF TGGDILRRTN 540
TGTFGDIRVN INPPFAQRYR VRIRYASTTD LQFHTSINGK AINQGNFSAT MNRGEDLDYK 600
TFRTVGFTTP FSFSDVQSTF TIGAWNFSSG NEVYIDRIEF VPVEVTYEAE YDFEKAQEKV 660
TALFTSTNPR GLKTDVKDYH IDQVSNLVES LSDEFYLDEK RELFEIVKYA KQIHIERNM 719

SEQ ID NO: 239 moltype = AA length = 684
FEATURE Location/Qualifiers
source 1..684
mol_type = protein
organism = Bacillus thuringiensis
SEQUENCE: 239
MGGKGMNRNN QNEYEVIYAA TCGCPSDDVV KYPLASDPNA SLQNINYKDY LKISEGDYID 60
SYINPGNVRT GLQTGIDIVA LLVGTLGGPV GGILTGLLST LFGFLWPSND QAVWEAFIEQ 120
MEELIEQRIS DQVVRTALDD LTGIQNYYNQ YLLALEEWEE GPNSVRANLV LQRFENLHAL 180
FVSNMPSFGS GPGSQRFEAQ LLIVYAQAAN LHLLLLRDAE IYGARWGLRE SQIELYFDEL 240
QNNTRDYTNH CVNAYNNGLE KVRGTNAASW LKYHQFRREA TLTAMDLVAL FPYYNLRQYP 300
IAVNPQLTRE VYTDPLGVPF EESNPFPEIR CSRWQETSAM TFSNLENAIV RPPHLFDIIR 360
NLRIYTGTFR FNNNNLIEGW IGHSVTNNRL GISTEFTSNY GITTPIINSY NFANRDVYQI 420
NTRSNTSLIA FQNAPLFGIT RAQFQPGGTY SVNQRTSLLC EQNYNSTDEL PSLDPDEPIS 480
RSYSHRLSHI TSYLHRVLTI DGINIYSGNL PTYVWTHRDV DLTNTITADR ITHLPLIKSN 540
VQRSGRPVKG PGFTGGDVLR ISSSDADISI IGVSAGAPLT QQYRIRARYA SNVDVTIRFI 600
RHNTQSVIGS ASLSSTMNSG EESRYEAYRT VEVISNFRLN SSSEQIRIVT QGLRANGQLY 660
LDSLEFIPVN PTREAEEDLE AAKK 684

SEQ ID NO: 240 moltype = AA length = 649
FEATURE Location/Qualifiers
source 1..649
mol_type = protein
organism = Bacillus thuringiensis
SEQUENCE: 240
MKPNNQDNHE TLSNKVTVEK PFTDSLKNET TKNSNYEDCL KMSRHESVEP FVSVSTIQTG 60
IGIAGKILGS LGVPFAGQVA SLYSFILGEL WPKGKSQWEI FMEDVEKLVD QKISIYARNK 120
ALADLKGLGD ALAVYHESLE SWIENRNNRR ARSVVKDQYI ALELMFVQRL PSFAVSGEEV 180
PLLPIYAQAA NLHLLLLRDA SIFGEEWGFS TSEISTFYNR QSSRTIEYSD YCSGWYNTGL 240
NRLRGANAES WVRYNQFRRD MTLMVLDLVA LFPSYDTRTY PIKTSAQLTR EVYTDPNGIV 300
AGGNNNWFRN GASFSTIENA IIRQPHLYDF LTNLTIYTRI SRANPAYMNL WAGHRITSNR 360
IGSSNSSELV YGAITNPVST TNLSFVNRDV YRTESLAGGL GTLNGILYGL TRVDFDMIFR 420
NRPDIVTGLF YHPGHAGIAT QVKDSETELP PETTEQPNYR AFSHLLSHIS MGPTTQDVPP 480
VYSWTHQSAD RSNTIDSDRI TQIPLVKAHT LQSGTTVVKG PGFTGGDILR RTSGGPFAFS 540
NVNLDFNLSQ RYRARIRYAS TTDLRIYVTV AGERIYAGKF NKTMKKGDPL TFQSFSYATI 600
NTAFTFPERS SSLTVGADTF DSGNEVYVDR FELIPDTVTF EAESDLEKA 649

SEQ ID NO: 241 moltype = AA length = 723
FEATURE Location/Qualifiers
source 1..723
mol_type = protein
organism = Bacillus thuringiensis
SEQUENCE: 241
MNRNNQNEYE VIDAPHCGCP ADDVVKYPLT DDPNAGLQNM NYKEYLQTYG GDYTDPLINP 60
NLSVSGKDVI QVGINIVGRL LSFFGFPFSS QWVTVYTYLL NSLWPDDENS VWDAFMERVE 120
ELIDQKISEA VKGRALDDLT GLQYNYNLYV EALDEWLNRP NGARASLVSQ RFNILDSLFT 180
QFMPSFGSGP GSQNYATILL PVYAQAANLH LLLLKDADIY GARWGLNQTQ IDQFHSRQQS 240
LTQTYTNHCV TAYNDGLAEL RGTSVASWLK YHQYRREMTV TAMDLVALFP YYNVRQYPNG 300
ANPQLTREVY TDPIVFNPPE RPSGAFCESF YTIRAARERL TFSQLEHAII RPPRLFERFQ 360
ALGIYTGEAR LNANSAPMNY WIGHFIRNTR LGDSTTITTN YGTTNNRLTN FSMPSDVYQI 420
NSTSSNLAAI LGTLYGVTRA QFHFGSGSFS TYVGQNSVLP QCHQNYNSIE ELPNQSDEPT 480
VRSYSHRLSH ITSFNFNVQL NNPLISAGNM PVYVWTHRSV DLTNRISSDR ITQIPVVKAY 540
ELSSGATVVK GPGFTGGDVI RRTNTGGFGA IRVLVTGPLT QRYRIRFRYA STIDFDFFVT 600
RGGTTINNFR FTRTMNRGQE SRYESYRTVE FTTPFNFTQS QDIIRTSIQG LSGNGEVYLD 660
RIEIIPVNPT REAEEDLEAA KKAVASLFTR TRDGLQVNVT DYQVDQAANL VSCLSDEQYG 720
HDK 723

SEQ ID NO: 242 moltype = AA length = 771
FEATURE Location/Qualifiers
source 1..771
mol_type = protein

```
                        organism = Bacillus thuringiensis
SEQUENCE: 242
MNRNNQNDYE VIDASNCGCA SGDVVKYPLT NDPNAGLQNI NYKEYLQMSD ENYTDSYINP    60
SLSISGKSVI QVGINIVGRL LSFFGFPFAN QVVAVYSYLL NTLWPNNDTE VWESFMAQVE   120
ELVDQKISEA VVGTALDHLS GLNYNYELYV EALEEWLERP NAARANLVFN RFTTLDSLFT   180
QFMPSFGSGP GSNRYADSLL SVYAQAANLH LLFLKDADIY GARWGLNQTQ IDQYHNRQQT   240
LTRNYTNHCV TTFNDGLEKI RNTSAESWFK YNQYRREMTL MAMDLVALFP YYNVREYSMA   300
VNPQLTREVY TDPIAFDPSE QPNTQLCRKW YTARFVQNNV NFSQLENAFI RSPHLFERLH   360
SLEINFINGA NWWWHKVRNQ LLNNSLILER DYGTSTVNSP TTQLTVNTSN ADIYQVRSRA   420
ENPTAAAGTY YSVRGVEFYL SSGVKREFSG TTVAPLACQE LRNSIDELPS LEPNEPIIRN   480
YSHRLSHITW YQFSGRQSGN PTTNNGDIPT YVWTHRDVDF NNTITPNRIT QIPWIKASEI   540
AANTTVVKGP GFTGGDILRS TIPGTVGTIR ANVMAPLTQQ YRIRLRYAST TNFVVNLFVN   600
NSASGFTLPS TMVQNESLTY ESFNTEEVTR TIRFSQSDTT LRLGIFSFDP GQEVYVDKLE   660
IVPINPAREA EEDLEAAKKA VASLFTRTRD GLQVNVTDYQ VDQAANLVSC LSDEQYGHDK   720
KMLLEAVRAA KRLSRERNLL QDPDFNEINS TEENGWKASS GVTISEGGPF F            771

SEQ ID NO: 243          moltype = AA length = 652
FEATURE                 Location/Qualifiers
source                  1..652
                        mol_type = protein
                        organism = Bacillus thuringiensis
SEQUENCE: 243
MKPNNQNNHQ TLSSNMTVNK TSTDSLKNET TMELKNSNYK DCLKMSEHES IEPFVSVSTI    60
QTGIGIAGKI LGSLGVPFSG QVASLYSFIL GELWPKGKSQ WEIFMEHVEE LVAQKISTYA   120
RNKALADLKG LGDALAVYHE SLESWIKDRN NTRVRSVVKN QYINLELMFV QKLPSFAVSG   180
EEVPLLPIYA QAANLHLLLL RDASTFGKEW GFSTSEISTF YKRQSSRTRE YSDYCSEWYN   240
TGLNRLKGTN AASWVRYNQF RRDMTLMVLD LVALFPCYDT HMYPIPTSVQ LTREVYTDPN   300
GAVGVNNTGW FQNGASFSAI ENAIIRQPHL YDFITNLTIY TRRSQVGTAI LNLWAGHKIN   360
FNRIGSSNSS ELVYGASTNP VSTNSLSFVN QDVFRTISLL GINGSVSGLT YGLTRVDFDI   420
RNRNFTNIIS SVTYNSGHQN IGTQTRDSET ELPPETTEQP NYEANSHLLS HISMSPTTAA   480
TPPVYSWTHH SADRTNTISS DRITQIPLVK AHTLQSGTTV VKGPGFTGGD ILRRTSGGPF   540
AFSNVNLDFN LSQRYRARIR YASTTNLRIY ITVAGERILA GQFNKTMEKG DPLTFQSFSY   600
ATINTAFTFP TRSSSLTVGA DTFDSGNEVY VDRFELIPDT SKFEAESDLE KA           652

SEQ ID NO: 244          moltype = AA length = 627
FEATURE                 Location/Qualifiers
source                  1..627
                        mol_type = protein
                        organism = Bacillus thuringiensis
SEQUENCE: 244
MDLSLDARIE DSLCIAEGNS INPLVSASTV QTGINIAGRI LGVLGVPFAG QLASFYSFLV    60
GELWPRGRDQ WEIFLEHVEQ LINQQITENA RNTALARLQG LGDSFRAYQQ SLEDWLENRD   120
DARTRSVLYT QYIALELDFL NAMPLFAIRN QEVPLLMVYA QAANLHLLLL RDASLFGSKF   180
GLTSQEIQRY YERQVERTRD YSDYCVEWYN TGLNSLRGTN AASWVRYNQF RRDLTLGVLD   240
LVALFPSYDT RTYPINTSAQ LTREVYTDAI GTVHPSQAFA STTWYNNNAP SLSAIEAAVI   300
RSPHLLDFPE QLTIYSTLSR WSNTQYMNIW VGHRLESRTI GGSLNTSTQG STNTSINPVR   360
LQFTARDVYR TESLAGLNIF LTQPVNGVPW VRFNWRNPLN SLRGSLLYTI GYTGVGTQLQ   420
DSETELPPET TERPNYESYS HRLSHIGLIS SSHVRALVYS WTHRSADRTN TIGPNRITQI   480
PLVKALNLHS GATVVRGPGF TGGDILRRTN TGTFGDIRLN INVPLSQRYR VRIRYASTTD   540
LQFFTRINGT TVNIGNFSRT MNRGDNLESR SFRAAGFSTP FNFSNAQSTF TLGAQSFSNQ   600
EVYIDRVEFV PAEVTFEAEY DLERAQE                                      627

SEQ ID NO: 245          moltype = AA length = 656
FEATURE                 Location/Qualifiers
source                  1..656
                        mol_type = protein
                        organism = Bacillus thuringiensis
SEQUENCE: 245
MPPKNQNKYQ SLSKNATVDK ISTDSLKNET DRELKNIYNE DCLRMSEHES MEPFVSASTI    60
QTGIGIAGKI LGNLGVPFAG QVASLYSFIL DELWPKGKSQ WEIFMEHVEE LIAQKISTYA   120
RNKALADLKG LGDALAVYHE SLESWIKNRN NTRARSVVKN QYIALELMFV QALPSFAVSG   180
EEVPLLPIYA QAANLHLLLL RDASIFGKEW GLSDSEISTF YNRQSGRSRE YSDHCVKWYN   240
TGLNRLRGTN AESWVRYNQF RRDMTLMVLD LVALFPSYDT HMYPIKTTAQ LTREVYTNPI   300
GVVGGVSWFE NAASFAAIEN AVIRQPHLYD FMTDLTIYTR LSRALPRYMN LWAGHRINFN   360
TIRGSTSREM VYGAITNPVS TTPLSFVNQD IYRTQSIAGV LLNNLSSRFYG VPRVDFDIRN   420
RNYPNIINRL TYNPGYAEIA TQVKDSETEL PPETTEQPNY EAASHLLCHI GMPPTGSGTG   480
SATPPVYSWT HRSAGRTNII NSDSITQIPL VKANNLHSGA TVVKGPGFTG GDILRRTSAG   540
TFVDLPVNLI SWQLSQSYRV RIRYASTTDL QFHTSINGRA INQGNFSATM NRGDALESRT   600
FRTVGFTTPF NFSDAQSTFT ISAWNFSSSN EVYIDRIEFV PAEVTLEAES LERAQK       656

SEQ ID NO: 246          moltype = AA length = 659
FEATURE                 Location/Qualifiers
source                  1..659
                        mol_type = protein
                        organism = Bacillus thuringiensis
SEQUENCE: 246
MPSYQNKNEY EILDASENTV NALNRYPFAN NPYSSIFSSC PRSGPGNWIN ILGNAVSEAV    60
SISQDIISLL TQPSISGIIS MAFSLLSRMI GSNGRSISEL SMCDLLAIID LRVNQSVLDD   120
GVADFNGSLV IYRNYLEALQ RWNNNPNPAN AEEVRTRFRE SDTIFDLILT QGSLTNGGSL   180
```

```
ARNNAQILLL PSFANAAYFH LLLLRDANVY GNNWGLFGVT PNINYESKLL NLIRLYTNYC   240
THWYNQGLNE LRNRGSNATA WLEFHRFRRD MTLMVLDIVS SFSSLDITRY PRATDFQLSR   300
IIYTDPIGFV NRSDPSAPRT WFSFHNQANF SALESGIPSP SFSQFLDSMR ISTGPLSLPA   360
SPNIHRARVW YGNQNNFNGS SSQTFGEITN DNQTISGLNI FRIDSQAVNL NNTTFGVSRA   420
EFYHDASQGS QRSIYQGFVD TGGASTAVAQ NIQTFFPGEN SSIPTPQDYT HILSRSTNLT   480
GGLRQVASGR RSSLVLHGWT HKSLSRQNRV EPNRITQVPA VKASSPSNCT VIAGPGFTGG   540
DLVRMSSNCS VSYNFTPADQ QVVIRLRYAC QGTASLRITF GNGSSQIIPL VSTTSSINNL   600
QYENFSFASG PNSVNFLSAG TSITIQNIST NSNVVLDRIE IVPEQPIPII PGDLEAAKK    659

SEQ ID NO: 247          moltype = AA  length = 5
FEATURE                 Location/Qualifiers
source                  1..5
                        mol_type = protein
                        organism = Bacillus thuringiensis
SEQUENCE: 247
QIEQL                                                                5

SEQ ID NO: 248          moltype = AA  length = 5
FEATURE                 Location/Qualifiers
SITE                    3
                        note = misc_feature - Xaa can be any naturally occurring
                         amino acid
source                  1..5
                        mol_type = protein
                        organism = Bacillus thuringiensis
SEQUENCE: 248
DPXNP                                                                5

SEQ ID NO: 249          moltype = AA  length = 5
FEATURE                 Location/Qualifiers
source                  1..5
                        mol_type = protein
                        organism = Bacillus thuringiensis
SEQUENCE: 249
SLQPG                                                                5

SEQ ID NO: 250          moltype = AA  length = 5
FEATURE                 Location/Qualifiers
source                  1..5
                        mol_type = protein
                        organism = Bacillus thuringiensis
SEQUENCE: 250
ANLHL                                                                5

SEQ ID NO: 251          moltype = AA  length = 5
FEATURE                 Location/Qualifiers
source                  1..5
                        mol_type = protein
                        organism = Bacillus thuringiensis
SEQUENCE: 251
WTHRS                                                                5

SEQ ID NO: 252          moltype = AA  length = 5
FEATURE                 Location/Qualifiers
source                  1..5
                        mol_type = protein
                        organism = Bacillus thuringiensis
SEQUENCE: 252
ITQIP                                                                5

SEQ ID NO: 253          moltype = AA  length = 5
FEATURE                 Location/Qualifiers
source                  1..5
                        mol_type = protein
                        organism = Bacillus thuringiensis
SEQUENCE: 253
GFTGG                                                                5

SEQ ID NO: 254          moltype = AA  length = 5
FEATURE                 Location/Qualifiers
source                  1..5
                        mol_type = protein
                        organism = Bacillus thuringiensis
SEQUENCE: 254
RYASS                                                                5

SEQ ID NO: 255          moltype = AA  length = 5
FEATURE                 Location/Qualifiers
source                  1..5
```

```
                                mol_type = protein
                                organism = Bacillus thuringiensis
SEQUENCE: 255
KTMEI                                                                    5

SEQ ID NO: 256          moltype = AA   length = 5
FEATURE                 Location/Qualifiers
source                  1..5
                        mol_type = protein
                        organism = Bacillus thuringiensis
SEQUENCE: 256
TFRYT                                                                    5

SEQ ID NO: 257          moltype = AA   length = 5
FEATURE                 Location/Qualifiers
source                  1..5
                        mol_type = protein
                        organism = Bacillus thuringiensis
SEQUENCE: 257
PFSFR                                                                    5

SEQ ID NO: 258          moltype = AA   length = 5
FEATURE                 Location/Qualifiers
source                  1..5
                        mol_type = protein
                        organism = Bacillus thuringiensis
SEQUENCE: 258
GQRWG                                                                    5

SEQ ID NO: 259          moltype = AA   length = 189
FEATURE                 Location/Qualifiers
source                  1..189
                        mol_type = protein
                        organism = Bacillus thuringiensis
SEQUENCE: 259
SHRLSHIGLI SASHVKALVY SWTHRSADRT NTIEPNSITQ IPLVKAFNLS SGAAVVRGPG         60
FTGGDILRRK NTGTFGDIRV NINPPFAQRY RVRIRYASTT DLQFHTSING KAINQGNFSA        120
TMNRGEDLDY KTFRTVGFTT PFSFSDVQST FTIGAWNFSS GNEVYIDRIE FVPVEVTYEA        180
EYDFEKAQE                                                               189

SEQ ID NO: 260          moltype = AA   length = 192
FEATURE                 Location/Qualifiers
source                  1..192
                        mol_type = protein
                        organism = Bacillus thuringiensis
SEQUENCE: 260
SHRLCHATFV QRSGTPFLTT GPVFSWTHRS ATDRNIIYPD VINQIPLVKA FNLTSGTSVV         60
RGPGFTGGDI IRTNVNGSVL SMSLNFSNTT LQRYRVRVRY AASQTMVMSV TVGGSTTGNQ        120
GFPSTMSANG ALTSQSFRFA EFPVGISASG SQGASISISN NVGRQMFHLD RIEFLPVTST        180
FEEEYDLERA QE                                                           192

SEQ ID NO: 261          moltype = AA   length = 196
FEATURE                 Location/Qualifiers
source                  1..196
                        mol_type = protein
                        organism = Bacillus thuringiensis
SEQUENCE: 261
SHVLNHVTFV RWPGEISGSD SWRAPMFSWT HRSATPTNTI DPERITQIPL VKAHTLQSGT         60
TVVRGPGFTG GDILRRTSGG PFAYTIVNIN GQLPQRYRAR IRYASTTNLR IYVTVAGERI        120
FAGQFNKTMD TGDPLTFQSF SYATINTAFT FPMSQSSFTV GADTFSSGNE VYIDRFELIP        180
VTATFEAEYD LERAQK                                                       196

SEQ ID NO: 262          moltype = AA   length = 198
FEATURE                 Location/Qualifiers
source                  1..198
                        mol_type = protein
                        organism = Bacillus thuringiensis
SEQUENCE: 262
FNLLSHVTFL RFNTTQGGPL ATVGFVPTYV WTRQDVDFNN IITPNRITQI PVVKAYELSS         60
GATVVKGPGF TGGDVIRRTN TGGFGAIRVS VTGPLTQRYR IRFRYASTID FDFFVTRGGT        120
TINNRFRFTRT MNRGEQESRYE SYRTVEFTTP FNFTQSQDII RTSIQGLSGN GEVYLDRIEI      180
IPVNPTREAE EDLEAAKK                                                     198

SEQ ID NO: 263          moltype = AA   length = 196
FEATURE                 Location/Qualifiers
source                  1..196
                        mol_type = protein
                        organism = Bacillus thuringiensis
SEQUENCE: 263
```

-continued

```
SHRLSHVSMF RSGFSNSSVS IIRAPMFSWI HRSAEFNNII PSSQITQIPL TKSTNLGSGT  60
SVVKGPGFTG GDILRRTSPG QISTLRVNIT APLSQRYRVR IRYASTTNLQ FHTSIDGRPI  120
NQGNFSATMS SGGNLQSGSF RTVGFTTPFN FSNGSSVFTL SAHVFNSGNE VYIDRIEFVP  180
AEVTFEAEYD LERAQE                                                 196

SEQ ID NO: 264          moltype = AA  length = 188
FEATURE                 Location/Qualifiers
source                  1..188
                        mol_type = protein
                        organism = Bacillus thuringiensis
SEQUENCE: 264
SHRLSHIGLI IGNTLRAPVY SWTHRSADRT NTIGPNRITQ IPLVKALNLH SGVTVVGGPG  60
FTGGDILRRT NTGTFGDIRL NINVPLSQRY RVRIRYASTT DLQFFTRING TTVNIGNFSR  120
TMNRGDNLEY RSFRTAGFST PFNFLNAQST FTLGAQSFSN QEVYIDRVEF VPAEVTFEAE  180
YDLERAQK                                                          188

SEQ ID NO: 265          moltype = AA  length = 205
FEATURE                 Location/Qualifiers
source                  1..205
                        mol_type = protein
                        organism = Bacillus thuringiensis
SEQUENCE: 265
SHRLCHATFV QRSGTPFLTT GVVFSWTDRS ATLTNTIDPE RINQIPLVKG FRVWGGTSVI  60
TGPGFTGGDI LRRNTFGDFV SLQVNINSPI TQRYRLRFRY ASSRDARVIV LTGAASTGVG  120
GQVSVNMPLQ KTMEIGENLT SRTFRYTDFS NPFSFRANPD IIGISEQPLF GAGSISSGEL  180
YIDKIEIILA DATFEAESDL ERAQE                                       205

SEQ ID NO: 266          moltype = AA  length = 5
FEATURE                 Location/Qualifiers
source                  1..5
                        mol_type = protein
                        organism = Bacillus thuringiensis
SEQUENCE: 266
QLTRE                                                             5

SEQ ID NO: 267          moltype = AA  length = 5
FEATURE                 Location/Qualifiers
source                  1..5
                        mol_type = protein
                        organism = Bacillus thuringiensis
SEQUENCE: 267
SHRLS                                                             5

SEQ ID NO: 268          moltype = AA  length = 187
FEATURE                 Location/Qualifiers
source                  1..187
                        mol_type = protein
                        organism = Bacillus thuringiensis
SEQUENCE: 268
SHRLCHATFL ERISGPRIAG TVFSWTHRSA SPTNEVSPSR ITQIPWVKAH TLASGASVIK  60
GPGFTGGDIL TRNSMGELGT LRVTFTGRLP QSYYIRFRYA SVANRSGTFR YSQPPSYGIS  120
FPKTMDAGEP LTSRSFAHTT LFTPITFSRA QEEFDLYIQS GVYIDRIEFI PVTATFEAEY  180
DLERAQK                                                           187

SEQ ID NO: 269          moltype = AA  length = 167
FEATURE                 Location/Qualifiers
source                  1..167
                        mol_type = protein
                        organism = Bacillus thuringiensis
SEQUENCE: 269
WTHRSATTTN TINPNAIIQI PLVKAFNLHS GATVVRGPGF TGGDILRRTN TGTFADMRVN  60
ITGPLSQRYR VRIRYASTTD LQFFTRINGT SVNQGNFQRT MNRGDNLESG NFRTAGFSTP  120
FSFSNAQSTF TLGTQAFSNQ EVYIDRIEFV PAEVTFEAES DLERAQK               167

SEQ ID NO: 270          moltype = AA  length = 168
FEATURE                 Location/Qualifiers
source                  1..168
                        mol_type = protein
                        organism = Bacillus thuringiensis
SEQUENCE: 270
WTHRSADRTN TIEPNSITQI PLVKAFNLSS GAAVVRGPGF TGGDILRRKN TGTFGDIRVN  60
INPPFAQRYR VRIRYASTTD LQFHTSINGK AINQGNFSAT MNRGEDLDYK TFRTVGFTTP  120
FSFSDVQSTF TIGAWNFSSG NEVYIDRIEF VPVEVTYEAE YDFEKAQE              168

SEQ ID NO: 271          moltype = DNA  length = 2010
FEATURE                 Location/Qualifiers
misc_feature            1..2010
                        note = Artificial Sequence
source                  1..2010

```
                    mol_type = other DNA
                    organism = unidentified
SEQUENCE: 271
atgcctcgaa ataatcaaaa tgaatatgaa attattgacg cttccacttg tggttgttcg    60
tcagatgatg ttgttcaata ccctttggca agagatcgaa atgctgtatt ccaaaatatg   120
cattataaag attatttgca aacgtatgat ggagactata caggttctct tataaatcct   180
aacttatcta ttaatcctag agatgtactg caaactggaa ttaatattgt gggaagatta   240
ctaggatttc taggtgttcc atttgctggt cagttagtta cttttctatac ctttcttta    300
aatcaactgt ggccaacaaa tgataatgca gtatgggaag cttttatggc acaaaatagaa  360
gagcttatta atcaaagaat atccgaagca gtagtaggga cagcagcgga tcatttaacg   420
ggattacacg ataattatga gttatatgta gaggcattgg aggaatggct ggaaagaccg   480
aatgctgcta gaactaatct acttttaat agatttacca ccctagatag tcttttttaca   540
caatttatgc caagctttgg tactggacct ggaagtcaaa actacgcagt tccattactt   600
acagtatacg cacaagcagc gaaccttcat ttgttattat taaaggatgc tgaaatatat   660
ggagcaagat ggggactgaa ccaaaatcag attaactcat tccatacgcg ccaacaagaa   720
cgtactcaat attatacaaa tcattgcgta acgacgtata ataccggttt agatagatta   780
agaggcacaa atactgaaag ttggttaaat tatcatcgtt tccgtagaga gatgacatta   840
atggcaatgg atttagtagc gctattccca tattataatg tacgacaata tccaaatgga   900
gcaaatcctc agctgacccg tgaagtttac actgacccga tcgttttcaa cccgccggct   960
aacgttggcc tgtgccgccg ttggggcacc aacccgtata acacgttctc cgaactggaa  1020
aacgctttta tccgtccacc gcacctgttc gatcgcctga actccctgac gatttcctct  1080
aaccgttttc cggtgtcttc taacttttatg gactattgt ccggtcacac gctcgccgc   1140
tcttacctga atgactccgc cgttcaagag gattcttatg gtctgatcac caccactcgt  1200
gcgaccatca acccaggcgt ggatggcacc aaccgtattg aaagcactgc agttgacttc  1260
cgtagcgcac tgatcggcat ctacggtgtt aatcgtgcat cttttgttcc gggcggtctg  1320
tttaacggta ccacctcccc ggcaaacggc ggctgccgg acctgtatga tacgaacgat  1380
gagctgccgc cggatgagtc cactggctct tccactcacc gtctgtccca cgtaactttt  1440
ttcagcttcc agaccaatca agcaggttct attgcaaacg ccggctccgt tccgacctat  1500
gtgtggaccc gccgtgatgt tgatctgaat aacaccatta cgccgaaccg tatcaatcaa  1560
attccggtgg taaaggcata tgagctaagt agtggtgcta ctgtcgtgaa aggtccagga  1620
ttcacaggag gagatgtaat ccgaagaaca aatattggtg ggttcggagc aataagggtg  1680
tcggtcactg gaccgctaac acaacgatat cgcataaggt tccgttatgc ttcgacaata  1740
gattttgatt tctttgtaac acgtggagga actactataa ataattttag atttacacgt  1800
acaatgaaca ggggacagga atcaagatat gaatcctatc gtactgtgga gtttacaact  1860
ccttttaact ttacacaaag tcaagatata attcgaacat ctatccaggg acttagtgga  1920
aatggggaag tataccttga tagaattgaa atcatccctg taaatccaac acgagaagcg  1980
gaagaggatc tagaagcagc aaagaaataa                                    2010

SEQ ID NO: 272        moltype = DNA    length = 2001
FEATURE               Location/Qualifiers
misc_feature          1..2001
                      note = Artificial Sequence
source                1..2001
                      mol_type = other DNA
                      organism = unidentified
SEQUENCE: 272
atgcctcgaa ataatcaaaa tgaatatgaa attattgacg cttccacttg tggttgttcg    60
tcagatgatg ttgttcaata ccctttggca agagatccga atgctgtatt ccaaaatatg   120
cattataaag attatttgca aacgtatgat ggagactata caggttctct tataaatcct   180
aacttatcta ttaatcctag agatgtactg caaactggaa ttaatattgt gggaagatta   240
ctaggatttc taggtgttcc atttgctggt cagttagtta cttttctatac ctttcttta    300
aatcaactgt ggccaacaaa tgataatgca gtatgggaag cttttatggc acaaaatagaa  360
gagcttatta atcaaagaat atccgaagca gtagtaggga cagcagcgga tcatttaacg   420
ggattacacg ataattatga gttatatgta gaggcattgg aggaatggct ggaaagaccg   480
aatgctgcta gaactaatct acttttaat agatttacca ccctagatag tcttttttaca   540
caatttatgc caagctttgg tactggacct ggaagtcaaa actacgcagt tccattactt   600
acagtatacg cacaagcagc gaaccttcat ttgttattat taaaggatgc tgaaatatat   660
ggagcaagat ggggactgaa ccaaaatcag attaactcat tccatacgcg ccaacaagaa   720
cgtactcaat attatacaaa tcattgcgta acgacgtata ataccggttt agatagatta   780
agaggcacaa atactgaaag ttggttaaat tatcatcgtt tccgtagaga gatgacatta   840
atggcaatgg atttagtagc gctattccca tattataatg tacgacaata tccaaatgga   900
gcaaatcctc agctgacccg tgaatctac actgacccga tcgtttataa cccgccggct   960
aaccaaggca tctgccgccg ttggggcaac aacccgtata acacgttctc cgaactggaa  1020
aacgctttta tccgtccacc gcacctgttc gaacgcctga accgcctgac gatttcccgc  1080
aaccgttaca ctgcgccgac cactaacagc ttcctggact attggtctgg tcatacgctg  1140
cagagccagc acgcgaataa cccgactact tacgagacgt cttatggtca gatcacttct  1200
aacacccgtc tgttcaatac gaccaacggc gctcgtgcga ttgatagccg tgcccgcaac  1260
ttcggtaacc tgtacgccaa cctgtacggt gttagctctc tgaacatctt cccgaccggt  1320
gttatgtccg aaatcaccaa cgcagcgaac acctgccgac cacgaccgaa  1380
gagctgccgc tggagaacaa caacttcaac ctgctgtccc acgtaacttt cctgcgtttc  1440
aacaccaccc agggtggccc gctggctacc ctgggcttcg tgcctactta cgtttggacc  1500
cgtgaagacg tagactttac caataccatt actgcagatc gcatcaatca aattccggtg  1560
gtaaaggcat atgagctaag tagtggtgct actgtcgtga aaggtccagg attcacagga  1620
ggagatgtaa tccgaagaac aaatattggt gggttcggag caataagggt gtcggtcact  1680
ggaccgctaa cacaacgata tcgcataagg ttccgttatg cttcgacaat agattttgat  1740
ttctttgtaa cacgtggagg aactactata ataattttta gatttacacg tacaatgaac  1800
aggggacagg aatcaagata tgaatcctat cgtactgtgg agtttacaac tcctttttaac  1860
tttacacaaa gtcaagatat aattcgaaca tctatccagg gacttagtgg aaatggggaa  1920
gtataccttg atagaattga aatcatccct gtaaatccaa cacgagaagc ggaagaggat  1980
```
ctagaagcag caaagaaata a 2001

SEQ ID NO: 273    moltype = DNA  length = 2034
FEATURE           Location/Qualifiers
misc_feature      1..2034
                  note = Artificial Sequence
source            1..2034
                  mol_type = other DNA
                  organism = unidentified
SEQUENCE: 273
atgcctcgaa ataatcaaaa tgaatatgaa attattgacg cttccacttg tggttgttcg 60
tcagatgatg ttgttcaata ccctttggca agagatccga atgctgtatt ccaaaatatg 120
cattataaag attatttgca aacgtatgat ggagactata caggttctct tataaatcct 180
aacttatcta ttaatcctag agatgtactg caaactggaa ttaatattgt gggaagatta 240
ctaggatttc taggtgttcc atttgctggt cagttagtta cttctctatac ctttctttta 300
aatcaactgt ggccaacaaa tgataatgca gtatgggaag cttttatggc acaaatagaa 360
gagcttatta atcaaagaat atccgaagca gtagtaggga cagcagcgga tcatttaacg 420
ggattacacg ataattatga gttatatgta gaggcattgg aggaatggct ggaaagaccg 480
aatgctgcta gaactaatct acttttaat agatttacca ccctagatag tcttttttaca 540
caatttatgc caagctttgg tactggacct ggaagtcaaa actacgcagt tccattactt 600
acagtatacg cacaagcagc gaaccttcat ttgttattat taaaggatgc tgaaatatat 660
ggagcaagat ggggactgaa ccaaaatcag attaactcat tccatacgcg ccaacaagaa 720
cgtactcaat attatacaaa tcattgcgta acgacgtata ataccggttt agatagatta 780
agaggcacaa atactgaaag ttggttaaat tatcatcgtt tccgtagaga gatgacatta 840
atggcaatgg atttagtagc gctattccca tattataatg tacgacaata tccaaatgga 900
gcaaatcctc agctgacccg tgaaatttat acagatccga ttggttttgt aaatcgtggt 960
acttcaagta gattaagctg gtttgattgg caaaatagag ctaattttttc agaattgaa 1020
agggcaatac cagatcccgt actttcgcaa ttttttaaata gtattcgtat atatactggt 1080
atactgtcat tacctgtttc tccaaatacc gttagaggac gggtatggta tgggaatcaa 1140
aatcaggtta gtagtgctaa ttcacaagat gttttcaatg agactttggc ccaagtaaca 1200
aatgatagac aaaacctttc aggattaaat atatttaggg ttgattcgca agcagctaat 1260
ctaaataatt ctttgtatgg tgtaagtaga gctgaatttt tccacgatgc tagccaaggg 1320
tctagaaggt ccgtatatca agggtatatt agaactagcg ggctagataa ccctgtaacg 1380
cagactattc gaacttttttt accaggagag aattcggata caccaactcc agaagattat 1440
actcatgtat taagtgctgc aataaattta actggcggcc ttcgacaacc agtaactaat 1500
cgtcgttctt ctgtggtgat gtatggatgg acacatagga gcctaagtcg tgaaaataca 1560
atattttcag atagaatcaa tcaaattccg gtggtaaagg catatgagct aagtagtggt 1620
gctactgtcg tgaaaggtcc aggattcaca ggaggagatg taatccgaag aacaaatatt 1680
ggtgggttcg gagcaataag ggtgtcggtc actggaccgc taacacaacg atatcgcata 1740
aggttccgtt atgcttcgac aatagatttt gatttctttg taacacgtgg aggaactact 1800
ataaataatt ttagatttac acgtacaatg aacagggac aggaatcaag atatgaatcc 1860
tatcgtactg tggagtttac aactcctttt aactttcac aaagtcaaga tataattcga 1920
acatctatcc agggacttag tggaaatggg gaagtatacc ttgatagaat tgaaatcatc 1980
cctgtaaatc caacacgaga agcggaagag gatctagaag cagcaaagaa ataa 2034

SEQ ID NO: 274    moltype = DNA  length = 2043
FEATURE           Location/Qualifiers
misc_feature      1..2043
                  note = Artificial Sequence
source            1..2043
                  mol_type = other DNA
                  organism = unidentified
SEQUENCE: 274
atgcctcgaa ataatcaaaa tgaatatgaa attattgacg cttccacttg tggttgttcg 60
tcagatgatg ttgttcaata ccctttggca agagatccga atgctgtatt ccaaaatatg 120
cattataaag attatttgca aacgtatgat ggagactata caggttctct tataaatcct 180
aacttatcta ttaatcctag agatgtactg caaactggaa ttaatattgt gggaagatta 240
ctaggatttc taggtgttcc atttgctggt cagttagtta cttctctatac ctttctttta 300
aatcaactgt ggccaacaaa tgataatgca gtatgggaag cttttatggc acaaatagaa 360
gagcttatta atcaaagaat atccgaagca gtagtaggga cagcagcgga tcatttaacg 420
ggattacacg ataattatga gttatatgta gaggcattgg aggaatggct ggaaagaccg 480
aatgctgcta gaactaatct acttttaat agatttacca ccctagatag tcttttttaca 540
caatttatgc caagctttgg tactggacct ggaagtcaaa actacgcagt tccattactt 600
acagtatacg cacaagcagc gaaccttcat ttgttattat taaaggatgc tgaaatatat 660
ggagcaagat ggggactgaa ccaaaatcag attaactcat tccatacgcg ccaacaagaa 720
cgtactcaat attatacaaa tcattgcgta acgacgtata ataccggttt agatagatta 780
agaggcacaa atactgaaag ttggttaaat tatcatcgtt tccgtagaga gatgacatta 840
atggcaatgg atttagtagc gctattccca tattataatg tacgacaata tccaaatgga 900
gcaaatcctc agctgacccg tgaagtttac actgacccga tcgttttcaa cccgccggct 960
aacgttggcc tgtgccgccg ttggggcacc aaccgtata acacgttctc cgaactggaa 1020
aacgcttttta tccgtccacc gcacctgttc gatcgcctga actccctgac gatttcctct 1080
aaccgttttc cggtgtcttc taactttatg gactattggt ccgtcacac gctgcgccgc 1140
tcttacctga atgactccgc cgttcaagag gattcttatg gtctgatcac caccactcgt 1200
gcgaccatca acccaggcgt ggatgccacc aacgtattg aaagcactg agttgacttc 1260
cgtagcgcac tgatcggcat ctacggtgtt aatcgtgcat cttttgttcc gggcggtctg 1320
tttaacggta ccacctcccc ggcaaacggc ggctgccgtg acctgtatga tacgaacgat 1380
gagctgccgc cggatgagtc cactggctct tccactcacc gtctgtccca cgtaactttt 1440
ttcagcttcc agaccaatca agcaggttct attgcaaacg ccggctccgt tccgacctat 1500
gtgtggaccc gccgtgatgt tgatctgaat aacaccatta cgccgaaccg tatcaatcaa 1560

```
attccgctgg tgaagggctt tcgtgtttgg ggcggcactt ccgtaatcac tggtccgggt    1620
ttcacgggtg gcgatattct cgtcgcaac acgttcggcg acttcgtttc cctgcaggta    1680
aacatcaact ctccgatcac ccagcgctac cgcctcgct  tccgttacgc ctcttctcgt    1740
gatgcacgtg ttatcgtcct gaccggcgca gcaagcaccg cgttggtgg  tcaagttttct   1800
gtgaacatgc cactgcagaa aaccatggaa atcggcgac  acctgacgtc ccgcactttc    1860
cgctataccg attttagcaa tccgttctcc tttcgtgcaa acccggacat cattggcatc    1920
tctgagcaac cgctgttcgg tgctggttcc atctcctctg gtgagctgta tatcgacaag    1980
atcgaaatta tcctggcgga cgctaccttc gaagcggaga cgacctgga  acgcgcgcag    2040
taa                                                                  2043

SEQ ID NO: 275         moltype = AA   length = 669
FEATURE                Location/Qualifiers
REGION                 1..669
                       note = Artificial Sequenec
source                 1..669
                       mol_type = protein
                       organism = unidentified
SEQUENCE: 275
MPRNNQNEYE IIDASTCGCS SDDVVQYPLA RDPNAVFQNM HYKDYLQTYD GDYTGSLINP     60
NLSINPRDVL QTGINIVGRL LGFLGVPFAG QLVTFYTFLL NQLWPTNDNA VWEAFMAQIE    120
ELINQRISEA VVGTAADHLT GLHDNYELYV EALEEWLERP NAARTNLLFN RFTTLDSLFT    180
QFMPSFGTGP GSQNYAVPLL TVYAQAANLH LLLLKDAEIY GARWGLNQNQ INSFHTRQQE    240
RTQYYTNHCV TTYNTGLDRL RGTNTESWLN YHRFRREMTL MAMDLVALFP YYNVRQYPNG    300
ANPQLTREVY TDPIVFNPPA NVGLCRRWGT NPYNTFSELE NAFIRPPHLF DRLNSLTISS    360
NRFPVSSNFM DYWSGHTLRR SYLNDSAVQE DSYGLITTTR ATINPGVDGT NRIESTAVDF    420
RSALIGIYGV NRASFVPGGL FNGTTSPANG GCRDLYDTND ELPPDESTGS STHRLSHVTF    480
FSFQTNQAGS IANAGSVPTY VWTRRDVDLN NTITPNRINQ IPVVKAYELS SGATVVKGPG    540
FTGGDVIRRT NIGGFGAIRV SVTGPLTQRY RIRPFRYASTI DFDFFVTRGG TTINNFRFTR   600
TMNRGQESRY ESYRTVEFTT PFNFTQSQDI IRTSIQGLSG NGEVYLDRIE IIPVNPTREA    660
EEDLEAAKK                                                           669

SEQ ID NO: 276         moltype = AA   length = 666
FEATURE                Location/Qualifiers
REGION                 1..666
                       note = Artificial Sequence
source                 1..666
                       mol_type = protein
                       organism = unidentified
SEQUENCE: 276
MPRNNQNEYE IIDASTCGCS SDDVVQYPLA RDPNAVFQNM HYKDYLQTYD GDYTGSLINP     60
NLSINPRDVL QTGINIVGRL LGFLGVPFAG QLVTFYTFLL NQLWPTNDNA VWEAFMAQIE    120
ELINQRISEA VVGTAADHLT GLHDNYELYV EALEEWLERP NAARTNLLFN RFTTLDSLFT    180
QFMPSFGTGP GSQNYAVPLL TVYAQAANLH LLLLKDAEIY GARWGLNQNQ INSFHTRQQE    240
RTQYYTNHCV TTYNTGLDRL RGTNTESWLN YHRFRREMTL MAMDLVALFP YYNVRQYPNG    300
ANPQLTREIY TDPIVYNPPA NQGICRRWGN NPYNTFSELE NAFIRPPHLF ERLNRLTISR    360
NRYTAPTTNS FLDYWSGHTL QSHANNPTT  YETSYGQITS NTRLFNTTNG ARAIDSRARN    420
FGNLYANLYG VSSLNIFPTG VMSEITNAAN TCRQDLTTTE ELPLENNNFN LLSHVTFLRF    480
NTTQGGPLAT LGFVPTYVWT REDVDFTNTI TADRINQIPV VKAYELSSGA TVVKGPGFTG    540
GDVIRRTNIG GFGAIRVSVT GPLTQRYRIR FRYASTIDFD FFVTRGGTTI NNFRFTRTMN    600
RGQESRYESY RTVEFTTPFN FTQSQDIIRT SIQGLSGNGE VYLDRIEIIP VNPTREAEED    660
LEAAKK                                                              666

SEQ ID NO: 277         moltype = AA   length = 677
FEATURE                Location/Qualifiers
REGION                 1..677
                       note = Artificial Sequence
source                 1..677
                       mol_type = protein
                       organism = unidentified
SEQUENCE: 277
MPRNNQNEYE IIDASTCGCS SDDVVQYPLA RDPNAVFQNM HYKDYLQTYD GDYTGSLINP     60
NLSINPRDVL QTGINIVGRL LGFLGVPFAG QLVTFYTFLL NQLWPTNDNA VWEAFMAQIE    120
ELINQRISEA VVGTAADHLT GLHDNYELYV EALEEWLERP NAARTNLLFN RFTTLDSLFT    180
QFMPSFGTGP GSQNYAVPLL TVYAQAANLH LLLLKDAEIY GARWGLNQNQ INSFHTRQQE    240
RTQYYTNHCV TTYNTGLDRL RGTNTESWLN YHRFRREMTL MAMDLVALFP YYNVRQYPNG    300
ANPQLTREIY TDPIGFVNRG TSSRLSWFDW QNRANFSELE RAIPDPVLSQ FLNSIRIYTG    360
ILSLPVSPNT VRGRVWYGNQ NQVSSANSQD VFNQTFGQVT NDRQNLSGLN IFRVDSQAAN    420
LNNSLYGVSR AEFFHDASQG SRRSVYQGYI RTSGLDNPVT QTIRTFLPGE NSDTPTPEDY    480
THVLSAAINL TGGLRQPVTN RRSSVVMYGW THRSLSRENT IFSDRINQIP VVKAYELSSG    540
ATVVKGPGFT GGDVIRRTNI GGFGAIRVSV TGPLTQRYRI RFRYASTIDF DFFVTRGGTT    600
INNFRFTRTM NRGQESRYES YRTVEFTTPF NFTQSQDIIR TSIQGLSGNG EVYLDRIEII    660
PVNPTREAEE DLEAAKK                                                  677

SEQ ID NO: 278         moltype = AA   length = 680
FEATURE                Location/Qualifiers
REGION                 1..680
                       note = Artificial Sequence
source                 1..680
                       mol_type = protein
```

```
                organism = unidentified
SEQUENCE: 278
MPRNNQNEYE IIDASTCGCS SDDVVQYPLA RDPNAVFQNM HYKDYLQTYD GDYTGSLINP   60
NLSINPRDVL QTGINIVGRL LGFLGVPFAG QLVTFYTFLL NQLWPTNDNA VWEAFMAQIE  120
ELINQRISEA VVGTAADHLT GLHDNYELYV EALEEWLERP NAARTNLLFN RFTTLDSLFT  180
QFMPSFGTGP GSQNYAVPLL TVYAQAANLH LLLLKDAEIY GARWGLNQNQ INSFHTRQQE  240
RTQYYTNHCV TTYNTGLDRL RGTNTESWLN YHRFRREMTL MAMDLVALFP YYNVRQYPNG  300
ANPQLTREVY TDPIVFNPPA NVGLCRRWGT NPYNTFSELE NAFIRPPHLF DRLNSLTISS  360
NRFPVSSNFM DYWSGHTLRR SYLNDSAVQE DSYGLITTTR ATINPGVDGT NRIESTAVDF  420
RSALIGIYGV NRASFVPGGL FNGTTSPANG GCRDLYDTND ELPPDESTGS STHRLSHVTF  480
FSFQTNQAGS IANAGSVPTY VWTRRDVDLN NTITPNRINQ IPLVKGFRVW GGTSVITGPG  540
FTGGDILRRN TFGDFVSLQV NINSPITQRY RLRFRYASSR DARVIVLTGA ASTGVGGQVS  600
VNMPLQKTME IGENLTSRTF RYTDFSNPFS FRANPDIIGI SEQPLFGAGS ISSGELYIDK  660
IEIILADATF EAESDLERAQ                                             680
```

INSECTICIDAL PROTEINS AND METHODS FOR THEIR USE

CROSS-REFERENCE TO RELATED APPLICATIONS

This application is a divisional application of U.S. patent application Ser. No. 17/269,314, filed Feb. 18, 2021, which is a National Stage application of International Patent Application No. PCT/US2019/047660, filed Aug. 22, 2019, which claims the benefit of U.S. Provisional Application No. 62/724,276, filed Aug. 29, 2018, the disclosures of each of which are is hereby incorporated herein by reference in their entireties.

REFERENCE TO SEQUENCE LISTING SUBMITTED ELECTRONICALLY

An XML formatted sequence listing having the file name "105995 SequenceListing.xml" created on Aug. 9, 2023, and having a size of 553.915 bytes is filed in computer readable form concurrently with the specification. The sequence listing contained in this XML formatted document is part of the specification and is herein incorporated by reference in its entirety.

FIELD

This disclosure relates to the field of molecular biology. Provided are novel genes that encode pesticidal proteins. These pesticidal proteins and the nucleic acid sequences that encode them are useful in preparing pesticidal formulations and in the production of transgenic pest-resistant plants. Methods to create or alter pesticidal proteins are provided for altered or enhanced pesticidal activity.

BACKGROUND

Biological control of insect pests of agricultural significance using a microbial agent, such as fungi, bacteria or another species of insect affords an environmentally friendly and commercially attractive alternative to synthetic chemical pesticides. Generally speaking, the use of biopesticides presents a lower risk of pollution and environmental hazards and biopesticides provide greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a range of insect pests including Lepidoptera, Diptera, Coleoptera, Hemiptera and others. *Bacillus thuringiensis* (Bt) and *Bacillus popilliae* are among the most successful biocontrol agents discovered to date. Insect pathogenicity has also been attributed to strains of *B. larvae, B. lentimorbus, B. sphaericus* and *B. cereus*. Microbial insecticides, particularly those obtained from *Bacillus* strains, have played an important role in agriculture as alternatives to chemical pest control.

Crop plants have been developed with enhanced insect resistance by genetically engineering crop plants to produce pesticidal proteins from *Bacillus*. For example, corn and cotton plants have been genetically engineered to produce pesticidal proteins isolated from strains of *Bacillus thuringiensis*. These genetically engineered crops are now widely used in agriculture and have provided the farmer with an environmentally friendly alternative to traditional insect-control methods. While they have proven to be very successful commercially, these genetically engineered, insect-resistant crop plants may provide resistance to only a narrow range of the economically important insect pests. In some cases, insects can develop resistance to different insecticidal compounds, which raises the need to identify alternative biological control agents for pest control.

Accordingly, there remains a need for new pesticidal proteins with different ranges of insecticidal activity against insect pests, e.g., insecticidal proteins which are active against a variety of insects in the order Lepidoptera and the order Coleoptera, including but not limited to insect pests that have developed resistance to existing insecticides.

SUMMARY

In one aspect compositions and methods for conferring pesticidal activity to bacteria, plants, plant cells, tissues and seeds are provided. Compositions include nucleic acid molecules encoding sequences for pesticidal and insecticidal polypeptides, vectors comprising those nucleic acid molecules, and host cells comprising the vectors. Compositions also include the pesticidal polypeptide sequences and antibodies to those polypeptides. Compositions also comprise transformed bacteria, plants, plant cells, tissues and seeds.

In another aspect isolated or recombinant nucleic acid molecules are provided encoding a shuffled Cry toxin polypeptide including amino acid substitutions, deletions, insertions, and fragments thereof. Provided are isolated or recombinant nucleic acid molecules capable of encoding shuffled Cry toxin polypeptides of SEQ ID NOS: 57-112 and 275-278, as well as amino acid substitutions, deletions, insertions, fragments thereof, and combinations thereof. In certain embodiments, polynucleotides are provided that encode insecticidal polypeptides, wherein the polynucleotides comprise a nucleic acid sequence as set forth in any one of SEQ ID NOS: 57-112, 214-246, and 275-278. Nucleic acid sequences that are complementary to a nucleic acid sequence of the embodiments or that hybridize to a sequence of the embodiments are also encompassed. The nucleic acid sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant.

In another aspect shuffled Cry toxin polypeptides are encompassed. Also provided are isolated or recombinant shuffled Cry toxin polypeptides of SEQ ID NO: 57-112 and 275-278, as well as amino acid substitutions, deletions, insertions, fragments thereof and combinations thereof.

In another aspect methods are provided for producing the polypeptides and for using those polypeptides for controlling or killing a Lepidopteran, Coleopteran, nematode, fungi, and/or Dipteran pests. The transgenic plants of the embodiments express one or more of the pesticidal sequences disclosed herein. In various embodiments, the transgenic plant further comprises one or more additional genes for insect resistance, for example, one or more additional genes for controlling Coleopteran, Lepidopteran, Hemipteran or nematode pests. It will be understood by one of skill in the art that the transgenic plant may comprise any gene imparting an agronomic trait of interest.

In another aspect methods for detecting the nucleic acids and polypeptides of the embodiments in a sample are also included. A kit for detecting the presence of a shuffled Cry toxin polypeptide or detecting the presence of a polynucleotide encoding a shuffled Cry toxin polypeptide in a sample is provided. The kit may be provided along with all reagents and control samples necessary for carrying out a method for detecting the intended agent, as well as instructions for use.

In another aspect the compositions and methods of the embodiments are useful for the production of organisms with enhanced pest resistance or tolerance. These organisms and compositions comprising the organisms are desirable for agricultural purposes. The compositions of the embodiments are also useful for generating altered or improved proteins that have pesticidal activity or for detecting the presence of shuffled Cry toxin polypeptides.

In another aspect methods for shuffling Cry toxin polypeptides comprising swapping alpha loop domains of domain 1 (Dm1) from a first Cry toxin into a second Cry toxin are provided. In some embodiments, the shuffled Cry toxin polypeptide has an altered spectrum of activity. In another embodiment, the shuffled Cry toxin polypeptide has an altered amount of pesticidal activity. In some embodiments, the shuffled cry toxin polypeptide has an altered mode of action or site of action. In some embodiments, the shuffling comprises swapping alpha loops 2, 3, 4, 5, and/or 6 from a first Cry toxin into a second Cry toxin. In some embodiments the Cry toxin is a native Cry toxin. In some embodiments, the Cry toxin is a shuffled or hybrid Cry toxin.

BRIEF DESCRIPTION OF THE FIGURES

FIG. 1 shows different holotype Bt Cry toxin domain fragments (Dm1, Dm2 and Dm3) that were optimized for *E. coli* expression and synthesized and used for some shuffling reactions and templated for fragment PCR. The border sequences are shown for the junctions of Dm1, Dm2, and Dm3 (SEQ ID NOs: 266 and 267 respectively).

FIG. 3 shows a library design to shuffle several hybrid domain 1 (Dm1) with Cry1Ea domain 2 (Dm2) and Cry1Ca domain 3 (Dm3) at three different cross over points having different lengths of Cry1Ca Dm3. Hybrid Dm1s differ at alpha 3-5 region. Along with 9 hybrid Dm1s, three Cry1Ea-like Dm1 hybrids were designed. Dm1 and Dm1 alpha fragments of different Cry toxins were mixed with Cry1Ea and Cry1Ca Dm2-Dm3 fusion fragment to create different novel Cry toxin variants. Cry1Ea and Cry1Ca Dm2s were fused at different crossover points; WTHRS (ECF2 library, SEQ ID NO: 251), ITQIP (ECF3 library, SEQ ID NO: 252) and GFTGG (ECF4 library, SEQ ID NO: 253).

FIG. 7 shows a list of all IPRS-C variants generated using different Cry toxin fragment shuffling. Domain composition of all variants indicated. Dm2 and Dm3 fusion crossover points (F) were also indicated. Specific activities (IC50 and LC50) of all these variants were determined against CEW, FAW and ECB and listed as tested. Variants in the table are divided based on their activity against FAW, CEW, or both.

FIG. 8 shows a fragment of Dm1 (Alpha loop 3—part of Alpha loop 5) shuffled in examples 1, 2 and 3. Shaded areas are anchor sequences where the shuffled fragment was fused to the backbone. Usually, the 5' anchor sequence motif is QIEQL (SEQ ID NO:247) and 3' anchor sequence motif is ANLHL (SEQ ID NO:250). Diversity at each of these anchor sequence positions was also listed below the normal anchor sequence motif in columns.

FIG. 10 shows IPRS variant produced (with associated SEQ ID NOs.) as described in the Examples.

FIG. 11 shows Cry toxin Alpha loop (with associated SEQ ID NOs.) that may be used for Alpha loop swapping.

FIG. 12 shows proprietary Cry toxins showing insecticidal activity (with associated SEQ ID NOs.) that may be used for shuffling as described herein.

FIG. 13 shows Cry toxin Dm3 regions (with associated SEQ ID NOs.) that showed altered activity when swapped to another Cry toxin.

DETAILED DESCRIPTION

Figure 2:
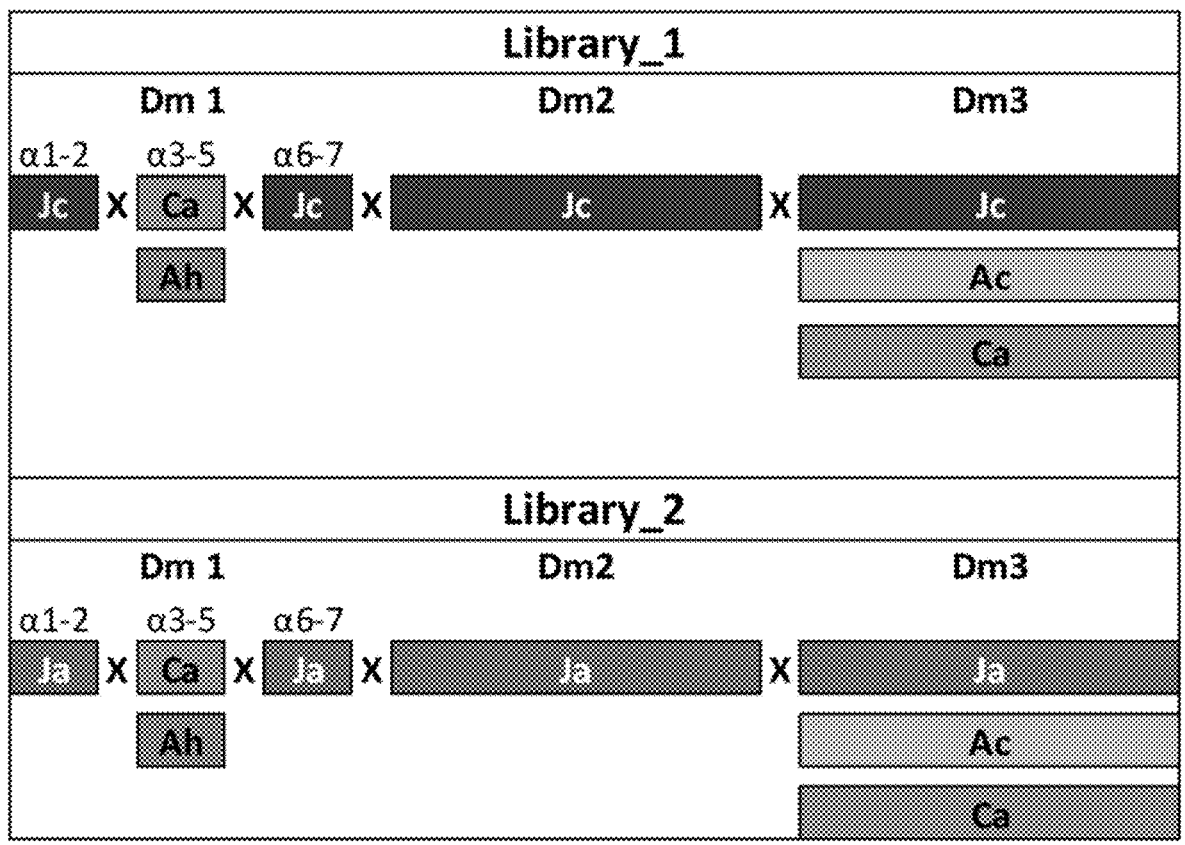
FIG. 2 shows a library schematic of 12 constructs that were synthesized as described in Example 2 for swapping of alpha loops 3-5 of various shuffled Cry toxins. In Library-1, Dm1 alpha fragments of Cry1Jc, Cry1Ca and Cry1Ah were mixed with Dm3 fragments of Cry1Jc, Cry1Ac and Cry1Ca along with Cry1Jc Dm2. Six constructs were synthesized. In Library-2, Dm1 alpha fragments of Cry1Ja, Cry1Ca and Cry1Ah were mixed with Dm3 fragments of Cry1Ja, Cry1Ac and Cry1Ca along with Cry1Ja Dm2. Six constructs were synthesized.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof, and so forth. All technical and scientific terms used herein have the same meaning as commonly understood to one of ordinary skill in the art to which this disclosure belongs unless clearly indicated otherwise.

The present disclosure is drawn to compositions and methods for controlling pests. The methods involve transforming organisms with nucleic acid sequences encoding shuffled Cry toxin polypeptides. In particular, the nucleic acid sequences of the embodiments are useful for preparing plants and microorganisms that possess pesticidal activity. Thus, transformed bacteria, plants, plant cells, plant tissues and seeds are provided. The compositions include pesticidal nucleic acids and proteins of bacterial species. The nucleic acid sequences find use in the construction of expression vectors for subsequent transformation into organisms of interest, as probes for the isolation of other homologous (or partially homologous) genes, and for the generation of altered shuffled Cry toxin polypeptides by utilizing aspects of certain methods known in the art, such as site directed mutagenesis, domain swapping, or DNA shuffling. The shuffled Cry toxin polypeptides find use in controlling or killing Lepidopteran, Coleopteran, Dipteran, fungal, Hemipteran and nematode pest populations and for producing compositions with pesticidal activity. Insect pests of interest include, but are not limited to, Lepidoptera species including but not limited to: Corn Earworm, (CEW) (*Helicoverpa zea*), European Corn Borer (ECB) (*Ostrinia nubialis*), diamond-back moth, e.g., *Helicoverpa zea* Boddie; soybean looper, e.g., *Pseudoplusia includens* Walker; and velvet bean caterpillar e.g., *Anticarsia gemmatalis* Hübner and Coleoptera species including but not limited to Western corn rootworm (*Diabrotica virgifera*)—WCRW, Southern corn rootworm (*Diabrotica undecimpunctata howardi*)—SCRW, and Northern corn rootworm (*Diabrotica barberi*)—NCRW.

By "pesticidal toxin" or "pesticidal protein" is used herein to refer to a toxin that has toxic activity against one or more pests. For example, pests may include members of the Lepidoptera, Diptera, Hemiptera and Coleoptera orders or the Nematoda phylum or a protein that has homology to such a protein. Pesticidal proteins have been isolated from organisms including, for example, *Bacillus* sp., *Bacillus thurengiensis* ("Bt"), *Pseudomonas* sp., *Photorhabdus* sp., *Xenorhabdus* sp., *Clostridium bifermentans* and *Paenibacillus popilliae*.

In some embodiments a shuffled Cry toxin polypeptide includes an amino acid sequence deduced from the full-length nucleic acid sequence disclosed herein and amino acid sequences that are shorter than the full-length sequences, either due to the use of an alternate downstream start site or due to processing that produces a shorter protein having pesticidal activity. Processing may occur in the organism in which the protein is expressed in or in the pest after ingestion of the protein.

In another aspect, methods are provided for shuffling a Cry toxin polypeptide comprising swapping or shuffling alpha loop domains of domain 1 (Dm1) from a first Cry toxin into a second Cry toxin, creating a heterologous alpha loop region in the second shuffled Cry toxin.

In some embodiments, the methods and compositions disclosed herein relate to shuffling or swapping all or parts of a domain 3 (Dm3) from a first Cry toxin (a heterologous portion) into a second Cry toxin, creating a heterologous domain 3 region in the second Cry shuffled or swapped toxin. In some embodiments, the shuffled or swapped domain 3 occurs at any one of the crossover points as set forth in SEQ ID NOs: 250-257. In some embodiments, the heterogous portion of domain 3 comprises a fragment derived from a Cry1If, Cry1Cb, Cry1Fa, Cry9Eb, Cry1Ae, Cry1Ja, Cry1Da, Cry1Bb, or Cry1Ca toxin or any one of SEQ ID NOs: 259-265 or 268-270.

In some embodiments, the shuffled Cry toxin polypeptide has an altered spectrum of activity. In another embodiment, the shuffled Cry toxin polypeptide has an altered amount of pesticidal activity. In some embodiments, the shuffled cry toxin polypeptide has an altered mode of action or site of action. In some embodiments, the shuffled cry toxin polypeptide has an altered solubility.

In some embodiments, the shuffling comprises swapping or shuffling whole or portions of alpha loops 2, 3, 4, 5, and/or 6 from a first Cry toxin into a second Cry toxin, which creates a heterologous alpha loop region. In some embodiments the Cry toxin is a native Cry toxin. In some embodiments, the Cry toxin is a shuffled or hybrid Cry toxin derived from a native Cry toxin. In some embodiments, the alpha loop swapping or shuffling occurs at a sequence motif comprising at least 90% or having at least 95% sequence identity to any one of SEQ ID NOs: 247-250.

In another embodiment, the alpha loop swapping or shuffling occurs at a sequence motif comprising variant of SEQ ID NO: 247, wherein the variant comprises 1) a histidine or arginine at position 1 of SEQ ID NO: 247; 2) a valine, methionine, or leucine at position 2 of SEQ ID NO: 247; 3) a leucine at position 3 of SEQ ID NO: 247; 4) an arginine, glutamic acid, leucine, or serine at position 4 of SEQ ID NO: 247; or 5) an isoleucine at position 5 of SEQ ID NO: 247.

In another embodiment, the alpha loop swapping or shuffling occurs at a sequence motif comprising variant of SEQ ID NO: 250, wherein the variant comprises 1) a valine position 1 of SEQ ID NO: 250; 2) a phenylalanine at position 2 of SEQ ID NO: 250; or 3) a phenylalanine at position 3 of SEQ ID NO: 250.

In another embodiment, the alpha loop swapping or shuffling occurs at a sequence motif comprising variant of SEQ ID NO: 248, wherein the variant comprises 1) a asparagin, serine, threonine, or arginine at position 1 of SEQ ID NO: 248; 2) an arginine at position 2 of SEQ ID NO: 248; 3) an aspartic acid, glycine, or alanine at position 4 of SEQ ID NO: 248; 4) an arginine, glutamic acid, leucine, or serine at position 4 of SEQ ID NO: 248; or 5) an alanine, serine, threonine, glutamic acid, or valine at position 5 of SEQ ID NO: 248.

In another embodiment, the alpha loop swapping or shuffling occurs at a sequence motif comprising variant of SEQ ID NO: 249, wherein the variant comprises 1) an arginine, alanine, threonine, lysine, or glycine at position 1 of SEQ ID NO: 249; 2) a threonine, serine, valine, isoleucine, or glutamic acid at position 2 of SEQ ID NO: 249; 3) a serine, isoleucine, proline, alanine, arginine, threonine, glycine, or asparagine at position 3 of SEQ ID NO: 249; 4) an asparagine, glutamine, glutamic acid, glycine, aspartic acid, serine, or threonine at position 4 of SEQ ID NO: 249; or 5) a phenylalanine, glutamic acid, tyrosine, or glutamine at position 5 of SEQ ID NO: 249.

In another embodiment, the alpha loop swapping or shuffling occurs at a sequence motif comprising variant of SEQ ID NO: 258, wherein the variant comprises 1) a glutamic acid, alanine, serine, arginine, lysine, or threonine at position 2 of SEQ ID NO: 258; 2) an alanine, glycine, or glutamic acid at position 3 of SEQ ID NO: 258; or 3) a serine or phenylalanine at position 4 of SEQ ID NO: 258.

Thus, provided herein are isolated or recombinant nucleic acid sequences encoding shuffled Cry toxin polypeptides conferring pesticidal activity. Also provided are the amino acid sequences of shuffled Cry toxin polypeptides. The polypeptides resulting from translation of these shuffled Cry toxin genes allows cells to control or kill pests that ingest it.

Members of *B. thuringiensis* insecticidal protein classes are known to one skilled in the art (see, Crickmore, et al., Microbiology and Molecular Biology Reviews (1998) Vol 62: 807-813; and Crickmore, et al., "*Bacillus thuringiensis* toxin nomenclature" (2016), at btnomenclature.info/ which can be accessed on the world-wide web using the "www" prefix). As used herein, a "Bt Cry toxin," or a "Cry toxin"

refers to a parasporal inclusion (crystal) protein from *B. thuringiensis* that exhibits some experimentally verifiable toxic effect to a target organism, or any protein that has obvious sequence similarity to a known Cry protein (Crickmore, et al., Microbiology and Molecular Biology Reviews (1998) Vol 62: 807).

Shuffled Cry Toxin Proteins and Variants and Fragments Thereof

Shuffled Cry toxin polypeptides are encompassed by the disclosure. "Shuffled Cry toxin polypeptide," and "shuffled Cry toxin protein" as used herein interchangeably refers to a polypeptide(s) having insecticidal activity including but not limited to insecticidal activity against one or more insect pests of the Lepidoptera and/or Coleoptera orders, and has been shuffled from one or more native *Bacillus thurengiensis* Cry toxin polypeptides. In some embodiments, the shuffled Cry toxin polypeptide comprises a shuffled Cry toxin, wherein the shuffling comprises a heterologous alpha loop swap in domain 1 ("Dm1") or a heterologous fragment of domain 3 ("Dm 3"). A variety of shuffled Cry toxin polypeptides are contemplated. Sources of shuffled Cry toxin polypeptides or related proteins include bacterial species selected from but not limited to *Bacillus thurengiensis* (Bt) species.

"Sufficiently identical" is used herein to refer to an amino acid sequence that has at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity. In one embodiment the shuffled Cry toxin polypeptide has at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to any one of SEQ ID NOs: 57-112, 214-246, and 275-278. The term "about" when used herein in context with percent sequence identity means +/−1.0%.

A "recombinant protein" is used herein to refer to a protein that is no longer in its natural environment, for example in vitro or in a recombinant bacterial or plant host cell.

"Substantially free of cellular material" as used herein refers to a polypeptide including preparations of protein having less than about 30%, 20%, 10% or 5% (by dry weight) of non-pesticidal protein (also referred to herein as a "contaminating protein").

"Fragments" or "biologically active portions" include polypeptide fragments comprising amino acid sequences sufficiently identical to a shuffled Cry toxin polypeptide and that exhibit insecticidal activity. "Fragments" or "biologically active portions" of shuffled Cry toxin polypeptides includes fragments comprising amino acid sequences sufficiently identical to the amino acid sequence set forth in any one of SEQ ID NOs: 57-112, 214-246, and 275-278 wherein the shuffled Cry toxin polypeptide has insecticidal activity. Such biologically active portions can be prepared by recombinant techniques and evaluated for insecticidal activity. In some embodiments, the shuffled Cry toxin polypeptide fragment is an N-terminal and/or a C-terminal truncation of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more amino acids from the N-terminus and/or C-terminus relative to any one of SEQ ID NOs: 57-112, 214-246, and 275-278, e.g., by proteolysis, by insertion of a start codon, by deletion of the codons encoding the deleted amino acids and concomitant insertion of a start codon, and/or insertion of a stop codon. In some embodiments, the shuffled Cry toxin polypeptide fragment is an N-terminal truncation of at least 1, 2, 3, 4, 5, 6, 7, 8, 9, 10, 11, 12, 13, 14, 15, 16, 17, 18, 19, 20, 21, 22, 23, 24 amino acids from the N-terminus of any one of SEQ ID NOs: 57-112, 214-246, and 275-278. In some embodiments, the shuffled Cry toxin polypeptide fragment is an N-terminal and/or a C-terminal truncation of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or more amino acids from the N-terminus and/or C-terminus relative to any one of SEQ ID NOs: 57-112, 214-246, and 275-278.

"Variants" as used herein refers to proteins or polypeptides having an amino acid sequence that is at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater identical to the parental amino acid sequence.

In some embodiments an shuffled Cry toxin polypeptide comprises an amino acid sequence having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to the full length or a fragment of the amino acid sequence of any one of SEQ ID NOs: 57-112, 214-246, and 275-278, wherein the shuffled Cry toxin polypeptide has insecticidal activity.

In some embodiments an shuffled Cry toxin polypeptide comprises an amino acid sequence of any one or more of SEQ ID NOS: 57-112, 214-246, and 275-278 having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95 or more amino acid substitutions compared to the amino acid at the corresponding position of any one or more of the respective SEQ ID NOS: 57-112, 214-246, and 275-278.

Methods for such manipulations are generally known in the art. For example, amino acid sequence variants of a shuffled Cry toxin polypeptide can be prepared by mutations in the DNA. This may also be accomplished by one of several forms of mutagenesis, such as for example site-specific double strand break technology, and/or in directed evolution. In some aspects, the changes encoded in the amino acid sequence will not substantially affect the function of the protein. Such variants will possess a desired pesticidal activity. However, it is understood that the ability of a shuffled Cry toxin polypeptide to confer pesticidal activity or other polypeptide physical property may be improved or altered by the use of such techniques upon the compositions of this disclosure.

Conservative amino acid substitutions may be made at one or more predicted nonessential amino acid residues. A "nonessential" amino acid residue is a residue that can be altered from the wild-type sequence of a shuffled Cry toxin polypeptide without altering the biological activity. A "conservative amino acid substitution" is one in which the amino acid residue is replaced with an amino acid residue having a similar side chain. Families of amino acid residues having similar side chains have been defined in the art. These families include: amino acids with basic side chains (e.g., lysine, arginine, histidine); acidic side chains (e.g., aspartic acid, glutamic acid); polar, negatively charged residues and their amides (e.g., aspartic acid, asparagine, glutamic, acid, glutamine; uncharged polar side chains (e.g., glycine, asparagine, glutamine, serine, threonine, tyrosine, cysteine); small aliphatic, nonpolar or slightly polar residues (e.g., Alanine, serine, threonine, proline, glycine); nonpolar side chains (e.g., alanine, valine, leucine, isoleucine, proline, phenylalanine, methionine, tryptophan); large aliphatic, nonpolar residues (e.g., methionine, leucine, isoleucine, valine, cystine); beta-branched side chains (e.g., threonine, valine, isoleucine); aromatic side chains (e.g., tyrosine, phenylalanine, tryptophan, histidine); large aromatic side chains (e.g., tyrosine, phenylalanine, tryptophan).

Amino acid substitutions may be made in nonconserved regions that retain function. In general, such substitutions would not be made for conserved amino acid residues or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the embodiments (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the embodiments (e.g., residues that have only conservative substitutions between all proteins contained in the alignment homologous proteins). However, one of skill in the art would understand that functional variants may have minor conserved or nonconserved alterations in the conserved residues.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity or epitope to facilitate either protein purification, protein detection or other experimental uses known in the art (3) target secretion or translation of a protein to a subcellular organelle, such as the periplasmic space of Gram-negative bacteria, mitochondria or chloroplasts of plants or the endoplasmic reticulum of eukaryotic cells, the latter of which often results in glycosylation of the protein.

Variant nucleotide and amino acid sequences of the disclosure also encompass sequences derived from mutagenic and recombinogenic procedures such as DNA shuffling. With such a procedure, one or more different shuffled Cry toxin polypeptide coding regions can be used to create a new shuffled Cry toxin polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene and other known pesticidal genes to obtain a new gene coding for a protein with an improved property of interest, such as an increased insecticidal activity. Strategies for such DNA shuffling are known in the art. See, for example, Stemmer, (1994) Proc. Natl. Acad. Sci. USA 91:10747-10751; Stemmer, (1994) Nature 370:389-391; and U.S. Pat. Nos. 5,605,793 and 5,837,458.

Domain swapping as shuffling is another mechanism for generating altered Cry toxin polypeptides. Domains may be swapped between shuffled Cry toxin polypeptides resulting in hybrid or chimeric toxins with altered insecticidal activity or target spectrum. Methods for generating recombinant proteins and testing them for pesticidal activity are known in the art (see, for example, Naimov, et al., (2001) Appl. Environ. Microbiol. 67:5328-5330; de Maagd, et al., (1996) Appl. Environ. Microbiol. 62:1537-1543; Ge, et al., (1991) J. Biol. Chem. 266:17954-17958; Schnepf, et al., (1990) J. Biol. Chem. 265:20923-21010; Rang, et al., 91999) Appl. Environ. Microbiol. 65:2918-2925).

In some embodiments the shuffled Cry toxin polypeptide has a modified physical property. As used herein, the term "physical property" refers to any parameter suitable for describing the physical-chemical characteristics of a protein. As used herein, "physical property of interest" and "property of interest" are used interchangeably to refer to physical properties of proteins that are being investigated and/or modified. Examples of physical properties include, but are not limited to, net surface charge and charge distribution on the protein surface, net hydrophobicity and hydrophobic residue distribution on the protein surface, surface charge density, surface hydrophobicity density, total count of surface ionizable groups, surface tension, protein size and its distribution in solution, melting temperature, heat capacity, and second virial coefficient. Examples of physical properties also include, shuffled Cry toxin polypeptide having increased expression, increased solubility, decreased phytotoxicity, and digestibility of proteolytic fragments in an insect gut. Models for digestion by simulated gastric fluids are known to one skilled in the art (Fuchs, R. L. and J. D. Astwood. Food Technology 50: 83-88, 1996; Astwood, J. D., et al Nature Biotechnology 14: 1269-1273, 1996; Fu T J et al J. Agric Food Chem. 50: 7154-7160, 2002).

In some embodiments variants include polypeptides that differ in amino acid sequence due to mutagenesis. Variant proteins encompassed by the disclosure are biologically active, that is they continue to possess a desired biological activity (i.e. pesticidal activity) of the native protein. In some embodiment the variant will have at least about 10%, at least about 30%, at least about 50%, at least about 70%, at least about 80% or more of the insecticidal activity of the native protein. In some embodiments, the variants may have improved activity over the native protein.

Bacterial genes quite often possess multiple methionine initiation codons in proximity to the start of the open reading frame. Often, translation initiation at one or more of these start codons will lead to generation of a functional protein. These start codons can include ATG codons. However, bacteria such as Bacillus sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present disclosure and may be used in the methods of the present disclosure. It will be understood that, when expressed in plants, it will be necessary to alter the alternate start codon to ATG for proper translation.

In some embodiments a shuffled Cry toxin polypeptide comprises the amino acid sequence of any one or more of SEQ ID NOS: 57-112 and 275-278.

In some embodiments, chimeric polypeptides are provided comprising regions of at least two different shuffled Cry toxin polypeptides of the disclosure.

In some embodiments, chimeric polypeptides are provided comprising regions of at least two different shuffled Cry toxin polypeptides selected from any one or more of SEQ ID NOS: 57-112, 214-246, and 275-278.

In some embodiments, chimeric shuffled Cry toxin polypeptide(s) are provided comprising an N-terminal Region of a first shuffled Cry toxin polypeptide of the disclosure operably fused to a C-terminal Region of a second shuffled Cry toxin polypeptide of the disclosure.

In other embodiments the shuffled Cry toxin polypeptide may be expressed as a precursor protein with an intervening sequence that catalyzes multi-step, post translational protein splicing. Protein splicing involves the excision of an intervening sequence from a polypeptide with the concomitant joining of the flanking sequences to yield a new polypeptide (Chong, et al., (1996) *J. Biol. Chem.*, 271:22159-22168). This intervening sequence or protein splicing element, referred to as inteins, which catalyze their own excision through three coordinated reactions at the N-terminal and C-terminal splice junctions: an acyl rearrangement of the N-terminal cysteine or serine; a transesterfication reaction between the two termini to form a branched ester or thioester intermediate and peptide bond cleavage coupled to cyclization of the intein C-terminal asparagine to free the intein (Evans, et al., (2000) *J. Biol. Chem.*, 275:9091-9094).

In another embodiment fusion proteins are provided that include within its amino acid sequence an amino acid sequence comprising a shuffled Cry toxin polypeptide of the disclosure. Methods for design and construction of fusion proteins (and polynucleotides encoding same) are known to those of skill in the art. Polynucleotides encoding a shuffled Cry toxin polypeptide may be fused to signal sequences which will direct the localization of the shuffled Cry toxin polypeptide to particular compartments of a prokaryotic or eukaryotic cell and/or direct the secretion of the shuffled Cry toxin polypeptide of the embodiments from a prokaryotic or eukaryotic cell.

For example, in *E. coli*, one may wish to direct the expression of the protein to the periplasmic space. Examples of signal sequences or proteins (or fragments thereof) to which the shuffled Cry toxin polypeptide may be fused in order to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic *E. coli* heat-labile enterotoxin B-subunit and the signal sequence of alkaline phosphatase. Several vectors are commercially available for the construction of fusion proteins which will direct the localization of a protein, such as the pMAL series of vectors (particularly the pMAL-p series) available from New England Biolabs. In a specific embodiment, the shuffled Cry toxin polypeptide may be fused to the pelB pectate lyase signal sequence to increase the efficiency of expression and purification of such polypeptides in Gram-negative bacteria (see, U.S. Pat. Nos. 5,576,195 and 5,846,818).

Plant plastid transit peptide/polypeptide fusions are known in the art. Apoplast transit peptides such as rice or barley alpha-amylase secretion signal are also known in the art. The plastid transit peptide is generally fused N-terminal to the polypeptide to be targeted (e.g., the fusion partner). In one embodiment, the fusion protein consists essentially of the plastid transit peptide and the shuffled Cry toxin polypeptide to be targeted. In another embodiment, the fusion protein comprises the plastid transit peptide and the polypeptide to be targeted. In such embodiments, the plastid transit peptide is preferably at the N-terminus of the fusion protein. However, additional amino acid residues may be N-terminal to the plastid transit peptide providing that the fusion protein is at least partially targeted to a plastid. In a specific embodiment, the plastid transit peptide is in the N-terminal half, N-terminal third or N-terminal quarter of the fusion protein. Most or all of the plastid transit peptide is generally cleaved from the fusion protein upon insertion into the plastid. The position of cleavage may vary slightly between plant species, at different plant developmental stages, as a result of specific intercellular conditions or the particular combination of transit peptide/fusion partner used. In one embodiment, the plastid transit peptide cleavage is homogenous such that the cleavage site is identical in a population of fusion proteins. In another embodiment, the plastid transit peptide is not homogenous, such that the cleavage site varies by 1-10 amino acids in a population of fusion proteins. The plastid transit peptide can be recombinantly fused to a second protein in one of several ways. In some embodiments the shuffled Cry toxin polypeptide is fused to a heterologous signal peptide or heterologous transit peptide.

In some embodiments fusion proteins are provide comprising a shuffled Cry toxin polypeptide or chimeric Cry toxin polypeptide of the disclosure represented by a formula selected from the group consisting of:

$$R^1\text{-L-}R^2, R^2\text{-L-}R^1, R^1\text{-}R^2 \text{ or } R^2\text{-}R^1$$

wherein $R^1$ is an shuffled Cry toxin polypeptide or chimeric shuffled Cry toxin polypeptide of the disclosure and $R^2$ is a protein of interest. In some embodiments $R^1$ and $R^2$ are a shuffled Cry toxin polypeptide or chimeric shuffled Cry toxin polypeptide of the disclosure. The $R^1$ polypeptide is fused either directly or through a linker (L) segment to the $R^2$ polypeptide. The term "directly" defines fusions in which the polypeptides are joined without a peptide linker. Thus "L" represents a chemical bound or polypeptide segment to which both $R^1$ and $R^2$ are fused in frame, most commonly L is a linear peptide to which $R^1$ and $R^2$ are bound by amide bonds linking the carboxy terminus of $R^1$ to the amino terminus of L and carboxy terminus of L to the amino terminus of $R^2$. By "fused in frame" is meant that there is no translation termination or disruption between the reading frames of $R^1$ and $R^2$. The linking group (L) is generally a polypeptide of between 1 and 500 amino acids in length. The linkers joining the two molecules are preferably designed to (1) allow the two molecules to fold and act independently of each other, (2) not have a propensity for developing an ordered secondary structure which could interfere with the functional domains of the two proteins, (3) have minimal hydrophobic or charged characteristic which could interact with the functional protein domains and (4) provide steric separation of $R^1$ and $R^2$ such that $R^1$ and $R^2$ could interact simultaneously with their corresponding receptors on a single cell. Typically surface amino acids in flexible protein regions include Gly, Asn and Ser. Virtually any permutation of amino acid sequences containing Gly, Asn and Ser would be expected to satisfy the above criteria for a linker sequence. Other neutral amino acids, such as Thr and Ala, may also be used in the linker sequence. Additional amino acids may also be included in the linkers due to the addition of unique restriction sites in the linker sequence to facilitate construction of the fusions.

In some embodiments the linkers comprise sequences selected from the group of formulas: $(Gly_3Ser)_n$, $(Gly_4Ser)_n$, $(Gly_5Ser)_n$, $(Gly_nSer)_n$, or $(AlaGlySer)_n$ where n is an integer. One example of a highly-flexible linker is the (GlySer)-rich spacer region present within the pIII protein of the filamentous bacteriophages, e.g. bacteriophages M13 or fd (Schaller, et al., 1975). This region provides a long, flexible spacer region between two domains of the pIII surface protein. Also included are linkers in which an endopeptidase recognition sequence is included. Such a cleavage site may be valuable to separate the individual components of the fusion to determine if they are properly folded and active in vitro. Examples of various endopeptidases include, but are not limited to, Plasmin, Enterokinase, Kallikerin, Urokinase, Tissue Plasminogen activator, clostripain, Chymosin, Collagenase, Russell's Viper Venom Protease, Postproline cleavage enzyme, V8 protease, Thrombin and factor Xa. In some embodiments the linker comprises the amino acids from the multi-gene expression vehicle (MGEV), which is cleaved by vacuolar proteases as disclosed in US Patent Application Publication Number US 2007/0277263. In other embodiments, peptide linker segments from the hinge region of heavy chain immunoglobulins IgG, IgA, IgM, IgD or IgE provide an angular relationship between the attached polypeptides. Especially useful are those hinge regions where the cysteines are replaced with serines. Linkers of the present disclosure include sequences derived from murine IgG gamma 2b hinge region in which the cysteines have been changed to serines. The fusion proteins are not limited by the form, size or number of linker sequences employed and the only requirement of the linker is that functionally it does not interfere adversely with the folding and function of the individual molecules of the fusion.

Nucleic Acid Molecules, and Variants and Fragments Thereof

Isolated or recombinant nucleic acid molecules comprising nucleic acid sequences encoding Cry toxin polypeptides or biologically active portions thereof, as well as nucleic acid molecules sufficient for use as hybridization probes to identify nucleic acid molecules encoding proteins with regions of sequence homology are provided. As used herein, the term "nucleic acid molecule" refers to DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule (or DNA) is used herein to refer to a nucleic acid sequence (or DNA) that is no longer in its natural environment, for example in vitro. A "recombinant" nucleic acid molecule (or DNA) is used herein to refer to a nucleic acid sequence (or DNA) that is in a recombinant bacterial or plant host cell. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the disclosure, "isolated" or "recombinant" when used to refer to nucleic acid molecules excludes isolated chromosomes. For example, in various embodiments, the recombinant nucleic acid molecules encoding Cry toxin polypeptides can contain less than about 5 kb, 4 kb, 3 kb, 2 kb, 1 kb, 0.5 kb or 0.1 kb of nucleic acid sequences that naturally flank the nucleic acid molecule in genomic DNA of the cell from which the nucleic acid is derived.

In some embodiments an isolated nucleic acid molecule encoding Cry toxin polypeptides has one or more change in the nucleic acid sequence compared to the native or genomic nucleic acid sequence. In some embodiments the change in the native or genomic nucleic acid sequence includes but is not limited to: changes in the nucleic acid sequence due to the degeneracy of the genetic code; changes in the nucleic acid sequence due to the amino acid substitution, insertion, deletion and/or addition compared to the native or genomic sequence; removal of one or more intron; deletion of one or more upstream or downstream regulatory regions; and deletion of the 5' and/or 3' untranslated region associated with the genomic nucleic acid sequence. In some embodiments the nucleic acid molecule encoding a Cry toxin polypeptide is a non-genomic sequence.

A variety of polynucleotides that encode Cry toxin polypeptides or related proteins are contemplated. Such polynucleotides are useful for production of Cry toxin polypeptides in host cells when operably linked to a suitable promoter, transcription termination and/or polyadenylation sequences. Such polynucleotides are also useful as probes for isolating homologous or substantially homologous polynucleotides that encode Cry toxin polypeptides or related proteins.

Polynucleotides Encoding Polypeptides

One source of polynucleotides that encode Cry toxin polypeptides or related proteins is a *Bacillus* bacterium which may contain a Cry toxin polynucleotide of any one of SEQ ID NOs: 1-56, 181-213, and 271-274, encoding a Cry toxin polypeptide of SEQ ID NOs: 57-112, 214-246, and 271-274, respectively. The polynucleotides of any one or more of SEQ ID NOS: 1-56, 181-213, and 271-274, can be used to express Cry toxin polypeptides in recombinant bacterial hosts that include but are not limited to *Agrobacterium, Bacillus, Escherichia, Salmonella, Lysinibacillus, Acetobacter, Pseudomonas* and *Rhizobium* bacterial host cells. The polynucleotides are also useful as probes for isolating homologous or substantially homologous polynucleotides encoding Cry toxin polypeptides or related proteins. Such probes can be used to identify homologous or substantially homologous polynucleotides, or portions thereof, derived from *Bacillus thurengiensis*.

Polynucleotides encoding Cry toxin polypeptides can also be synthesized de novo from a Cry toxin polypeptide sequence. The sequence of the polynucleotide gene can be deduced from a Cry toxin polypeptide sequence through use of the genetic code. Computer programs such as "Back-Translate" (GCG™ Package, Acclerys, Inc. San Diego, Calif) can be used to convert a peptide sequence to the corresponding nucleotide sequence encoding the peptide. Examples of Cry toxin polypeptide sequences that can be used to obtain corresponding nucleotide encoding sequences include, but are not limited to the Cry toxin polypeptides of SEQ ID NOS: 57-112, 214-246, and 275-278. Furthermore, synthetic Cry toxin polynucleotide sequences of the disclosure can be designed so that they will be expressed in plants.

In some embodiments the nucleic acid molecule encoding a Cry toxin polypeptide is a polynucleotide having the sequence set forth in any one of SEQ ID NOS: 1-56, 181-213 and 271-274, and variants, fragments and complements thereof "Complement" is used herein to refer to a nucleic acid sequence that is sufficiently complementary to a given nucleic acid sequence such that it can hybridize to the given nucleic acid sequence to thereby form a stable duplex. "Polynucleotide sequence variants" is used herein to refer to a nucleic acid sequence that except for the degeneracy of the genetic code encodes the same polypeptide.

In some embodiments the nucleic acid molecule encoding the Cry toxin polypeptide is a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments the non-genomic nucleic acid molecule is a synthetic nucleic acid sequence.

In some embodiments the nucleic acid molecule encoding a Cry toxin polypeptide disclosed herein is a non-genomic polynucleotide having a nucleotide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity, to the nucleic acid sequence of any one of SEQ ID NOS: 1-56, 181-213 and 271-274, wherein the Cry toxin polypeptide has insecticidal activity.

In some embodiments the nucleic acid molecule encodes a Cry toxin polypeptide variant comprising one or more amino acid substitutions to the amino acid sequence of any one of SEQ ID NOS: 57-112, 214-246, and 275-278.

Also provided are nucleic acid molecules that encode transcription and/or translation products that are subsequently spliced to ultimately produce functional Cry toxin polypeptides. Splicing can be accomplished in vitro or in vivo, and can involve cis- or trans-splicing. The substrate for splicing can be polynucleotides (e.g., RNA transcripts) or polypeptides. An example of cis-splicing of a polynucleotide is where an intron inserted into a coding sequence is removed and the two flanking exon regions are spliced to generate a Cry toxin polypeptide encoding sequence. An example of trans-splicing would be where a polynucleotide is encrypted by separating the coding sequence into two or more fragments that can be separately transcribed and then spliced to form the full-length pesticidal encoding sequence. The use of a splicing enhancer sequence, which can be introduced into a construct, can facilitate splicing either in cis or trans-splicing of polypeptides (U.S. Pat. Nos. 6,365,377 and 6,531,316). Thus, in some embodiments the polynucleotides do not directly encode a full-length Cry toxin polypeptide, but rather encode a fragment or fragments of a Cry toxin polypeptide. These polynucleotides can be used to express a functional Cry toxin polypeptide through a mechanism involving splicing, where splicing may occur at the level of polynucleotide (e.g., intron/exon) and/or polypeptide (e.g., intein/extein). This may be useful, for example, in controlling expression of pesticidal activity, since a functional pesticidal polypeptide will only be expressed if all required fragments are expressed in an environment that permits splicing processes to generate functional product. In another example, introduction of one or more insertion sequences into a polynucleotide can facilitate recombination with a low homology polynucleotide; use of an intron or intein for the insertion sequence facilitates the removal of the intervening sequence, thereby restoring function of the encoded variant.

Nucleic acid molecules that are fragments of these nucleic acid sequences encoding Cry toxin polypeptides are also encompassed by the embodiments. "nucleotide fragment" as used herein refers to a portion of the nucleic acid sequence encoding a Cry toxin polypeptide. A nucleotide fragment of a nucleic acid sequence may encode a biologically active portion of a Cry toxin polypeptide or it may be a fragment that can be used as a hybridization probe or PCR primer using methods disclosed below. Nucleic acid molecules that are fragments of a nucleic acid sequence encoding a Cry toxin polypeptide comprise at least about 150, 180, 210, 240, 270, 300, 330, 360, 400, 450, or 500 contiguous nucleotides or up to the number of nucleotides present in a full-length nucleic acid sequence encoding a Cry toxin polypeptide disclosed herein, depending upon the intended use. "Contiguous nucleotides" is used herein to refer to nucleotide residues that are immediately adjacent to one another. Fragments of the nucleic acid sequences of the embodiments will encode protein fragments that retain the biological activity of the Cry toxin polypeptide and, hence, retain insecticidal activity. "Retains insecticidal activity" is used herein to refer to a polypeptide having at least about 10%, at least about 30%, at least about 50%, at least about 70%, 80%, 90%, 95% or higher of the insecticidal activity of any one of the full-length Cry toxin polypeptides set forth in SEQ ID NOS: 57-112, 214-246, and 275-278. In some embodiments, the insecticidal activity is against a Lepidopteran species. In one embodiment, the insecticidal activity is against a Coleopteran species. In some embodiments, the insecticidal activity is against one or more insect pests of the corn rootworm complex: western corn rootworm, *Diabrotica virgifera*; northern corn rootworm, *D. barberi*: Southern corn rootworm or spotted cucumber beetle; *Diabrotica undecimpunctata howardi, Diabrotica speciosa*, and the Mexican corn rootworm, *D. virgifera zeae*. In one embodiment, the insecticidal activity is against a *Diabrotica* species.

In some embodiments the Cry toxin polypeptide is encoded by a nucleic acid sequence sufficiently homologous to any one of the nucleic acid sequences of SEQ ID NOS: 1-56, 181-213, and 271-274.

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST, BLAST-2. Those skilled in the art can determine appropriate parameters for aligning sequences, including any algorithms needed to achieve maximal alignment over the full length of the sequences being compared. The percent identity between the two sequences is a function of the number of identical positions shared by the sequences (e.g., percent identity of query sequence=number of identical positions between query and subject sequences/total number of positions of query sequence×100).

In some embodiments a Cry toxin polynucleotide encodes a Cry toxin polypeptide comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater sequence identity across the entire length of the amino acid sequence of any one of SEQ ID NOS: 57-112, 214-246, and 275-278.

In some embodiments polynucleotides are provided encoding chimeric polypeptides comprising regions of at least two different Cry toxin polypeptides of the disclosure.

In some embodiments polynucleotides are provided encoding chimeric polypeptides comprising an N-terminal Region of a first Cry toxin polypeptide of the disclosure operably fused to a C-terminal Region of a second Cry toxin polypeptide of the disclosure.

The embodiments also encompass nucleic acid molecules encoding Cry toxin polypeptide variants. "Variants" of the Cry toxin polypeptide encoding nucleic acid sequences include those sequences that encode the Cry toxin polypeptides disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleic acid sequences also include synthetically derived nucleic acid sequences that have been generated, for example, by using site-directed mutagenesis but which still encode the Cry toxin polypeptides disclosed as discussed below.

The present disclosure provides isolated or recombinant polynucleotides that encode any of the Cry toxin polypeptides disclosed herein. Those having ordinary skill in the art will readily appreciate that due to the degeneracy of the genetic code, a multitude of nucleotide sequences encoding Cry toxin polypeptides of the present disclosure exist.

The skilled artisan will further appreciate that changes can be introduced by mutation of the nucleic acid sequences thereby leading to changes in the amino acid sequence of the encoded Cry toxin polypeptides, without altering the biological activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

Alternatively, variant nucleic acid sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

The polynucleotides of the disclosure and fragments thereof are optionally used as substrates for a variety of recombination and recursive recombination reactions, in addition to standard cloning methods as set forth in, e.g., Ausubel, Berger and Sambrook, i.e., to produce additional pesticidal polypeptide homologues and fragments thereof with desired properties. A variety of such reactions are known. Methods for producing a variant of any nucleic acid listed herein comprising recursively recombining such polynucleotide with a second (or more) polynucleotide, thus forming a library of variant polynucleotides are also embodiments of the disclosure, as are the libraries produced, the cells comprising the libraries and any recombinant polynucleotide produced by such methods. Additionally, such methods optionally comprise selecting a variant polynucleotide from such libraries based on pesticidal activity, as is wherein such recursive recombination is done in vitro or in vivo.

A variety of diversity generating protocols, including nucleic acid recursive recombination protocols are available and fully described in the art. The procedures can be used separately, and/or in combination to produce one or more variants of a nucleic acid or set of nucleic acids, as well as variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties or that encode proteins with or which confer desirable properties. Following diversification by one or more of the methods herein or otherwise available to one of skill, any nucleic acids that are produced can be selected for a desired activity or property, e.g. pesticidal activity or, such activity at a desired pH, etc. This can include identifying any activity that can be detected, for example, in an automated or automatable format, by any of the assays in the art, see, e.g., discussion of screening of insecticidal activity, infra. A variety of related (or even unrelated) properties can be evaluated, in serial or in parallel, at the discretion of the practitioner.

Descriptions of a variety of diversity generating procedures for generating modified nucleic acid sequences, e.g., those coding for polypeptides having pesticidal activity or fragments thereof, are found in the following publications and the references cited therein: Soong, et al., (2000) *Nat Genet* 25(4):436-439; Stemmer, et al., (1999) *Tumor Targeting* 4:1-4; Ness, et al., (1999) *Nat Biotechnol* 17:893-896; Chang, et al., (1999) *Nat Biotechnol* 17:793-797; Minshull and Stemmer, (1999) *Curr Opin Chem Biol* 3:284-290; Christians, et al., (1999) *Nat Biotechnol* 17:259-264; Crameri, et al., (1998) *Nature* 391:288-291; Crameri, et al., (1997) *Nat Biotechnol* 15:436-438; Zhang, et al., (1997) *PNAS USA* 94:4504-4509; Patten, et al., (1997) *Curr Opin*

Biotechnol 8:724-733; Crameri, et al., (1996) *Nat Med* 2:100-103; Crameri, et al., (1996) *Nat Biotechnol* 14:315-319; Gates, et al., (1996) *J Mol Biol* 255:373-386; Stemmer, (1996) "Sexual PCR and Assembly PCR" In: *The Encyclopedia of Molecular Biology*. VCH Publishers, New York. pp. 447-457; Crameri and Stemmer, (1995) *BioTechniques* 18:194-195; Stemmer, et al., (1995) *Gene*, 164:49-53; Stemmer, (1995) *Science* 270: 1510; Stemmer, (1995) *Bio/Technology* 13:549-553; Stemmer, (1994) *Nature* 370:389-391 and Stemmer, (1994) *PNAS USA* 91:10747-10751.

Mutational methods of generating diversity include, for example, site-directed mutagenesis (Ling, et al., (1997) *Anal Biochem* 254(2):157-178; Dale, et al., (1996) *Methods Mol Biol* 57:369-374; Smith, (1985) *Ann Rev Genet* 19:423-462; Botstein and Shortle, (1985) *Science* 229:1193-1201; Carter, (1986) *Biochem J* 237:1-7 and Kunkel, (1987) "The efficiency of oligonucleotide directed mutagenesis" in *Nucleic Acids & Molecular Biology* (Eckstein and Lilley, eds., Springer Verlag, Berlin)); mutagenesis using uracil containing templates (Kunkel, (1985) *PNAS USA* 82:488-492; Kunkel, et al., (1987) *Methods Enzymol* 154:367-382 and Bass, et al., (1988) *Science* 242:240-245); oligonucleotide-directed mutagenesis (Zoller and Smith, (1983) *Methods Enzymol* 100:468-500; Zoller and Smith, (1987) *Methods Enzymol* 154:329-350 (1987); Zoller and Smith, (1982) *Nucleic Acids Res* 10:6487-6500), phosphorothioate-modified DNA mutagenesis (Taylor, et al., (1985) *Nucl Acids Res* 13:8749-8764; Taylor, et al., (1985) *Nucl Acids Res* 13:8765-8787 (1985); Nakamaye and Eckstein, (1986) *Nucl Acids Res* 14:9679-9698; Sayers, et al., (1988) *Nucl Acids Res* 16:791-802 and Sayers, et al., (1988) *Nucl Acids Res* 16:803-814); mutagenesis using gapped duplex DNA (Kramer, et al., (1984) *Nucl Acids Res* 12:9441-9456; Kramer and Fritz, (1987) *Methods Enzymol* 154:350-367; Kramer, et al., (1988) *Nucl Acids Res* 16:7207 and Fritz, et al., (1988) *Nucl Acids Res* 16:6987-6999).

Additional suitable methods include point mismatch repair (Kramer, et al., (1984) *Cell* 38:879-887), mutagenesis using repair-deficient host strains (Carter, et al., (1985) *Nucl Acids Res* 13:4431-4443 and Carter, (1987) *Methods in Enzymol* 154:382-403), deletion mutagenesis (Eghtedarzadeh and Henikoff, (1986) *Nucl Acids Res* 14:5115), restriction-selection and restriction-purification (Wells, et al., (1986) *Phil Trans R Soc Lond A* 317:415-423), mutagenesis by total gene synthesis (Nambiar, et al., (1984) *Science* 223:1299-1301; Sakamar and Khorana, (1988) *Nucl Acids Res* 14:6361-6372; Wells, et al., (1985) *Gene* 34:315-323 and Grundström, et al., (1985) *Nucl Acids Res* 13:3305-3316), double-strand break repair (Mandecki, (1986) *PNAS USA*, 83:7177-7181 and Arnold, (1993) *Curr Opin Biotech* 4:450-455). Additional details on many of the above methods can be found in *Methods Enzymol* Volume 154, which also describes useful controls for trouble-shooting problems with various mutagenesis methods.

The nucleotide sequences of the embodiments can also be used to isolate corresponding sequences from a bacterial source, including but not limited to a *Pseudomonas* species. In this manner, methods such as PCR, hybridization, and the like can be used to identify such sequences based on their sequence homology to the sequences set forth herein. Sequences that are selected based on their sequence identity to the entire sequences set forth herein or to fragments thereof are encompassed by the embodiments. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, New York), hereinafter "Sambrook". See also, Innis, et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

To identify potential Cry toxin polypeptides from bacterium collections, the bacterial cell lysates can be screened with antibodies generated against Cry toxin polypeptides using Western blotting and/or ELISA methods. This type of assay can be performed in a high throughput fashion. Positive samples can be further analyzed by various techniques such as antibody based protein purification and identification. Methods of generating antibodies are well known in the art as discussed infra.

Alternatively, mass spectrometry based protein identification method can be used to identify homologs of Cry toxin polypeptides using protocols in the literatures (Scott Patterson, (1998), 10.22, 1-24, *Current Protocol in Molecular Biology* published by John Wiley & Son Inc). Specifically, LC-MS/MS based protein identification method is used to associate the MS data of given cell lysate or desired molecular weight enriched samples (excised from SDS-PAGE gel of relevant molecular weight bands to Cry toxin polypeptides) with sequence information of a Cry toxin polypeptide disclosed herein. Any match in peptide sequences indicates the potential of having the homologous proteins in the samples. Additional techniques (protein purification and molecular biology) can be used to isolate the protein and identify the sequences of the homologs.

In hybridization methods, all or part of the pesticidal nucleic acid sequence can be used to screen cDNA or genomic libraries. Methods for construction of such cDNA and genomic libraries are generally known in the art and are disclosed in Sambrook and Russell, (2001), supra. The so-called hybridization probes may be genomic DNA fragments, cDNA fragments, RNA fragments or other oligonucleotides and may be labeled with a detectable group such as 32P or any other detectable marker, such as other radioisotopes, a fluorescent compound, an enzyme or an enzyme co-factor. Probes for hybridization can be made by labeling synthetic oligonucleotides based on the known Cry toxin polypeptide-encoding nucleic acid sequences disclosed herein. Degenerate primers designed on the basis of conserved nucleotides or amino acid residues in the nucleic acid sequence or encoded amino acid sequence can additionally be used. The probe typically comprises a region of nucleic acid sequence that hybridizes under stringent conditions to at least about 12, at least about 25, at least about 50, 75, 100, 125, 150, 175 or 200 consecutive nucleotides of nucleic acid sequences encoding Cry toxin polypeptides of the disclosure or a fragment or variant thereof. Methods for the preparation of probes for hybridization and stringency conditions are generally known in the art and are disclosed in Sambrook and Russell, (2001), supra, herein incorporated by reference.
Antibodies Antibodies to a Cry toxin polypeptide of the embodiments or to variants or fragments thereof are also encompassed. The antibodies of the disclosure include polyclonal and monoclonal antibodies as well as fragments thereof which retain their ability to bind to a Cry toxin polypeptide. An antibody, monoclonal antibody or fragment thereof is said to be capable of binding a molecule if it is capable of specifically reacting with the molecule to thereby bind the molecule to the antibody, monoclonal antibody or fragment thereof. The term "antibody" (Ab) or "monoclonal antibody" (Mab) is meant to include intact molecules as well as fragments or binding regions or domains thereof (such as, for example, Fab and F(ab).sub.2 fragments) which are capable of binding hapten. Such fragments are typically produced by proteolytic cleavage, such as papain or pepsin. Alternatively, hapten-binding fragments can be produced through the application of recombinant DNA technology or through synthetic chemistry. Methods for the preparation of the antibodies of the present disclosure are generally known in the art. For example, see, Antibodies, A Laboratory Manual, Ed Harlow and David Lane (eds.) Cold Spring Harbor Laboratory, N.Y. (1988), as well as the references cited therein. Standard reference works setting forth the general principles of immunology include: Klein, J. Immunology: The Science of Cell-Noncell Discrimination, John Wiley & Sons, N.Y. (1982); Dennett, et al., Monoclonal Antibodies, Hybridoma: A New Dimension in Biological Analyses, Plenum Press, N.Y. (1980) and Campbell, "Monoclonal Antibody Technology," In Laboratory Techniques in Biochemistry and Molecular Biology, Vol. 13, Burdon, et al., (eds.), Elsevier, Amsterdam (1984). See also, U.S. Pat. Nos. 4,196,265; 4,609,893; 4,713,325; 4,714,681; 4,716,111; 4,716,117 and 4,720,459. Antibodies against Cry toxin polypeptides or antigen-binding portions thereof can be produced by a variety of techniques, including conventional monoclonal antibody methodology, for example the standard somatic cell hybridization technique of Kohler and Milstein, (1975) *Nature* 256:495. Other techniques for producing monoclonal antibody can also be employed such as viral or oncogenic transformation of B lymphocytes. An animal system for preparing hybridomas is a murine system. Immunization protocols and techniques for isolation of immunized splenocytes for fusion are known in the art. Fusion partners (e.g., murine myeloma cells) and fusion procedures are also known. The antibody and monoclonal antibodies of the disclosure can be prepared by utilizing a Cry toxin polypeptide as antigens.

A kit for detecting the presence of a Cry toxin polypeptide or detecting the presence of a nucleotide sequence encoding a Cry toxin polypeptide in a sample is provided. In one embodiment, the kit provides antibody-based reagents for detecting the presence of a Cry toxin polypeptide in a tissue sample. In another embodiment, the kit provides labeled nucleic acid probes useful for detecting the presence of one or more polynucleotides encoding a Cry toxin polypeptide. The kit is provided along with appropriate reagents and controls for carrying out a detection method, as well as instructions for use of the kit.

Receptor Identification and Isolation

Receptors to the Cry toxin polypeptides of the embodiments or to variants or fragments thereof are also encompassed. Methods for identifying receptors are known in the art (see, Hofmann, et. al., (1988) *Eur. J. Biochem.* 173:85-91; Gill, et al., (1995) *J. Biol. Chem.* 27277-27282) and can be employed to identify and isolate the receptor that recognizes the Cry toxin polypeptide using the brush-border membrane vesicles from susceptible insects. In addition to the radioactive labeling method listed in the cited literatures, a Cry toxin polypeptide can be labeled with fluorescent dye and other common labels such as streptavidin. Brush-border membrane vesicles (BBMV) of susceptible insects such as soybean looper and stink bugs can be prepared according to the protocols listed in the references of Hofmann and Gill above and separated on SDS-PAGE gel and blotted on suitable membrane. Labeled Cry toxin polypeptide can be incubated with blotted membrane of BBMV and labeled Cry toxin polypeptide can be identified with the labeled reporters. Identification of protein band(s) that interact with the Cry toxin polypeptide can be detected by N-terminal amino acid gas phase sequencing or mass spectrometry based protein identification method (Patterson, (1998) 10.22, 1-24, Current Protocol in Molecular Biology published by John Wiley & Son Inc). Once the protein is identified, the corresponding gene can be cloned from genomic DNA or cDNA library of the susceptible insects and binding affinity can be measured directly with the Cry toxin polypeptide. Receptor function for insecticidal activity by the Cry toxin polypeptide can be verified by RNAi type of gene knock out method (Rajagopal, et al., (2002) *J. Biol. Chem.* 277:46849-46851).

Nucleotide Constructs, Expression Cassettes and Vectors

The use of the term "nucleotide constructs" herein is not intended to limit the embodiments to nucleotide constructs comprising DNA. Those of ordinary skill in the art will recognize that nucleotide constructs, particularly polynucleotides and oligonucleotides composed of ribonucleotides and combinations of ribonucleotides and deoxyribonucleotides, may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

A further embodiment relates to a transformed organism such as an organism selected from plant and insect cells, bacteria, yeast, baculovirus, protozoa, nematodes and algae. The transformed organism comprises a DNA molecule of the embodiments, an expression cassette comprising the DNA molecule or a vector comprising the expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and where necessary to join two protein coding regions in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the Cry toxin polypeptide gene sequence of the disclosure to be under the transcriptional regulation of the regulatory regions. The DNA construct may additionally contain selectable marker genes.

The DNA construct will generally include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter or any other nucleotide or amino acid sequence is "foreign" or "heterologous" to the sequence of the embodiments, it is intended that the nucleotide or amino acid sequence is not the native or naturally occurring promoter or nucleotide sequence for the operably linked sequence of the embodiments. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

In some embodiments the DNA construct comprises a polynucleotide encoding a Cry toxin polypeptide of the embodiments. In some embodiments the DNA construct comprises a polynucleotide encoding a fusion protein comprising a Cry toxin polypeptide of the embodiments.

In some embodiments the DNA construct may also include a transcriptional enhancer sequence. As used herein, the term an "enhancer" refers to a DNA sequence which can stimulate promoter activity, and may be an innate element of the promoter or a heterologous element inserted to enhance the level or tissue-specificity of a promoter. Various enhancers are known in the art including for example, introns with gene expression enhancing properties in plants (US Patent Application Publication Number 2009/0144863, the ubiquitin intron (i.e., the maize ubiquitin intron 1 (see, for example, NCBI sequence S94464)), the omega enhancer or the omega prime enhancer (Gallie, et al., (1989) *Molecular Biology of RNA* ed. Cech (Liss, New York) 237-256 and Gallie, et al., (1987) *Gene* 60:217-25), the CaMV 35S enhancer (see, e.g., Benfey, et al., (1990) *EMBO J.* 9:1685-96) and the enhancers of U.S. Pat. No. 7,803,992 may also be used. The above list of transcriptional enhancers is not meant to be limiting. Any appropriate transcriptional enhancer can be used in the embodiments.

The termination region may be native with the transcriptional initiation region, may be native with the operably linked DNA sequence of interest, may be native with the plant host or may be derived from another source (i.e., foreign or heterologous to the promoter, the sequence of interest, the plant host or any combination thereof).

Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2: 1261-1272; Munroe, et al., (1990) *Gene* 91:151-158; Ballas, et al., (1989) *Nucleic Acids Res.* 17:7891-7903 and Joshi, et al., (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred usage. For example, although nucleic acid sequences of the embodiments may be expressed in both monocotyledonous and dicotyledonous plant species, sequences can be modified to account for the specific preferences and GC content preferences of monocotyledons or dicotyledons as these preferences have been shown to differ (Murray et al. (1989) *Nucleic Acids Res.* 17:477-498). Thus, the maize-preferred for a particular amino acid may be derived from known gene sequences from maize. Maize usage for 28 genes from maize plants is listed in Table 4 of Murray, et al., supra. Methods are available in the art for synthesizing plant-preferred genes. See, for example, Murray, et al., (1989) *Nucleic Acids Res.* 17:477-498, and Liu H et al. *Mol Bio Rep* 37:677-684, 2010, herein incorporated by reference. A *Zea maize* usage table can be also found at kazusa.or.jp//cgi-bin/show.cgi?species=4577, which can be accessed using the www prefix. A *Glycine max* usage table can be found at kazusa.or.jp//cgi-bin/show.cgi?species=3847&aa=1&style=N, which can be accessed using the www prefix.

In some embodiments the recombinant nucleic acid molecule encoding a Cry toxin polypeptide has maize optimized codons.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli* or eukaryotic cells such as yeast, insect, amphibian or mammalian cells or monocotyledonous or dicotyledonous plant cells. An example of a monocotyledonous host cell is a maize host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus), human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA*, ed. Cech (Liss, New York), pp. 237-256) and maize chlorotic mottle virus leader (MCMV) (Lommel, et al., (1991) *Virology* 81:382-385). See also, Della-Cioppa, et al., (1987) *Plant Physiol.* 84:965-968. Such constructs may also contain a "signal sequence" or "leader sequence" to facilitate co-translational or post-translational transport of the peptide to certain intracellular structures such as the chloroplast (or other plastid), endoplasmic reticulum or Golgi apparatus.

"Signal sequence" as used herein refers to a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are proteolytically activated in the gut of the target pest (Chang, (1987) *Methods Enzymol.* 153:507-516). In some embodiments, the signal sequence is located in the native sequence or may be derived from a sequence of the embodiments. "Leader sequence" as used herein refers to any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like. Nuclear-encoded proteins targeted to the chloroplast thylakoid lumen compartment have a characteristic bipartite transit peptide, composed of a stromal targeting signal peptide and a lumen targeting signal peptide. The stromal targeting information is in the amino-proximal portion of the transit peptide. The lumen targeting signal peptide is in the carboxyl-proximal portion of the transit peptide, and contains all the information for targeting to the lumen. Recent research in proteomics of the higher plant chloroplast has achieved in the identification of numerous nuclear-encoded lumen proteins (Kieselbach et al. *FEBS LETT* 480:271-276, 2000; Peltier et al. Plant Cell 12:319-341, 2000; Bricker et al. *Biochim. Biophys Acta* 1503:350-356, 2001), the lumen targeting signal peptide of which can potentially be used in accordance with the present disclosure. About 80 proteins from *Arabidopsis*, as well as homologous proteins from spinach and garden pea, are reported by Kieselbach et al., *Photosynthesis Research,* 78:249-264, 2003. In particular, Table 2 of this publication, which is incorporated into the description herewith by reference, discloses 85 proteins from the chloroplast lumen, identified by their accession number (see also US Patent Application Publication 2009/09044298).

Suitable chloroplast transit peptides (CTP) are well known to one skilled in the art also include chimeric CT's comprising but not limited to, an N-terminal domain, a central domain or a C-terminal domain from a CTP from *Oryza sativa* 1-decoy-D xylose-5-Phosphate Synthase *Oryza sativa*-Superoxide dismutase *Oryza sativa*-soluble starch synthase *Oryza sativa*-NADP-dependent Malic acid enzyme *Oryza sativa*-Phospho-2-dehydro-3-deoxyheptonate Aldolase 2 *Oryza sativa*-L-Ascorbate peroxidase 5 *Oryza sativa*-Phosphoglucan water dikinase, *Zea Mays* ssRUBISCO, *Zea Mays*-beta-glucosidase, *Zea Mays*-Malate dehydrogenase, *Zea Mays* Thioredoxin M-type (See US Patent Application Publication 2012/0304336).

The Cry toxin polypeptide gene to be targeted to the chloroplast may be optimized for expression in the chloroplast to account for differences in usage between the plant nucleus and this organelle. In this manner, the nucleic acids of interest may be synthesized using chloroplast-preferred sequences.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible or other promoters for expression in the host organism. Suitable constitutive promoters for use in a plant host cell include, for example, the core promoter of the Rsyn7 promoter and other constitutive promoters disclosed in WO 1999/43838 and U.S. Pat. No. 6,072,050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026) and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142 and 6,177,611.

Depending on the desired outcome, it may be beneficial to express the gene from an inducible promoter. Of particular interest for regulating the expression of the nucleotide sequences of the embodiments in plants are wound-inducible promoters. Such wound-inducible promoters, may respond to damage caused by insect feeding, and include potato proteinase inhibitor (pin II) gene (Ryan, (1990) *Ann. Rev. Phytopath.* 28:425-449; Duan, et al., (1996) *Nature Biotechnology* 14:494-498); wun1 and wun2, U.S. Pat. No. 5,428,148; win1 and win2 (Stanford, et al., (1989) *Mol. Gen. Genet.* 215:200-208); systemin (McGurl, et al., (1992) *Science* 225:1570-1573); WIP1 (Rohmeier, et al., (1993) *Plant Mol. Biol.* 22:783-792; Eckelkamp, et al., (1993) *FEBS Letters* 323:73-76); MPI gene (Corderok, et al., (1994) *Plant J.* 6(2):141-150) and the like.

Additionally, pathogen-inducible promoters may be employed in the methods and nucleotide constructs of the embodiments. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi, et al., (1983) *Neth. J. Plant Pathol.* 89:245-254; Uknes, et al., (1992) *Plant Cell* 4: 645-656 and Van Loon, (1985) *Plant Mol. Virol.* 4:111-116. See also, WO 1999/43819.

Of interest are promoters that are expressed locally at or near the site of pathogen infection. See, for example, Marineau, et al., (1987) *Plant Mol. Biol.* 9:335-342; Matton, et al., (1989) *Molecular Plant-Microbe Interactions* 2:325-331; Somsisch, et al., (1986) *Proc. Natl. Acad. Sci. USA* 83:2427-2430; Somsisch, et al., (1988) *Mol. Gen. Genet.* 2:93-98 and Yang, (1996) *Proc. Natl. Acad. Sci. USA* 93:14972-14977. See also, Chen, et al., (1996) *Plant J.* 10:955-966; Zhang, et al., (1994) *Proc. Natl. Acad. Sci. USA* 91:2507-2511; Warner, et al., (1993) *Plant J.* 3:191-201;

Siebertz, et al., (1989) *Plant Cell* 1:961-968; U.S. Pat. No. 5,750,386 (nematode-inducible) and the references cited therein. Of particular interest is the inducible promoter for the maize PRms gene, whose expression is induced by the pathogen *Fusarium moniliforme* (see, for example, Cordero, et al., (1992) *Physiol. Mol. Plant Path.* 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena, et al., (1991) *Proc. Natl. Acad. Sci. USA* 88:10421-10425 and McNellis, et al., (1998) *Plant J.* 14(2):247-257) and tetracycline-inducible and tetracycline-repressible promoters (see, for example, Gatz, et al., (1991) *Mol. Gen. Genet.* 227:229-237 and U.S. Pat. Nos. 5,814,618 and 5,789,156).

Tissue-preferred promoters can be utilized to target enhanced Cry toxin polypeptide expression within a particular plant tissue. Tissue-preferred promoters include those discussed in Yamamoto, et al., (1997) *Plant J.* 12(2)255-265; Kawamata, et al., (1997) *Plant Cell Physiol.* 38(7): 792-803; Hansen, et al., (1997) *Mol. Gen Genet.* 254(3): 337-343; Russell, et al., (1997) *Transgenic Res.* 6(2):157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524; Yamamoto, et al., (1994) *Plant Cell Physiol.* 35(5): 773-778; Lam, (1994) *Results Probl. Cell Differ.* 20:181-196; Orozco, et al., (1993) *Plant Mol Biol.* 23(6):1129-1138; Matsuoka, et al., (1993) *Proc Natl. Acad. Sci. USA* 90(20): 9586-9590 and Guevara-Garcia, et al., (1993) *Plant J.* 4(3):495-505. Such promoters can be modified, if necessary, for weak expression.

Leaf-preferred promoters are known in the art. See, for example, Yamamoto, et al., (1997) *Plant J.* 12(2):255-265; Kwon, et al., (1994) *Plant Physiol.* 105:357-67; Yamamoto, et al., (1994) *Plant Cell Physiol.* 35(5):773-778; Gotor, et al., (1993) *Plant J.* 3:509-18; Orozco, et al., (1993) *Plant Mol. Biol.* 23(6):1129-1138 and Matsuoka, et al., (1993) *Proc. Natl. Acad. Sci. USA* 90(20):9586-9590.

Root-preferred or root-specific promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner, (1991) *Plant Cell* 3(10):1051-1061 (root-specific control element in the GRP 1.8 gene of French bean); Sanger, et al., (1990) *Plant Mol. Biol.* 14(3):433-443 (root-specific promoter of the mannopine synthase (MAS) gene of *Agrobacterium tumefaciens*) and Miao, et al., (1991) *Plant Cell* 3(1):11-22 (full-length cDNA clone encoding cytosolic glutamine synthetase (GS), which is expressed in roots and root nodules of soybean). See also, Bogusz, et al., (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi, (1991) describe their analysis of the promoters of the highly expressed rolC and rolD root-inducing genes of *Agrobacterium rhizogenes* (see, *Plant Science* (Limerick) 79(1):69-76). They concluded that enhancer and tissue-preferred DNA determinants are dissociated in those promoters. Teeri, et al., (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see, *EMBO J.* 8(2): 343-350). The TR1' gene fused to nptII (neomycin phosphotransferase II) showed similar characteristics. Additional root-preferred promoters include the VfENOD-GRP3 gene promoter (Kuster, et al., (1995) *Plant Mol. Biol.* 29(4):759-772) and rolB promoter (Capana, et al., (1994) *Plant Mol. Biol.* 25(4):681-691. See also, U.S. Pat. Nos. 5,837,876; 5,750,386; 5,633,363; 5,459,252; 5,401,836; 5,110,732 and 5,023,179. *Arabidopsis thaliana* root-preferred regulatory sequences are disclosed in US20130117883.

"Seed-preferred" promoters include both "seed-specific" promoters (those promoters active during seed development such as promoters of seed storage proteins) as well as "seed-germinating" promoters (those promoters active during seed germination). See, Thompson, et al., (1989) *BioEssays* 10:108. Such seed-preferred promoters include, but are not limited to, Cim1 (cytokinin-induced message); cZ19B1 (maize 19 kDa zein); and milps (myo-inositol-1-phosphate synthase) (see, U.S. Pat. No. 6,225,529). Gamma-zein and Glb-1 are endosperm-specific promoters. For dicots, seed-specific promoters include, but are not limited to, Kunitz trypsin inhibitor 3 (KTi3) (Jofuku and Goldberg, (1989) *Plant Cell* 1:1079-1101), bean β-phaseolin, napin, β-conglycinin, glycinin 1, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also, WO 2000/12733, where seed-preferred promoters from end1 and end2 genes are disclosed. In dicots, seed specific promoters include but are not limited to seed coat promoter from *Arabidopsis*, pBAN; and the early seed promoters from *Arabidopsis*, p26, p63, and p63tr (U.S. Pat. Nos. 7,294,760 and 7,847,153). A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of between about 1/1000 transcripts to about 1/100,000 transcripts to about 1/500,000 transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 1999/43838 and U.S. Pat. No. 6,072,050), the core 35S CaMV promoter, and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142 and 6,177,611.

The above list of promoters is not meant to be limiting. Any appropriate promoter can be used in the embodiments.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones and 2,4-dichlorophenoxyacetate (2,4-D). Additional examples of suitable selectable marker genes include, but are not limited to, genes encoding resistance to chloramphenicol (Herrera Estrella, et al., (1983) *EMBO J.* 2:987-992); methotrexate (Herrera Estrella, et al., (1983) *Nature* 303:209-213 and Meijer, et al., (1991) *Plant Mol. Biol.* 16:807-820); streptomycin (Jones, et al., (1987) *Mol. Gen. Genet.* 210:86-91); spectinomycin (Bretagne-Sagnard, et al., (1996) *Transgenic Res.* 5:131-137); bleomycin (Hille, et al., (1990) *Plant Mol. Biol.* 7:171-176); sulfonamide (Guerineau, et al., (1990) *Plant Mol. Biol.* 15:127-136); bromoxynil (Stalker, et al., (1988) *Science* 242:419-423); glyphosate (Shaw, et al., (1986) *Science* 233:478-481 and U.S. patent application Ser. No. 10/004,357 and Ser. No. 10/427,692); phosphinothricin (De-Block, et al., (1987) *EMBO J.* 6:2513-2518). See generally, Yarranton, (1992) *Curr. Opin. Biotech.* 3:506-511; Christopherson, et al., (1992) *Proc. Natl. Acad. Sci. USA* 89:6314-6318; Yao, et al., (1992) *Cell* 71:63-72; Reznikoff, (1992) *Mol. Microbiol.* 6:2419-2422; Barkley, et al., (1980) in *The Operon*, pp. 177-220; Hu, et al., (1987) *Cell* 48:555-566; Brown, et al., (1987) *Cell* 49:603-612; Figge, et al., (1988) *Cell* 52:713-722; Deuschle, et al., (1989) *Proc. Natl. Acad. Sci. USA* 86:5400-5404; Fuerst, et al., (1989) *Proc. Natl. Acad. Sci. USA* 86:2549-2553; Deuschle, et al., (1990) *Science* 248:480-483; Gossen, (1993) Ph.D. Thesis, University of Heidelberg; Reines, et al., (1993) *Proc. Natl. Acad. Sci. USA* 90:1917-1921; Labow, et al., (1990) *Mol. Cell. Biol.* 10:3343-3356; Zambretti, et al., (1992) *Proc. Natl. Acad. Sci. USA* 89:3952-3956; Bairn, et al., (1991) *Proc. Natl. Acad. Sci. USA* 88:5072-5076; Wyborski, et al., (1991) *Nucleic Acids Res.* 19:4647-4653; Hillenand-Wissman, (1989) *Topics Mol. Struc. Biol.* 10:143-162; Degenkolb, et al., (1991) *Antimicrob. Agents Chemother.* 35:1591-1595; Kleinschmidt, et al., (1988) *Biochemistry* 27:1094-1104; Bonin, (1993) Ph.D. Thesis, University of Heidelberg; Gossen, et al., (1992) *Proc. Natl. Acad. Sci. USA* 89:5547-5551; Oliva, et al., (1992) *Antimicrob. Agents Chemother.* 36:913-919; Hlavka, et al., (1985) *Handbook of Experimental Pharmacology*, Vol. 78 (Springer-Verlag, Berlin) and Gill, et al., (1988) *Nature* 334:721-724.

The above list of selectable marker genes is not meant to be limiting. Any selectable marker gene can be used in the embodiments.

Plant Transformation

The methods of the embodiments involve introducing a polypeptide or polynucleotide into a plant. "Introducing" as used herein means presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide(s) or polypeptide(s) gains access to the interior of at least one cell of the plant. Methods for introducing polynucleotide(s) or polypeptide(s) into plants are known in the art including, but not limited to, stable transformation methods, transient transformation methods, and virus-mediated methods.

"Stable transformation" as used herein means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant. "Plant" as used herein refers to whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells and pollen).

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (U.S. Pat. Nos. 5,563,055 and 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244 and 5,932,782; Tomes, et al., (1995) in *Plant Cell, Tissue, and Organ Culture: Fundamental Methods*, ed. Gamborg and Phillips, (Springer-Verlag, Berlin) and McCabe, et al., (1988) *Bio/technology* 6:923-926) and Lec1 transformation (WO 00/28058). For potato transformation see, Tu, et al., (1998) *Plant Molecular Biology* 37:829-838 and Chong, et al., (2000) *Transgenic Research* 9:71-78. Additional transformation procedures can be found in Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature (London)* 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (Longman, New York), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*).

In specific embodiments, the sequences of the embodiments can be provided to a plant using a variety of transient transformation methods. Such transient transformation methods include, but are not limited to, the introduction of the Cry toxin polynucleotide or variants and fragments thereof directly into the plant or the introduction of the Cry toxin polypeptide transcript into the plant. Such methods include, for example, microinjection or particle bombardment. See, for example, Crossway, et al., (1986) *Mol Gen. Genet.* 202:179-185; Nomura, et al., (1986) *Plant Sci.* 44:53-58; Hepler, et al., (1994) *Proc. Natl. Acad. Sci.* 91:2176-2180 and Hush, et al., (1994) *The Journal of Cell Science* 107:775-784. Alternatively, the Cry toxin polynucleotide can be transiently transformed into the plant using techniques known in the art. Such techniques include viral vector system and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

Methods are known in the art for the targeted insertion of a polynucleotide at a specific location in the plant genome. In one embodiment, the insertion of the polynucleotide at a desired genomic location is achieved using a site-specific recombination system. See, for example, WO 1999/25821, WO 1999/25854, WO 1999/25840, WO 1999/25855 and WO 1999/25853. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

Plant transformation vectors may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux, (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g., immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g., Hiei, et al., (1994) *The Plant Journal* 6:271-282; Ishida, et al., (1996) *Nature Biotechnology* 14:745-750). Explants are typically transferred to a fresh supply of the same medium and cultured routinely. A general description of the techniques and methods for generating transgenic plants are found in Ayres and Park, (1994) *Critical Reviews in Plant Science* 13:219-239 and Bommineni and Jauhar, (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

The cells that have been transformed may be grown into plants in accordance with conventional ways. See, for example, McCormick, et al., (1986) *Plant Cell Reports* 5:81-84. These plants may then be grown, and either pollinated with the same transformed strain or different strains, and the resulting hybrid having constitutive or inducible expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The nucleotide sequences of the embodiments may be provided to the plant by contacting the plant with a virus or viral nucleic acids. Generally, such methods involve incorporating the nucleotide construct of interest within a viral DNA or RNA molecule. It is recognized that the recombinant proteins of the embodiments may be initially synthesized as part of a viral polyprotein, which later may be processed by proteolysis in vivo or in vitro to produce the desired Cry toxin polypeptide. It is also recognized that such a viral polyprotein, comprising at least a portion of the amino acid sequence of a Cry toxin polypeptide of the embodiments, may have the desired pesticidal activity. Such viral polyproteins and the nucleotide sequences that encode for them are encompassed by the embodiments. Methods for providing plants with nucleotide constructs and producing the encoded proteins in the plants, which involve viral DNA or RNA molecules, are known in the art. See, for example, U.S. Pat. Nos. 5,889,191; 5,889,190; 5,866,785; 5,589,367 and 5,316,931.

Methods for transformation of chloroplasts are known in the art. See, for example, Svab, et al., (1990) Proc. Natl. Acad. Sci. USA 87:8526-8530; Svab and Maliga, (1993) Proc. Natl. Acad. Sci. USA 90:913-917; Svab and Maliga, (1993) EMBO J. 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride, et al., (1994) Proc. Natl. Acad. Sci. USA 91:7301-7305.

The embodiments further relate to plant-propagating material of a transformed plant of the embodiments including, but not limited to, seeds, tubers, corms, bulbs, leaves and cuttings of roots and shoots.

The embodiments may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tuhpa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the embodiments include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants (for example, corn, alfalfa, sunflower, *Brassica*, soybean, cotton, safflower, peanut, sorghum, wheat, millet, tobacco, etc.), such as corn and soybean plants.

Turf grasses include, but are not limited to: annual bluegrass (*Poa annua*); annual ryegrass (*Lolium multiflorum*); Canada bluegrass (*Poa compressa*); Chewing's fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerata*); perennial ryegrass (*Lolium perenne*); red fescue (*Festuca rubra*); redtop (*Agrostis alba*); rough bluegrass (*Poa trivialis*); sheep fescue (*Festuca ovina*); smooth bromegrass (*Bromus inermis*); tall fescue (*Festuca arundinacea*); timothy (*Phleum pratense*); velvet bentgrass (*Agrostis canna*); weeping alkaligrass (*Puccinellia distans*); western wheatgrass (*Agropyron smithii*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive, etc. Leguminous plants include beans and peas. Beans include guar, locust bean, fenugreek, soybean, garden beans, cowpea, mung bean, lima bean, fava bean, lentils, chickpea, etc.

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell, (2001) Molecular Cloning: A Laboratory Manual. Cold Spring Harbor Laboratory Press, Cold Spring Harbor, NY). PCR is carried out using oligonucleotide primers specific to the gene of interest or *Agrobacterium* vector background, etc.

Plant transformation may be confirmed by Southern blot analysis of genomic DNA (Sambrook and Russell, (2001) supra). In Northern blot analysis, RNA is isolated from specific tissues of transformant, fractionated in a formaldehyde agarose gel, and blotted onto a nylon filter according to standard procedures that are routinely used in the art (Sambrook and Russell, (2001) supra). Expression of RNA encoded by the pesticidal gene is then tested by hybridizing the filter to a radioactive probe derived from a pesticidal gene, by methods known in the art (Sambrook and Russell, (2001) supra). Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the Cry toxin polypeptide.

Methods to Introduce Genome Editing Technologies into Plants

In some embodiments, the disclosed Cry toxin polynucleotide compositions can be introduced into the genome of a plant using genome editing technologies, or previously introduced Cry toxin polynucleotides in the genome of a plant may be edited using genome editing technologies. For example, the disclosed polynucleotides can be introduced into a desired location in the genome of a plant through the use of double-stranded break technologies such as TALENs, meganucleases, zinc finger nucleases, CRISPR-Cas, and the like. For example, the disclosed polynucleotides can be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing traits of interest could be either an endogenous trait or a previously introduced trait.

In some embodiments, where the disclosed Cry toxin polynucleotide has previously been introduced into a genome, genome editing technologies may be used to alter or modify the introduced polynucleotide sequence. Site specific modifications that can be introduced into the disclosed Cry toxin polynucleotide compositions include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. Such technologies can be used to modify the previously introduced polynucleotide through the insertion, deletion or substitution of nucleotides within the introduced polynucleotide. Alternatively, double-stranded break technologies can be used to add additional nucleotide sequences to the introduced polynucleotide. Additional sequences that may be added include, additional expression elements, such as enhancer and promoter sequences. In another embodiment, genome editing technologies may be used to position additional insecticidally-active proteins in close proximity to the disclosed Cry toxin polynucleotide compositions disclosed herein within the genome of a plant, in order to generate molecular stacks of insecticidally-active proteins.

An "altered target site," "altered target sequence." "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Stacking of Traits in Transgenic Plant

Transgenic plants may comprise a stack of one or more insecticidal polynucleotides disclosed herein with one or more additional polynucleotides resulting in the production or suppression of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and co-transformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853, all of which are herein incorporated by reference.

In some embodiments, one or more of the polynucleotides encoding the Cry toxin polypeptide(s) disclosed herein, alone or stacked with one or more additional insect resistance traits can be stacked with one or more additional input traits (e.g., herbicide resistance, fungal resistance, virus resistance, stress tolerance, disease resistance, male sterility, stalk strength, and the like) or output traits (e.g., increased yield, modified starches, improved oil profile, balanced amino acids, high lysine or methionine, increased digestibility, improved fiber quality, drought resistance, and the like). Thus, the polynucleotide embodiments can be used to provide a complete agronomic package of improved crop quality with the ability to flexibly and cost effectively control any number of agronomic pests.

Transgenes useful for stacking include but are not limited to: transgenes that confer resistance to an herbicide; transgenes that confer or contribute to an altered grain characteristic; genes that control male-sterility; genes that create a site for site specific dna integration; genes that affect abiotic stress resistance; genes that confer increased yield genes that confer plant digestibility; and transgenes that confer resistance to insects or disease.

Examples of transgenes that confer resistance to insects include genes encoding a *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC® Accession Numbers 40098, 67136, 31995 and 31998. Other non-limiting examples of *Bacillus thuringiensis* transgenes being genetically engineered are given in the following patents and patent applications: U.S. Pat. Nos. 5,188,960; 5,689,052; 5,880,275; 5,986,177; 6,023,013, 6,060,594, 6,063,597, 6,077,824, 6,620,988, 6,642,030, 6,713,259, 6,893,826, 7,105,332; 7,179,965, 7,208,474; 7,227,056, 7,288,643, 7,323,556, 7,329,736, 7,449,552, 7,468,278, 7,510,878, 7,521,235, 7,544,862, 7,605,304, 7,696,412, 7,629,504, 7,705,216, 7,772,465, 7,790,846, 7,858,849 and WO 1991/14778; WO 1999/31248; WO 2001/12731; WO 1999/24581 and WO 1997/40162.

Genes encoding pesticidal proteins may also be stacked including but are not limited to: insecticidal proteins from *Pseudomonas* sp. such as PSEEN3174 (Monalysin, (2011) *PLoS Pathogens*, 7:1-13), from *Pseudomonas protegens* strain CHA0 and Pf-5 (previously fluorescens) (Pechy-Tarr, (2008) *Environmental Microbiology* 10:2368-2386: GenBank Accession No. EU400157); from *Pseudomonas taiwanensis* (Liu, et al., (2010) *J. Agric. Food Chem.* 58:12343-12349) and from *Pseudomonas pseudoalcaligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxinology Journal* 3:101-118 and Morgan, et al., (2001) *Applied and Envir. Micro.* 67:2062-2069), U.S. Pat. Nos. 6,048,838, and 6,379, 946; a PIP-1 polypeptide of U.S. Pat. No. 9,688,730; an AfIP-1A and/or AfIP-1B polypeptide of U.S. Pat. No. 9,475, 847; a PIP-47 polypeptide of US Publication Number US20160186204; an IPD045 polypeptide, an IPD064 polypeptide, an IPD074 polypeptide, an IPD075 polypeptide, and an IPD077 polypeptide of PCT Publication Number WO 2016/114973; an IPD080 polypeptide of PCT Serial Number PCT/US17/56517; an IPD078 polypeptide, an IPD084 polypeptide, an IPD085 polypeptide, an IPD086 polypeptide, an IPD087 polypeptide, an IPD088 polypeptide, and an IPD089 polypeptide of Serial Number PCT/US17/54160; PIP-72 polypeptide of US Patent Publication Number US20160366891; a PtIP-50 polypeptide and a PtIP-65 polypeptide of US Publication Number US20170166921; an IPD098 polypeptide, an IPD059 polypeptide, an IPD108 polypeptide, an IPD109 polypeptide of U.S. Ser. No. 62/521, 084; a PtIP-83 polypeptide of US Publication Number US20160347799; a PtIP-96 polypeptide of US Publication Number US20170233440; an IPD079 polypeptide of PCT Publication Number WO2017/23486; an IPD082 polypeptide of PCT Publication Number WO 2017/105987, an IPD090 polypeptide of Serial Number PCT/US17/30602, an IPD093 polypeptide of U.S. Ser. No. 62/434,020; an IPD103 polypeptide of Serial Number PCT/US17/39376; an IPD101 polypeptide of U.S. Ser. No. 62/438,179; an IPD121 polypeptide of U.S. Ser. No. 62/508,514, and δ-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry28, Cry29, Cry30, Cry31, Cry32, Cry33, Cry34, Cry35, Cry36, Cry37, Cry38, Cry39, Cry40, Cry41, Cry42, Cry43, Cry44, Cry45, Cry46, Cry47, Cry49, Cry50, Cry51, Cry52, Cry53, Cry54, Cry55, Cry56, Cry57, Cry58, Cry59, Cry60, Cry61, Cry62, Cry63, Cry64, Cry65, Cry66, Cry67, Cry68, Cry69, Cry70, Cry71, and Cry72 classes of δ-endotoxin genes and the *B. thuringiensis* cytolytic Cyt1 and Cyt2 genes.

Examples of δ-endotoxins also include but are not limited to Cry1A proteins of U.S. Pat. Nos. 5,880,275 and 7,858, 849; a DIG-3 or DIG-11 toxin (N-terminal deletion of α-helix 1 and/or α-helix 2 variants of Cry proteins such as Cry1A) of U.S. Pat. Nos. 8,304,604 and 8,304,605, Cry1B of U.S. patent application Ser. No. 10/525,318; Cry1C of U.S. Pat. No. 6,033,874; Cry1F of U.S. Pat. Nos. 5,188,960, 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as such as members of the Cry9A, Cry9B, Cry9C, Cry9D, Cry9E, and Cry9F families; a Cry15 protein of Naimov, et al., (2008) *Applied and Environmental Microbiology* 74:7145-7151; a Cry22, a Cry34Ab 1 protein of U.S. Pat. Nos. 6,127,180, 6,624,145 and 6,340,593; a CryET33 and CryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab 1 protein of U.S. Pat. Nos. 6,083,499, 6,548,291 and 6,340, 593; a Cry46 protein, a Cry51 protein, a Cry binary toxin; a TIC901 or related toxin; TIC807 of US 2008/0295207; ET29, ET37, TIC809, TIC810, TIC812, TIC127, TIC128 of PCT US 2006/033867; AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020, and AXMI-021 of WO 2006/083891; AXMI-010 of WO 2005/038032; AXMI-003 of WO 2005/021585; AXMI-008 of US 2004/0250311; AXMI-006 of US 2004/0216186; AXMI-007 of US 2004/0210965; AXMI-009 of US 2004/0210964; AXMI-014 of US 2004/0197917; AXMI-004 of US 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US20110023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063, and AXMI-064 of US 2011/0263488; AXMI-R1 and related proteins of US 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230, and AXMI231 of WO11/103247; AXMI-115, AXMI-113, AXMI-005, AXMI-163 and AXMI-184 of U.S. Pat. No. 8,334,431; AXMI-001, AXMI-002, AXMI-030, AXMI-035, and AXMI-045 of US 2010/0298211; AXMI-066 and AXMI-076 of US2009/0144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US 2010/0005543; and Cry proteins such as Cry1A and Cry3A having modified proteolytic sites of U.S. Pat. No. 8,319,019; and a Cry1Ac, Cry2Aa and Cry1Ca toxin protein from *Bacillus thuringiensis* strain VBTS 2528 of US Patent Application Publication Number 2011/0064710. Other Cry proteins are well known to one skilled in the art (see, Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix). The insecticidal activity of Cry proteins is well known to one skilled in the art (for review, see, van Frannkenhuyzen, (2009) *J. Invert. Path.* 101:1-16). The use of Cry proteins as transgenic plant traits is well known to one skilled in the art and Cry-transgenic plants including but not limited to Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb 1, Cry34Ab 1, Cry35Ab 1, Vip3A, mCry3A, Cry9c and CBI-Bt have received regulatory approval (see, Sanahuja, (2011) *Plant Biotech Journal* 9:283-300 and the CERA (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682), Cry1BE & Cry1F (US2012/0311746), Cry1CA & Cry1AB (US2012/0311745), Cry1F & CryCa (US2012/0317681), Cry1DA & Cry1BE (US2012/0331590), Cry1DA & Cry1Fa (US2012/0331589), Cry1AB & Cry1BE (US2012/0324606), and Cry1Fa & Cry2Aa, Cry1I or Cry1E (US2012/0324605). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279, 6,137,033, 7,244,820, 7,615,686, and 8,237,020, and the like. Other VIP proteins are well known to one skilled in the art (see, lifesci.sussex.ac.uk/home/Neil_Crickmore/Bt/vip.html which can be accessed on the world-wide web using the "www" prefix). Pesticidal proteins also include toxin complex (TC) proteins, obtainable from organisms such as *Xenorhabdus, Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but are not limited to lycotoxin-1 peptides and mutants thereof (U.S. Pat. No. 8,334,366).

Further transgenes that confer resistance to insects may down-regulation of expression of target genes in insect pest species by interfering ribonucleic acid (RNA) molecules through RNA interference. RNA interference refers to the process of sequence-specific post-transcriptional gene silencing in animals mediated by short interfering RNAs (siRNAs) (Fire, et al., (1998) *Nature* 391:806). RNAi transgenes may include but are not limited to expression of dsRNA, siRNA, miRNA, iRNA, antisense RNA, or sense RNA molecules that down-regulate expression of target genes in insect pests. PCT Publication WO 2007/074405 describes methods of inhibiting expression of target genes in invertebrate pests including Colorado potato beetle. PCT Publication WO 2005/110068 describes methods of inhibiting expression of target genes in invertebrate pests including in particular Western corn rootworm as a means to control insect infestation. Furthermore, PCT Publication WO 2009/091864 describes compositions and methods for the suppression of target genes from insect pest species including pests from the *Lygus* genus.

RNAi transgenes are provided for targeting the vacuolar ATPase H subunit, useful for controlling a coleopteran pest population and infestation as described in US Patent Application Publication 2012/0198586. PCT Publication WO 2012/055982 describes ribonucleic acid (RNA or double stranded RNA) that inhibits or down regulates the expression of a target gene that encodes: an insect ribosomal protein such as the ribosomal protein L19, the ribosomal protein L40 or the ribosomal protein S27A; an insect proteasome subunit such as the Rpn6 protein, the Pros 25, the Rpn2 protein, the proteasome beta 1 subunit protein or the Pros beta 2 protein; an insect β-coatomer of the COPI vesicle, the γ-coatomer of the COPI vesicle, the β'-coatomer protein or the ζ-coatomer of the COPI vesicle; an insect Tetraspanine 2 A protein which is a putative transmembrane domain protein; an insect protein belonging to the actin family such as Actin 5C; an insect ubiquitin-5E protein; an insect Sec23 protein which is a GTPase activator involved in intracellular protein transport; an insect crinkled protein which is an unconventional myosin which is involved in motor activity; an insect crooked neck protein which is involved in the regulation of nuclear alternative mRNA splicing; an insect vacuolar H+-ATPase G-subunit protein and an insect Tbp-1 such as Tat-binding protein. PCT publication WO 2007/035650 describes ribonucleic acid (RNA or double stranded RNA) that inhibits or down regulates the expression of a target gene that encodes Snf7. US Patent Application publication 2011/0054007 describes polynucleotide silencing elements targeting RPS10. PCT publication WO 2016/205445 describes polynucleotide silencing elements that reduce fecundity, with target polynucleotides, including NCLB, MAEL, BOULE, and VgR. US Patent Application publication 2014/0275208 and US2015/0257389 describes polynucleotide silencing elements targeting RyanR and PAT3. PCT publications WO/2016/138106, WO 2016/060911, WO 2016/060912, WO 2016/060913, and WO 2016/060914 describe polynucleotide silencing elements targeting COPI coatomer subunit nucleic acid molecules that confer resistance to Coleopteran and Hemipteran pests. US Patent Application Publications 2012/029750, US 20120297501, and 2012/0322660 describe interfering ribonucleic acids (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene. US Patent Application Publication 2012/0164205 describe potential targets for interfering double stranded ribonucleic acids for inhibiting invertebrate pests including: a Chd3 Homologous Sequence, a Beta-Tubulin Homologous Sequence, a 40 kDa V-ATPase Homologous Sequence, a EF1α Homologous Sequence, a 26S Proteosome Subunit p28 Homologous Sequence, a Juvenile Hormone Epoxide Hydrolase Homologous Sequence, a Swelling Dependent Chloride Channel Protein Homologous Sequence, a Glucose-6-Phosphate 1-Dehydrogenase Protein Homologous Sequence, an Act42A Protein Homologous Sequence, a ADP-Ribosylation Factor 1 Homologous Sequence, a Transcription Factor IIB Protein Homologous Sequence, a Chitinase Homologous Sequences, a Ubiquitin Conjugating Enzyme Homologous Sequence, a Glyceraldehyde-3-Phosphate Dehydrogenase Homologous Sequence, an Ubiquitin B Homologous Sequence, a Juvenile Hormone Esterase Homolog, and an Alpha Tubuliln Homologous Sequence.

Use in Pesticidal Control

General methods for employing strains comprising a nucleic acid sequence of the embodiments or a variant thereof, in pesticide control or in engineering other organisms as pesticidal agents are known in the art.

Microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the gene(s) expressing one or more of the Cry toxin polypeptides and desirably provide for improved protection of the pesticide from environmental degradation and inactivation.

Alternatively, the Cry toxin polypeptide is produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated Cry toxin polypeptides may then be formulated in accordance with conventional techniques for application to the environment hosting a target pest, e.g., soil, water, and foliage of plants. See, for example EPA 0192319, and the references cited therein.

Pesticidal Compositions

In some embodiments the active ingredients can be applied in the form of compositions and can be applied to the crop area or plant to be treated, simultaneously or in succession, with other compounds. These compounds can be fertilizers, weed killers, Cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient or an agrochemical composition that contains at least one of the Cry toxin polypeptide(s) produced by the bacterial strains include leaf application, seed coating and soil application. The number of applications and the rate of application depend on the intensity of infestation by the corresponding pest.

The composition may be formulated as a powder, dust, pellet, granule, spray, emulsion, colloid, solution or such like, and may be prepared by such conventional means as desiccation, lyophilization, homogenation, extraction, filtration, centrifugation, sedimentation or concentration of a culture of cells comprising the polypeptide. In all such compositions that contain at least one such pesticidal polypeptide, the polypeptide may be present in a concentration of from about 1% to about 99% by weight.

Lepidopteran, Dipteran, Heteropteran, nematode, Hemiptera or Coleopteran pests may be killed or reduced in numbers in a given area by the methods of the disclosure or may be prophylactically applied to an environmental area to prevent infestation by a susceptible pest. Preferably the pest ingests or is contacted with, a pesticidally-effective amount of the polypeptide. "Pesticidally-effective amount" as used herein refers to an amount of the pesticide that is able to bring about death to at least one pest or to noticeably reduce pest growth, feeding or normal physiological development. This amount will vary depending on such factors as, for example, the specific target pests to be controlled, the specific environment, location, plant, crop or agricultural site to be treated, the environmental conditions and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, Crystal and/or spore suspension or isolated protein component with the desired agriculturally-acceptable carrier. The compositions may be formulated prior to administration in an appropriate means such as lyophilized, freeze-dried, desiccated or in an aqueous carrier, medium or suitable diluent, such as saline or other buffer. The formulated compositions may be in the form of a dust or granular material or a suspension in oil (vegetable or mineral) or water or oil/water emulsions or as a wettable powder or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523. The plants can also be treated with one or more chemical compositions, including one or more herbicide, insecticides or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halo sulfuron Gowan, Paraquat, Propyzamide, Sethoxydim, Butafenacil, Halosulfuron, Indaziflam; Fruits/Vegetables Insecticides: Aldicarb, *Bacillus thuriengiensis*, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, FluaCrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinotoram, Thiodicarb, Flonicamid, Methiocarb, Emamectin-benzoate, Indoxacarb, Forthiazate, Fenamiphos, Cadusaphos, Pyriproxifen, Fenbutatin-oxid, Hexthiazox, Methomyl, 4-[[(6-Chlorpyridin-3-yl)methyl](2,2-difluoroethyl)amino]furan-2(5H)-on; Fruits/Vegetables Fungicides: Carbendazim, Chlorothalonil, EBDCs, Sulphur, Thiophanate-methyl, Azoxystrobin, Cymoxanil, Fluazinam, Fosetyl, Iprodione, Kresoxim-methyl, Metalaxyl/mefenoxam, Trifloxystrobin, Ethaboxam, Iprovalicarb, Trifloxystrobin, Fenhexamid, Oxpoconazole fumarate, Cyazofamid, Fenamidone, Zoxamide, Picoxystrobin, Pyraclostrobin, Cyflufenamid, Boscalid; Cereals Herbicides: Isoproturon, Bromoxynil, Ioxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, Iodosulfuron, Propoxycarbazone, Picolinafen, Mesosulfuron, Beflubutamid, Pinoxaden, Amidosulfuron, Thifensulfuron Methyl, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoxim-methyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Metamidophos, Oxidemethonmethyl, Pirimicarb, Methiocarb; Maize Herbicides: Atrazine, Alachlor, Bromoxynil, Acetochlor, Dicamba, Clopyralid, (S-) Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumoron, Tefluthrin, Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino]furan-2(5H)-on, Carbofuran, Benfuracarb; Rice Fungicides: Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-) Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2 (5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Carbendazim, Fludioxonil, Iprodione, Prochloraz, Vinclozolin; Canola Insecticides: Carbofuran organophosphates, Pyrethroids, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

In some embodiments the herbicide is Atrazine, Bromacil, Diuron, Chlorsulfuron, Metsulfuron, Thifensulfuron Methyl, Tribenuron, Acetochlor, Dicamba, Isoxaflutole, Nicosulfuron, Rimsulfuron, Pyrithiobac-sodium, Flumioxazin, Chlorimuron-Ethyl, Metribuzin, Quizalofop, S-metolachlor, Hexazinne or combinations thereof.

In some embodiments the insecticide is Esfenvalerate, Chlorantraniliprole, Methomyl, Indoxacarb, Oxamyl or combinations thereof.

Pesticidal and Insecticidal Activity

"Pest" includes but is not limited to, insects, fungi, bacteria, nematodes, mites, ticks and the like. Insect pests include insects selected from the orders Coleoptera, Diptera, Hymenoptera, Lepidoptera, Mallophaga, Homoptera, Hemiptera Orthroptera, Thysanoptera, Dermaptera, Isoptera, Anoplura, Siphonaptera, Trichoptera, etc., particularly Lepidoptera and Coleoptera.

Those skilled in the art will recognize that not all compounds are equally effective against all pests. Compounds of the embodiments display activity against insect pests, which may include economically important agronomic, forest, greenhouse, nursery ornamentals, food and fiber, public and animal health, domestic and commercial structure, household and stored product pests.

Larvae of the order Lepidoptera include, but are not limited to, armyworms, cutworms, loopers and heliothines in the family Noctuidae *Spodoptera frugiperda* J E Smith (fall armyworm); *S. exigua* Hübner (beet armyworm); *S. litura* Fabricius (tobacco cutworm, cluster caterpillar); *Mamestra configurata* Walker (bertha armyworm); *M. brassicae* Linnaeus (cabbage moth); *Agrotis Ipsilon* Hufnagel (black cutworm); *A. orthogonia* Morrison (western cutworm); *A. subterranea* Fabricius (granulate cutworm); *Alabama argillacea* Hübner (cotton leaf worm); *Trichoplusia ni* Hübner (cabbage looper); *Pseudoplusia includens* Walker (soybean looper); *Anticarsia gemmatalis* Hübner (velvetbean caterpillar); *Hypena scabra* Fabricius (green cloverworm); *Heliothis virescens* Fabricius (tobacco budworm); *Pseudaletia unipuncta* Haworth (armyworm); *Athetis mindara* Barnes and Mcdunnough (rough skinned cutworm); *Euxoa messoria* Harris (darksided cutworm); *Earias insulana* Boisduval (spiny bollworm); *E. vittella* Fabricius (spotted bollworm); *Helicoverpa armigera* Hübner (American bollworm); *H. zea* Boddie (corn earworm or cotton bollworm); *Melanchra picta* Harris (zebra caterpillar); *Egira* (*Xylomyges*) *curialis* Grote (citrus cutworm); borers, casebearers, webworms, coneworms, and skeletonizers from the family Pyralidae *Ostrinia nubilalis* Hübner (European corn borer); *Amyelois transitella* Walker (naval orangeworm); *Anagasta kuehniella* Zeller (Mediterranean flour moth); *Cadra cautella* Walker (almond moth); *Chilo suppressalis* Walker (rice stem borer); *C. partellus*, (sorghum borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Eoreuma loftini* Dyar (Mexican rice borer); *Ephestia elutella* Hübner (tobacco (cacao) moth); *Galleria mellonella* Linnaeus (greater wax moth); *Herpetogramma licarsisalis* Walker (sod webworm); *Homoeosoma electellum* Hulst (sunflower moth); *Elasmopalpus lignosellus* Zeller (lesser cornstalk borer); *Achroia grisella* Fabricius (lesser wax moth); *Loxostege sticticalis* Linnaeus (beet webworm); *Orthaga thyrisalis* Walker (tea tree web moth); *Maruca testulalis* Geyer (bean pod borer); *Plodia interpunctella* Hübner (Indian meal moth); *Scirpophaga incertulas* Walker (yellow stem borer); *Udea rubigalis* Guenée (celery leaftier); and leafrollers, budworms, seed worms and fruit worms in the family Tortricidae *Acleris gloverana* Walsingham (Western blackheaded budworm); *A. variana* Fernald (Eastern blackheaded budworm); *Archips argyrospila* Walker (fruit tree leaf roller); *A. rosana* Linnaeus (European leaf roller); and other *Archips* species, *Adoxophyes orana* Fischer von Rösslerstamm (summer fruit tortrix moth); *Cochylis hospes* Walsingham (banded sunflower moth); *Cydia latiferreana* Walsingham (filbertworm); *C. pomonella* Linnaeus (coding moth); *Platynota flavedana* Clemens (variegated leafroller); *P. stultana* Walsingham (omnivorous leafroller); *Lobesia botrana* Denis & Schiffermüller (European grape vine moth); *Spilonota ocellana* Denis & Schiffermüller (eyespotted bud moth); *Endopiza viteana* Clemens (grape berry moth); *Eupoecilia ambiguella* Hübner (vine moth); *Bonagota salubricola* Meyrick (Brazilian apple leafroller); *Grapholita molesta* Busck (oriental fruit moth); *Suleima helianthana* Riley (sunflower bud moth); *Argyrotaenia* spp.; *Choristoneura* spp.

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Méneville (Chinese Oak Tussah Moth); *Bombyx mori* Linnaeus (Silkworm); *Bucculatrix thurberiella* Busck (cotton leaf perforator); *Colias eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Euproctis chrysorrhoea* Linnaeus (browntail moth); *Harrisina americana* Guérin-Méneville (grapeleaf skeletonizer); *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugrubrosa* Hulst (Western hemlock looper); *Leucoma salicis* Linnaeus (satin moth); *Lymantria dispar* Linnaeus (gypsy moth); *Manduca quinquemaculata* Haworth (five spotted hawk moth, tomato hornworm); *M. sexta* Haworth (tomato hornworm, tobacco hornworm); *Operophtera brumata* Linnaeus (winter moth); *Paleacrita vernata* Peck (spring cankerworm); *Papilio cresphontes* Cramer (giant swallowtail orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval and Leconte (Southern cabbageworm); *Sabulodes aegrotata* Guenée (omnivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta*

*absoluta* Meyrick (tomato leafminer); *Yponomeuta padella* Linnaeus (ermine moth); *Heliothis subflexa* Guenée; *Malacosoma* spp. and *Orgyia* spp.

Of interest are larvae and adults of the order Coleoptera including weevils from the families Anthribidae, Bruchidae and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); *Cylindrocopturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug)); flea beetles, cucumber beetles, rootworms, leaf beetles, potato beetles and leafminers in the family Chrysomelidae (including, but not limited to: *Leptinotarsa decemlineata* Say (Colorado potato beetle); *Diabrotica virgifera virgifera* LeConte (western corn rootworm); *D. barberi* Smith and Lawrence (northern corn rootworm); *D. undecimpunctata howardi* Barber (southern corn rootworm); *Chaetocnema pulicaria* Melsheimer (corn flea beetle); *Phyllotreta cruciferae* Goeze (Crucifer flea beetle); *Phyllotreta striolata* (stripped flea beetle); *Colaspis brunnea* Fabricius (grape colaspis); *Oulema melanopus* Linnaeus (cereal leaf beetle); *Zygogramma exclamationis* Fabricius (sunflower beetle)); beetles from the family Coccinellidae (including, but not limited to: *Epilachna varivestis* Mulsant (Mexican bean beetle)); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle)); carpet beetles from the family Dermestidae; wireworms from the family Elateridae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebrionidae.

Adults and immatures of the order Diptera are of interest, including leafminers *Agromyza parvicornis* Loew (corn blotch leafminer); midges (including, but not limited to: *Contarinia sorghicola* Coquillett (sorghum midge); *Mayetiola destructor* Say (Hessian fly); *Sitodiplosis mosellana* Géhin (wheat midge); *Neolasioptera murtfeldtiana* Felt, (sunflower seed midge)); fruit flies (Tephritidae), *Oscinella frit* Linnaeus (fruit flies); maggots (including, but not limited to: *Delia platura* Meigen (seedcorn maggot); *D. coarctata* Fallen (wheat bulb fly) and other *Delia* spp., *Meromyza americana* Fitch (wheat stem maggot); *Musca domestica* Linnaeus (house flies); *Fannia canicularis* Linnaeus, *F. femoralis* Stein (lesser house flies); *Stomoxys calcitrans* Linnaeus (stable flies)); face flies, horn flies, blow flies, *Chrysomya* spp.; *Phormia* spp. and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds) and other *Brachycera*, mosquitoes *Aedes* spp.; Anopheles spp.; *Culex* spp.; black flies *Prosimulium* spp.; *Simulium* spp.; biting midges, sand flies, sciarids, and other *Nematocera*.

Included as insects of interest are adults and nymphs of the orders Hemiptera and Homoptera such as, but not limited to, adelgids from the family Adelgidae, plant bugs from the family Miridae, cicadas from the family Cicadidae, leafhoppers, *Empoasca* spp.; from the family Cicadellidae, planthoppers from the families Cixiidae, Flatidae, Fulgoroidea, Issidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Asterolecanidae, Coccidae, Dactylopiidae, Diaspididae, Eriococcidae Ortheziidae, Phoenicococcidae and Margarodidae, lace bugs from the family Tingidae, stink bugs from the family Pentatomidae, cinch bugs, *Blissus* spp.; and other seed bugs from the family Lygaeidae, spittlebugs from the family Cercopidae squash bugs from the family Coreidae and red bugs and cotton stainers from the family Pyrrhocoridae.

Agronomically important members from the order Homoptera further include, but are not limited to: *Acyrthisiphon pisum* Harris (pea aphid); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacorthum solani* Kaltenbach (foxglove aphid); *Chaetosiphon fragaefolii* Cockerell (strawberry aphid); *Diuraphis noxia* Kurdjumov/Mordvilko (Russian wheat aphid); *Dysaphis plantaginea* Paaserini (rosy apple aphid); *Eriosoma lanigerum* Hausmann (woolly apple aphid); *Brevicoryne brassicae* Linnaeus (cabbage aphid); *Hyalopterus pruni* Geoffroy (mealy plum aphid); *Lipaphis erysimi* Kaltenbach (turnip aphid); *Metopolophium dirrhodum* Walker (cereal aphid); *Macrosiphum euphorbiae* Thomas (potato aphid); *Myzus persicae* Sulzer (peach-potato aphid, green peach aphid); *Nasonovia ribisnigri* Mosley (lettuce aphid); *Pemphigus* spp. (root aphids and gall aphids); *Rhopalosiphum maidis* Fitch (corn leaf aphid); *R. padi* Linnaeus (bird cherry-oat aphid); *Schizaphis graminum* Rondani (greenbug); *Sipha flava* Forbes (yellow sugarcane aphid); *Sitobion avenae* Fabricius (English grain aphid); *Therioaphis maculata* Buckton (spotted alfalfa aphid); *Toxoptera aurantii* Boyer de Fonscolombe (black citrus aphid) and *T. chricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly); *B. argentifolli* Bellows & Perring (silverleaf whitefly); *Dialeurodes citri* Ashmead (citrus whitefly); *Trialeurodes abuhloneus* (bandedwinged whitefly) and *T. vaporariorum* Westwood (greenhouse whitefly); *Empoasca fabae* Harris (potato leafhopper); *Laodelphax striatellus* Fallen (smaller brown planthopper); *Macrolestes quadrihneatus* Forbes (aster leafhopper); *Nephotettix cinticeps* Uhler (green leafhopper); *N. nigropictus* Stal (rice leafhopper); *Nilaparvata lugens* Stål (brown planthopper); *Peregrinus maidis* Ashmead (corn planthopper); *Sogatella furcifera* Horvath (white-backed planthopper); *Sogatodes orizicola* Muir (rice delphacid); *Typhlocyba pomaria* McAtee (white apple leafhopper); *Erythroneoura* spp. (grape leafhoppers); *Magicicada septendecim* Linnaeus (periodical cicada); *Icerya purchasi* Maskell (cottony cushion scale); *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla); *Trioza diospyri* Ashmead (persimmon psylla).

Agronomically important species of interest from the order Hemiptera include, but are not limited to: *Acrosternum hilare* Say (green stink bug); *Anasa tristis* De Geer (squash bug); *Blissus leucopterus leucopterus* Say (chinch bug); *Corythuca gossypii* Fabricius (cotton lace bug); *Cyrtopeltis modesta* Distant (tomato bug); *Dysdercus suturellus* Herrich-Schäffer (cotton stainer); *Euschistus servus* Say (brown stink bug); *E. variolarius* Palisot de Beauvois (one-spotted stink bug); *Graptostethus* spp. (complex of seed bugs); *Leptoglossus corculus* Say (leaf-footed pine seed bug); *Lygus lineolaris* Palisot de Beauvois (tarnished plant bug); *L. Hesperus* Knight (Western tarnished plant bug); *L. pratensis* Linnaeus (common meadow bug); *L. ruguhpennis* Poppius (European tarnished plant bug); *Lygocoris pabuhnus* Linnaeus (common green capsid); *Nezara viridula* Linnaeus (southern green stink bug); *Oebalus pugnax* Fabricius (rice stink bug); *Oncopeltus fasciatus* Dallas (large milkweed bug); *Pseudatomoscelis seriatus* Reuter (cotton fleahopper).

Furthermore, embodiments may be effective against Hemiptera such, *Calocoris norvegicus* Gmelin (strawberry bug); *Orthops campestris* Linnaeus; *Plesiocoris rugicollis* Fallen (apple capsid); *Cyrtopeltis modestus* Distant (tomato bug); *Cyrtopeltis notatus* Distant (suckfly); *Spanagonicus albofasciatus* Reuter (whitemarked fleahopper); *Diaphnocoris chlorionis* Say (honeylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus* Fabricius (four-lined plant bug); *Nysius ericae* Schilling (false chinch bug); *Nysius raphanus* Howard (false chinch bug); *Nezara viridula* Linnaeus (Southern green stink bug); *Eurygaster* spp.; *Coreidae* spp.; *Pyrrhocoridae* spp.; *Tinidae* spp.; *Blostomatidae* spp.; *Reduviidae* spp. and *Cimicidae* spp.

Also included are adults and larvae of the order Acari (mites) such as *Aceria tosichella* Keifer (wheat curl mite); *Petrobia latens* Müller (brown wheat mite); spider mites and red mites in the family Tetranychidae, *Panonychus ulmi* Koch (European red mite); *Tetranychus urticae* Koch (two spotted spider mite); (*T. mcdanieli* McGregor (McDaniel mite); *T. cinnabarinus* Boisduval (carmine spider mite); *T. turkestani* Ugarov & Nikolski (strawberry spider mite); flat mites in the family Tenuipalpidae, *Brevipalpus lewisi* McGregor (citrus flat mite); rust and bud mites in the family Eriophyidae and other foliar feeding mites and mites important in human and animal health, i.e., dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick) and scab and itch mites in the families Psoroptidae, Pyemotidae and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch and Mulaik (brown recluse spider) and the *Latrodectus mactans* Fabricius (black widow spider) and centipedes in the order Scutigeromorpha such as *Scutigera coleoptrata* Linnaeus (house centipede).

Insect pest of interest include the superfamily of stink bugs and other related insects including but not limited to species belonging to the family Pentatomidae (*Nezara viridula, Halyomorpha halys, Piezodorus guildini, Euschistus servus, Acrosternum hilare, Euschistus heros, Euschistus tristigmus, Acrosternum hilare, Dichelops furcatus, Dichelops melacanthus*, and *Bagrada hilaris* (Bagrada Bug)), the family Plataspidae (*Megacopta cribraria*—Bean plataspid) and the family Cydnidae (*Scaptocoris castanea*—Root stink bug) and Lepidoptera species including but not limited to: diamond-back moth, e.g., *Helicoverpa zea* Boddie; soybean looper, e.g., *Pseudoplusia includens* Walker and velvet bean caterpillar e.g., *Anticarsia gemmatalis* Hübner.

Methods for measuring pesticidal activity are well known in the art. See, for example, Czapla and Lang, (1990) *J. Econ. Entomol.* 83:2480-2485; Andrews, et al., (1988) *Biochem. J.* 252:199-206; Marrone, et al., (1985) *J. of Economic Entomology* 78:290-293 and U.S. Pat. No. 5,743,477. Generally, the protein is mixed and used in feeding assays. See, for example Marrone, et al., (1985) *J. of Economic Entomology* 78:290-293. Such assays can include contacting plants with one or more pests and determining the plant's ability to survive and/or cause the death of the pests.

Nematodes include parasitic nematodes such as root-knot, cyst and lesion nematodes, including *Heterodera* spp., *Meloidogyne* spp. and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode) and *Globodera rostochiensis* and *Globodera pailida* (potato cyst nematodes). Lesion nematodes include *Pratylenchus* spp.

Seed Treatment

To protect and to enhance yield production and trait technologies, seed treatment options can provide additional crop plan flexibility and cost effective control against insects, weeds and diseases. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematocides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., Published by the British Crop Production Council.

Some seed treatments that may be used on crop seed include, but are not limited to, one or more of abscisic acid, acibenzolar-S-methyl, avermectin, amitrol, azaconazole, azospirillum, azadirachtin, azoxystrobin, *Bacillus* spp. (including one or more of *cereus, firmus, megaterium, pumilis, sphaericus, subtilis* and/or *thuringiensis* species), *bradyrhizobium* spp. (including one or more of *betae, canariense, elkanii, iriomotense, japonicum, liaonigense, pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB, penflufen, penicillium, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, trichoderma, trifloxystrobin, triticonazole and/or zinc. PCNB seed coat refers to EPA Registration Number 00293500419, containing quintozen and terrazole. TCMTB refers to 2-(thiocyanomethylthio) benzothiazole.

Seed varieties and seeds with specific transgenic traits may be tested to determine which seed treatment options and application rates may complement such varieties and transgenic traits in order to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

Methods for Killing an Insect Pest and Controlling an Insect Population

In some embodiments methods are provided for killing an insect pest, comprising contacting the insect pest, either simultaneously or sequentially, with an insecticidally-effective amount of a recombinant Cry toxin polypeptide of the disclosure. In some embodiments methods are provided for killing an insect pest, comprising contacting the insect pest with an insecticidally-effective amount of one or more of a recombinant pesticidal protein of SEQ ID NOS: 57-112, 214-246, and 275-278, or a variant or insecticidally active fragment thereof.

In some embodiments methods are provided for controlling an insect pest population, comprising contacting the insect pest population, either simultaneously or sequentially, with an insecticidally-effective amount of one or more of a recombinant Cry toxin polypeptide of the disclosure. In some embodiments, methods are provided for controlling an insect pest population, comprising contacting the insect pest population with an insecticidally-effective amount of one or more of a recombinant Cry toxin polypeptide of SEQ ID NOS: 57-112, 214-246, and 275-278, or a variant or insecticidally active fragment thereof. As used herein, "controlling a pest population" or "controls a pest" refers to any effect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack or deterring the pests from eating the plant.

In some embodiments methods are provided for controlling an insect pest population resistant to a pesticidal protein, comprising contacting the insect pest population, either simultaneously or sequentially, with an insecticidally-effective amount of one or more of a recombinant Cry toxin polypeptide of the disclosure. In some embodiments, methods are provided for controlling an insect pest population resistant to a pesticidal protein, comprising contacting the insect pest population with an insecticidally-effective amount of one or more of a recombinant Cry toxin polypeptide of SEQ ID NOS: 57-112, 214-246, and 275-278, or a variant or insecticidally active fragment thereof.

In some embodiments methods are provided for protecting a plant from an insect pest, comprising expressing in the plant or cell thereof at least one recombinant polynucleotide encoding a Cry toxin polypeptide of the disclosure. In some embodiments methods are provided for protecting a plant from an insect pest, comprising expressing in the plant or cell thereof a recombinant polynucleotide encoding one or more Cry toxin polypeptides of SEQ ID NOS: 57-112, 214-246, and 275-278, or variants or insecticidally active fragments thereof.

Insect Resistance Management (IRM) Strategies

Expression of B. thuringiensis δ-endotoxins in transgenic corn plants has proven to be an effective means of controlling agriculturally important insect pests (Perlak, et al., 1990; 1993). However, in certain instances insects have evolved that are resistant to B. thuringiensis δ-endotoxins expressed in transgenic plants. Such resistance, should it become widespread, would clearly limit the commercial value of germplasm containing genes encoding such B. thuringiensis δ-endotoxins.

One way of increasing the effectiveness of the transgenic insecticides against target pests and contemporaneously reducing the development of insecticide-resistant pests is to use non-transgenic (i.e., non-insecticidal protein) refuges (a section of non-insecticidal crops/corn) with transgenic crops producing a single insecticidal protein active against target pests. The United States Environmental Protection Agency (epa.gov/oppbppdl/biopesticides/pips/bt_corn_refuge_2006.htm, which can be accessed using the www prefix) publishes the requirements for use with transgenic crops producing a single Bt protein active against target pests. In addition, the National Corn Growers Association, on their website: (ncga.com/insect-resistance-management-fact-sheet-bt-corn, which can be accessed using the www prefix) also provides similar guidance regarding refuge requirements. Due to losses to insects within the refuge area, larger refuges may reduce overall yield.

Another way of increasing the effectiveness of the transgenic insecticides against target pests and contemporaneously reducing the development of insecticide-resistant pests would be to have a repository of insecticidal genes that are effective against groups of insect pests and which manifest their effects through different modes of action.

Expression in a plant of two or more insecticidal compositions toxic to the same insect species, each insecticide being expressed at efficacious levels would be another way to achieve control of the development of resistance. This is based on the principle that evolution of resistance against two separate modes of action is far more unlikely than only one. Roush, for example, outlines two-toxin strategies, also called "pyramiding" or "stacking," for management of insecticidal transgenic crops. (The Royal Society. Phil. Trans. R. Soc. Lond. B. (1998) 353:1777-1786). Stacking or pyramiding of two different proteins each effective against the target pests and with little or no cross-resistance can allow for use of a smaller refuge. The US Environmental Protection Agency requires significantly less (generally 5%) structured refuge of non-Bt corn be planted than for single trait products (generally 20%). There are various ways of providing the IRM effects of a refuge, including various geometric planting patterns in the fields and in-bag seed mixtures, as discussed further by Roush.

In some embodiments the Cry toxin polypeptides of the disclosure are useful as an insect resistance management strategy in combination (i.e., pyramided) with other pesticidal proteins or other transgenes (i.e., an RNAi trait) including but not limited to Bt toxins, Xenorhabdus sp. or Photorhabdus sp. insecticidal proteins, other insecticidally active proteins, and the like.

Provided are methods of controlling Lepidoptera and/or Coleoptera insect infestation(s) in a transgenic plant that promote insect resistance management, comprising expressing in the plant at least two different insecticidal proteins having different modes of action.

In some embodiments the methods of controlling Lepidoptera and/or Coleoptera insect infestation in a transgenic plant and promoting insect resistance management comprises the presentation of at least one of the Cry toxin polypeptide insecticidal proteins to insects in the order Lepidoptera and/or Coleoptera.

In some embodiments the methods of controlling Lepidoptera and/or Coleoptera insect infestation in a transgenic plant and promoting insect resistance management comprises the presentation of at least one of the Cry toxin polypeptides of SEQ ID NOS: 57-112, 214-246, and 275-278, or variants or insecticidally active fragments thereof, insecticidal to insects in the order Lepidoptera and/or Coleoptera.

Also provided are methods of reducing likelihood of emergence of Lepidoptera and/or Coleoptera insect resistance to transgenic plants expressing in the plants insecticidal proteins to control the insect species, comprising expression of at least one of a Cry toxin polypeptide insecticidal to the insect species in combination with a second insecticidal protein to the insect species having different modes of action.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with a pest against which the polypeptide has pesticidal activity. In some embodiments, the polypeptide has pesticidal activity against a Lepidopteran, Coleopteran, Dipteran, Hemipteran or nematode pest, and the field is infested with a Lepidopteran, Hemipteran, Coleopteran, Dipteran or nematode pest.

As defined herein, the "yield" of the plant refers to the quality and/or quantity of biomass produced by the plant. "Biomass" as used herein refers to any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

In specific methods, plant yield is increased as a result of improved pest resistance of a plant expressing at least one Cry toxin polypeptide disclosed herein. Expression of the Cry toxin polypeptide(s) results in a reduced ability of a pest to infest or feed on the plant, thus improving plant yield.

Methods of Processing

Further provided are methods of processing a plant, plant part or seed to obtain a food or feed product from a plant, plant part or seed comprising at least one Cry toxin polynucleotide. The plants, plant parts or seeds provided herein, can be processed to yield oil, protein products and/or by-products that are derivatives obtained by processing that have commercial value. Non-limiting examples include transgenic seeds comprising a nucleic acid molecule encoding one or more Cry toxin polypeptides which can be processed to yield soy oil, soy products and/or soy by-products.

"Processing" refers to any physical and chemical methods used to obtain any soy product and includes, but is not limited to, heat conditioning, flaking and grinding, extrusion, solvent extraction or aqueous soaking and extraction of whole or partial seeds The following examples are offered by way of illustration and not by way of limitation.

EXAMPLES

Example 1: Synthesis of Various Cry Toxin Domain Fragments

Whole domain fragments (Dm1, Dm2 and Dm3) of 42 holotype Cry toxins were optimized for *E. coli* expression and synthesized (See FIG. 1). All domain fragments were cloned into pUC19 sub cloning for expression. These fragments were used as starting materials for many of block shuffling libraries. All holotype Cry toxin protein information was obtained from NCBI Gen Bank, Crickmore, et al., "*Bacillus thuringiensis* toxin nomenclature" (2011), at life-sci.sussex.ac.uk/home/Neil_Crickmore/Bt/ which can be accessed on the world-wide web using the "www" prefix, and btnomenclature.info/ which can be accessed on the world-wide web using the "www" prefix. Table 1 lists holotype toxin fragments that were synthesized.

TABLE 1

Holotype Bt Toxin Synthesized Fragments
List of Cry1 and Cry9 holotype (WT)
synthesized as domain fragments Cry1Aa
Cry1Ab
Cry1Ac
Cry1Ad
Cry1Ae
Cry1Af
Cry1Ag
Cry1Ah
Cry1Ai
Cry1Ba
Cry1Bb
Cry1Bd
Cry1Be
Cry1Bf
Cry1Bg
Cry1Bh
Cry1Ca
Cry1Cb
Cry1Da
Cry1Db
Cry1Dc
Cry1Ea
Cry1Eb
Cry1Fa
Cry1Fb
Cry1Ga
Cry1Gb
Cry1Gc
Cry1Ha
Cry1Hb
Cry1Ia
Cry1Ib
Cry1Ic
Cry1Id
Cry1Ie
Cry1If
Cry1Ka
Cry1La TABLE 1-continued

| Holotype Bt Toxin Synthesized Fragments List of Cry1 and Cry9 holotype (WT) synthesized as domain fragments |
|---|
| Cry1Ma |
| Cry9Aa |
| Cry9Ba |
| Cry9Bb |
| Cry9Ca |
| Cry9Da |
| Cry9Db |
| Cry9Ea |
| Cry9Eb |
| Cry9Ec |
| Cry9Ed |

Example 2: Vector Insert and Backbone Assembly

PCR products for the inserts (Domain 1, 2, or 3, or sub domain fragments) were amplified using Q5 High-Fidelity DNA Polymerase (NEB M0491L), while plasmid backbones were amplified using Phusion High-Fidelity DNA Polymerase (ThermoFisher F530L or NEB M0530L), following the instructions for recommended temperatures and cycles in the respective DNA polymerase's protocol.

All libraries were cloned into pMAL vector pVER6805 to be expressed as His-MBP-toxin configuration. Following production of the insert (Dm1, 2 and 3) PCR fragments, the vector backbone (8 to 9 kb in length excluding the insert portion) containing His+MBP and additional essential vector elements were produced by inverse PCR.

Inserts and backbones were assembled into plasmids primarily with NEBuilder HiFi DNA Assembly Master Mix (NEB E2621L), using 10 ul reactions, which were scaled down from the original 20 ul protocol, and following the recommended incubation temperature and length.

NEBuilder assembly reactions were diluted 1:2 with deionized water and 1 ul was used in the transformation of 50 ul of electro competent BL21(DE3) cells (Lucigen E. cloni EXPRESS 60300-2) diluted 1:8. Alternatively, the GeneArt Seamless Cloning and Assembly Kit (Invitrogen A13288) was occasionally used for the assembly of inserts and backbones, following the directions for the reaction. For the transformation, 10 ul of the reaction was added to 50 ul of Invitrogen One Shot Chemically Competent TOP10 cells (included with the kit). Cultures were grown and plasmid DNA was prepared using a Miniprep Kit (Qiagen 27104). The plasmid DNA was then used to transform 50 ul of chemically competent BL21-Gold (DE3) cells (Agilent 230132).

BL21 cells were plated onto LB agar plates with carbenicillin selection at 100 ug/ml and grown overnight at 37 C. Starter cultures of 150-160 ul LB carb (100 ug/ml) were inoculated and grown overnight, shaking at 37 C. Magic Media cultures (Invitrogen K6803) were grown in deep-well plate format with 1 ml of Magic Media inoculated with 20 ul of starter culture. The Magic Media plates were cultured at 25 C for 8 hours, then 16 C for 64 hours, shaking at 250 rpm. The plates were spun at 4000 rpm for 15 minutes. The supernatant was discarded, a steel ball was added to each well and the plates were stored at −80 C overnight.

The plates were vortexed until the cell pellets were re-suspended and then shaken 250 rpm at 37 C for 1.5 to 2 hours. After storage at −80 C overnight, the plates were thawed and the steel balls removed with a large magnet, followed by a spin at 4000 rpm for 20 minutes at 4 C.

To prepare the samples for Western analysis, 7.5 ul of supernatant plus 7.5 ul of deionized water were combined with 5 ul of E-PAGE sample loading buffer (included with Invitrogen E-PAGE 96-well 6% gels EP09606) with 4% beta mercaptoethanol added. The samples were heated 70 C for 10 minutes and spun for 5 min at 4000 rpm at 4 C. A 96-well E-PAGE gel was then loaded with 5 ul of samples plus 15 ul of deionized water, along with 5 ul of E-PAGE See Blue Pre-Stained Standard (Invitrogen LC5700) plus 15 ul of deionized water. The gel was run on program EP of the E-Base gel device (Invitrogen EBM03 and EBD03) for 20 minutes.

The iBlot2 system (Invitrogen IB21001) was used to transfer the proteins from the gel to a nitrocellulose membrane (Invitrogen IB23001) according to the manufacturer's directions. The membrane was blocked with SuperBlock T20 (TBS) Blocking Buffer (ThermoFisher 37536) for an hour at room temperature and then incubated overnight at 4 C with Sigma Monoclonal Anti-Maltose Binding Protein-Alkaline Phosphatase antibody produced in mouse (A3963-5ML) diluted 1:2000 in SuperBlock T20. After 3 10-minute washes with TBS-T (0.05% Tween-20), the blots were developed with Bio-Rad Alkaline Phosphatase Conjugate Substrate Kit (170-6432) according to the manufacturer's protocol. Proteins that appeared to have good expression profiles were then advanced to screening by insect assay.

For production of the proteins that were advanced after expression screening, glycerol stocks were stamped onto LB carb (100 ug/ml) and incubated at 30 C or 37 C overnight. Colonies from these plates were used to inoculate 3 ml LB carb (100 ug/ml) starter cultures grown 37 C overnight. Magic Media cultures (Invitrogen K6803) of 100 ml to 200 ml were inoculated with 1 ml to 2 ml starter cultures, respectively (i.e., 1% of final volume) and shaken 25 C for 8 hours, then 16 C for 64 hours at 250 rpm. The cultures were spun down at 9000 rpm 10 min 4 C.

Shuffled insecticidal proteins ("IPRS" polypeptides or proteins) were expressed in a modified pMAL vector (Cat #E8000S from New England Biolabs) as a fusion with MBP (maltose binding protein). The pMAL vector was modified to attach a 6× His tag to the N-terminal end of MBP after methionine at position 1. The plasmid containing the insecticidal protein gene was cloned in *E. coli* BL21 (DE3). The BL21 cells were grown in MagicMedia™ (Life Technologies) in either 96 deep well plates or flasks in a shaker running at 250 rpm at 37° C. for 8 hrs followed by 16° C. for 64 hrs. During the 16° C. incubation, the MBP-toxin fusion protein was accumulated in the BL21 cell as a soluble protein.

In order to purify the fusion protein, the *E. coli* cells were harvested by centrifugation and treated in a lysozyme solution consisting of 2 mg/ml lysozyme in 50 ml sodium phosphate buffer at pH8 containing 300 mM NaCl, 2 U/ml endonuclease (Epicentre) and 5 mM MaCl2 for 3 hrs at 37° C. with gentle shaking. The lysozyme treated *E. coli* cells were then disrupted with 1% Triton X100 and clear lysate containing the toxins were prepared by centrifugation at 4000 rpm, 30 min (96 well plates) or 9000 rpm (flask produced samples). His tagged MBP-toxin proteins were purified from the clear lysate by affinity chromatography using NiNTA agarose from Qiagen™ following the manufacturer's standard procedure. For those clear lysate samples made in 96 well plates, Pall Corporation™ (25 Harbor Park Drive Port Washington, NY 11050) 96 deep well filter plates were used as affinity chromatography columns. The purified toxin proteins eluted from NiNTA agarose was passed through Sephadex G25 to change the phosphate buffer to 25 mM HEPES-NaOH, pH8 and used in insect bioassay for determining the insecticidal. MBP was digested with 1/100 (w/w) Factor Xa (New England Biolabs) at 25° C. for overnight and removed from the toxins by Superdex 200 column chromatography utilizing the size difference and a weak affinity of MBP to Superdex.

Protein concentrations were determined by capillary electrophoresis with the LabChip™ GXII device (Caliper Life-Sciences). The protein analysis was repeated at least 3 times until the final concentrations were considered to be reliable within the predetermined deviation, less than 10%.

The activity of IPRS polypeptide variants against major corn pests, European Corn Borer (ECB, *Ostrinia nubilalis*), Corn Earworm (ECW, *Helicoverpa zea*) and Fall Armyworm (FAW, *Spodoptera frugiperda*), was determined by feeding assay as described by Cong, R., et al. Proceedings of the 4th Pacific Rim Conferences on Biotechnology of *Bacillus thuringiensis* and its environmental impact, pp. 118-123, ed. by R. J. Akhurst, C. E. Beard and P. Hughes, published in 2002, Canberra, Australia. Briefly, the assays were conducted on an artificial diet containing the insecticidal proteins. The insecticidal proteins were prepared as described in Example 1, and 10 μL of protein samples were mixed with 40 μL of molten (40-50° C.) artificial insect diet prepared based on Southland Premix formulated for Lepidopteran insects (Southland Products, Lake Village, AR) with low temperature melting agarose. The diet-insecticidal protein mixture was placed in each well of a 96 well micro-titer plate. One or more neonate insect larvae were placed in each well to feed for 4 days for CEW and FAW and 5 days for ECB at 28° C.

Example 3: Cry1J Alpha Loop 3-5 Shuffling (for IPRS hits C21 and C51)

Figure 5:
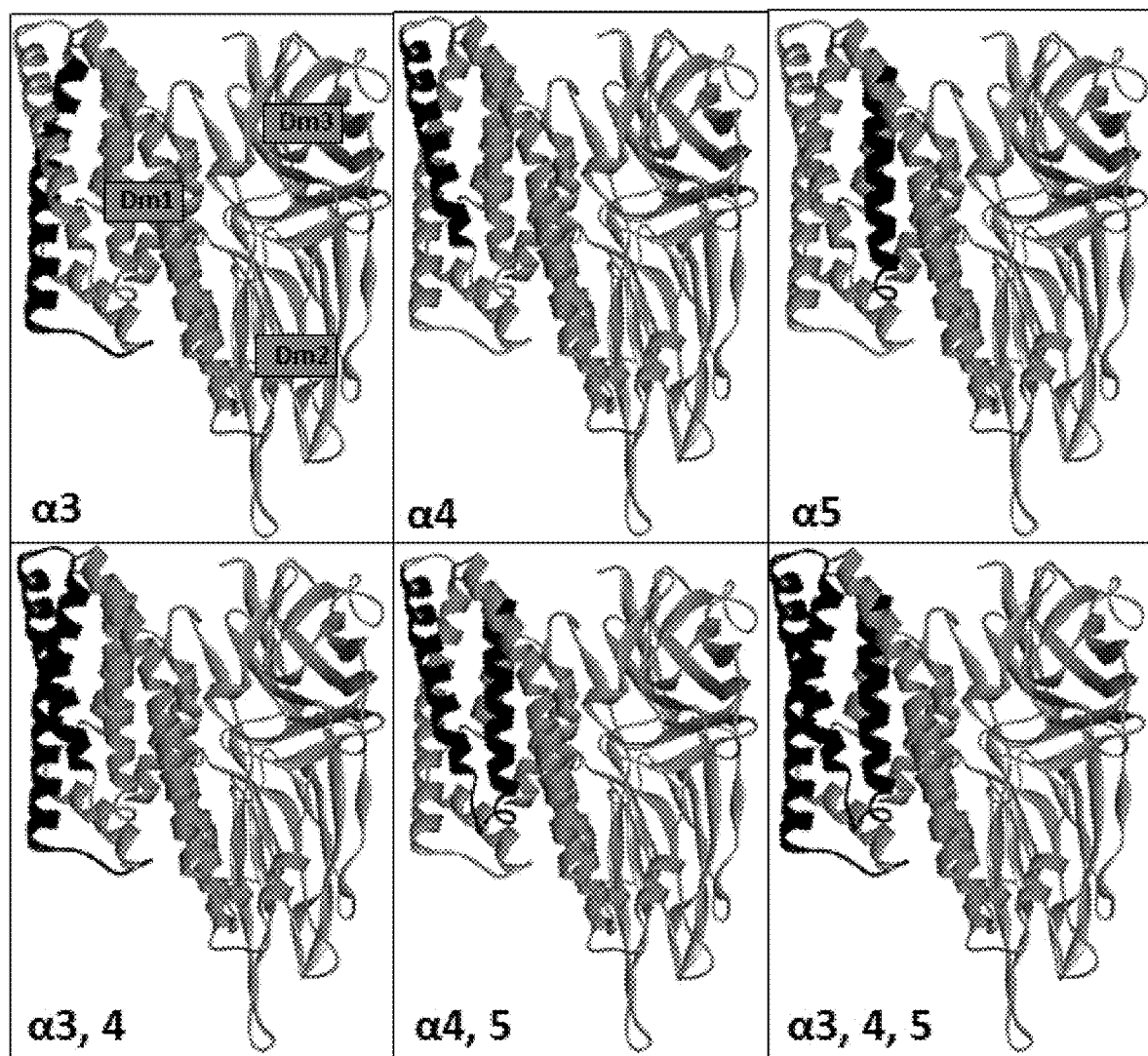
FIG. 5 shows a homology model of IPRS-C16 with different domains labeled. Shuffled alpha helices (both individual and combinations) are indicated in black and the remainder of the protein (rest of the Dm1, Dm2 and Dm3) is colored in gray. Alpha shuffling was done in IPRS-C16 and IPRS-C21.
Figure 6:
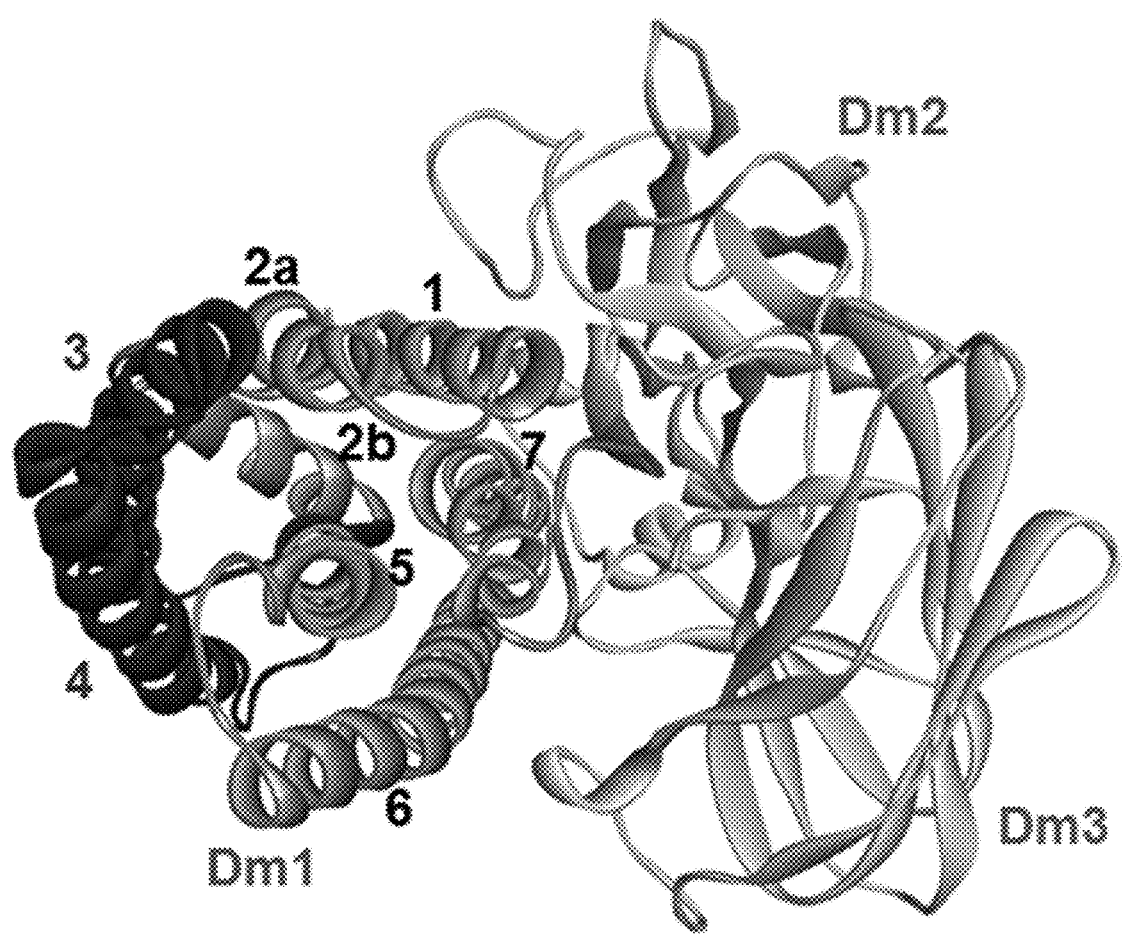
FIG. 6 shows a homology model (top view image) of IPRS-C16 showing the shuffled fragment of Dm1 (Alpha-3, Alpha-4 and part of Alpha-5 fragment) colored in black. Different alpha helices and domains are labeled. Location of helices was determined based on alignment of multiple Cry toxins and X-ray structural information of known Cry toxins.
Figure 9:
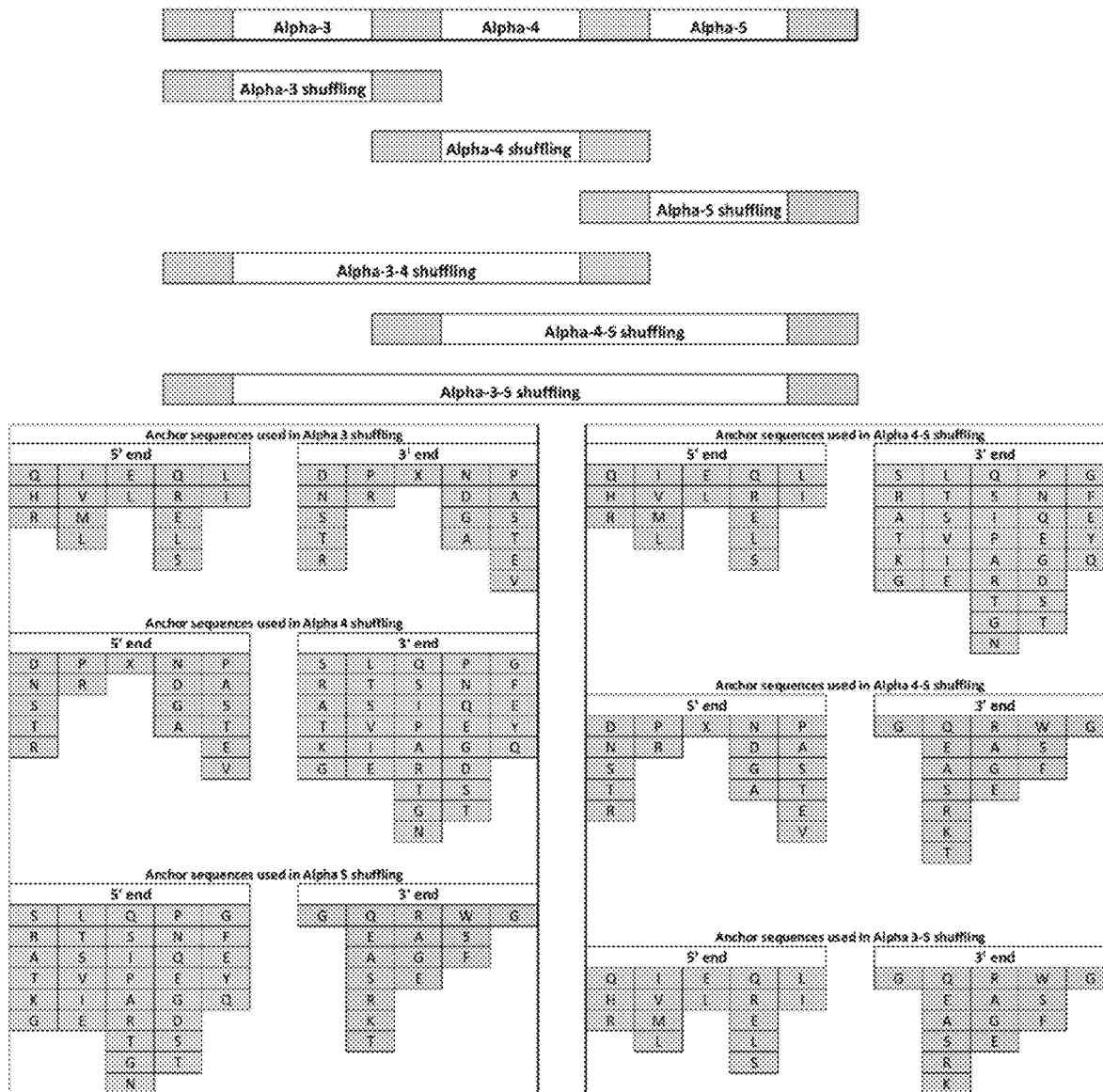
FIG. 9 shows fragments of Dm1 (Alpha loops 3, 4, 5, 3-4, 4-5, and 3-5) shuffled as described in the Examples. Shaded areas are anchor sequences where the shuffled fragment was fused to the backbone. Usually, the 5' anchor sequence motifs are QIEQL (SEQ ID NO: 247, for shuffling of alpha helix-3, 4&5 and 3&5), DPXNP (SEQ ID NO: 248, for shuffling alpha-4, 4&5) and SLQPG (SEQ ID NO: 249, for shuffling alpha-5). 3' anchor sequence motifs are DPXNP (SEQ ID NO: 248, for shuffling of alpha-3), SLQPG (SEQ ID NO: 249, for shuffling alpha-3&4) and GQRWG (SEQ ID NO: 268, for shuffling alpha-5, 4&5 and 3&5). Diversity at each of these anchor sequence positions was also listed below the normal anchor sequence motif in columns.

Whole domain 1 (Dm1) shuffling often resulted in very low soluble expression. Instead, data suggests the region encompassing alpha loops 3 to 5 of Dm has 1) minimal interaction with rest of the protein; and, 2) is exposed to solvent, was shuffled (See Tables 2, 3, and 10, and FIGS. 5 and 6). Therefore, shuffling of alpha loop 3-5 regions were predicted to have an impact on solubility of the shuffled polypeptides, as well as potentially altering insectidal activities. As a proof of concept library, two small libraries were made. In each library, the alpha loop 3-5 region of Cry1Jc and Cry1Ja was swapped with both the Cry1Ca and Cry1Ah Alpha loop 3-5 regions. The consensus region between QIEQL (SEQ ID NO: 247, at the end of alpha loop 2B) and ANLHL (SEQ ID NO: 251, in the middle of alpha loop 5) of the Dm1 was selected to shuffle. These five amino acid stretches (SEQ ID NOs: 247 and 251) are highly conserved among several Cry1 toxins (See FIGS. 8 and 9). Consensus regions between alpha loops 3 and 4 (SEQ ID NO: 248), and alpha loops 4 and 5 (SEQ ID NO: 249) were also identified for potential chimeric alpha loop swapping. In addition to Alpha loop 3-5 swapping, Domain 3 of Cry1Jc and Cry1Ja was also swapped with Domain 3 of Cry1Ac and Cry1Ca (see FIGS. 8 and 9). Total library size was 6 with 12 constructs in total for two backbones (See FIG. 2). All 12 constructs for the library were synthesized as described in Example 2. Alpha loop 3-5 amino acid sequence regions of various Cry toxins used in shuffling are set forth in SEQ ID NOs: 159-180 (encoded by DNA sequences as set forth in SEQ ID NOs: 137-158, respectively).

In order to express these genes as MBP-fusion proteins, they were cloned into pMal vector. Toxin sequences were PCR amplified from pUC19 vectors. Vector backbone was obtained by inverse PCR pMal vector. Then, both insert and vector backbones were ligated using homology based cloning kit Geneart and NEBuilder. These twelve clones were transformed into BL21 *E. Coli* cells and proceeded for protein purification directly without checking for expression.

Proteins were purified, quantified and submitted for insect assay against CEW and FAW. Initial testing was done for a Yes/No assay to assess activity. Based on initial results, selected clones were submitted for a dose response assay for specific activity. Later, the active clone(s) were tested for their activity against other lepidopteran pests (SBL, VBC and ECB) to determine their activity spectrum (See Table 2).

TABLE 2

Activity spectrum of active clones

| SEQ ID NO: | Variant name | Toxin Composition | | | | | Activity (ppm) | | | | | | |
|---|---|---|---|---|---|---|---|---|---|---|---|---|---|
| | | Dm1 | | | Dm2 | Dm3 | CEW | | FAW | | ECB | SBL | VBC |
| | | α1-2 | α3-5 | α6-7 | | | IC50 | LC50 | IC50 | LC50 | ILC50 | ILC50 | ILC50 |
| 88 | IPRS-C21 | Jc | Ca | Jc | Jc | Jc | 1.34 | 19.88 | N.A | | 1.91 | <1 | ~4000 |
| 87 | IPRS-C51 | Ja | Ca | Ja | Jc | Ja | N.A | | 376.73 | N.M | N.D | | |

*N.A. means not active as tested; N.M. means no mortality as tested; and N.D. means not determined

Example 4: Dm1 Alpha Loop 3-5 and Dm3 Shuffling on Cry1Ea Backbone for IPRS Hits: IPRS-C13, IPRS-14, IPRS-15, IPRS-16, IPRS-17, IPRS-19 and IPRS-31

Based on the success of alpha loop 3-5 library of 1Jc backbone, a library was designed to shuffle several hybrid domain 1 (Dm1) domains with Cry1Ea domain 2 (Dm2) and Cry1Ca domain 3 (Dm3) at three different cross over points having different lengths of hybrid domain 3. The hybrid Dm1s are similar to each other, except at alpha 3-5 region. Along with 9 hybrid Dm1s, three Cry1Ea-like Dm1s were also used in shuffling.

Eleven Dm1s (Two Cry1Ea-like Dm1s and 9 hybrid Dm1s) and three Cry1Ea Dm2-Cry1Ca Dm3 fragments (Cry1Ea Dm2 and Cry1Ca Dm3 fused at three different crossover points) were synthesized. Three libraries (ECF2, 3 and 4) were constructed (See FIG. 3). In the ECF2 library, 11 Dm1s were shuffled with Cry1Ea Dm2 and Cry1Ca Dm3. Cry1Ea Dm2 was fused with Cry1Ca Dm3 at crossover region 1 in Dm3 (SEQ ID NO: 251). In the ECF3 library, 11 Dm1s were shuffled with Cry1Ea Dm2 and Cry1Ca Dm3. Cry1Ea Dm2 was fused with Cry1Ca Dm3 at consensus crossover region 2 in Dm3 (SEQ ID NO: 252). In the ECF4 library, 11 Dm1s were shuffled with Cry1Ea Dm2 and Cry1Ca Dm3. Cry1Ea Dm2 was fused with Cry1Ca Dm3 at consensus crossover region 3 in Dm3 (SEQ ID NO: 253).

In order to express these genes as MBP-fusion proteins, all three libraries were made in pMal vector. The Dm1s and three Dm2-Dm3 fragments were PCR amplified from pUC19 vectors. Vector backbone was obtained by inverse PCR of pMal vector backbone. Then, both insert (Dm1, Dm2-Dm2) and vector backbones were assembled using homology based cloning kit Geneart and NEBuilder.

All 33 clones (11 clones/library) were sequence confirmed and transformed into BL21 *E. coli* cells and checked for expression using western blot. All 22 clones that were expressed grown in 200 ml cultures and proteins were purified, quantified and submitted for insect assay against FAW. Selected clones based on initial testing results were submitted for a dose response assay to get specific activity. Later, the most active clone under test conditions (IPRS-C16, SEQ ID NO: 62) was tested for its activity against other lepidopteran pests (SBL, VBC and ECB), along with certain other clones, to determine their activity spectra (See Tables 3 and 4).

Figure 4:
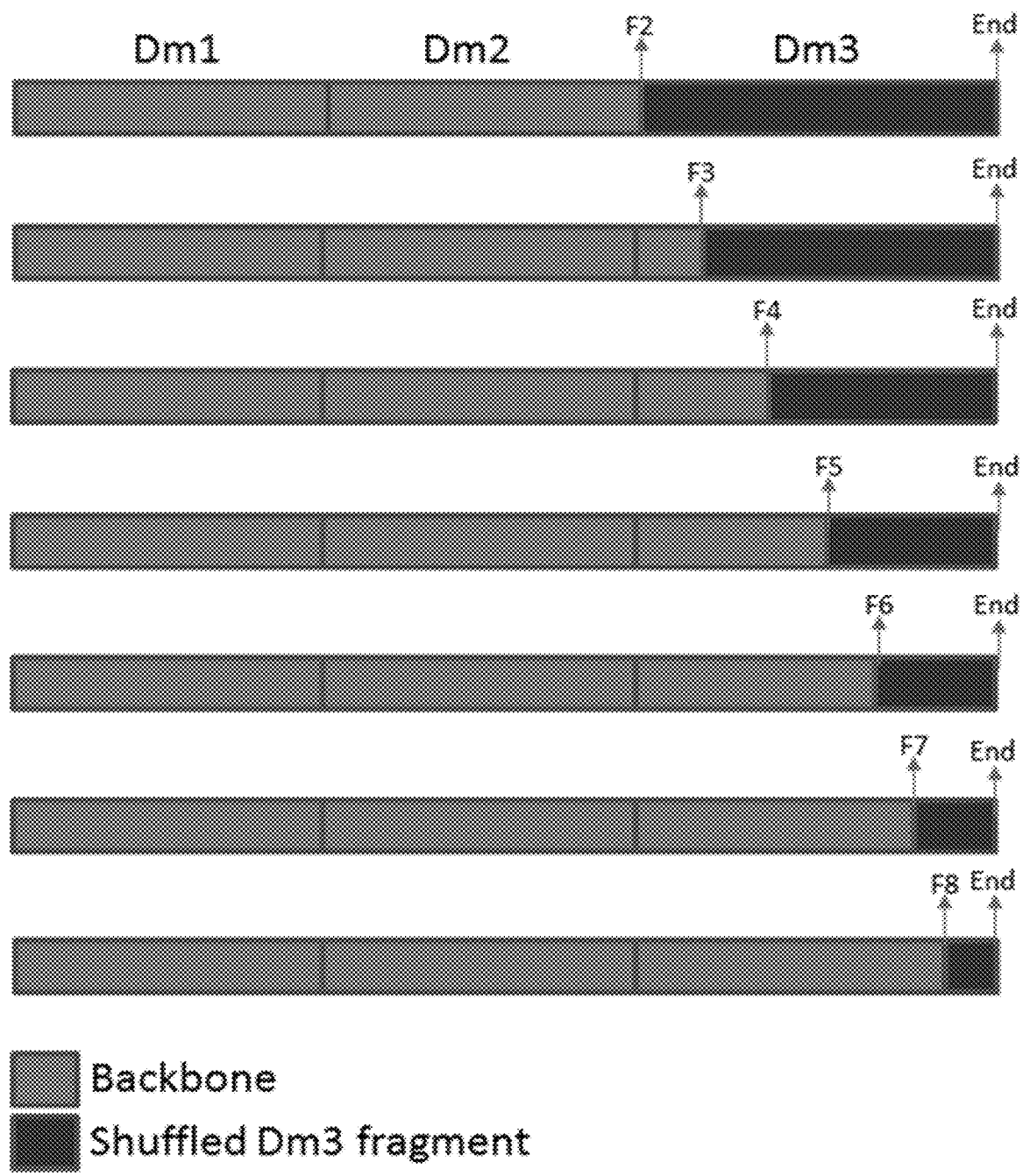
FIG. 4 shows a representation of an alignment of several Cry toxins with seven different cross over regions between Dm2 and Dm3 or just within Dm3, which are used as recombination sites for Dm3 fusions on C16, C18 and C21 Dm1-Dm2 backbones. Dm3 shuffling was done by fusing Dm3s to Dm1-Dm2 backbone at different crossover (fusion) points. Crossover points are labeled as F2 to F8 (SEQ ID NOs: 251-257).

53 different synthesized Cry toxin domain-3s were selected as sources of diversity. Seven fragments (crossover consensus regions 1-7, SEQ ID NOs: 251-257; See Table 5 and FIG. 4) of each domain were PCR amplified and pooled based on crossover point (each pool containing 53 PCR fragments). Two sets of Dm3 PCR fragment pools, each set containing 7 individual Dm3 fragments pools, were made. One set was made for IPRS-C21 backbone and another set for IPRS-C16 and IPRS-C18 backbones. Corresponding pools forming each set are identical except for cross over region homology (FIG. 4).

Seven (corssovers 1-7, also named F2-F8 respectively) vector backbones were made by inverse PCR of backbone excluding the region to be swapped using backbone specific PCR primers. Since IPRS-C16 and IPRS-C18 have identical Dm3s, common primers were used for these two backbones.

Each specific Dm3 pool was assembled with corresponding inverse PCR Vector backbone to obtain all variants in pMal vector backbone to be expressed as MBP fusion proteins. All variants were re-arrayed after sequence confirmation. Only those clones that were expressed in soluble fraction in *E. coli* were further purified and tested for their insect activity. IPRS-C16 and IPRS-C18 Dm3 variants were initially screened against FAW and IPRS-C21 variants were screened against CEW. Active variants were further tested for their activity spectrum on other lepidopteran pests (See Table 4 and FIG. 7). The Dm3 variants retained activity but, had decreased activity as tested against their respective target insect (IPRS-C16 and IPRS-C18: FAW, IPRS-C21: CEW) compared their parents.

TABLE 3

Activity spectrum of shuffled clones

| SEQ ID NO: | Variant name | Toxin Composition | | | | | Activity (ppm) | | | | | | | | | |
|---|---|---|---|---|---|---|---|---|---|---|---|---|---|---|---|---|
| | | Dm1 | | | | | CEW | | FAW | | ECB | | SBL | | VBC | |
| | | α1-2 | α3-5 | α6-7 | Dm2 | Dm3 | IC50 | LC50 | IC50 | LC50 | ILC50 | LC50 | ILC50 | LC50 | ILC50 | LC50 |
| 59 | C13 | 1Ea | Aa | 1Ea | 1Ea | 1Ca | N.A. | N.A. | 3.4 | 63 | N.A. | N.A. | <3 | <3 | <1 | 16 |
| 60 | C14 | 1Ea | Ab | 1Ea | 1Ea | 1Ca | N.D. | N.D. | 4.52 | 185 | N.D. | N.D. | N.D. | N.D. | N.D. | N.D. |
| 61 | C15 | 1Ea | Eb | 1Ea | 1Ea | 1Ca | N.D. | N.D. | 5.06 | 168 | N.D. | N.D. | N.D. | N.D. | N.D. | N.D. |
| 62 | C16 | 1Ea | MP294 | 1Ea | 1Ea | 1Ca | N.A. | N.A. | <1 | 25 | N.A. | N.A. | <3 | <3 | <1 | 4 |
| 63 | C17 | 1Ea | Ad | 1Ea | 1Ea | 1Ca | N.A. | N.A. | 4 | 69 | N.A. | N.A. | <2 | <2 | <1 | 4.5 |
| 64 | C19 | 1Ea | MP294 | 1Ea | 1Ea | 1Ca | N.D. | N.D. | 35 | 282 | N.D. | N.D. | N.D. | N.D. | N.D. | N.D. |
| 65 | C31 | 1Ea | Eb | 1Ea | 1Ea | 1Ca | N.D. | N.D. | 333 | N.M. | N.D. | N.D. | N.D. | N.D. | N.D. | N.D. |

*N.A. means not active as tested; and N.D. means not determined

Example 5: Dm3 Fragment Shuffling on C16 and C21

Domain 3 (Dm3) is believed to be involved in secondary receptor recognition. Therefore, Dm3 shuffling was done on IPRS-C16 (SEQ ID NO: 62), IPRS-C18 (SEQ ID NO: 66), and IPRS-C21 (SEQ ID NO: 88) to generate unique variants and potentially having different sites of action (SOA). Based on the alignment of several Cry toxins, seven different crossover regions between Dm2 and Dm3, which are generally conserved, were used as recombination sites for Dm3 fusion on IPRS-C16, IPRS-C18 and IPRS-C21 Dm1-Dm2 backbones.

TABLE 4

Dm3 swapping activity spectrum on other Lepidopteran pests

| SEQ ID NO: | Variant name | Toxin Composition | | | | | Activity (ppm) | | | | | | | | | |
|---|---|---|---|---|---|---|---|---|---|---|---|---|---|---|---|---|
| | | Dm1 | | | | | CEW | | FAW | | ECB | | SBL | | VBC | |
| | | α1-2 | α3-5 | α6-7 | Dm2 | Dm3 | IC50 | LC50 | IC50 | LC50 | ILC50 | LC50 | ILC50 | LC50 | ILC50 | LC50 |
| 66 | IPRS-C18 | 1Ea | MP294 | 1Ea | MP372 | 1CaF3 | N.A. | N.A. | <1 | 11 | N.A. | N.A. | <3 | <3 | <3 | <3 |
| 67 | IPRS-C32 | 1Ea | MP294 | 1Ea | 1Cb | 1CaF3 | N.A. | N.A. | 27.02 | N.M. | N.D. | N.D. | N.D. | N.D. | N.D. | N.D. |
| 73 | IPRS-C58 | 1Ea | MP294 | 1Ea | MP372_2F1 | 1CaF3 | N.D. | N.D. | 40 | N.M | N.D. | N.D. | N.D. | N.D. | N.D. | N.D. |
| 74 | IPRS-C59 | 1Ea | MP294 | 1Ea | 1Ga_2F1 | 1CaF3 | N.D. | N.D. | 168 | N.M | N.D. | N.D. | N.D. | N.D. | N.D. | N.D. |
| 75 | IPRS-C71 | 1Ea | MP294 | 1Ea | GS028_2F1 | 1CaF3 | N.D. | N.D. | 25 | 325 | N.D. | N.D. | N.D. | N.D. | N.D. | N.D. |
| 76 | IPRS-C72 | 1Ea | MP294 | 1Ea | 1Eb_2F1 | 1CaF3 | N.D. | N.D. | 7 | 47 | N.D. | N.D. | N.D. | N.D. | N.D. | N.D. |
| 77 | IPRS-C73 | 1Ea | MP294 | 1Ea | 1Eb_2F2 | 1CaF3 | N.D. | N.D. | 3.2 | 46 | N.D. | N.D. | N.D. | N.D. | N.D. | N.D. |
| 68 | IPRS-C33 | 1Ea | MP294 | 1Ea | 1Ea | IfF3 | N.D. | N.D. | 102 | N.M | N.D. | N.D. | N.D. | N.D. | N.D. | N.D. |
| 69 | IPRS-C34 | 1Ea | MP294 | 1Ea | 1Ea | 9EbF3 | N.D. | N.D. | 196 | N.M | N.D. | N.D. | N.D. | N.D. | N.D. | N.D. |

TABLE 4-continued

Dm3 swapping activity spectrum on other Lepidopteran pests

| SEQ ID NO: | Variant name | Toxin Composition | | | | | Activity (ppm) | | | | | | | | | |
|---|---|---|---|---|---|---|---|---|---|---|---|---|---|---|---|---|
| | | Dm1 | | | Dm2 | Dm3 | CEW | | FAW | | ECB | | SBL | | VBC | |
| | | α1-2 | α3-5 | α6-7 | | | IC50 | LC50 | IC50 | LC50 | ILC50 | LC50 | ILC50 | LC50 | ILC50 | LC50 |
| 70 | IPRS-C35 | 1Ea | MP294 | 1Ea | MP372 | 1CbF2 | N.D. | N.D. | 92 | N.M | N.D. | N.D. | N.D. | N.D. | N.D. | N.D. |
| 71 | IPRS-C56 | 1Ea | MP294 | 1Ea | MP372 | 1AeF3 | N.D. | N.D. | 27 | N.M | N.D. | N.D. | N.D. | N.D. | N.D. | N.D. |
| 72 | IPRS-C57 | 1Ea | MP294 | 1Ea | 1Ea | 1BbF3 | N.D. | N.D. | >200 | N.M | N.D. | N.D. | N.D. | N.D. | N.D. | N.D. |
| 89 | IPRS-C66 | 1Jc | 1Ca | 1Jc | 1Jc | 1F2F3 | 20 | N.M | N.A. | N.A. | N.A. | N.A. | 10 | 29 | 865 | N.M |
| 78 | IPRS-C74 | 1Ea | MP294 | 1Ea | GS028_2F2 | 1CaF3 | N.D. | N.D. | <1 | 24 | N.D. | N.D. | N.D. | N.D. | N.D. | N.D. |

*N.A. means not active as tested; N.M. means no mortality as tested; N.D. means not determined; and F number is the crossover point

TABLE 5

Cry toxin Dm3 fragments crossover points:

| SEQ ID NO: | amino acid consensus sequence at which Dm3 fragment fused to C16 and C18 backbones | Dm2-Dm3 Cross over point |
|---|---|---|
| 251 | WTHHS | F2 |
| 252 | ITQIP | F3 |
| 253 | GFTGG | F4 |
| 254 | RYASS | F5 |
| 255 | KTMEI | F6 |
| 256 | TFRYT | F7 |
| 257 | PFSFR | F8 |

Example 6: Sequential Alpha Loop 3-5 and Dm3 Shuffling on MP1068 Backbone

MP1068 (SEQ ID NO: 214) is a proprietary Cry toxin. It has 63% homology to Cry1Ac. Its Dm1 is 84% similar to Cry1Ac, Dm2 is unique with 45% homology to Cry1Nb and Dm3 has 79% homology to Cry1Bh. Since MP1068 Dm2 is very unique, variants based on MP1068 Dm2 as backbone were created. Initially, MP1068 toxin region was expressed as MBP fusion protein, but attempts were unsuccessful as all expressed protein was in insoluble fraction. To overcome the soluble expression problem, shuffling was performed on the alpha loop 3-5 fragment, which is exposed to solvents (see FIGS. 5 and 6), to generate variants of MP1068 with insect activity followed by Dm3 shuffling on that backbone to improve activity.

MP1068 in pMal vector backbone was obtained by inverse PCR backbone specific primers. This vector backbone has all vector components along MP1068 toxin except the alpha loop 3-5 region. 23 alpha loop 3-5 fragments were PCR amplified form synthesized Dm1 fragments (Table 5). Equal amounts of all alpha loop 3-5 fragments were pooled and gel purified. Alpha loop 3-5 PCR fragment pool and MP1068 vector backbone were assembled using Geneart (Invitrogen) homology based assembly kit. Assembled reaction was transformed into BL21 cells and plated. Three 96-well plates of colonies were collected and directly tested for their soluble expression. All expressed clones were re-arrayed and sent for sequencing to remove redundant sequences.

Sequencing data revealed that there were 9 unique MP1068 variants with different alpha loop 3-5 sequences swapped. All 9 variants were tested in a diet assay for their insect activity against CEW, FAW and ECB (Table 6 and FIG. 7).

TABLE 6

MP1068 alpha swapped variant insect activity

| SEQ ID NO: | Variant Name | Toxin Composition | | | | | Activity (ppm) | |
|---|---|---|---|---|---|---|---|---|
| | | Dm1 | | | Dm2 | Dm3 | CEW | |
| | | α1-2 | α3-5 | α6-7 | | | IC50 | LC50 |
| 100 | IPRS-C23 | MP1068 | 1Aa | MP1068 | MP1068 | MP1068 | 5.5 | 62 |

| SEQ ID NO: | Variant Name | Activity (ppm) | | | | | | | |
|---|---|---|---|---|---|---|---|---|---|
| | | FAW | | ECB | | SBL | | VBC | |
| | | IC50 | LC50 | ILC50 | LC50 | ILC50 | LC50 | ILC50 | LC50 |
| 100 | IPRS-C23 | 7.28 | N.M | 4.3 | 117 | N.D. | N.D. | N.D. | N.D. |

*N.A. means not active as tested; N.M. means no mortality as tested; and N.D. means not determined IPRS-C23 was selected as backbone for further Dm3 shuffling (See Example 5) as it was more active compared to two other active clones as tested. Six Dm3s, from Cry1Ca, Cry1Cb, Cry1Da, MP258 (See US 20160194364 A1, SEQ ID NO: 16, herein incorporated by reference), Cry1Bb, and Cry1Ja were selected as a source of diversity. Five fragments of (crossover points 1-4, also named F2 to F5 crossover points) of each Dm3 were obtained by PCR amplification. The individual fragments (for example, F2s of all Dm3s in the diversity) were pooled into 5 Dm3 pools (F2 to F5 pools). The vector backbone was obtained by inverse PCR excluding the region to be swapped. In order to facilitate homology based assembly, the ends of the vector backbone and the inserts (Dm3 pools) had a 15 bp identical sequence overlap. The insert pools and vector backbones were gel purified assembled using NEB builder or Gene Art assembly kits. The assembly reaction was then transformed into BL21 cells, and collected colonies were screened by sequencing. Individual unique clones were re-arrayed and checked for expression using Bio-Rad 96-well E-Page gel and blotting. Clones expressing hybrid toxins in soluble fraction were grown in 150 ml culture of magic media and purified by standard Ni-NTA purification and tested for their insect activity.

All possible 30 clones were purified and tested for their activity against CEW, FAW and ECB and 10 were found to be active variants as tested 6 of those 10 active variants showed improved activity against all three insects tested (Table 7).

Whole Dm1s from several proprietary Cry1 toxins were PCR amplified from their respective parent Cry toxins. All PCR amplified fragments were pooled and gel purified to remove any remnants of parent clones. Then, pooled Dm1 fragments were allowed to recombine using a PCR with natural amino acid diversity representing various Dm1 fragments. Four 50 µL assembly reactions containing 0.5-1.0 µM pooled library oligos and Dm1 fragments were assembled in a Herculase II (Stratagene) reaction. A subsequent PCR reaction to amplify the fully extended approximately 1 Kb gene was carried out by adding 0.5 µM of flanking primers with 30 bp homology to the pMal vector backbone containing GS062 Dm2, Dm3.

Vector backbone was obtained by inverse PCR of GS062 toxin in pMal vector. Inverse PCR primers were designed in such a way to exclude GS062 Dm1 from the PCR fragment, so, inverse PCR vector backbone fragment would include all pMal vector components along with MBP, GS062 Dm2 and Dm3.

Rescued Dm1 mixtures were assembled using Invitrogen Geneart DNA fragment assembly kit. The assembly reaction was transformed into Invitrogen Top10 chemically compe-

TABLE 7

C23 Dm3 shuffling activity

| SEQ ID NO: | Variant Name | Toxin Composition | | | | | Activity (ppm) CEW | |
|---|---|---|---|---|---|---|---|---|
| | | Dm1 | | | | | | |
| | | α1-2 | α3-5 | α6-7 | Dm2 | Dm3 | IC50 | LC50 |
| 102 | IPRS-C24 | MP1068 | 1Aa | MP1068 | MP1068 | 1Cb (F2) | 2 | 14 |
| 103 | IPRS-C25 | MP1068 | 1Aa | MP1068 | MP1068 | 1Cb (F3) | <1 | 15 |
| 104 | IPRS-C26 | MP1068 | 1Aa | MP1068 | MP1068 | 1Da (F3) | 17 | 260 |
| 105 | IPRS-C27 | MP1068 | 1Aa | MP1068 | MP1068 | 1Ja (F2) | 11 | N.M |
| 106 | IPRS-C28 | MP1068 | 1Aa | MP1068 | MP1068 | 1Ja (F3) | 9 | 580 |
| 107 | IPRS-C29 | MP1068 | 1Aa | MP1068 | MP1068 | MP258 (F4) | 2.19 | 27 |
| 108 | IPRS-C41 | MP1068 | 1Aa | MP1068 | MP1068 | MP258 (F2) | 5 | 100 |
| 109 | IPRS-C42 | MP1068 | 1Aa | MP1068 | MP1068 | MP258 (F3) | <1 | 25 |
| 110 | IPRS-C43 | MP1068 | 1Aa | MP1068 | MP1068 | MP258 (F5) | <1 | 31 |
| 111 | IPRS-C44 | MP1068 | 1Aa | MP1068 | MP1068 | 1Bb (F3) | 11.4 | 224 |

| SEQ ID NO: | Variant Name | Activity (ppm) | | | | | | |
|---|---|---|---|---|---|---|---|---|
| | | FAW | | ECB | | SBL | | VBC | |
| | | IC50 | LC50 | ILC50 | LC50 | ILC50 | LC50 | ILC50 | LC50 |
| 102 | IPRS-C24 | 7 | N.M | 1.12 | 930 | <3 | <3 | 2.3 | 3.5 |
| 103 | IPRS-C25 | 3 | N.M | 11 | 567 | <5 | <5 | 1 | 1 |
| 104 | IPRS-C26 | 148 | N.M | N.D | N.D. | N.D | N.D. | N.D | N.D. |
| 105 | IPRS-C27 | 5 | N.M | N.D | N.D. | N.D | N.D. | N.D | N.D. |
| 106 | IPRS-C28 | <1 | N.M | N.D | N.D. | N.D | N.D. | N.D | N.D. |
| 107 | IPRS-C29 | 5.5 | N.M | N.D | N.D. | N.D | N.D. | N.D | N.D. |
| 108 | IPRS-C41 | 16 | N.M | 1 | 269 | <3 | <3 | 47 | 124 |
| 109 | IPRS-C42 | 3.6 | N.M | 1.2 | 105 | <2 | <2 | 120 | 1020 |
| 110 | IPRS-C43 | 4.5 | N.M | 1 | 427 | <3 | <3 | 61 | 266 |
| 111 | IPRS-C44 | N.A. | N.A. | N.D. | N.D. | N.D. | N.D. | N.D. | N.D. |

*N.A. means not active as tested; N.M. means no mortality as tested; N.D. means not determined; and F number is the crossover point Example 7: Sequential Dm1 and Dm3 Shuffling on GS062 Backbone (C45, 46, 47, 48 and C49)

GS062 (SEQ ID NO: 224) is a proprietary toxin with 62% homology to Cry1Da. Domain analysis revealed that it is a hybrid toxin with domain-1 is Cry1Ac type (77%), Dm2 is Cry1Ca type (80%) and Dm3 is Cry1Hb type (79%). GS062 was active only on ECB but not on CEW and FAW as tested. Native GS062 was family shuffled Dm1 on GS062 backbone to improve ECB activity and then shuffled Dm3 to add CEW or FAW specificity.

tent cells. After sequence analysis, all colonies were pooled and made a mixed plasmid preparation. The mixed plasmid was transformed into Lucigen Electro competent BL21 cells for protein expression.

Approximately 3000 E. coli (BL21) colonies were collected and screened for full-length MBP-toxin protein expression using Western blotting. Approximately 400 clones expressing hybrid toxin in soluble fraction in E. Coli were collected and re-arrayed. Protein was purified from these clones and submitted for their ECB activity in a Yes/No assay. Then, 40 active clones, based on ECB activity, among the 400 clones screened were re-arrayed and sequenced. Upon sequencing, redundant clones (clones with same sequence) were removed and only 16 unique clones were re-arrayed, purified and tested for their specific activity on ECB and SBL in a dose response manner.

Due to lack of sufficient homology among Dm1s selected for shuffling, many clones have either whole Dm1 or Dm1 with random mutations swapped on to GS062 backbone (Dm2-Dm3). Dm1s of these16 hits comes from MP477 (SEQ ID NO: 223), GS128 (SEQ ID NO: 244), and GS002 (SEQ ID NO: 235). These 16 clones were tested for their ECB and SBL activity in dose response manner. None of these 16 clones yielded any measurable specific activity number (IC or LC50) on ECB as tested, but 1 clone with GS002 Dm1 showed good SBL activity (Table 8).

Example 8: Dm1 Alpha Loop Swaps (Alpha Loop 3, 4, 5, 3-4, 4-5, and 3-5 Shuffling) on C16 and C21

Based on the success of alpha loop 3-5 fragment shuffling strategy (employed in different block shuffling strategies), shuffled individual and combination of alpha helices were tested to show which alpha helix or helices may improve activity or soluble expression. Alpha loop 3-5 fragment shuffled in previous libraries included alpha loop 3, 4, and only a portion of alpha loop 5. In this library, shuffled alpha loop 3, Alpha loop 4, and whole Alpha loop 5 individually and in combination on two block shuffled variants C16 and C21. Alpha loop 3-5 fragment shuffled in this library was slightly longer than alpha loop 3-5 fragments shuffled in all previous libraries (See FIGS. 8 and 9).

Alpha loops 3, 4, 5, 3-4, 4-5, and 3-5 were PCR amplified from 45 synthesized Dm1 fragments (See FIG. 11). Different

TABLE 8

GS062 backbone swapped Dm1 Activity

| SEQ ID NO: | Variant Name | Toxin Composition | | | Activity (ppm) | | | | | | | | | |
|---|---|---|---|---|---|---|---|---|---|---|---|---|---|---|
| | | | | | CEW | | FAW | | ECB | | SBL | | VBC | |
| | | Dm1 | Dm2 | Dm3 | IC50 | LC50 | IC50 | LC50 | ILC50 | LC50 | ILC50 | LC50 | ILC50 | LC50 |
| 112 | IPRS-C49 | GS002 | GS062 | GS062 | N.A | N.A | N.A | N.A | 1300 | 1842 | 12 | 18 | 80 | N.M |

*N.A. means not active as tested; N.M. means no mortality as tested; and N.D. means not determined IPRS-C49 showed no activity on CEW and FAW as tested, but was highly active on SBL, moderately active on VBC, and slightly active on ECB (See Table 8).

IPRS-C49 (SEQ ID NO: 112) was selected as backbone for further Dm3 shuffling (See Example 3) as it was more active compared to three other active clones. Six Dm3s, from Cry1Ca, Cry1Cb, Cry1Da, Cry1Ab, Cry1Ac, and Cry1Be were selected as a sources of diversity.

All possible 30 clones were purified and tested for their activity against CEW and FAW. Four variants were active on CEW but not on FAW as tested. Two of the four active variants were selected for further Lepidopteran activity spectrum studies, and showed improved activity against ECB, SBL and VBC (Table 9).

alpha loop fragments of Cry1Ca were obtained from C21 which contained Cry1Ca alpha loop 3-5 fragment. Six different Individual and combinatorial alpha loop fragment pools per backbone (alpha loop 3 pool, 4 pool, 5 pool, 3-4 pool, 4-5 pool, and 3-5 pool) were made. Alpha fragments of Cry1Ea and Cry1Ca were not included in pools corresponding to C16 and C21 respectively to avoid generating parent backbones. All pools were digested with Dpn-1 and gel purified to avoid parent contamination. Table 10 shows which different domain 1 alpha helices were PCR amplified. Different alpha fragments of Cry1Ca were obtained as C21 contains Cry1Ca alpha loop 3-5 fragment.

C16 and C21 vector backbones for corresponding alpha loop 3, 4, 5, 3-4, 4-5, and 3-5 regions were generated by inverse PCR, excluding the region to be shuffled using backbone specific primers.

TABLE 9

C49 Dm3 shuffled variant activity.

| SEQ ID NO: | Variant Name | Toxin Composition | | | Activity (ppm) | | | | | | | | | |
|---|---|---|---|---|---|---|---|---|---|---|---|---|---|---|
| | | | | | CEW | | FAW | | ECB | | SBL | | VBC | |
| | | Dm1 | Dm2 | Dm3 | IC50 | LC50 | IC50 | LC50 | ILC50 | LC50 | ILC50 | LC50 | ILC50 | LC50 |
| 97 | IPRS-C45 | GS002 | GS062 | 1Cb (F2) | 28 | 120 | N.A. | N.A. | 65 | 320 | <3 | <3 | <3 | <3 |
| 99 | IPRS-C47 | GS002 | GS062 | 1Be (F3) | 20 | 70 | N.A. | N.A. | 24 | 119 | <3 | <3 | <3 | <3 |
| 96 | IPRS-C46 | GS002 | GS062 | 1Cb (F1) | 12 | 43 | N.D | N.D. | N.D | N.D. | N.D | N.D. | N.D. | N.D. |
| 98 | IPRS-C48 | GS002 | GS062 | 1Da (F2) | 40 | N.M | N.D | N.D. | N.D | N.D. | N.D | N.D. | N.D. | N.D. |

*N.A. means not active as tested; N.M. means no mortality as tested; N.D. means not determined; and F number is the crossover point Similar shuffling was completed using GS047 (SEQ ID NO: 228). All possible 30 clones were purified and tested for their activity against CEW and FAW. Four variants were active on FAW. All four showed FAW activity as tested (SEQ ID NOs: 275-278, encoded by SEQ ID NOs: 271-274 respectively).

Twelve assembly reactions (six pools/backbone) were performed. Gel purified vector backbones were assembled with respective alpha helix fragment pool to obtain all variants in pMal vector to be expressed as MBP-fusion proteins. All unique variants were re-arrayed after sequence confirmation, and only those clones that were expressed in the soluble fraction were further purified and tested for their insect activity. C16 based variants were tested against FAW, and C21 variants were tested against CEW as C16 and C21 are active on FAW and CEW respectively. Fourteen active variants were isolated (8 from C16 backbone and 6 from C21 backbone). Table 10 shows the tested activity of the variants.

TABLE 10

Insecticidal activity of C16 and C21 alpha loop 3, 4, 5, 3-4, 4-5, and 3-5 variants

| SEQ ID | Variant | Toxin Composition | | | | | | | Activity (ppm) | | | |
|---|---|---|---|---|---|---|---|---|---|---|---|---|
| | | Dm1 | | | | | | | FAW | | CEW | |
| NO: | name | α1-2 | α3 | α4 | α5 | α6-7 | Dm2 | Dm3 | IC50 | LC50 | IC50 | LC50 |
| 79 | IPRS-C36 | 1Ea | Da | MP294 | | 1Ea | 1Ea | 1CaF3 | 15 | 51 | N.D | |
| 80 | IPRS-C37 | 1Ea | MP294 | | Aa | 1Ea | 1Ea | 1CaF3 | 3.2 | N.M | N.D | |
| 81 | IPRS-C38 | 1Ea | MP294 | Ad | MP294 | 1Ea | 1Ea | 1CaF3 | 5.1 | N.M | N.D | |
| 82 | IPRS-C39 | 1Ea | MP294 | | Ae | 1Ea | 1Ea | 1CaF3 | 2.4 | N.M | N.D | |
| 83 | IPRS-C52 | 1Ea | MP294 | | Db | 1Ea | 1Ea | 1CaF3 | 17 | N.M | N.D | |
| 84 | IPRS-C53 | 1Ea | MP294 | | Dc | 1Ea | 1Ea | 1CaF3 | 6.2 | N.M | N.D | |
| 85 | IPRS-C54 | 1Ea | MP294 | | Eb | 1Ea | 1Ea | 1CaF3 | 4.1 | N.M | N.D | |
| 86 | IPRS-C55 | 1Ea | MP294 | | Hb | 1Ea | 1Ea | 1CaF3 | 42.5 | N.M | N.D | |
| 112 | IPRS-C49 | 1Jc | 1Aa | 1Ca | 1Ca | 1Jc | 1Jc | 1Jc | N.D | | 9.20 | N.M |
| 91 | IPRS-C61 | 1Jc | 1Jc | 1Ca | 1Ca | 1Jc | 1Jc | 1Jc | N.D | | 6.37 | N.M |
| 92 | IPRS-C62 | 1Jc | 1Ca | | 1Ah | 1Jc | 1Jc | 1Jc | N.D | | 3.95 | N.M |
| 93 | IPRS-C63 | 1Jc | 1Ca | | 1Ea | 1Jc | 1Jc | 1Jc | N.D | | 3.07 | N.M |
| 94 | IPRS-C64 | 1Jc | 1Ca | | 1Jc | 1Jc | 1Jc | 1Jc | N.D | | 4.18 | N.M |
| 95 | IPRS-C65 | 1Jc | 1Ca | | 1Jd | 1Jc | 1Jc | 1Jc | N.D | | 2.39 | N.M |

That which is claimed is:

1. An insecticidal polypeptide comprising an amino acid sequence having at least 90% sequence identity to SEQ ID NO: 70.

2. An isolated polynucleotide encoding the insecticidal polypeptide of claim 1.

3. The isolated polynucleotide of claim 2, wherein the isolated polynucleotide comprises a nucleic acid sequence having at least 90% sequence identity to SEQ ID NO: 14.

4. A DNA construct comprising the polynucleotide of claim 2.

5. A host cell comprising the DNA construct of claim 4.

6. The host cell of claim 5, wherein the host cell is a plant cell.

7. The host cell of claim 5, wherein the host cell is a bacterial cell.

8. A transgenic plant comprising the DNA construct of claim 4.

9. A recombinant insecticidal polypeptide having at least 95% sequence identity to the amino acid sequence of SEQ ID NO: 70.

10. A composition comprising at least one recombinant insecticidal polypeptide of claim 9.

11. A recombinant polynucleotide encoding the insecticidal polypeptide of claim 9.

12. The recombinant polynucleotide of claim 11, wherein the polynucleotide has codons optimized for expression in an agriculturally important crop.

13. The recombinant polynucleotide of claim 11, wherein the recombinant polynucleotide comprises a nucleic acid sequence having at least 95% sequence identity to SEQ ID NO: 14.

14. The recombinant polynucleotide of claim 11, wherein the recombinant polynucleotide is operably linked to a heterologous promoter.

15. A DNA construct comprising a polynucleotide encoding a polypeptide having at least 90% sequence identity to the amino acid sequence of SEQ ID NO: 70, and a heterologous regulatory element, wherein the heterologous regulatory element is operably linked to the polynucleotide.

16. A host cell transformed with the DNA construct of claim 15.

17. The host cell of claim 16, wherein the host cell is a bacterial cell or a plant cell.

18. The host cell of claim 17, wherein the plant cell is a monocot or a dicot.

19. A transgenic plant comprising the polynucleotide of claim 11.

20. A transgenic plant comprising the DNA construct of claim 15.

21. A method of inhibiting growth or killing an insect pest or pest population comprising expressing in a plant the recombinant polynucleotide of claim 11.

22. The DNA construct of claim 15, wherein the polynucleotide comprises a nucleic acid sequence having at least 90% sequence identity to SEQ ID NO: 14.

23. A method of inhibiting growth of, or killing, an insect pest or pest population, comprising contacting the insect pest or pest population with the insecticidal polypeptide of claim 1.

24. The method of claim 23, wherein the insect pest or pest population is resistant to at least one Cry insecticidal protein.

* * * * *